US012384841B2

(12) United States Patent
Bracken et al.

(10) Patent No.: US 12,384,841 B2
(45) Date of Patent: Aug. 12, 2025

(54) ANTI-PAR-2 ANTIBODIES AND METHODS OF USE THEREOF

(71) Applicant: Cephalon LLC, West Chester, PA (US)

(72) Inventors: Anna Mikaela Bracken, Lane Cove (AU); Adam Clarke, Riverstone (AU); Bridget A. Cooksey, Curl Curl (AU); Anthony Gerard Doyle, Macquarie Park (AU); Mark Terence Liddament, Victoria (AU); Matthew Pollard, Pullenvale (AU); Lynn Poulton, Macquarie Park (AU); Anna Maria Matilda Quigley, Macquarie Park (AU); Julia Rozenfeld, Macquarie Park (AU); Marta Szabat, Vancouver (CA)

(73) Assignee: Cephalon LLC, West Chester, PA (US)

( * ) Notice: Subject to any disclaimer, the term of this patent is extended or adjusted under 35 U.S.C. 154(b) by 0 days.

(21) Appl. No.: 18/338,946

(22) Filed: Jun. 21, 2023

(65) Prior Publication Data

US 2024/0150457 A1 May 9, 2024

Related U.S. Application Data

(62) Division of application No. 17/405,275, filed on Aug. 18, 2021, now Pat. No. 11,725,052.

(60) Provisional application No. 63/067,259, filed on Aug. 18, 2020.

(51) Int. Cl.
*G01N 33/53* (2006.01)
*A61P 17/10* (2006.01)
*A61P 29/00* (2006.01)
*A61P 35/04* (2006.01)
*C07K 16/28* (2006.01)

(52) U.S. Cl.
CPC .............. *C07K 16/28* (2013.01); *A61P 17/10* (2018.01); *A61P 29/00* (2018.01); *A61P 35/04* (2018.01); *C07K 2317/24* (2013.01); *C07K 2317/33* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,122,464 A | 6/1992 | Wilson et al. | |
| 5,223,409 A | 6/1993 | Ladner et al. | |
| 5,225,539 A | 7/1993 | Winter | |
| 5,403,484 A | 4/1995 | Ladner et al. | |
| 5,427,908 A | 6/1995 | Dower et al. | |
| 5,516,637 A | 5/1996 | Huang et al. | |
| 5,571,698 A | 11/1996 | Ladner et al. | |
| 5,580,717 A | 12/1996 | Dower et al. | |
| 5,658,727 A | 8/1997 | Barbas et al. | |
| 5,693,780 A | 12/1997 | Newman et al. | |
| 5,698,426 A | 12/1997 | Huse | |
| 5,733,743 A | 3/1998 | Johnson et al. | |
| 5,750,753 A | 5/1998 | Kimae et al. | |
| 5,780,225 A | 7/1998 | Wigler et al. | |
| 5,821,047 A | 10/1998 | Garrard et al. | |
| 5,837,242 A | 11/1998 | Holliger et al. | |
| 5,869,620 A | 2/1999 | Whitlow et al. | |
| 5,965,726 A | 10/1999 | Pavlakis et al. | |
| 5,969,108 A | 10/1999 | McCafferty et al. | |
| 5,989,830 A | 11/1999 | Davis et al. | |
| 6,132,992 A | 10/2000 | Ledbetter et al. | |
| 6,174,666 B1 | 1/2001 | Pavlakis et al. | |
| 6,291,664 B1 | 9/2001 | Pavlakis et al. | |
| 6,414,132 B1 | 7/2002 | Pavlakis et al. | |

(Continued)

FOREIGN PATENT DOCUMENTS

| | | |
|---|---|---|
| WO | WO-8605807 A1 | 10/1986 |
| WO | WO-8901036 A1 | 2/1989 |

(Continued)

OTHER PUBLICATIONS

Akers, I. A., et al., "Mast Cell Tryptase Stimulates Human Lung Fibroblast Proliferation via Protease-activated Receptor-2," American Journal of Physiology Lung Cellular and Molecular Physiology 278(1):L193-L201, American Physiological Society, United States (Jan. 2000).

Akiyama, T., et al., "Protease-activated Receptors and Itch," Handbook of Experimental Pharmacology 226:219-235, Springer-Verlag, Germany (2015).

Akiyama, T., et al., "Enhanced scratching evoked by PAR-2 agonist and 5-HT but not histamine in a mouse model of chronic dry skin itch," Pain 151(2):378-383, Elsevier, Netherlands (Nov. 2010).

Altschul, S. F., et al., "Basic Local Alignment Search Tool," Journal of Molecular Biology 215(3):403-410, Elsevier, United Kingdom (Oct. 1990).

Altschul, S. F., et al., "Gapped BLAST and PSI-BLAST: A New Generation of Protein Database Search Programs," Nucleic Acids Research 25(17):3389-3402, Oxford University Press, United Kingdom (Sep. 1997).

(Continued)

*Primary Examiner* — Maher M Haddad
(74) *Attorney, Agent, or Firm* — Sterne, Kessler, Goldstein & Fox P.L.L.C.

(57) ABSTRACT

The present disclosure provides antibodies and antigen-binding fragments thereof that specifically bind to human PAR-2 and compositions comprising such antibodies or antigen-binding fragments thereof. In a particular aspect, the antibodies or antigen-binding fragments thereof that specifically bind to human PAR-2 block the interaction between a PAR-2 activating ligand and an extracellular domain of PAR-2, and/or blocks PAR-2 activation by a PAR-2 activating ligand. In further aspects, the antibodies or antigen-binding fragments can be used to treat diseases or conditions associated with increased expression of PAR-2 and/or diseases or conditions that can be alleviated by antagonizing activation of PAR-2 by a PAR-2 activating ligand (e.g., airway diseases, skin diseases, cancer, orofacial granulomatosis, inflammatory conditions, and pain associated with various diseases or conditions).

3 Claims, 9 Drawing Sheets

Specification includes a Sequence Listing.

(56) References Cited

U.S. PATENT DOCUMENTS

| | | |
|---|---|---|
| 6,794,498 B2 | 9/2004 | Pavlakis et al. |
| 7,083,784 B2 | 8/2006 | Dall'Acqua et al. |
| 7,183,076 B2 | 2/2007 | Arathoon et al. |
| 7,217,797 B2 | 5/2007 | Hinton et al. |
| 7,888,482 B2 | 2/2011 | Virca et al. |
| 7,951,917 B1 | 5/2011 | Arathoon et al. |
| 8,101,724 B2 | 1/2012 | Macdonald et al. |
| 8,227,577 B2 | 7/2012 | Klein et al. |
| 8,357,367 B2 | 1/2013 | Virca et al. |
| 8,586,713 B2 | 11/2013 | Davis et al. |
| 8,927,503 B2 | 1/2015 | Fairlie et al. |
| 9,188,593 B2 | 11/2015 | Singhal et al. |
| 10,087,408 B2 | 10/2018 | Hansen et al. |
| 11,725,052 B2* | 8/2023 | Bracken .................. A61P 11/00 424/133.1 |
| 2004/0014194 A1 | 1/2004 | Beyer et al. |
| 2009/0068175 A1 | 3/2009 | Lazar et al. |
| 2009/0092599 A1 | 4/2009 | Lazar et al. |
| 2009/0142340 A1 | 6/2009 | Lazar et al. |
| 2011/0059095 A1 | 3/2011 | MacDonald et al. |
| 2012/0100140 A1 | 4/2012 | Reyes et al. |
| 2013/0122086 A1 | 5/2013 | Paterson et al. |
| 2016/0252495 A1 | 9/2016 | Ricicova et al. |
| 2018/0305450 A1 | 10/2018 | Dobson et al. |
| 2019/0292258 A1 | 9/2019 | Lippincott et al. |

FOREIGN PATENT DOCUMENTS

| | | |
|---|---|---|
| WO | WO-9002809 A1 | 3/1990 |
| WO | WO-9110737 A1 | 7/1991 |
| WO | WO-9201047 A1 | 1/1992 |
| WO | WO-9218619 A1 | 10/1992 |
| WO | WO-9311236 A1 | 6/1993 |
| WO | WO-9515982 A2 | 6/1995 |
| WO | WO-9520401 A1 | 8/1995 |
| WO | WO-9713844 A1 | 4/1997 |
| WO | WO-0042072 A2 | 7/2000 |
| WO | WO-2006127379 A2 | 11/2006 |
| WO | WO-2006127396 A1 | 11/2006 |
| WO | WO-2009036379 A2 | 3/2009 |
| WO | WO-2010017086 A1 | 2/2010 |
| WO | WO-2010105256 A1 | 9/2010 |
| WO | WO-2010132954 A1 | 11/2010 |
| WO | WO-2011031695 A1 | 3/2011 |
| WO | WO-2012009568 A2 | 1/2012 |
| WO | WO-2012010453 A1 | 1/2012 |
| WO | WO-2014020350 A1 | 2/2014 |
| WO | WO-2016005369 A1 | 1/2016 |
| WO | WO-2016154075 A1 | 9/2016 |
| WO | WO-2018167322 A1 | 9/2018 |
| WO | WO-2019157358 A1 | 8/2019 |

OTHER PUBLICATIONS

Ames, R. S., et al., "Conversion of Murine Fabs Isolated From a Combinatorial Phage Display Library to Full Length Immunoglobulins," Journal of Immunological Methods 184(2):177-186, Elsevier, Netherlands (Aug. 1995).

Amiable, N., et al., "Proteinase-Activated Receptor-2 Gene Disruption Limits the Effect of Osteoarthritis on Cartilage in Mice: A Novel Target in Joint Degradation," The Journal of Rheumatology 38(5):911-920, Journal Of Rheumatology Publishing Co, Canada (May 2011).

An, Z., et al., "IgG2m4, an Engineered Antibody Isotype with Reduced Fc Function," Mabs 1(6):572-579, Taylor & Francis, United States (Nov.-Dec. 2009).

Andersen, H. H., et al., "Nonhistaminergic and Mechanical Itch Sensitization in Atopic Dermatitis," Pain 158(9):1780-1791, Lippincott Williams & Wilkins, United States (Sep. 2017).

Asaduzzaman, M., et al., "Functional Inhibition of Par2 Alleviates Allergen-induced Airway Hyperresponsiveness and Inflammation," Clin Exp Allergy 45(12):1844-1855, Blackwell Scientific Publications, United Kingdom (Dec. 2015).

Asosingh, K., et al., "Endothelial Cells in the Innate Response to Allergens and Initiation of Atopic Asthma," The Journal of Clinical Investigation, 128(7):3116-3128, American Society for Clinical Investigation, United States (Jul. 2018).

Aubier, M., et al., "Airway Smooth Muscle Enlargement Is Associated With Protease-activated Receptor 2/ligand Overexpression in Patients With Difficult-to-control Severe Asthma," J Allergy Clin Immunol 138(3):729-739, Mosby, United States (Sep. 2016).

Bagher, M., et al., "Mast Cells and Mast Cell Tryptase Enhance Migration of Human Lung Fibroblasts Through Protease-activated Receptor 2," Cell Commun Signal 16(1):59, BioMed Central, United Kingdom (Sep. 2018).

Bao, Y., et al., "Protease-Activated Receptor 2 Antagonist Potentiates Analgesic Effects of Systemic Morphine in a Rat Model of Bone Cancer Pain," Regional Anesthesia and Pain Medicine 40(2):158-165, BMJ, United Kingdom (Mar.-Apr. 2015).

Barratt, S. L., et al., "Idiopathic Pulmonary Fibrosis (IPF): An Overview," Journal of Clinical Medicine 7(8):201, MDPI AG, Switzerland (Aug. 2018).

Berger, P., et al., "Tryptase and Agonists of Par-2 Induce the Proliferation of Human Airway Smooth Muscle Cells," J Appl Physiol 91(3):1372-1379, American Physiological Society, United States (Sep. 2001).

Bird, R. E., et al., "Single-chain Antigen-binding Proteins," Science 242(4877):423-426, Association for the Advancement of Science, United States (Oct. 1988).

Borensztajn, K., et al., "Protease-Activated Receptor-2 Induces Myofibroblast Differentiation and Tissue Factor Up-regulation During Bleomycin-induced Lung Injury: Potential Role in Pulmonary Fibrosis," The American Journal of Pathology 177(6):2753-2764, Elsevier, United States (Dec. 2010).

Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).

Bricogne, G., "Direct phase determination by entropy maximization and likelihood ranking: status report and perspectives," Acta Crystallogr D Biol Crystallogr 49(Pt 1): 37-60, John Wiley and Sons Inc., United States (Jan. 1993).

Bricogne, G., "Bayesian Statistical Viewpoint on Structure Determination: Basic Concepts and Examples," Methods in Enzymology 276:361-423, Academic Press, United States (1997).

Brinkmann, U., et al., "Phage Display of Disulfide-stabilized Fv Fragments," Journal of Immunological Methods 182(1):41-50, Elsevier, Netherlands (May 1995).

Briot, A., et al., "Par2 inactivation inhibits early production of TSLP, but not cutaneous inflammation, in Netherton syndrome adult mouse model," Journal of Investigative Dermatology 130(12):2736-2742, Elsevier, United States (Dec. 2010).

Brummell, D. A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (Feb. 1993).

Burks, E. A., et al., "In vitro Scanning Saturation Mutagenesis of an Antibody Binding Pocket," Proceedings of the National Academy of Sciences USA 94(2):412-417, Plenum Publishing Corporation, United States (Jan. 1997).

Burton, D. R., and Barbas, C. F., 3rd., "Human Antibodies From Combinatorial Libraries," Advances in Immunology 57:191-280, Academic Press, United States (1994).

Busso, N., et al., "Evaluation of protease-activated receptor 2 in murine models of arthritis," Arthritis & Rheumatology 56(1):101-107, John Wiley and Sons Ltd., United Kingdom (Jan. 2007).

Camateros, P., et al., "Toll-Like Receptor 7/8 Ligand, S28463, Suppresses Ascaris suum-induced Allergic Asthma in Nonhuman Primates," American Journal of Respiratory Cell and Molecular Biology 58(1):55-65, American Thoracic Society, United States (Jan. 2018).

Cenac, N., et al., "Role for protease activity in visceral pain in irritable bowel syndrome," Journal of Clinical Investigation 117(3):636-647, American Society for Clinical Investigation, United States (Mar. 2007).

(56) References Cited

OTHER PUBLICATIONS

Cenac, N., "Protease-activated receptors as therapeutic targets in visceral pain," Current Neuropharmacology 11(6):598-605, Bentham Science Publishers, United Arab Emirates (Dec. 2013).
Cevikbas, F., et al., "Role of protease-activated receptors in human skin fibrosis and scleroderma," Experimental Dermatology 20(1):69-71, John Wiley and Sons Inc., United States (Jan. 2011).
Chayen, N. E., "The role of oil in macromolecular crystallization," Structure 5(10):1269-1274, Cell Press, United States (Oct. 1997).
Chen, Y., et al., "Proteinase-activated receptor 2 sensitizes transient receptor potential vanilloid 1, transient receptor potential vanilloid 4, and transient receptor potential ankyrin 1 in paclitaxel-induced neuropathic pain," Neuroscience 193:440-451, Elsevier Science, United States (Oct. 2011).
Chen, K., et al., "Blocking PAR2 attenuates oxaliplatin-induced neuropathic pain via TRPVI and releases of substance P and CGRP in superficial dorsal horn of spinal cord," Journal of the Neurological Sciences 352(1-2):62-67, Elsevier, Netherlands (May 2015).
Chen, D., et al., "Blocking PAR2 Alleviates Bladder Pain and Hyperactivity via TRPA1 Signal," Translational Neuroscience 7(1):133-138, Walter de Gruyter GmbH, Germany (Nov. 2016).
Cheng, R. K. Y., et al., "Structural insight into allosteric modulation of protease-activated receptor 2," Nature 545(7652):112-115, Nature Publishing Group, United Kingdom (May 2017).
Cheung, R. C., et al., "Epitope-specific antibody response to the surface antigen of duck hepatitis B virus in infected ducks," Virology 176(2):546-552, Academic Press, United States (Jun. 1990).
Chien, Y. H., et al., "The genetics of atopic dermatitis," Clinical Reviews in Allergy & Immunology 33(3):178-190, Humana Press, United States (Dec. 2007).
Cho, Y. M., et al., "The IRE1α-XBP1s pathway promotes insulin-stimulated glucose uptake in adipocytes by increasing PPARγ activity," Experimental & Molecular Medicine 50(8):102, 15 pages, Nature Publishing Group, United Kingdom (Aug. 2018).
Choi, J., E., and Nardo, A.D., "Skin Neurogenic Inflammation," Review Seminars Immunopathology 40(3):249-259, Springer, Germany (May 2018).
Cockett, M. I., et al., "High Level Expression of Tissue Inhibitor of Metalloproteinases in Chinese Hamster Ovary Cells Using Glutamine Synthetase Gene Amplification," Biotechnology 8(7):662-667, Nature Publishing Company, United States (Jul. 1990).
Cocks, T. M., et al., "A Protective Role for Protease-activated Receptors in the Airways," Nature 398(6723):156-160, Nature Publishing Group, United Kingdom (Mar. 1999).
Cocks, T. M., et al., "Protease-activated Receptor-2 (PAR2) in the Airways," Pulmonary Pharmacology & Therapeutics, 14(3):183-191, Academic Press, United Kingdom (2001).
Crilly, A., et al., "PAR(2) expression in peripheral blood monocytes of patients with rheumatoid arthritis," Annals of the Rheumatic Diseases 71(6):1049-1054, BMJ, United Kingdom (Jun. 2012).
Cunningham, B. C., and Wells, J. A., "High-resolution epitope mapping of hGH-receptor interactions by alanine-scanning mutagenesis," Science 244(4908):1081-1085, American Association for the Advancement of Science, United States (Jun. 1989).
D'Andrea, M. R., et al., "Characterization of protease-activated receptor-2 immunoreactivity in normal human tissues," The Journal of Histochemistry and Cytochemistry 46(2):157-164, SAGE Publications, United States (Feb. 1998).
Davidson, E., and Doranz, B. J., "A high-throughput shotgun mutagenesis approach to mapping B-cell antibody epitopes," Immunology 143(1):13-20, John Wiley & Sons Ltd., United States (Sep. 2014).
De Boer, J. D., "Protease-activated receptor-2 deficient mice have reduced house dust mite-evoked allergic lung inflammation," Innate Immunity 20(6):618-625, Sage Publications, United States (Aug. 2014).

Demir, I. E., et al., "Perineural mast cells are specifically enriched in pancreatic neuritis and neuropathic pain in pancreatic cancer and chronic pancreatitis," PLoS One 8(3):e60529, Public Library of Science, United States (2013).
Devine, J. F., "Chronic obstructive pulmonary disease: an overview," American Health & Drug Benefits 1(7):34-42, Engage Healthcare Communications, Inc., United States (Sep. 2008).
Ducroc, R., et al., "Trypsin is produced by and activates protease-activated receptor-2 in human cancer colon cells: evidence for new autocrine loop," Life Sciences 70(12):1359-1367, Elsevier, Netherlands (Feb. 2012).
Dumet, C., et al., "Insights into the IgG heavy chain engineering patent landscape as applied to IgG4 antibody development," MAbs 11(8):1341-1350, Taylor & Francis, United States (Dec. 2019).
Dutra-Oliveira, A., et al., "Protease-activated receptor-2 (PAR2) mediates VEGF production through the ERK1/2 pathway in human glioblastoma cell lines," Biochemical and Biophysical Research Communications 421(2):221-227, Elsevier, United States (May 2012).
Dux, M., et al., "Involvement of capsaicin-sensitive afferent nerves in the proteinase-activated receptor 2-mediated vasodilatation in the rat dura mater," Neuroscience 161(3):887-894, Elsevier Science, United States (Jul. 2009).
Edelman, G. M., et al., "The covalent structure of an entire gammaG immunoglobulin molecule," Proceedings of the National Academy of Sciences USA 63(1):78-85, National Academy of Sciences, United States (May 1969).
Elmariah, S. B., et al., "Cathepsin S signals via PAR2 and generates a novel tethered ligand receptor agonist," PLoS One 9(6):e99702, Public Library of Science, United States (Jun. 2014).
Ferrell, W. R., et al., "Essential role for proteinase-activated receptor-2 in arthritis," The Journal of Clinical Investigation 111(1):35-41, American Society for Clinical Investigation, United States (Jan. 2017).
Flatters, S. J. L., et al., "Clinical and preclinical perspectives on Chemotherapy-Induced Peripheral Neuropathy (CIPN): a narrative review," British Journal of Anaesthesia 119(4):737-749, Elsevier, United Kingdom (Oct. 2017).
Foecking, M. K., et al., "Powerful and versatile enhancer-promoter unit for mammalian expression vectors," Gene 45(1):101-105, Elsevier, Netherlands (1986).
Frateschi, S., et al., "PAR2 absence completely rescues inflammation and ichthyosis caused by altered CAP1/Prss8 expression in mouse skin," Nature Communications 18(2):161, Nature Publishing Group, United Kingdom (Jan. 2011).
Gatheral, T. L., et al., "Personalised asthma action plans for adults with asthma," The Cochrane Database of Systematic Reviews 4(4):CD011859, Cochrane Library, United Kingdom (Apr. 2017).
Ge, L., et al., "Constitutive protease-activated receptor-2-mediated migration of MDA MB-231 breast cancer cells requires both beta-arrestin-1 and -2," The Journal of Biological Chemistry 279(53):55419-55424, Elsevier, United States (Dec. 2004).
Gessler, F., et al., "Inhibition of tissue factor/protease-activated receptor-2 signaling limits proliferation, migration and invasion of malignant glioma cells," Neuroscience 165(4):1312-1322, Elsevier Science, United States (Feb. 2010).
Gieger, R., et al., "Crystallogenesis of biological macromolecules: facts and perspectives," Acta Crystallographica. Section D, Biological Crystallography 50(Pt4):339-350, Wiley-Blackwell, United States (Jul. 1994).
Glennie, M. J., et al., "Preparation and performance of bispecific F(ab' gamma)2 antibody containing thioether-linked Fab' gamma fragments," Journal of Immunology 139(7):2367-2375, American Association of Immunologists, United States (Oct. 1987).
Hachem, J. P., et al., "Serine protease signaling of epidermal permeability barrier homeostasis," Journal Of Investigative Dermatology 126(9):2074-2086, Elsevier, United States (Sep. 2006).
Hammerling, G. J., et al., eds., "Appendix: Production of Antibody-Producing Hybridomas in the RodentSystems" in Monoclonal Antibodies and T-Cell Hybridomas: Perspectives and Technical Advances, pp. 563-587, Elsevier, Netherlands (1981).
Hassler, S. N., et al., "Protease activated receptor 2 (PAR2) activation causes migraine-like pain behaviors in mice," Cephalalgia:

(56) References Cited

OTHER PUBLICATIONS

An International Journal of Headache 39(1):111-122, SAGE Journals, United Kingdom (Jan. 2019).
Henehan, M., et al., "Update on protease-activated receptor 2 in cutaneous barrier, differentiation, tumorigenesis and pigmentation, and its role in related dermatologic diseases," Experimental Dermatology 28(8):877-885, Copenhagen, Denmark (Aug. 2019).
Hollenberg, M. D., and Compton, S. J., "Proteinase-Activated Receptor Domains and Signaling," Drug Development Research, 59(4):344-349, Wiley-Liss, Inc., United States (2003).
Hoogerwerf, W. A., "Trypsin Mediates Nociception via the Proteinase-Activated Receptor 2: A Potentially Novel Role in Pancreatic Pain," Gastroenterology 127(3):883-891, W.B. Saunders, United States (Sep. 2004).
Hovnanian, A., "Netherton Syndrome: Skin Inflammation and Allergy by Loss of Protease Inhibition," Cell And Tissue Research 351(2):289-300, Springer-Verlag, Germany (Feb. 2013).
Howells, G. L., "Proteinase-Activated Receptor-2: Expression by Human Neutrophils," Journal of Cell Science 110 (Pt 7):881-887, Company of Biologists, United Kingdom (Apr. 1997).
Huesa, C., et al., "Proteinase-Activated Receptor 2 Modulates OA-Related Pain, Cartilage and Bone Pathology," Annals of the Rheumatic Diseases, 75(11): 1989-1997, BMJ, United Kingdom (Nov. 2016).
Huston, J. S., et al., "Protein Engineering of Antibody Binding Sites: Recovery of Specific Activity in an Anti-digoxin Single-chain Fv Analogue Produced in *Escherichia coli,*" Proceedings of the National Academy of Sciences USA 85(16):5879-5883, National Academy of Sciences, United States (Aug. 1988).
International Search Report and Written Opinion for International Application PCT/US2021/046552, European Patent Office, Munich, mailed Dec. 21, 2021, 13 pages.
Ito, M., "Prostanoid-Dependent Spontaneous Pain and PAR2-Dependent Mechanical Allodynia Following Oral Mucosal Trauma: Involvement of TRPV1, TRPA1, and TRPV4," Molecular Pain 13:1-17, Sage Publications, United Kingdom (Jan. 2017).
Iwaki, K., et al., "A Small Interfering RNA Targeting Proteinase-Activated Receptor-2 Is Effective in Suppression of Tumor Growth in a Pancl Xenograft Model," International Journal of Cancer 122:658-663, Wiley-Liss, United States (Feb. 2008).
Jefferis, R., and Lefranc, M. P., "Human Immunoglobulin Allotypes: Possible Implications for Immunogenicity," MAbs 1(4):332-338, Taylor & Francis, United States (Jul.-Aug. 2009).
Jimenez-Vargas, N. N., et al., "Protease-Activated Receptor-2 in Endosomes Signals Persistent Pain of Irritable Bowel Syndrome," Proceedings of the National Academy of Sciences of the United States of America 115(31):E7438-E7447, National Academy of Sciences, United States (Jul. 2018).
Jones, P. T., et al., "Replacing The Complementarity-Determining Regions In A Human Antibody With Those From a Mouse," Nature 321(6069):522-525, Nature Publishing Group, United Kingdom (May 1986).
Kabat, E. A., and Wu, T. T., "Attempts to Locate Complementarity-Determining Residues in the Variable Positions of Light and Heavy Chains," Annals of the New York Academy of Sciences 190:382-393, Blackwell, United States (Dec. 1971).
Kaplanski, G., "Interleukin-18: Biological Properties and Role in Disease Pathogenesis," Immunological Reviews 281(1):138-153, Blackwell, United Kingdom (Jan. 2018).
Karpovsky, B., et al., "Production of target-specific effector cells using hetero-cross-linked aggregates containing anti-target cell and anti-Fc gamma receptor antibodies," The Journal of Experimental Medicine 160(6):1686-1701, Rockefeller University Press, United States (Dec. 1984).
Kaufmann, R., et al., "Met Receptor Tyrosine Kinase Transactivation Is Involved in Proteinase-Activated Receptor-2-mediated Hepatocellular Carcinoma Cell Invasion," Carcinogenesis 30:1487-1496, IRL Press At Oxford University Press, United Kingdom (Sep. 2009).
Kawabata, A., and Kawao, N., "Physiology and pathophysiology of proteinase-activated receptors (PARs): PARs in the respiratory system: cellular signaling and physiological/pathological roles," Journal of Pharmacological Sciences 97(1):20-24, Japanese Pharmacological Society, Japan (Jan. 2005).
Kawagoe, K., et al., "Effect of Protease-Activated Receptor-2 Deficiency on Allergic Dermatitis in the Mouse Ear," Japanese Journal of Pharmacology, 88(1):77-84, Japanese Pharmacological Society, Japan (Jan. 2002).
Kelso, E. B., et al., "Expression and proinflammatory role of proteinase-activated receptor 2 in rheumatoid synovium: ex vivo studies using a novel proteinase-activated receptor 2 antagonist," Arthritis & Rheumatology 56(3):765-771, Wiley-Blackwell, United States (Mar. 2007).
Kempkes, C., et al., "Proteinase-activated receptors 1 and 2 regulate invasive behavior of human melanoma cells via activation of protein kinase D1," The Journal of Investigative Dermatology 132:375-384, Elsevier, United States (Feb. 2012).
Ketabchi, S., et al., "Expression of Protease-Activated Receptor-1 and -2 in Orofacial Granulomatosis," Oral Diseases 13(4):419-425, Copenhagen, Denmark (Jul. 2007).
Kettleborough, C. A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (Apr. 1994).
Kirkland, T. N., et al., "Analysis of the Fine Specificity and Cross-reactivity of Monoclonal Anti-lipid A Antibodies," Journal of Microbiology 137(11):3614-3619, Microbiological Society of Korea, Korea (Dec. 1986).
Knight, D. A., et al., "Protease-activated receptors in human airways: upregulation of PAR-2 in respiratory epithelium from patients with asthma," Allergy Clin Immunol 108(5):797-803, Mosby, United States (Nov. 2001).
Knight, V., et al., "Protease-activated receptor 2 promotes experimental liver fibrosis in mice and activates human hepatic stellate cells," Hepatology 55(3):879-887, Williams & Wilkins, United States (Mar. 2012).
Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United Kingdom (Oct. 1999).
Kohler, G., and Milstein, C., "Continuous Cultures of Fused Cells Secreting Antibody of Predefined Specificity," Nature 256(5517):495-497, Nature Publishing Group, United Kingdom (Aug. 1975).
Kostelny, S. A., et al., "Formation of a Bispecific Antibody by the Use of Leucine Zippers," The Journal of Immunology 148(5):1547-1553, American Association of Immunologists, United States (Mar. 1992).
Kouzaki, H., et al., "Proteases induce production of thymic stromal lymphopoietin by airway epithelial cells through protease-activated receptor-2," J Immunol 183(2):1427-1434, American Association of Immunologists, United States (Jul. 2009).
Kwapiszewska, G., et al., "PAR-2 Inhibition Reverses Experimental Pulmonary Hypertension," Circulation Research 110(9):1179-1191, Lippincott Williams & Wilkins, United States (Apr. 2012).
Labrijn, A. F., et al., "Therapeutic IgG4 Antibodies Engage in Fab-Arm Exchange with Endogenous Human IgG4 in Vivo," Nature Biotechnology 27(8):767-771, Nature America Publishing, United States (Aug. 2009).
Lam, D. K., and Schmidt, B. L., "Serine Proteases and Protease-Activated Receptor 2-Dependent Allodynia: A Novel Cancer Pain Pathway," Pain 149(2):263-272, Lippincott Williams & Wilkins, United States (May 2010).
Lam, D. K., et al., "Novel Animal Models of Acute and Chronic Cancer Pain: A Pivotal Role for PAR2," The Journal of Neuroscience 32(41):14178-14183, Society for Neuroscience, United States (Oct. 2012).
Lam, D., et al., "TMPRSS2, A Novel Membrane-Anchored Mediator in Cancer Pain," Pain 156(5):923-930, Lippincott Williams & Wilkins, United States (May 2015).
Larsen, K. S., et al., "Engineering of substrate selectivity for tissue factor.factor VIIa complex signaling through protease-activated receptor 2," The Journal of Biological Chemistry, 285(26):19959-

(56) References Cited

OTHER PUBLICATIONS

19966, Elsevier Inc. on behalf of American Society for Biochemistry and Molecular Biology, United States (Jun. 2010).

Lau, C., et al., "Chimeric anti-CD14 IGG2/4 Hybrid antibodies for therapeutic intervention in pig and human models of inflammation," Journal of Immunology 91(9):4769-4777, American Association of Immunologists, United States (Nov. 2013).

Lee, S. E., et al., "Protease and protease-activated receptor-2 signaling in the pathogenesis of atopic dermatitis," Yonsei Medical Journal 51(6):808-822, Yonsei University, Korea (Nov. 2010).

Lee, J. H., et al., "A synonymous variation in protease-activated receptor-2 is associated with atopy in Korean children," The Journal of Allergy and Clinical Immunology 128(6):1326-1334, Mosby, United States (Dec. 2011).

Lee, H. J., et al., "Protease-activated receptor 2 mediates mucus secretion in the airway submucosal gland," PLoS One 7(8):e43188, Public Library of Science, United States (2012).

Lee, K. H., et al., "Cigarette smoke extract enhances neutrophil elastase-induced IL-8 production via proteinase-activated receptor-2 upregulation in human bronchial epithelial cells," Experimental & Molecular Medicine 50(7):1-9, Nature Publishing Group, United Kingdom (Jul. 2018).

Li, W., et al., "Simultaneous Generation and Germline Transmission of Multiple Gene Mutations in Rat Using CRISPR-Cas systems," Nature Biotechnology 31(8):684-6, Nature America Publishing, United States (Aug. 2013).

Liang, G., et al., "Naive T cells sense the cysteine protease allergen papain through protease-activated receptor 2 and propel TH2 immunity," The Journal of Allergy and Clinical Immunology, 129(5):1377-1386, Mosby, United States (May 2012).

Liang, W. J., et al., "Tryptase and Protease-Activated Receptor 2 Expression Levels in Irritable Bowel Syndrome," Gut Liver 10(3):382-390, Editorial Office of Gut and Liver, Korea (May 2016).

Lin, K. W., et al., "Protease-activated receptor-2 (PAR-2) is a weak enhancer of mucin secretion by human bronchial epithelial cells in vitro," Int J Biochem Cell Biol 40(6-7):1379-1388, Elsevier, Netherlands (2008).

Lin, C., et al., "Pharmacological Targeting of Protease-Activated Receptor 2 Affords Protection from Bleomycin-Induced Pulmonary Fibrosis," Molecular Medicine 21(1):576-583, BioMed Central, United Kingdom (Jun. 2015).

Linder, J. R., et al., "Delayed Onset of Inflammation in Protease-Activated Receptor-2-Deficient Mice," Journal of Immunology, 165(11):6504-6510, American Association of Immunologists, United States (Dec. 2000).

Liu, M. A., et al., "Heteroantibody duplexes target cells for lysis by cytotoxic T lymphocytes," Proceedings of the National Academy of Sciences of the United States of America 82(24):8648-8652, National Academy of Sciences, United States (Dec. 1985).

Liu, H., et al., "Role of mast cells, stem cell factor and protease-activated receptor-2 in tubulointerstitial lesions in IgA nephropathy," Inflammation Research Journal 59(7):551-559, Basel, Switzerland (Jul. 2010).

Liu, S., et al., "Protease-activated receptor 2 in dorsal root ganglion contributes to peripheral sensitization of bone cancer pain," European Journal of Pain 18(3):326-337, Wiley, United Kingdom (Mar. 2014).

Lonberg, N., "Human Antibodies From Transgenic Animals," Nature Biotechnology, 23(9):1117-1125, Nature America Publishing, United States (Sep. 2005).

Lourbakos, A., et al., "Cleavage and activation of proteinase-activated receptor-2 on human neutrophils by gingipain-R from Porphyromonas gingivalis," FEBS Letters 435(1):45-48, John Wiley & Sons Ltd, United Kingdom (Sep. 1998).

Matej, R., et al., "Proteinase-activated receptor-2 expression in breast cancer and the role of trypsin on growth and metabolism of breast cancer cell line MDA MB-231," Physiological Research 56:475-484, Institute of Physiology of the Czechoslovak Academy of Sciences by Academia, Czech Republic (2007).

McCulloch, K., et al., "Rheumatic Disease: Protease-Activated Receptor-2 in Synovial Joint Pathobiology," Frontiers in Endocrinology 9:257, Lausanne, Switzerland (May 2018).

McPherson, A., "Current Approaches to Macromolecular Crystallization," European Journal of Biochemistry 189(1):1-23, Blackwell Science Ltd, United Kingdom (Apr. 1990).

Miike, S., et al., "Trypsin induces activation and inflammatory mediator release from human eosinophils through protease-activated receptor-2," J Immunol 167(11):6615-6622, American Association of Immunologists, United States (Dec. 2001).

Milner, J. M., et al., "Matriptase Is a Novel Initiator of Cartilage Matrix Degradation in Osteoarthritis," Arthritis and Rheumatism 62(7):1955-1966, Wiley-Blackwell, United States (Jul. 2010).

Miotto, D. M., et al., "Expression of protease activated receptor-2 (PAR-2) in central airways of smokers and non-smokers," Thorax 57(2):146-151, British Medical Assn, United Kingdom (Feb. 2002).

Miyata, S., et al., "Trypsin stimulates integrin alpha(5)beta(1)-dependent adhesion to fibronectin and proliferation of human gastric carcinoma cells through activation of proteinase-activated receptor-2," The Journal of Biological Chemistry 275: 4592-4598, Elsevier, United States (Feb. 2000).

Moldenhauer, G., et al., "Identity of HML-1 antigen on intestinal intraepithelial T cells and of B-ly7 antigen on hairy cell leukaemia," Scandinavian Journal of Immunology 32(2):77-82, Blackwell Scientific Publications, United Kingdom (Aug. 1990).

Morel, G. A., et al., "Monoclonal Antibodies to Bovine Serum Albumin: Affinity and Specificity Determinations," Molecular Immunology 25(1):7-15, Pergamon Press, United Kingdom (Jan. 1988).

Morgan, C. R., "Changes in Proteinase-Activated Receptor 2 Expression in the Human Tooth Pulp in Relation to Caries and Pain," Journal of Orofacial Pain 3(3): 265-274, Quintessence Pub. Co, United States (2009).

Moussa, L., et al., "Protease-activated receptor-2 augments experimental crescentic glomerulonephritis," The American Journal of Pathology 171(3):800-808, Elsevier, United States (Sep. 2007).

Mrozkova, P., et al., "The Role of Protease-Activated Receptor Type 2 in Nociceptive Signaling and Pain," Physiological Research 65(3):357-367, Institute of Physiology of the Czechoslovak Academy of Sciences by Academia, Pub. House of the Academy, Czech Republic (Jul. 2016).

Mußbach, F., et al., "Proteinase-activated receptor 2 ($PAR_2$) in hepatic stellate cells—evidence for a role in hepatocellular carcinoma growth in vivo," Molecular Cancer 15:54, BioMed Central, United Kingdom (Jul. 2016).

Muley, M., et al., "Prophylactic inhibition of neutrophil elastase prevents the development of chronic neuropathic pain in osteoarthritic mice," Journal of Neuroinflammation 14:168, BioMed Central, United Kingdom (Aug. 2017).

Murray, D. B., et al., "Tryptase Activates Isolated Adult Cardiac Fibroblasts via Protease Activated Receptor-2 (PAR-2)," Journal of Cell Communication and Signalling 6(1):45-51, Springer, Germany (Mar. 2012).

Myers, E. W., and Miller, W., "Optimal Alignments in linear space," Computer Applications in the Biosciences 4(1):11-17, Oxford University Press, United Kingdom (Mar. 1988).

Nadeem, A., et al., "Proteinase activated receptor-2-mediated dual oxidase-2 up-regulation is involved in enhanced airway reactivity and inflammation in a mouse model of allergic asthma," Immunology 145(3):391-403, Blackwell Scientific Publications, United Kingdom (Jul. 2015).

Nadeem, A., et al., "Protease activated receptor-2 mediated upregulation of IL-17 receptor signaling on airway epithelial cells is responsible for neutrophilic infiltration during acute exposure of house dust mite allergens in mice," Chem Biol Interact 304:52-60, Elsevier, Netherlands (May 2019).

Namkung, W., et al., "Protease-activated receptor 2 exerts local protection and mediates some systemic complications in acute pancreatitis," Gastroenterology 126(7):1844-1859, W.B. Saunders, United States (Jun. 2004).

Needleman, S. B., and Wunsch, C. D., "A General Method Applicable to the Search for Similarities in the Amino Acid Sequence of Two Proteins," Journal of Molecular Biology 48(3):443-453, Academic Press, United Kingdom (Mar. 1970).

(56) References Cited

OTHER PUBLICATIONS

Nichols, H. L., et al., "β-Arrestin-2 Mediates the Proinflammatory Effects of Proteinase-activated Receptor-2 in the Airway," Proc Natl Acad Sci USA 109(41):16660-16665, National Academy of Sciences, United States (Oct. 2012).
Nishimura, S., et al., "The proteinase/proteinase-activated receptor-2/transient receptor potential vanilloid-1 cascade impacts pancreatic pain in mice," Life Science 87(19-22):643-650, Elsevier, Netherlands (Nov. 2010).
O'Brien, P. J., et al., "Thrombin responses in human endothelial cells. Contributions from receptors other than PAR1 include the transactivation of PAR2 by thrombin-cleaved PAR1," J Biol Chem 275(18):13502-13509, Elsevier Inc. on Behalf of American Society for Biochemistry and Molecular Biology, United States (May 2000).
Pal, K., et al., "Divergent β-Arrestin-dependent Signaling Events Are Dependent Upon Sequences Within G-protein-coupled Receptor C Termini," J Biol Chem 288(5):3265-3274, Biochemistry and Molecular Biology, United States (Feb. 2013).
Palikhe, N. S., et al., "Increased Protease-Activated Receptor-2 (PAR-2) Expression on CD14++CD16+ Peripheral Blood Monocytes of Patients with Severe Asthma," PLoS One 10(12):e0144500, Public Library of Science, United States (Dec. 2015).
Park, Y. S., et al., "Clinical Implication of Protease-activated Receptor-2 in Idiopathic Pulmonary Fibrosis," Respiratory Medicine 107(2):256-262, Oxford University Press, United Kingdom (Feb. 2013).
Paulus, H., et al., "Preparation and biomedical applications of bispecific antibodies," Behring Institute Mitteilungen 78:118-132, Behringwerke AG, Germany (Dec. 1985).
Persic, L., et al., "An Integrated Vector System for the Eukaryotic Expression of Antibodies or Their Fragments After Selection From Phage Display Libraries," Gene 187(1):9-18, Elsevier/North-Holland, Netherlands (Mar. 1997).
Portenoy, R. K., et al., "Breakthrough Pain: Characteristics and Impact in Patients with Cancer Pain," Pain 81(1-2):129-134, Lippincott Williams & Wilkins, United States (May 1999).
Quirt, J., et al., "Asthma," Allergy Asthma Clin Immunol, 12:14(Suppl 2):50, BioMed Central, United Kingdom (Sep. 2018).
Rabe, K. F., et al., "Global strategy for the diagnosis, management, and prevention of chronic obstructive pulmonary disease: GOLD executive summary," American Journal of Respiratory and Critical Care Medicine 176(6):532-555, American Thoracic Society, United States (Sep. 2007).
Ramachandran, R., et al., "Neutrophil elastase acts as a biased agonist for proteinase-activated receptor-2 (PAR2)," J Biol Chem 286(28):24638-24648, Elsevier Inc. on behalf of American Society for Biochemistry and Molecular Biology, United States (Jul. 2011).
Riechmann, L., et al., "Reshaping Human Antibodies for Therapy," Nature 332(6162):323-327, Nature Publishing Group, United States (Mar. 1988).
Roguska, M. A., et al., "Humanization of Murine Monoclonal Antibodies through Variable Domain Resurfacing," Proceedings of the National Academy of Sciences USA 91(3):969-973, National Academy of Sciences, United States (Feb. 1994).
Roguska, M. A., et al., "A Comparison of Two Murine Monoclonal Antibodies Humanized by CDR-grafting and Variable Domain Resurfacing," Protein Engineering 9(10):895-904, Oxford University Press, United Kingdom (1996).
Rothmeier, A. S., and Ruf, W., "Protease-activated receptor 2 signaling in inflammation," Semin Immunopathol 34(1):133-149, Springer, Germany (Jan. 2012).
Roux, K. H., et al., "Comparisons of the ability of human IgG3 hinge mutants, IgM, IgE, and IgA2, to form small immune complexes: a role for flexibility and geometry," J Immunol 161(8):4083-4090, American Association of Immunologists, United States (Oct. 1998).
Roversi, P., et al., "Modelling Prior Distributions of Atoms for Macromolecular Refinement and Completion," Acta Crystallographica. Section D, Biological Crystallography 56(Pt10):1316-1323, International Union of Crystallography by Munksgaard, United States (Oct. 2000).
Sakamoto, A., et al., "Involvement of Mast Cells and Proteinase-Activated Receptor 2 in Oxaliplatin-Induced Mechanical Allodynia in Mice," Pharmacological Research 105:84-92, Elsevier, Netherlands (Mar. 2016).
Schaffner, F., & Ruf, W., "Tissue factor and PAR2 signaling in the tumor microenvironment," Arteriosclerosis, Thrombosis, and Vascular Biology 29(12): 1999-2004, Lippincott Williams & Wilkins, United States (Aug. 2009).
Schaffner, F., et al., "Cooperation of tissue factor cytoplasmic domain and PAR2 signaling in breast cancer development," Blood 116:6106-6113, American Society of Hematology, United States (Dec. 2010).
Schmidlin, F., et al., "Protease-activated receptor 2 mediates eosinophil infiltration and hyperreactivity in allergic inflammation of the airway", Journal of Immunology 169(9):5315-5321, American Association of Immunologists, United States (Nov. 2002).
Sharma, A., et al., "Protection against acute pancreatitis by activation of protease-activated receptor-2," American Journal of Physiology. Gastrointestinal and Liver Physiology 288(2):G388-395, American Physiological Society, United States (Feb. 2005).
Silva, J. P., et al., "The S228P mutation prevents in vivo and in vitro IgG4 Fab-arm exchange as demonstrated using a combination of novel quantitative immunoassays and physiological matrix preparation," J Biol Chem 290(9):5462-5469, Elsevier Inc. on behalf of American Society for Biochemistry and Molecular Biology, United States (Feb. 2015).
Songsivilai, S., and Lachmann, P. J., "Bispecific Antibody: A Tool for Diagnosis and Treatment of Disease," Clinical and Experimental Immunology 79(3):315-321, Blackwell Scientific Publications, United Kingdom (Mar. 1990).
Stahli, C., et al., "Distinction of Epitopes by Monoclonal Antibodies," Methods in Enzymology 92:242-253, Academic Press, United States (1983).
Steinhoff, M., et al., "Proteinase-activated receptor-2 in human skin: tissue distribution and activation of keratinocytes by mast cell tryptase," Experimental Dermatology 8:282-294, Munksgaard, Denmark (Aug. 1999).
Suckow, K. S., et al., "NMDA receptor subunit expression and PAR2 receptor activation in colospinal afferent neurons (CANs) during inflammation induced visceral hypersensitivity," Molecular Pain 5:54, Sage Publications, United States (Sep. 2009).
Tam, S. H., et al., "Functional, Biophysical, and Structural Characterization of Human IgG1 and IgG4 Fc Variants with Ablated Immune Functionality," Antibodies (Basel) 6(3):12, MDPI, Switzerland (Sep. 2017).
Terada, Y., et al., "Contribution of TRPA1 as a downstream signal of proteinase-activated receptor-2 to pancreatic pain," Journal of Pharmacological Sciences 123(3):284-287, Japanese Pharmacological Society, Japan (2013).
Tian, L., et al., "Role of PAR2 in regulating oxaliplatin-induced neuropathic pain via TRPA1," Translational Neuroscience 6(1):111-116, Walter de Gruyter GmbH, Germany (Mar. 2015).
Tindell, A. G., et al., "Correlation of protease-activated receptor-2 expression and synovitis in rheumatoid and osteoarthritis," Rheumatology International 32(10):3077-3086, Springer International, Germany (Oct. 2012).
Tsai, M. C., et al., "The Role of Protease-Activated Receptor 2 in Hepatocellular Carcinoma after Hepatectomy," Medicina (Kaunas) 57(6):574, MDPI, Switzerland (Jun. 2021).
Tsubota, M., et al., "Prostanoid-dependent bladder pain caused by proteinase-activated receptor-2 activation in mice: Involvement of TRPV1 and T-type Ca 2+ channels," Journal Of Pharmacological Sciences 136(1):46-49, Japanese Pharmacological Society, Japan (Jan. 2018).
UniProt, "PERV-A receptor-2," UniProt.org, Accession No. E5FAJ7, accessed at URL:[https://www.uniprot.org/uniprot/E5FAJ7] on Nov. 3, 2021, 4 pages.
UniProt, "Immunoglobulin heavy constant gamma 2," UniProt.org, Accession No. P01859, accessed at URL:[https://www.uniprot.org/uniprot/P01859] on Nov. 3, 2021, 8 pages.

(56) References Cited

OTHER PUBLICATIONS

UniProt, "Immunoglobulin heavy constant gamma 4," UniProt.org, Accession No. P01861, accessed at URL:[https://www.uniprot.org/uniprot/P01861] on Nov. 3, 2021, 7 pages.
UniProt, "Proteinase-activated receptor 2," UniProt.org, Accession No. P55085-1, accessed at URL:[https://www.uniprot.org/uniprot/Q63645] on Nov. 3, 2021, 7 pages.
UniProt, "Proteinase-activated receptor 2," UniProt.org, Accession No. Q63645, accessed at URL:[https://www.uniprot.org/uniprot/P55085] on Nov. 3, 2021, 10 pages.
Vafa, O., et al., "An engineered Fc variant of an IgG eliminates all immune effector functions via structural perturbations," Methods 65(1):114-126, Academic Press, United States (Jan. 2014).
Vasilopoulos, Y., et al., "Genetic association between an AACC insertion in the 3'UTR of the stratum corneum chymotryptic enzyme gene and atopic dermatitis," Journal of Investigative Dermatology 123(1):62-66, Nature Publishing Group, United Kingdom (Jul. 2004).
Vergnolle, N., et al., "Proteinase-activated Receptor-2 and Hyperalgesia: a Novel Pain Pathway," Nat Med 7(7):821-826, Nature Publishing Company, United States (Jul. 2001).
Vergnolle, N., "Modulation of Visceral Pain and Inflammation by Protease-Activated Receptors," British Journal of Pharmacology 141(8):1264-1274, Wiley, United Kingdom (Apr. 2004).
Verhoeyen, M., et al., "Reshaping Human Antibodies: Grafting an Antilysozyme Activity," Science 239(4847):1534-1536, American Association for the Advancement of Science, United States (Mar. 1988).
Vidarsson, G., et al., "IgG subclasses and allotypes: from structure to effector functions," Front Immunology 5:520, Frontiers Research Foundation, Switzerland (Oct. 2014).
Wang, Q., et al., "Inhibition of PAR2 and TRPA1 signals alleviates neuropathic pain evoked by chemotherapeutic bortezomib," Journal of Biological Regulators and Homeostatic Agents 31(4):977-983, Biolif, Italy (Oct.-Dec. 2017).
Wang, X., et al., "IgG Fc engineering to modulate antibody effector functions," Protein Cell 9(1):63-73, Higher Education Press, Germany (Jan. 2018).
Ward, E. S., et al., "Binding Activities of a Repertoire of Single Immunoglobulin Variable Domains Secreted from *Escherichia coli*," Nature 341(6242):544-546, Nature Publishing Group, United Kingdom (Oct. 1989).
Weiszer, I., et al., "Ascaris Hypersensitivity in the Rhesus Monkey. I. A Model for the Study of Immediate Type Thypersensitity in the Primate," Journal of Allergy 41(1):14-22, Mosby, United States (Jan. 1968).
Wilson, S. R., et al., "Amplification of MMP-2 and MMP-9 production by prostate cancer cell lines via activation of protease-activated receptors," Prostate 60:168-174, Wiley-Liss, United States (Jul. 2004).
Wojtukiewicz, M. Z., et al., "Protease-activated Receptors (PARs)—biology and Role in Cancer Invasion and Metastasis," Cancer Metastasis Reviews 34:775-796, Kluwer Academic, Netherlands (Dec. 2015).
Wyckoff, H. W., "Diffractometry," Methods in Enzymology 114:330-386, Academic Press, United States (1985).
Wygrecka, M., et al., "Role of Protease-Activated Receptor-2 in Idiopathic Pulmonary Fibrosis," American Journal of Respiratory and Critical Care Medicine 183(12):1703-1714, American Thoracic Society, United States (Jun. 2011).
Xiang, Y., et al., "Expression of proteinase-activated receptors (PAR)-2 in articular chondrocytes is modulated by IL-1beta, TNF-alpha and TGF-beta," Osteoarthritis Cartilage 14(11):1163-1173, W. B. Saunders for the Osteoarthritis Research Society, United Kingdom (Nov. 2006).
Xu, W., et al., "Electroacupuncture Relieves Visceral Hypersensitivity by Inactivating Protease-Activated Receptor 2 in a Rat Model of Postinfectious Irritable Bowel Syndrome," Evidence-Based Complementary and Alternative Medicine 2018:7048584, Hindawi Publishing Corporation, United States (Oct. 2018).
Yau, M-K., et al., "Protease activated receptor 2 (PAR2) modulators: a patent review (2010-2015)," Expert Opinion on Therapeutic Patents 26(4):471-483, Informa UK Limited, United Kingdom (2016).
Yoon, H., et al., "Protease Activated Receptor 2 Controls Myelin Development, Resiliency and Repair," Glia 65(12):2070-2086, Wiley-Liss, United States (Dec. 2017).
Younger, J., et al., "Pain Outcomes: A Brief Review of Instruments and Techniques," Current Pain and Headache Reports 13(1):39-43, Current Science Inc., United States (Feb. 2009).
Zhang, W., et al., "Proteinase-activated receptor 2 mediates thermal hyperalgesia and is upregulated in a rat model of chronic pancreatitis," Pancreas 40(2):300-307, Lippincott Williams & Wilkins, United States (Mar. 2011).
Zhou, B., et al., "Activation of PAR2 or/and TLR4 promotes SW620 cell proliferation and migration via phosphorylation of ERK1/2," Oncology Reports 25:503-511, Spandidos, Greece (Feb. 2013).
Zhou, J., et al., "Neutrophil elastase induces MUC5AC secretion via protease-activated receptor 2," Molecular and Cellular Biochemistry 377(1-2):75-85, Springer, Netherlands (May 2013).
Zhu, J., et al., "Trypsin-protease activated receptor-2 signaling contributes to pancreatic cancer pain," Oncotarget 8(37):61810-61823, Impact Journals, United States (Jun. 2017).
Edwards, B.M., et al., "The remarkable flexibility of the human antibody repertoire; isolation of over one thousand different antibodies to a single protein, BLyS," J Mol Biol 334(1):103-118, Elsevier, Netherlands (Nov. 2003).
Lloyd, C., et al., "Modelling the human immune response: performance of a 1011 human antibody repertoire against a broad panel of therapeutically relevant antigens," Protein Eng Des Sel 22(3):159-168, Oxford University Press, United Kingdom (Mar. 2009).
Goel, M., et al., "Plasticity within the antigen-combining site may manifest as molecular mimicry in the humoral immune response," J Immunol 173(12):7358-7367, American Association of Immunologists, United States (Dec. 2004).
Kanyavuz, A., et al., "Breaking the law: unconventional strategies for antibody diversification," Nat Rev Immunol 19(6):355-368, Nature Portfolio, Germany (Jun. 2019).
Damiano, B.P., "Increased expression of protease activated receptor-2 (PAR-2) in balloon-injured rat carotid artery," Thromb Haemost 81(5):808-814, Wiley, United States (May 1999).
Kopruszinski, C.M., et al., "Characterization and preclinical evaluation of a protease activated receptor 2 (PAR2) monoclonal antibody as a preventive therapy for migraine," Cephalalgia 40(14):1535-1550, Sage Publishing, United States (Dec. 2020).

* cited by examiner

FIG. 1A
Variable heavy chain sequences of humanized variants of Antibody 309

FIG. 1B
Variable light chain sequences of humanized variants of Antibody 309

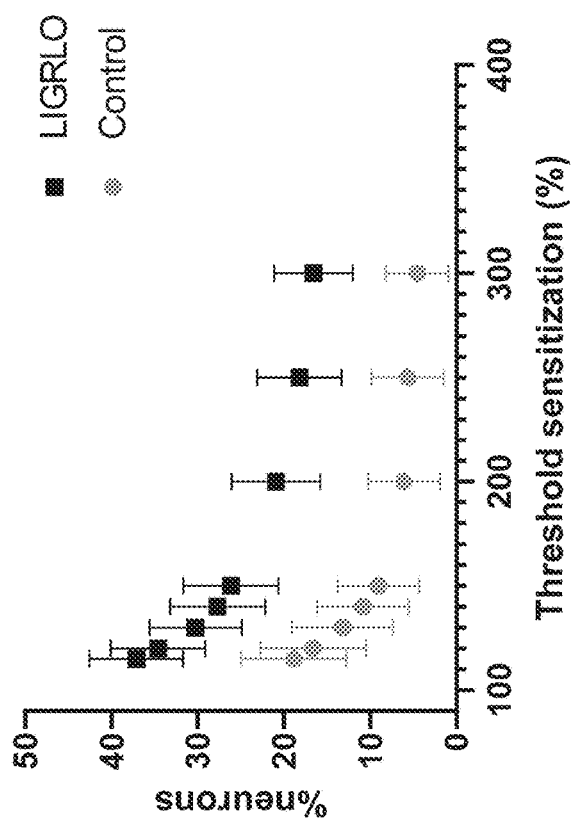
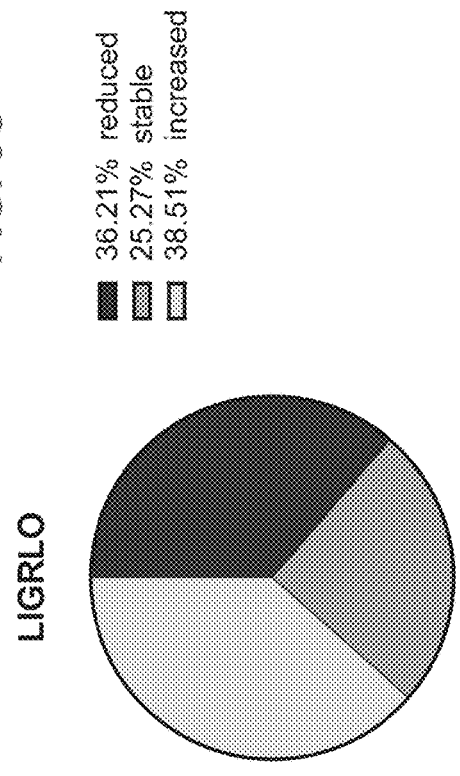
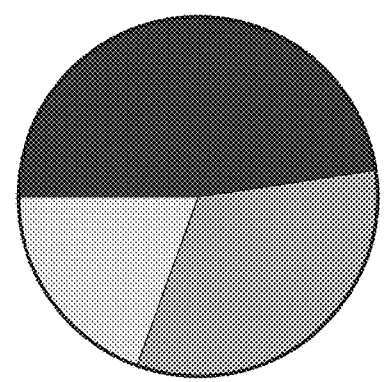
FIG. 6A
FIG. 6B
FIG. 6C

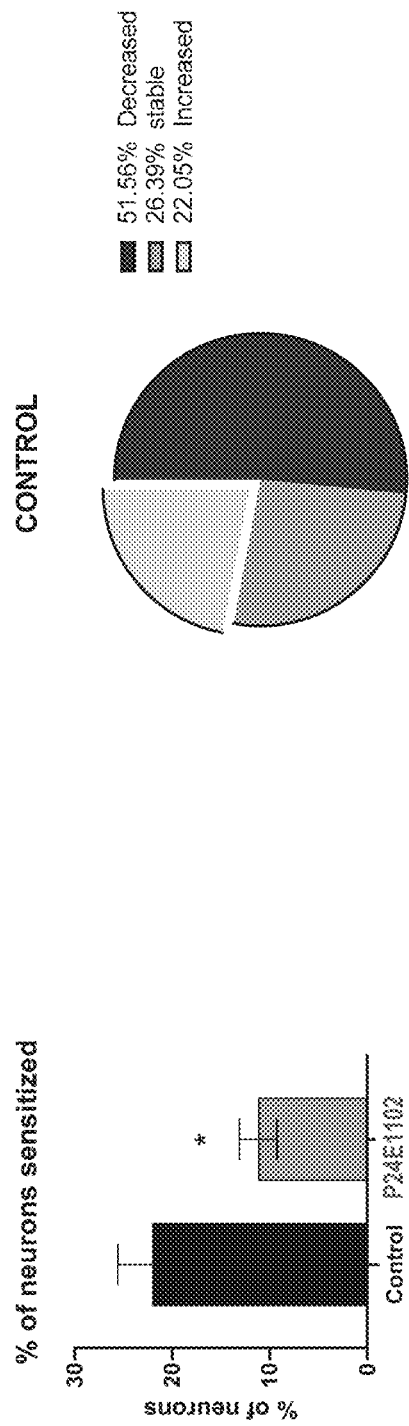
FIG. 7A
FIG. 7B
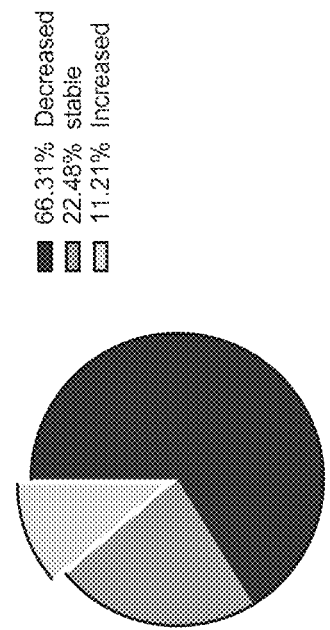
FIG. 7C

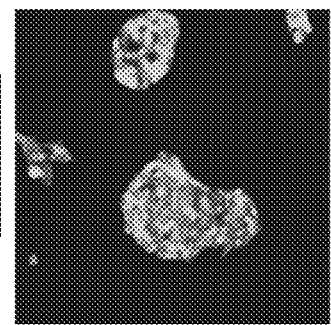
FIG. 9A Untreated
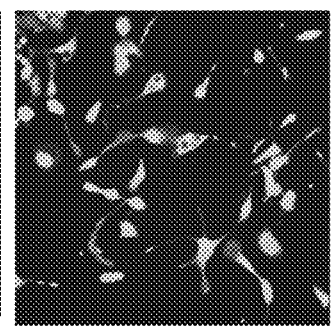
FIG. 9B SLIGKV (270 µM)
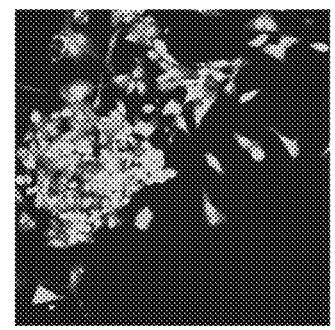
FIG. 9C SLIGKV + 500 nM P24E1102
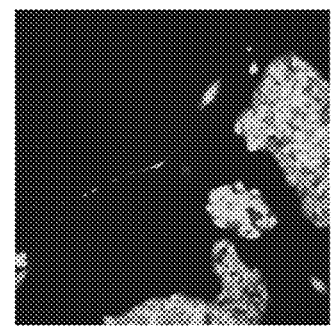
FIG. 9D SLIGKV + 2000 nM P24E1102

SEQUENCE LISTING

```
Sequence total quantity: 162
SEQ ID NO: 1          moltype = AA  length = 10
FEATURE               Location/Qualifiers
VARIANT               5
                      note = X is N or S
VARIANT               6
                      note = X is S or Y
VARIANT               8
                      note = X is G or A
VARIANT               9
                      note = X is V, G, or I
VARIANT               10
                      note = X is I or S
source                1..10
                      mol_type = protein
```

-continued

```
                        note = VH CDR1
                        organism = synthetic construct
SEQUENCE: 1
GFSLXXYXXX                                                              10

SEQ ID NO: 2            moltype = AA  length = 11
FEATURE                 Location/Qualifiers
VARIANT                 6
                        note = X is G or Q
VARIANT                 8
                        note = X is V or T
VARIANT                 11
                        note = X is N, A, G, or Y
source                  1..11
                        mol_type = protein
                        note = VH CDR2
                        organism = synthetic construct
SEQUENCE: 2
VIWGNXNXYY X                                                            11

SEQ ID NO: 3            moltype = AA  length = 11
FEATURE                 Location/Qualifiers
VARIANT                 2
                        note = X is R or K
VARIANT                 4
                        note = X is Y, W, or F
VARIANT                 7
                        note = X is Y or H
source                  1..11
                        mol_type = protein
                        note = VH CDR3
                        organism = synthetic construct
SEQUENCE: 3
WXGXKDXPFD Y                                                            11

SEQ ID NO: 4            moltype = AA  length = 11
FEATURE                 Location/Qualifiers
VARIANT                 1
                        note = X is K or R
VARIANT                 6
                        note = X is I or V
VARIANT                 9
                        note = X is Y, W, or F
source                  1..11
                        mol_type = protein
                        note = VL CDR1
                        organism = synthetic construct
SEQUENCE: 4
XASQNXYKXL D                                                            11

SEQ ID NO: 5            moltype =     length =
SEQUENCE: 5
000

SEQ ID NO: 6            moltype = AA  length = 8
FEATURE                 Location/Qualifiers
VARIANT                 1
                        note = X is L or Q
VARIANT                 4
                        note = X is N, G, or H
VARIANT                 5
                        note = X is S or H
source                  1..8
                        mol_type = protein
                        note = VL CDR3
                        organism = synthetic construct
SEQUENCE: 6
XQHXXGWT                                                                8

SEQ ID NO: 7            moltype = AA  length = 10
FEATURE                 Location/Qualifiers
source                  1..10
                        mol_type = protein
                        note = Anti-PAR-2 (309) Heavy Chain CDR1
                        organism = synthetic construct
SEQUENCE: 7
GFSLNSYGVI                                                              10

SEQ ID NO: 8            moltype = AA  length = 11
```

```
FEATURE              Location/Qualifiers
source               1..11
                     mol_type = protein
                     note = Anti-PAR-2 (309) Heavy Chain CDR2
                     organism = synthetic construct
SEQUENCE: 8
VIWGNGNTYY N                                                              11

SEQ ID NO: 9         moltype = AA  length = 11
FEATURE              Location/Qualifiers
source               1..11
                     mol_type = protein
                     note = Anti-PAR-2 (309 and 309-4e) Heavy Chain CDR3
                     organism = synthetic construct
SEQUENCE: 9
WRGYKDYPFD Y                                                              11

SEQ ID NO: 10        moltype = AA  length = 10
FEATURE              Location/Qualifiers
source               1..10
                     mol_type = protein
                     note = Anti-PAR-2 (P24E1102, P24E976, P24E1099, and
                       P24E1103) Heavy Chain CDR1
                     organism = synthetic construct
SEQUENCE: 10
GFSLSSYAIS                                                                10

SEQ ID NO: 11        moltype = AA  length = 11
FEATURE              Location/Qualifiers
source               1..11
                     mol_type = protein
                     note = Anti-PAR-2 (P24E1102, P24E976, P24E1099, and
                       P24E1103) Heavy Chain CDR2
                     organism = synthetic construct
SEQUENCE: 11
VIWGNQNVYY A                                                              11

SEQ ID NO: 12        moltype = AA  length = 11
FEATURE              Location/Qualifiers
source               1..11
                     mol_type = protein
                     note = Anti-PAR-2 (P24E1102, P24E976, P24E1099, and
                       P24E1103) Heavy Chain CDR3
                     organism = synthetic construct
SEQUENCE: 12
WKGYKDYPFD Y                                                              11

SEQ ID NO: 13        moltype = AA  length = 11
FEATURE              Location/Qualifiers
source               1..11
                     mol_type = protein
                     note = Anti-PAR-2 (309 and 309-4e) Light Chain CDR1
                     organism = synthetic construct
SEQUENCE: 13
KASQNIYKYL D                                                              11

SEQ ID NO: 14        moltype = AA  length = 7
FEATURE              Location/Qualifiers
source               1..7
                     mol_type = protein
                     note = Anti-PAR-2 (309 and 309-4e) Light Chain CDR2
                     organism = synthetic construct
SEQUENCE: 14
NTNSLHT                                                                    7

SEQ ID NO: 15        moltype = AA  length = 8
FEATURE              Location/Qualifiers
source               1..8
                     mol_type = protein
                     note = Anti-PAR-2 (309 and 309-4e) Light Chain CDR3
                     organism = synthetic construct
SEQUENCE: 15
LQHNSGWT                                                                   8

SEQ ID NO: 16        moltype = AA  length = 11
FEATURE              Location/Qualifiers
source               1..11
                     mol_type = protein
                     note = Anti-PAR-2 (P24E1102, P24E976, P24E1099, and
```

```
                        P24E1103) Light Chain CDR1
                        organism = synthetic construct
SEQUENCE: 16
RASQNVYKWL D                                                            11

SEQ ID NO: 17           moltype = AA  length = 7
FEATURE                 Location/Qualifiers
source                  1..7
                        mol_type = protein
                        note = Anti-PAR-2 (P24E1102) Light Chain CDR2
                        organism = synthetic construct
SEQUENCE: 17
NANTRAT                                                                 7

SEQ ID NO: 18           moltype = AA  length = 8
FEATURE                 Location/Qualifiers
source                  1..8
                        mol_type = protein
                        note = Anti-PAR-2 (P24E1102, P24E976, P24E1099, and
                         P24E1103) Light Chain CDR3
                        organism = synthetic construct
SEQUENCE: 18
QQHHSGWT                                                                8

SEQ ID NO: 19           moltype = AA  length = 7
FEATURE                 Location/Qualifiers
source                  1..7
                        mol_type = protein
                        note = Anti-PAR-2 (P24E976) Light Chain CDR2
                        organism = synthetic construct
SEQUENCE: 19
NAYSRAT                                                                 7

SEQ ID NO: 20           moltype = AA  length = 119
FEATURE                 Location/Qualifiers
source                  1..119
                        mol_type = protein
                        note = Anti-PAR-2 (309-4e) Variable Heavy Chain sequence
                        organism = synthetic construct
SEQUENCE: 20
QVQLVQSGAE VKKPGSSVKV SCKASGFSLN SYGVIWVRQA PGQGLEWMGV IWGNGNTYYN        60
QKFQGRVTIT ADESTSTAYM ELSSLRSEDT AVYYCARWRG YKDYPFDYWG QGTLVTVSS        119

SEQ ID NO: 21           moltype = AA  length = 119
FEATURE                 Location/Qualifiers
source                  1..119
                        mol_type = protein
                        note = Anti-PAR-2 (P24E1102, P24E976, P24E1099, and
                         P24E1103) Variable Heavy Chain sequence
                        organism = synthetic construct
SEQUENCE: 21
QVQLVQSGAE VKKPGSSVKV SCKASGFSLS SYAISWVRQA PGQGLEWMGV IWGNQNVYYA        60
QKFQGRVTIT ADESTSTAYM ELSSLRSEDT AVYYCARWKG YKDYPFDYWG QGTLVTVSS        119

SEQ ID NO: 22           moltype = AA  length = 7
FEATURE                 Location/Qualifiers
source                  1..7
                        mol_type = protein
                        note = Anti-PAR-2 (P24E1103) Light Chain CDR2
                        organism = synthetic construct
SEQUENCE: 22
NANNRAT                                                                 7

SEQ ID NO: 23           moltype = AA  length = 106
FEATURE                 Location/Qualifiers
source                  1..106
                        mol_type = protein
                        note = Anti-PAR-2 (309-4e) Variable Light Chain Sequence
                        organism = synthetic construct
SEQUENCE: 23
EIVLTQSPAT LSLSPGERAT LSCKASQNIY KYLDWYQQKP GQAPRLLIYN TNSLHTGIPA        60
RFSGSGSGRD FTLTISSLEP EDFAVYYCLQ HNSGWTFGGG TKVEIK                     106

SEQ ID NO: 24           moltype = AA  length = 106
FEATURE                 Location/Qualifiers
source                  1..106
                        mol_type = protein
                        note = Anti-PAR-2 (P24E1102) Variable Light Chain Sequence
                        organism = synthetic construct
```

```
SEQUENCE: 24
EIVLTQSPAT LSLSPGERAT LSCRASQNVY KWLDWYQQKP GQAPRLLIYN ANTRATGIPA    60
RFSGSGSGRD FTLTISSLEP EDFAVYYCQQ HHSGWTFGGG TKVEIK                 106

SEQ ID NO: 25           moltype = AA   length = 106
FEATURE                 Location/Qualifiers
source                  1..106
                        mol_type = protein
                        note = Anti-PAR-2 (P24E976) Light Chain Sequence
                        organism = synthetic construct
SEQUENCE: 25
EIVLTQSPAT LSLSPGERAT LSCRASQNVY KWLDWYQQKP GQAPRLLIYN AYSRATGIPA    60
RFSGSGSGRD FTLTISSLEP EDFAVYYCQQ HHSGWTFGGG TKVEIK                 106

SEQ ID NO: 26           moltype = AA   length = 106
FEATURE                 Location/Qualifiers
source                  1..106
                        mol_type = protein
                        note = Anti-PAR-2 (P24E1099) Variable Light Chain Sequence
                        organism = synthetic construct
SEQUENCE: 26
EIVLTQSPAT LSLSPGERAT LSCRASQNVY KWLDWYQQKP GQAPRLLIYN ANSRATGIPA    60
RFSGSGSGRD FTLTISSLEP EDFAVYYCQQ HHSGWTFGGG TKVEIK                 106

SEQ ID NO: 27           moltype = AA   length = 106
FEATURE                 Location/Qualifiers
source                  1..106
                        mol_type = protein
                        note = Anti-PAR-2 (P24E1103) Variable Light Chain Sequence
                        organism = synthetic construct
SEQUENCE: 27
EIVLTQSPAT LSLSPGERAT LSCRASQNVY KWLDWYQQKP GQAPRLLIYN ANNRATGIPA    60
RFSGSGSGRD FTLTISSLEP EDFAVYYCQQ HHSGWTFGGG TKVEIK                 106

SEQ ID NO: 28           moltype = AA   length = 397
FEATURE                 Location/Qualifiers
source                  1..397
                        mol_type = protein
                        note = human PAR-2
                        organism = synthetic construct
SEQUENCE: 28
MRSPSAAWLL GAAILLAASL SCSGTIQGTN RSSKGRSLIG KVDGTSHVTG KGVTVETVFS    60
VDEFSASVLT GKLTTVFLPI VYTIVFVVGL PSNGMALWVF LFRTKKKHPA VIYMANLALA   120
DLLSVIWFPL KIAYHIHGNN WIYGEALCNV LIGFFYGNMY CSILFMTCLS VQRYWVIVNP   180
MGHSRKKANI AIGISLAIWL LILLVTIPLY VVKQTIFIPA LNITTCHDVL PEQLLVGDMF   240
NYFLSLAIGV FLFPAFLTAS AYVLMIRMLR SSAMDENSEK KRKRAIKLIV TVLAMYLICF   300
TPSNLLLVVH YFLIKSQGQS HVYALYIVAL CLSTLNSCID PFVYYFVSHD FRDHAKNALL   360
CRSVRTVKQM QVSLTSKKHS RKSSSYSSSS TTVKTSY                            397

SEQ ID NO: 29           moltype = AA   length = 7
FEATURE                 Location/Qualifiers
source                  1..7
                        mol_type = protein
                        note = Anti-PAR-2 ("P24E1099") Light Chain CDR2
                        organism = synthetic construct
SEQUENCE: 29
NANSRAT                                                              7

SEQ ID NO: 30           moltype = AA   length = 438
FEATURE                 Location/Qualifiers
source                  1..438
                        mol_type = protein
                        note = Cynomolgus monkey PAR-2
                        organism = synthetic construct
SEQUENCE: 30
LGHLVLTHLL VALFGMGSWA AVNGIWVELP VVVKDLPEGW SLPSYLSVIV ALGNLGLLVV    60
TLWRRLAPGK GERVPIQVVQ VLSVVGTALL APLWHHVAPV AGQLHSVAFL TLALVLALAC   120
CTSNVTFLPF LSHLPPPFLR SFFLGQGLSA LLPCVLALVQ GVGRLECSPA PTNGTSGPPL   180
NFPERFPAST FFWALTALLV TSAAAFQGLL LLLPSLPSVT TGGAGPELPL GSPGAEEEEK   240
EEEEALPLQE PPSQAAGTIP GPDPEAHQLF SAHGAFLLGL LAITSALTNG VLPAVQSFSC   300
LPYGRLAYHL AVVLGSAANP LACFLAMGVL CRSLAGLVGL SLLGMLFGAY LMVLAILSPC   360
PPLVGTTAGV VLVVLSWVLC LCVFSYVKVA ASSLLHGGGR PALLAXGVAI QVGSLLGAGT   420
MFPPTSIYHV FQSRKDCV                                                438

SEQ ID NO: 31           moltype = AA   length = 418
FEATURE                 Location/Qualifiers
source                  1..418
                        mol_type = protein
                        note = Cynomolgus monkey PAR-2 (without the signal sequence)
```

```
                    organism = synthetic construct
SEQUENCE: 31
AVNGIWVELP VVVKDLPEGW SLPSYLSVIV ALGNLGLLVV TLWRRLAPGK GERVPIQVVQ    60
VLSVVGTALL APLWHHVAPV AGQLHSVAFL TLALVLALAC CTSNVTFLPF LSHLPPPFLR   120
SFFLGQGLSA LLPCVLALVQ GVGRLECSPA PTNGTSGPPL NFPERFPAST FFWALTALLV   180
TSAAAFQGLL LLLPSLPSVT TGGAGPEPLL GSPGAEEEEK EEEEALPLQE PPSQAAGTIP   240
GPDPEAHQLF SAHGAFLLGL LAITSALTNG VLPAVQSFSC LPYGRLAYHL AVVLGSAANP   300
LACFLAMGVL CRSLAGLVGL SLLGMLFGAY LMVLAILSPC PPLVGTTAGV VLVVLSWVLC   360
LCVFSYVKVA ASSLLHGGGR PALLAXGVAI QVGSLLGAGT MFPPTSIYHV FQSRKDCV    418

SEQ ID NO: 32           moltype = AA  length = 397
FEATURE                 Location/Qualifiers
source                  1..397
                        mol_type = protein
                        note = Rat PAR-2
                        organism = synthetic construct
SEQUENCE: 32
MRSLSLAWLL GGITLLAASA SCNRTVNAPG PNSKGRSLIG RLDTPPPITG KGAPVEPGFS    60
VDEFSASVLT GKLTTVFLPV IYIIVFVIGL PSNGMALWVF FFRTKKKHPA VIYMANLALA   120
DLLSVIWFPL KISYHLHGND WTYGDALCKV LIGFFYGNMY CSILFMTCLS VQRYWVIVNP   180
MGHSRKRANI AVGVSLAIWL LIFLVTIPLY VMRQTIYIPA LNITTCHDVL PEEVLVGDMF   240
SYFLSLAIGV FLFPALLTAS AYVLMIKTLR SSAMDEHSEK KRRRAIRLII TVLSMYFICF   300
APSNVLLVVH YFLIKSQRQS HVYALYLVAL CLSTLNSCID PFVYYFVSKD FRDQARNALL   360
CRSVRTVKRM QISLTSNKFS RKSSSYSSSS TSVKTSY                           397

SEQ ID NO: 33           moltype = AA  length = 327
FEATURE                 Location/Qualifiers
source                  1..327
                        mol_type = protein
                        note = Human heavy chain IgG4 constant region
                        organism = synthetic construct
SEQUENCE: 33
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 34           moltype = AA  length = 326
FEATURE                 Location/Qualifiers
source                  1..326
                        mol_type = protein
                        note = human heavy chain IgG4 constant region (with S228P
                         and terminal lysine deletion)
                        organism = synthetic construct
SEQUENCE: 34
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLG                                       326

SEQ ID NO: 35           moltype = AA  length = 330
FEATURE                 Location/Qualifiers
source                  1..330
                        mol_type = protein
                        note = Human heavy chain IgG1 constant region
                        organism = synthetic construct
SEQUENCE: 35
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 36           moltype = AA  length = 326
FEATURE                 Location/Qualifiers
source                  1..326
                        mol_type = protein
                        note = Human heavy chain IgG2 constant region
                        organism = synthetic construct
SEQUENCE: 36
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
```

```
QVSLTCLVKG FYPSDISVEW ESNGQPENNY KTTPPMLDSD GSFFLYSKLT VDKSRWQQGN    300
VFSCSVMHEA LHNHYTQKSL SLSPGK                                        326

SEQ ID NO: 37           moltype = AA  length = 107
FEATURE                 Location/Qualifiers
source                  1..107
                        mol_type = protein
                        note = human kappa light chain constant region
                        organism = synthetic construct
SEQUENCE: 37
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 38           moltype = AA  length = 232
FEATURE                 Location/Qualifiers
source                  1..232
                        mol_type = protein
                        note = IgG1 Fc domain
                        organism = synthetic construct
SEQUENCE: 38
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 39           moltype = AA  length = 231
FEATURE                 Location/Qualifiers
source                  1..231
                        mol_type = protein
                        note = Human IgG1 Fc domain (without C-terminal lysine
                           residue)
                        organism = synthetic construct
SEQUENCE: 39
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP G             231

SEQ ID NO: 40           moltype = AA  length = 232
FEATURE                 Location/Qualifiers
source                  1..232
                        mol_type = protein
                        note = IgG1 Fc
                        organism = synthetic construct
SEQUENCE: 40
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSS KAFPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 41           moltype = AA  length = 232
FEATURE                 Location/Qualifiers
source                  1..232
                        mol_type = protein
                        note = IgG1 Fc domain (with K322A)
                        organism = synthetic construct
SEQUENCE: 41
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCAVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 42           moltype = AA  length = 229
FEATURE                 Location/Qualifiers
source                  1..229
                        mol_type = protein
                        note = human IgG4 Fc
                        organism = synthetic construct
SEQUENCE: 42
ESKYGPPCPS CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGK                229

SEQ ID NO: 43           moltype = AA  length = 229
FEATURE                 Location/Qualifiers
source                  1..229
                        mol_type = protein
                        note = human IgG4 Fc (with S228P)
```

```
                          organism = synthetic construct
SEQUENCE: 43
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 44             moltype = AA  length = 228
FEATURE                   Location/Qualifiers
source                    1..228
                          mol_type = protein
                          note = IgG4 Fc (with S228P and without terminal lysine
                            residue)
                          organism = synthetic construct
SEQUENCE: 44
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG              228

SEQ ID NO: 45             moltype = AA  length = 6
FEATURE                   Location/Qualifiers
source                    1..6
                          mol_type = protein
                          note = PAR-2 activating ligand
                          organism = synthetic construct
SEQUENCE: 45
SLIGKV                                                              6

SEQ ID NO: 46             moltype = AA  length = 6
FEATURE                   Location/Qualifiers
source                    1..6
                          mol_type = protein
                          note = PAR-2
                          organism = synthetic construct
SEQUENCE: 46
SLIGRL                                                              6

SEQ ID NO: 47             moltype = AA  length = 55
FEATURE                   Location/Qualifiers
source                    1..55
                          mol_type = protein
                          note = human PAR-1
                          organism = synthetic construct
SEQUENCE: 47
MGPRRLLLVA ACFSLCGPLL SARTRARRPE SKATNATLDP RSFLLRNPND KYEPF       55

SEQ ID NO: 48             moltype = AA  length = 398
FEATURE                   Location/Qualifiers
source                    1..398
                          mol_type = protein
                          note = Nt-PAR-2
                          organism = synthetic construct
SEQUENCE: 48
MRSPSAAWLL GAAILLAASL SCSGTIQGTN RSSKGRSLIG KVDGTSHVTG KGVTVETVFS   60
VDEFSASVLT GKLTTLFVPS VYTGVFVVSL PLNIMAIVVF ILKMVKKPA  VVYMLHLATA  120
DVLFVSVLPF KISYYFSGSD WQFGSELCRF VTAAFYCNMY ASILLMTVIS IDRFLAVVYP  180
MQSLSWRTLG RASFTCLAIW ALAIAGVVPL LLKEQTIQVP GLNITTCHDV LNETLLEGYY  240
AYYFSAFSAV FFFVPLIIST VCYVSIIRCL SSSAVANRSK KSRALFLSAA VPCIFIICFG  300
PTNVLLIAHY SFLSHTSTTE AAYFAYLLCV CVSSISCCID PLIYYASSE  CQRYVYSILC  360
CKESSDPSSY NSSGQLMASK MDTCSSNLNN SIYKKLLT                         398

SEQ ID NO: 49             moltype = AA  length = 106
FEATURE                   Location/Qualifiers
source                    1..106
                          mol_type = protein
                          note = Anti-PAR-2 antibody Ab1 light chain
                          organism = synthetic construct
SEQUENCE: 49
QIVLSQSPAI LSASPGEKVT MTCRASSSLP YIHWYQQKPG SSPRPWIYAT SNLASGVPAR   60
FSGRGSGTSY SLTISRMEAE DAATYYCQQW SSTPPTFGGG SKLEIK                106

SEQ ID NO: 50             moltype = AA  length = 121
FEATURE                   Location/Qualifiers
source                    1..121
                          mol_type = protein
                          note = Anti-PAR-2 antibody Ab1 heavy chain
                          organism = synthetic construct
SEQUENCE: 50
```

```
EVQLVEFGGG LVQPKGSLKL SCAASGFTFN TNAMHWVRQA PGKGLEWVAR IGSKSSYFAT    60
YYADSVKDRF TISRDDSRSM FYLQMNNLKT EDTAMYYCVR EDYYGSSFDL WGQGTTLTVS   120
S                                                                  121

SEQ ID NO: 51           moltype = AA   length = 111
FEATURE                 Location/Qualifiers
source                  1..111
                        mol_type = protein
                        note = Anti-PAR-2 antibody Ab5 light chain
                        organism = synthetic construct
SEQUENCE: 51
DIVLTQSPTS LAVSLGQRAT ISCRASESVD SYGNSFLHWY QQKAGQPPKL LIYRTSNLES    60
GIPARFSGSG SRTDFTLTIN PVEADDVATY FCQQSNEDPY TFGGGTKLEL K            111

SEQ ID NO: 52           moltype = AA   length = 123
FEATURE                 Location/Qualifiers
source                  1..123
                        mol_type = protein
                        note = Anti-PAR-2 antibody Ab5 heavy chain
                        organism = synthetic construct
SEQUENCE: 52
QVQLQQPGSE LVKPGASVKL SCKASGYTFT NYWMHWVKQR PGQGLEWIGM IHPNSDFSNY    60
NEKFKKKATL TVDKSSSTAY MQLSSLTSED SAVYFCAKGP NYYGSRYWYF DVWGTGTTVT   120
VSS                                                                123

SEQ ID NO: 53           moltype = AA   length = 106
FEATURE                 Location/Qualifiers
source                  1..106
                        mol_type = protein
                        note = Anti-PAR-2 antibody Ab20 light chain
                        organism = synthetic construct
SEQUENCE: 53
QIVLSQSPAI LSASPGEKVT MTCRTSSSVI YIHWYQQKSG SSPKPWIYAT SNLASGVPTR    60
FSGSGSGTSY SLTISRVEAE DAATYYCHHW RSNPPTFGGG TKLEIK                  106

SEQ ID NO: 54           moltype = AA   length = 121
FEATURE                 Location/Qualifiers
source                  1..121
                        mol_type = protein
                        note = Anti-PAR-2 antibody Ab20 heavy chain
                        organism = synthetic construct
SEQUENCE: 54
EVQLVESGGG LVQPKGSLKL SCAASGFTFN IYAMHWVRQA PGKGLEWVAR IGSKSSNYAT    60
NYADSVKDRF TISRDDSQSM LCLQMNNLKT EDTAMYYCVR EDYYGNSFDS WGQGTTLAVS   120
S                                                                  121

SEQ ID NO: 55           moltype = AA   length = 106
FEATURE                 Location/Qualifiers
source                  1..106
                        mol_type = protein
                        note = Anti-PAR-2 antibody Ab39 light chain
                        organism = synthetic construct
SEQUENCE: 55
QIVLSQSPVI LSTSPGEKVT MTCRANSRVI YVHWYQQKPG SSPKPWIFAT SNLASGVPSR    60
FSGSGSGTSY SLTISRVETE DAATYYCQHC GNNPPTFGSG TKLEIK                  106

SEQ ID NO: 56           moltype = AA   length = 121
FEATURE                 Location/Qualifiers
source                  1..121
                        mol_type = protein
                        note = Anti-PAR-2 antibody Ab39 heavy chain
                        organism = synthetic construct
SEQUENCE: 56
EVQLVESGGG LVQPKGSLKL SCAASGFTFN TYAMHWVRQA PGKGLEWVAR IGSKSSYYAT    60
YYADSVKDRF TISRADSQSM LYLQMNNLKT EDTAIYYCVR EDYYGCSFDY WGQGTTLTVS   120
S                                                                  121

SEQ ID NO: 57           moltype = AA   length = 107
FEATURE                 Location/Qualifiers
source                  1..107
                        mol_type = protein
                        note = Anti-PAR-2 antibody Ab77 light chain
                        organism = synthetic construct
SEQUENCE: 57
DIVMTQSHKF MSISVGDRVS ITCKASQDVG TAVAWHQQKA GQSPKLLIYW ASARHTGVPD    60
RFTGSGSGTD FTLTISNVQS EDLTDFFCQQ YSNYPFTFGS GTKLEIK                 107

SEQ ID NO: 58           moltype = AA   length = 121
FEATURE                 Location/Qualifiers
```

```
source                  1..121
                        mol_type = protein
                        note = Anti-PAR-2 antibody Ab77 heavy chain
                        organism = synthetic construct
SEQUENCE: 58
EVQLVGSGGG LVQPKGSLKL SCAASGFTFN TYAMHWVRQA PGKGLEWVAR IGSKSSYYAT   60
YYADSVKDRF TISRDDSQSM LYLQMNNLKT EDTAMYYCVR EDYYGSSYDY WGQGTTLTVS  120
S                                                                 121

SEQ ID NO: 59           moltype = AA  length = 107
FEATURE                 Location/Qualifiers
source                  1..107
                        mol_type = protein
                        note = Anti-PAR-2 antibody Ab84 light chain
                        organism = synthetic construct
SEQUENCE: 59
DIVMTQSHKF MSTSVGDRVS ITCKASQDVG SAVAWHQQKP GQSPKLLIYW TSNRHTGVPD   60
RFTGRRSGTD FTLTISNVQS EDLADYFCQQ YSTYPFTFGS GTKLEIK                107

SEQ ID NO: 60           moltype = AA  length = 121
FEATURE                 Location/Qualifiers
source                  1..121
                        mol_type = protein
                        note = Anti-PAR-2 antibody Ab84 heavy chain
                        organism = synthetic construct
SEQUENCE: 60
EVQLIESGGG LVQPKGSLKL SCAASGFTFN SYAMHWVRQA PGKGLEWVAR IRSKNVHYAT   60
YYADSVKDRF TISRDDSQSM LYLQMNNLKT EDTAMYFCVR EDYYGSSYDY WGQGTTLTVS  120
S                                                                 121

SEQ ID NO: 61           moltype = AA  length = 107
FEATURE                 Location/Qualifiers
source                  1..107
                        mol_type = protein
                        note = Anti-PAR-2 antibody Ab86 light chain
                        organism = synthetic construct
SEQUENCE: 61
DIVMTQSHKF MSTSLGDRVS ITCKASQDVG SAVAWHQQKP GQSPKVLIYW ASNRHTGVPD   60
RFTGSGSGTD FTLTISNVQS EDLADYFCQQ YSSYPFTFGS GTKLEIK                107

SEQ ID NO: 62           moltype = AA  length = 121
FEATURE                 Location/Qualifiers
source                  1..121
                        mol_type = protein
                        note = Anti-PAR-2 antibody Ab86 heavy chain
                        organism = synthetic construct
SEQUENCE: 62
EVQLVESGGG LVQPKGSLKL SCAASGFTFN TYAMHWVRQA PGKGLEWVAR IRSKNVHYAT   60
YYADSVKDRF TISRDDSQNM LYLQMNNLKT EDTAMYYCVR EDYYGSSYDY WGQGTTLTVS  120
S                                                                 121

SEQ ID NO: 63           moltype = AA  length = 107
FEATURE                 Location/Qualifiers
source                  1..107
                        mol_type = protein
                        note = Anti-PAR-2 antibody Ab87 light chain
                        organism = synthetic construct
SEQUENCE: 63
DIVMTQSHKF MSTSVGDRVS ITCKASQDVR SAVAWHQQKP GQSPKLLIYW ASNRHTGVPD   60
RFTGSGSGTD FTLTISNVQS EDLADYFCQQ YSSYPFTFGS GTKLEIK                107

SEQ ID NO: 64           moltype = AA  length = 121
FEATURE                 Location/Qualifiers
source                  1..121
                        mol_type = protein
                        note = Anti-PAR-2 antibody Ab87 heavy chain
                        organism = synthetic construct
SEQUENCE: 64
EVQLVESGGG LVQPKGSLKL SCAASGFTFY SYAMHWVRQA PGRGLEWVAR IRSKNVHYAT   60
YYADSVKDRF TISRDDSQNM LYLQMNNLKT EDTAMYYCVR EDYYGSSYDY WGQGTTLTVS  120
S                                                                 121

SEQ ID NO: 65           moltype = AA  length = 107
FEATURE                 Location/Qualifiers
source                  1..107
                        mol_type = protein
                        note = Anti-PAR-2 antibody Ab114 light chain
                        organism = synthetic construct
SEQUENCE: 65
```

```
DVQITQSPSY LAASPGETIT INCRASKSIS RYLAWYQEKP GKTNKLLIYS GSTLQSGVPS    60
RFSGSGFGTD FTLTISSLEP EDFAMYYCQQ HNKYPLTFGA GTKLELK                107

SEQ ID NO: 66           moltype = AA  length = 123
FEATURE                 Location/Qualifiers
source                  1..123
                        mol_type = protein
                        note = Anti-PAR-2 antibody Ab114 heavy chain
                        organism = synthetic construct
SEQUENCE: 66
QVQLQQSGPE LVKPGASVKI SCKTSGFTFT SYYIHWVKQR PGQGLEWIGW IYPGSGNTYY    60
NERFKGKATL TADTSSSTAS MQLSSLTSED SAVYYCANGP LFYGSSYWYF DVWGTGTTVT   120
VSS                                                                123

SEQ ID NO: 67           moltype = AA  length = 108
FEATURE                 Location/Qualifiers
source                  1..108
                        mol_type = protein
                        note = Anti-PAR-2 antibody Ab140 light chain
                        organism = synthetic construct
SEQUENCE: 67
QIVLTQSPAI MSASLGERVT MTCTASSSVS SSYLHWYQQK PGSSPKLWIY ATSNLASGVP    60
ARFSGSGSGT SYSLTISSME AEDAATYYCH QYHRSPLTFG AGTKLELK                108

SEQ ID NO: 68           moltype = AA  length = 121
FEATURE                 Location/Qualifiers
source                  1..121
                        mol_type = protein
                        note = Anti-PAR-2 antibody Ab140 heavy chain
                        organism = synthetic construct
SEQUENCE: 68
EVQLVESGGG LVQPKGSLKL SCAASGFTFN SYAMHWVRQA PGKGLEWVAC IRSKSSYYAT    60
YYADSVKDRF TISRHDSQSM LYLQMNNLKT EDTAMYYCVR EDYYGSSYDY WGQGTTLTVS   120
S                                                                  121

SEQ ID NO: 69           moltype = AA  length = 108
FEATURE                 Location/Qualifiers
source                  1..108
                        mol_type = protein
                        note = Anti-PAR-2 antibody Ab189 light chain
                        organism = synthetic construct
SEQUENCE: 69
QIVLTQSPAI MSASLGERVT MTCTASSSVI SSYLHWYQQK PGSSPKLWIF STSNLASGVP    60
ARFSGSGSGT SYSLTISTME AEDAATYYCH QYHRSPLTFG AGTKLELK                108

SEQ ID NO: 70           moltype = AA  length = 121
FEATURE                 Location/Qualifiers
source                  1..121
                        mol_type = protein
                        note = Anti-PAR-2 antibody Ab189 heavy chain
                        organism = synthetic construct
SEQUENCE: 70
EVQLVESGGG LVQPKGSLKL SCAASGFTFN TYAMHWVRQA PGKGLEWVAR IRSKTTNYAT    60
YYADSVKDRF TISRDDSQSM LYLQISNLKT EDTAMYYCVR EDYYGSSLDY WGQGTTLTVS   120
S                                                                  121

SEQ ID NO: 71           moltype = AA  length = 106
FEATURE                 Location/Qualifiers
source                  1..106
                        mol_type = protein
                        note = Anti-PAR-2 antibody Ab192 light chain
                        organism = synthetic construct
SEQUENCE: 71
ENVLTQSPAI MSASLGEKVT MSCRASSSVN YMYWYQQKSD ASPKLWIYYT SNLAPGVPAR    60
FSGSGSGTSY SLTISSMEGE DAATYYCQQF TTSPYTFGGG TKLEIK                 106

SEQ ID NO: 72           moltype = AA  length = 121
FEATURE                 Location/Qualifiers
source                  1..121
                        mol_type = protein
                        note = Anti-PAR-2 antibody Ab192 heavy chain
                        organism = synthetic construct
SEQUENCE: 72
QVQLQQPGTE LVKPGASVKL SCKASGYTFT SYWMHWIKQR PGQGLEWIGN INPSSGGTNY    60
NEKFKTKATL TVDKSSSTAY MQLSSLTSED SAVYYCAGEA YSNYVAWFAY WGQGTLVTVS   120
S                                                                  121

SEQ ID NO: 73           moltype = AA  length = 107
FEATURE                 Location/Qualifiers
```

```
source                          1..107
                                mol_type = protein
                                note = Anti-PAR-2 antibody Ab201 light chain
                                organism = synthetic construct
SEQUENCE: 73
EVQITQSPSY LAASPGETIT INCRASKSIS KYLAWYQEKP GKTNKLLIYS GSTLQSGIPS    60
RFSGSGSGTD FTLTISSLEP EDFAMYYCQQ HNKYPLTFGA GTRLELK                 107

SEQ ID NO: 74                   moltype = AA  length = 123
FEATURE                         Location/Qualifiers
source                          1..123
                                mol_type = protein
                                note = Anti-PAR-2 antibody Ab201 heavy chain
                                organism = synthetic construct
SEQUENCE: 74
QVQLQQSGPE LVKPGASVKI SCKASGFSFT SFYIHWVNQR PGQGLEWIGW IYPGSGNTLY    60
NEKFKGKATL TADTSSSTAY IHLSSLTSED SAVYYCTRGP LFYGSSHWYF DVWGMGTTVT   120
VSS                                                                 123

SEQ ID NO: 75                   moltype = AA  length = 106
FEATURE                         Location/Qualifiers
source                          1..106
                                mol_type = protein
                                note = Anti-PAR-2 antibody Ab209 light chain
                                organism = synthetic construct
SEQUENCE: 75
ENVLTQSPAI MSASLGEKVT MSCRASSSVN YMYWYRQKSD ASPKLWIYYT SNLAPGVPTR    60
FSGSGSGTSY SLTISSMEGE DAATYYCQQF TTSPYTFGGG TKLEIK                  106

SEQ ID NO: 76                   moltype = AA  length = 121
FEATURE                         Location/Qualifiers
source                          1..121
                                mol_type = protein
                                note = Anti-PAR-2 antibody Ab209 heavy chain
                                organism = synthetic construct
SEQUENCE: 76
QVQLQQPGTE LVKPGASVKL SCKASGYTFT SYWMHWIKQR PGQGLEWIGN INPSTGSTNF    60
NVKFKTKATL TVDKSSSTTY MQLNSLTSED SAVYYCAGEA YSNYVAWFAY WGQGTLVTVS   120
S                                                                   121

SEQ ID NO: 77                   moltype = AA  length = 106
FEATURE                         Location/Qualifiers
source                          1..106
                                mol_type = protein
                                note = Anti-PAR-2 antibody Ab225 light chain
                                organism = synthetic construct
SEQUENCE: 77
EIVLTQSPTT MAASPGEKVT ITCRASSSVR SMYWYQQKSG ASPKPWIYET SKLTSGVPDR    60
FSGSGSGTSY SFTISSMGTE DAGTYYCHQW TTTPYTFGAG TKLELK                  106

SEQ ID NO: 78                   moltype = AA  length = 118
FEATURE                         Location/Qualifiers
source                          1..118
                                mol_type = protein
                                note = Anti-PAR-2 antibody Ab225 heavy chain
                                organism = synthetic construct
SEQUENCE: 78
QVQLKESGPG LVQPSQTLSL TCTVSGFSLT SYHVSWVRQS PGKGLEWMGI IWTGGSTAYN    60
SLLKSRLSIS RDTSKSQVFL KMNSLQTEDT ATYYCARRGA YPFYFDYWGQ GVMVTVSS     118

SEQ ID NO: 79                   moltype = AA  length = 107
FEATURE                         Location/Qualifiers
source                          1..107
                                mol_type = protein
                                note = Anti-PAR-2 antibody Ab227 light chain
                                organism = synthetic construct
SEQUENCE: 79
DIQMTQSPHS LSASLGETVS IECLASEGIS NYLAWFQQKP GKSPQLLIYY ASSLQDGVPS    60
RFSGSGSGTQ YSLKISNMQP EDEGVYYCQQ GYKYPWTFGG GTELELK                 107

SEQ ID NO: 80                   moltype = AA  length = 121
FEATURE                         Location/Qualifiers
source                          1..121
                                mol_type = protein
                                note = Anti-PAR-2 antibody Ab227 heavy chain
                                organism = synthetic construct
SEQUENCE: 80
EVQLVESGGG LVQPGRSLKL SCVASGFTFN NYWMTWIRQA PGKGLEWVAS ITNSGGRTYY    60
PDSVKGRFTV SRDAKSTLY LQMNSLRSED TATYYCTRDR IIRGSTWFTY WGQGTLVTVS   120
```

```
S                                                                       121

SEQ ID NO: 81             moltype = AA  length = 107
FEATURE                   Location/Qualifiers
source                    1..107
                          mol_type = protein
                          note = Anti-PAR-2 antibody Ab228 light chain
                          organism = synthetic construct
SEQUENCE: 81
DIQMTQSPHS LSASLGETVS IECLASEGIS NYLAWYQQKP GKSPQLLIYY ASSLQDGVPS    60
RFSGSGSGTQ YSLKISNMQP EDEGVYYCHQ GYKYPWTFGG GTKLELK                 107

SEQ ID NO: 82             moltype = AA  length = 121
FEATURE                   Location/Qualifiers
source                    1..121
                          mol_type = protein
                          note = Anti-PAR-2 antibody Ab228 heavy chain
                          organism = synthetic construct
SEQUENCE: 82
EVQLVESGGG LVQPGRSLKL SCVVSGFTFN NYWMTWIRQA PGKGLEWVAS ITNSGGNTYY    60
PDSVKGRFTI SRDNAKSTLY LQMNSLRSED TATYYCTRDR IIRGSTWFAY WGQGTLVTVS   120
S                                                                   121

SEQ ID NO: 83             moltype = AA  length = 106
FEATURE                   Location/Qualifiers
source                    1..106
                          mol_type = protein
                          note = Anti-PAR-2 antibody Ab234 light chain
                          organism = synthetic construct
SEQUENCE: 83
EIVLTQSPTT MAASPGEKVT LTCRASSSVI YMHWYQQRSG ASPKLWIYET SKLASGVPNR    60
FGGSGSGTSY SLTINSMETE DAATYYCQQG SYYPWTFGGG TKLELK                  106

SEQ ID NO: 84             moltype = AA  length = 120
FEATURE                   Location/Qualifiers
source                    1..120
                          mol_type = protein
                          note = Anti-PAR-2 antibody Ab234 heavy chain
                          organism = synthetic construct
SEQUENCE: 84
EVQLVETGGG LVQPGRSLKL SCVASGFTFN NYWLYWIRQA PGKGLEWVSS INNDGGGTYY    60
PDSVKGRFTV SRDNAENTVY LQMNSLRSED TATYYCARDR AFIRGRFAYW GQGTLVTVSS   120

SEQ ID NO: 85             moltype = AA  length = 106
FEATURE                   Location/Qualifiers
source                    1..106
                          mol_type = protein
                          note = Anti-PAR-2 antibody Ab245 light chain
                          organism = synthetic construct
SEQUENCE: 85
EVVLTQSPTT MAASPGEKVT ITCRATSSVS HMYWYQQKSG ASPKPWIYET SKLASGVPDR    60
FRGSGSGTSY SFTISSMETE DVATYYCHQW SSFPYTFGPG TKLELK                  106

SEQ ID NO: 86             moltype = AA  length = 118
FEATURE                   Location/Qualifiers
source                    1..118
                          mol_type = protein
                          note = Anti-PAR-2 antibody Ab245 heavy chain
                          organism = synthetic construct
SEQUENCE: 86
QVQLKESGPG LVQPSQTLFL TCTVSGFSLT SYHVSWVRQP PGKGLEWMGI IWTGGSTAYN    60
SLLKPRLTIS RDTSKSQVFL KMNSLRTEDT ATYYCARRGL YPFYFDYWGQ GVMVTVSS     118

SEQ ID NO: 87             moltype = AA  length = 106
FEATURE                   Location/Qualifiers
source                    1..106
                          mol_type = protein
                          note = Anti-PAR-2 antibody Ab248 light chain
                          organism = synthetic construct
SEQUENCE: 87
EIVLTQSPTT LAASPGEKVT ITCRASSRVS NMYWYQQKSG ASPKAWIYET SKLASGVPDR    60
FSGSGSGTSY SFTISSMETE DAATYYCHQW TSTPYTFGAG TKLELK                  106

SEQ ID NO: 88             moltype = AA  length = 118
FEATURE                   Location/Qualifiers
source                    1..118
                          mol_type = protein
                          note = Anti-PAR-2 antibody Ab248 heavy chain
                          organism = synthetic construct
```

```
SEQUENCE: 88
QVQLKESGPG LVQPSQTLSL TCTVSGFSLT NYHVSWVRQP PGKGLEWMGI IWTGGSTAYN   60
SLLKSRLSIS RDTSKSQVFL KMNSLQTEDT ATYYCARRGL YPYYFDYWGQ GVMVTVSS    118

SEQ ID NO: 89             moltype = AA   length = 107
FEATURE                   Location/Qualifiers
source                    1..107
                          mol_type = protein
                          note = Anti-PAR-2 antibody Ab261 light chain
                          organism = synthetic construct
SEQUENCE: 89
DIQMTQSPHS LSASLGETVS IECLASEGIS NYLAWFQQKP GKSPQLLIYY ASSLQDGVPS   60
RFSGSGSGTQ YSLKISNMQP EDEGVYYCQQ GYKYPWTFGG GTKLELK              107

SEQ ID NO: 90             moltype = AA   length = 121
FEATURE                   Location/Qualifiers
source                    1..121
                          mol_type = protein
                          note = Anti-PAR-2 antibody Ab261 heavy chain
                          organism = synthetic construct
SEQUENCE: 90
EVQLVESGGG LVQPGRSLKL SCVASGFTFN NYWMTWIRQA PGKGLEWVAS ITNTGGNTYY   60
PDSVKGRFTI SRDNAKSTLY LQMNSLRSED TATYYCTRDR IIRGADWFAY WGQGTLVTVS  120
S                                                                 121

SEQ ID NO: 91             moltype = AA   length = 106
FEATURE                   Location/Qualifiers
source                    1..106
                          mol_type = protein
                          note = Anti-PAR-2 antibody Ab303 light chain
                          organism = synthetic construct
SEQUENCE: 91
DIQMTQSPSF LSASVGERVT LSCKTSQKIN RYLDWYQQKL GEAPKLLIYN TNNLHTGIPS   60
RFSGSGSGTD YTLTISSLQP EDVATYFCLQ HSSWPTFGAG TKLELK               106

SEQ ID NO: 92             moltype = AA   length = 120
FEATURE                   Location/Qualifiers
source                    1..120
                          mol_type = protein
                          note = Anti-PAR-2 antibody Ab303 heavy chain
                          organism = synthetic construct
SEQUENCE: 92
QVTLKESGPG ILQPSHTLSL TCSFSGFSLS TYGMGVSWIR QPSGKGLEWL ASIWWNGNTY   60
NNPSLKSRLT VSKDTSNNQA FLKVTSVDTA DTATYYCAHT PNLGNWFAYW GQGTLVTVSS  120

SEQ ID NO: 93             moltype = AA   length = 106
FEATURE                   Location/Qualifiers
source                    1..106
                          mol_type = protein
                          note = Anti-PAR-2 antibody Ab311 light chain
                          organism = synthetic construct
SEQUENCE: 93
DIQMTQSPSF LSASVGDRVT INCKASQNIY KYLDWYQQKL GEAPKLLIYN SNILHTGVPS   60
RFSGSGSGTD FTLSISSLQP EDVATYFCLQ HNSGWTFGGG SKLELR               106

SEQ ID NO: 94             moltype = AA   length = 119
FEATURE                   Location/Qualifiers
source                    1..119
                          mol_type = protein
                          note = Anti-PAR-2 antibody Ab311 heavy chain
                          organism = synthetic construct
SEQUENCE: 94
QVQLKESGPG LVQPSQTLSL SCTVSGFSLT TYGVIWVRQP PGKGLMWMGV IWGNGNTYYN   60
SPLKSRLSIS RDTSKSQVFL KMNNLQSEDT AMYFCGRWRW YKDYPFDYWG QGVKVTVSS   119

SEQ ID NO: 95             moltype = AA   length = 106
FEATURE                   Location/Qualifiers
source                    1..106
                          mol_type = protein
                          note = Anti-PAR-2 antibody Ab313 light chain
                          organism = synthetic construct
SEQUENCE: 95
DIQMTQSPSV LSASVGDRVI LNCKASQKIN KYLNWYQQKL GEAPKLLIYT TNNLQTGIPS   60
RFSGSGSGTD FTLTISSLQP EDFATYFCFQ HSSWPTFGAG TKLELK               106

SEQ ID NO: 96             moltype = AA   length = 118
FEATURE                   Location/Qualifiers
source                    1..118
                          mol_type = protein
```

```
                         note = Anti-PAR-2 antibody Ab313 heavy chain
                         organism = synthetic construct
SEQUENCE: 96
EVQLKESGPG LVQPSQTLSL TCTVSGFSLT DYSVHWVRQP PGKGLEWMGV MWSGGSTSYN    60
SPLKSRLSIS RDTSKSQVFL KTNSLQTEDT AIYYCTRARP TVATLDYWGQ GVMVTVSS     118

SEQ ID NO: 97            moltype = AA  length = 106
FEATURE                  Location/Qualifiers
source                   1..106
                         mol_type = protein
                         note = Anti-PAR-2 antibody Ab323 light chain
                         organism = synthetic construct
SEQUENCE: 97
DIQMTQSPSF LSASVGDRVT INCKASQNIY KYLDWYQQKL GEAPKLLMYN TNTLHTGIPS    60
RFSGSGSGTD FTLTISSLQP EDVATYFCLQ HNSGWTFGGG TKLELK                 106

SEQ ID NO: 98            moltype = AA  length = 119
FEATURE                  Location/Qualifiers
source                   1..119
                         mol_type = protein
                         note = Anti-PAR-2 antibody Ab323 heavy chain
                         organism = synthetic construct
SEQUENCE: 98
QVQLKESGPG LVQPSQTLSL TCSVSGFSLS TYGIIWVRQP PGKGLEWMGV IWGNGNTHYN    60
SALKSRLSIT RDTSKSQVFL KMNNLQTEDT AMYFCGRWRG YKDYPFDYWG QGVMVTVSS    119

SEQ ID NO: 99            moltype = AA  length = 106
FEATURE                  Location/Qualifiers
source                   1..106
                         mol_type = protein
                         note = Anti-PAR-2 antibody Ab335 light chain
                         organism = synthetic construct
SEQUENCE: 99
DIQMTQSPSF LSASVGDRVT INCKASRNIY KYLDWYQQKL GEAPKLLIYN TNNLHTGIPS    60
RFSGSGSGTD FTLTISSLQP EDVATYFCLQ HNSGWTFGGG TKLELK                 106

SEQ ID NO: 100           moltype = AA  length = 119
FEATURE                  Location/Qualifiers
source                   1..119
                         mol_type = protein
                         note = Anti-PAR-2 antibody Ab335 heavy chain
                         organism = synthetic construct
SEQUENCE: 100
QVQLKESGPG LVQPSQTLSL SCTVSGFSLS TYGIVWVRQP PGKGLEWMGV IWGNGNTNYN    60
SALKSRLSIS RDTSKSQVFL KMNNLQSEDT AMYFCGRWRG YKDYPFDYWG QGVKVTVSS    119

SEQ ID NO: 101           moltype = AA  length = 106
FEATURE                  Location/Qualifiers
source                   1..106
                         mol_type = protein
                         note = Anti-PAR-2 antibody Ab342 light chain
                         organism = synthetic construct
SEQUENCE: 101
DIQMTQTPSF LSASVGDRVT INCRASQNIY KYLDWYQLKL GEAPKLLIYN TNTLHTGIPS    60
RFSGSGSGTD FTLTISSLQP EDVATYFCLQ HNSGWAFGGG TKLELK                 106

SEQ ID NO: 102           moltype = AA  length = 119
FEATURE                  Location/Qualifiers
source                   1..119
                         mol_type = protein
                         note = Anti-PAR-2 antibody Ab342 heavy chain
                         organism = synthetic construct
SEQUENCE: 102
QVQLKESGPG LVQPSQTLSL SCTVSGFSLN TYGIVWVRQP PGKGLDWMGV IWGNGNTYYD    60
SALKSRLSIS RDTSKSQIFL KMNNLQSEDT AMYFCGRWRG FKDYPFDYWG QGVKVTVSS    119

SEQ ID NO: 103           moltype = AA  length = 107
FEATURE                  Location/Qualifiers
source                   1..107
                         mol_type = protein
                         note = Anti-PAR-2 antibody Ab343 light chain
                         organism = synthetic construct
SEQUENCE: 103
DIQMTQSPHS LSASLGETVS IECLASEAIS NYLAWYQQKP GKSPQLLIYY ASSLKDGVPS    60
RISGSGSGTQ YSLKISNMQP EDEGVYYCQQ GYKYPRTFGG GTKLELK                107

SEQ ID NO: 104           moltype = AA  length = 121
FEATURE                  Location/Qualifiers
source                   1..121
```

```
                         mol_type = protein
                         note = Anti-PAR-2 antibody Ab343 heavy chain
                         organism = synthetic construct
SEQUENCE: 104
EVQLVESGGG LVQPGRSLKL SCVASGFTFN NYWMSWIRQA PGKGLEWVAS ITNTGGRIFY    60
PDSVKGRFTI SRDNAQNTLY LQMNSLRSED AATYYCTRDR LYYGSNWFTY WGQGTLVTVS   120
S                                                                  121

SEQ ID NO: 105           moltype = AA  length = 106
FEATURE                  Location/Qualifiers
source                   1..106
                         mol_type = protein
                         note = Anti-PAR-2 antibody Ab348 light chain
                         organism = synthetic construct
SEQUENCE: 105
DIQMTQSPSF LSASVGDRVT INCKASQNIY KYLDWYQQKL GEAPKLLIYN TNSLHTGIPS    60
RFSGSGSGTD FTLTISSLQP EDVATYFCLQ HNSGWTFGGG TKLELK                 106

SEQ ID NO: 106           moltype = AA  length = 119
FEATURE                  Location/Qualifiers
source                   1..119
                         mol_type = protein
                         note = Anti-PAR-2 antibody Ab348 heavy chain
                         organism = synthetic construct
SEQUENCE: 106
QVQLKESGPG LVQPSQTLSL TCSVSGFSLS SYGVIWVRQP PGKGLEWMGV VWGNGNTAYN    60
FTLKSRLTIS RDTSKSQVFL KMNNLQTEDT AMYFCGRWRG FKDYPFDYWG QGVMVTVSS    119

SEQ ID NO: 107           moltype = AA  length = 105
FEATURE                  Location/Qualifiers
source                   1..105
                         mol_type = protein
                         note = Anti-PAR-2 antibody Ab360 light chain
                         organism = synthetic construct
SEQUENCE: 107
DTVLTQSPAL AVSPGERVTI SCRASESVRT RMHWYQQRPG QQPKLLIYGA SNPESGVPAR    60
FSGSGSGTDF TLTIDPVEAD DSATYFCHQS WNEYTFGAGT KLELK                  105

SEQ ID NO: 108           moltype = AA  length = 120
FEATURE                  Location/Qualifiers
source                   1..120
                         mol_type = protein
                         note = Anti-PAR-2 antibody Ab360 heavy chain
                         organism = synthetic construct
SEQUENCE: 108
EVQLVESGGG LVQPGRSLKL SCVASGFTFN NYWMTWIRQA PGKGLEWVAS ITNTGGSTYY    60
PDSVKGRFTI SRDNAKSTLY LQMNSLRSED TATYYCTREG IRGTGWFAYW GQGTLVTVSS   120

SEQ ID NO: 109           moltype = AA  length = 372
FEATURE                  Location/Qualifiers
source                   1..372
                         mol_type = protein
                         note = human PAR-2 (without the signal sequence)
                         organism = synthetic construct
SEQUENCE: 109
IQGTNRSSKG RSLIGKVDGT SHVTGKGVTV ETVFSVDEFS ASVLTGKLTT VFLPIVYTIV    60
FVVGLPSNGM ALWVFLFRTK KKHPAVIYMA NLALADLLSV IWFPLKIAYH IHGNNWIYGE   120
ALCNVLIGFF YGNMYCSILF MTCLSVQRYW VIVNPMGHSR KKANIAIGIS LAIWLLILLV   180
TIPLYVVKQT IFIPALNITT CHDVLPEQLL VGDMFNYFLS LAIGVFLFPA FLTASAYVLM   240
IRMLRSSAMD ENSEKKRKRA IKLIVTVLAM YLICFTPSNL LLVVHYFLIK SQGQSHVYAL   300
YIVALCLSTL NSCIDPFVYY FVSHDFRDHA KNALLCRSVR TVKQMQVSLT SKKHSRKSSS   360
YSSSSTTVKT SY                                                      372

SEQ ID NO: 110           moltype = AA  length = 107
FEATURE                  Location/Qualifiers
source                   1..107
                         mol_type = protein
                         note = Anti-PAR-2 antibody Ab380 light chain
                         organism = synthetic construct
SEQUENCE: 110
DIQMTQSPHS LSASLGETVS IECLASEGIS NYLAWFQQKP GKSPQLLIYY ASSLQDGVPS    60
RFSGSGSGTQ YSLKISNMQP EDEGVYYCQQ GYKYPWTFGG GTKLELK                107

SEQ ID NO: 111           moltype = AA  length = 121
FEATURE                  Location/Qualifiers
source                   1..121
                         mol_type = protein
                         note = Anti-PAR-2 antibody Ab380 heavy chain
                         organism = synthetic construct
```

```
SEQUENCE: 111
EVQLVESGGG LVQPGRSLKL SCVATGFTFN NYWMTWIRQA PGKGLEWVAS ITNSGGNTYY    60
PDSVKGRFTI SRDDAKSTLY LQMNSLRSED TATYYCTRVR VYYGSNWFVY WGQGTLVTVS   120
S                                                                   121

SEQ ID NO: 112          moltype = AA   length = 107
FEATURE                 Location/Qualifiers
source                  1..107
                        mol_type = protein
                        note = Anti-PAR-2 antibody Ab392 light chain
                        organism = synthetic construct
SEQUENCE: 112
DIQMTQSPHS LSASLGEGVS IECLASEGIS NYLAWFQQKP GKSPQLLIYY ASSLQDGVPS    60
RFSGSGSGTQ YSLKISNMQP EDEGVYYCQQ GYKYPWTFGG GTKLELK                 107

SEQ ID NO: 113          moltype = AA   length = 121
FEATURE                 Location/Qualifiers
source                  1..121
                        mol_type = protein
                        note = Anti-PAR-2 antibody Ab392 heavy chain
                        organism = synthetic construct
SEQUENCE: 113
EVQLVESGGG LVQPGRSLKL SCVASGFTFN NKWMTWIRQA PGKGLEWIAS ITNTGGRTFY    60
PDSVKGRFTI SRDDAKSTLY LQMNSLRSED TATYYCTRAT IRRGASYFDY WGQGVMVTVS   120
S                                                                   121

SEQ ID NO: 114          moltype = AA   length = 107
FEATURE                 Location/Qualifiers
source                  1..107
                        mol_type = protein
                        note = Anti-PAR-2 antibody Ab435 light chain
                        organism = synthetic construct
SEQUENCE: 114
DIQMTQSPHS LSASLGETVS IECLASEGIS NYLAWYQQKP GKSPQLLIYY ASSLQDGVPS    60
RFSGSGSGTQ YSLKISNMQP EDEGIYYCQQ HYKYPWTFGG GTKLELK                 107

SEQ ID NO: 115          moltype = AA   length = 121
FEATURE                 Location/Qualifiers
source                  1..121
                        mol_type = protein
                        note = Anti-PAR-2 antibody Ab435 heavy chain
                        organism = synthetic construct
SEQUENCE: 115
EVQLVESGGG LVQPGRSLKL SCVGSGFTFN NYWMTWIRQA PGWGLEWVAS ITNTGGRTYY    60
PDSVKGRFTI SRDNAKSTLY LQMNSLRSED TATYYCTRDR VYYGSNWFVY WGQGTLVTVS   120
S                                                                   121

SEQ ID NO: 116          moltype = AA   length = 119
FEATURE                 Location/Qualifiers
source                  1..119
                        mol_type = protein
                        note = Anti-PAR-2 antibody (309) Variable heavy CHain
                          Sequence
                        organism = synthetic construct
SEQUENCE: 116
QVQLKESGPG LVQPSQTLSL TCTVSGFSLN SYGVIWARQP PGKGLDWMGV IWGNGNTYYN    60
SDLKSRLSIS RDTSKSQVFL KMNNLQAEDT ALYFCARWRG YKDYPFDYWG QGVMVTVSS   119

SEQ ID NO: 117          moltype = AA   length = 106
FEATURE                 Location/Qualifiers
source                  1..106
                        mol_type = protein
                        note = Anti-PAR-2 antibody (309) Variable Light CHain
                          Sequence
                        organism = synthetic construct
SEQUENCE: 117
DIQMTQSPSF LSASVGDRVT FNCKASQNIY KYLDWYQQKL GEAPKLLIYN TNSLHTGIPS    60
RFSGSGFGTD FTLTISSLQP EDVATYFCLQ HNSGWTFGGG TKLELR                 106

SEQ ID NO: 118          moltype = AA   length = 119
FEATURE                 Location/Qualifiers
source                  1..119
                        mol_type = protein
                        note = Anti-PAR-2 antibody (309-6e and 309-6i) Variable
                          Heavy Chain Sequence
                        organism = synthetic construct
SEQUENCE: 118
EVQLVESGGG LVQPGGSLRL SCAASGFSLN SYGVIWVRQA PGKGLEWVSV IWGNGNTYYN    60
DSVKGRFTIS RDNSKNTLYL QMNSLRAEDT AVYYCARWRG YKDYPFDYWG QGTLVTVSS   119
```

```
SEQ ID NO: 119           moltype = AA  length = 119
FEATURE                  Location/Qualifiers
source                   1..119
                         mol_type = protein
                         note = Anti-PAR-2 antibody (309-11e and 309-11i) Variable
                           Heavy Chain Sequence
                         organism = synthetic construct
SEQUENCE: 119
QVQLQESGPG LVKPSETLSL TCTVSGFSLN SYGVIWIRQP PGKGLEWIGV IWGNGNTYYN   60
PSLKSRVTIS VDTSKNQFSL KLSSVTAADT AVYYCARWRG YKDYPFDYWG QGTLVTVSS   119

SEQ ID NO: 120           moltype = AA  length = 119
FEATURE                  Location/Qualifiers
source                   1..119
                         mol_type = protein
                         note = Anti-PAR-2 antibody (309-12e and 309-12i) Variable
                           Heavy Chain Sequence
                         organism = synthetic construct
SEQUENCE: 120
QVQLQQWGAG LLKPSETLSL TCAVYGFSLN SYGVIWIRQP PGKGLEWIGV IWGNGNTYYN   60
PSLKSRVTIS VDTSKNQFSL KLSSVTAADT AVYYCARWRG YKDYPFDYWG QGTLVTVSS   119

SEQ ID NO: 121           moltype = AA  length = 106
FEATURE                  Location/Qualifiers
source                   1..106
                         mol_type = protein
                         note = Anti-PAR-2 antibody (309-4i, 309-6i, 309-11i, and
                           309-12i) Variable Light Chain Sequence
                         organism = synthetic construct
SEQUENCE: 121
DIQMTQSPSS LSASVGDRVT ITCKASQNIY KYLDWYQQKP GKAPKRLIYN TNSLHTGVPS   60
RFSGSGSGTE FTLTISSLQP EDFATYYCLQ HNSGWTFGGG TKVEIK                 106

SEQ ID NO: 122           moltype = AA  length = 119
FEATURE                  Location/Qualifiers
source                   1..119
                         mol_type = protein
                         note = Anti-PAR-2 antibody P24E5 Variable Heavy Chain
                           Sequence
                         organism = synthetic construct
SEQUENCE: 122
QVQLVQSGAE VKKPGSSVKV SCKASGFSLS SYGVIWVRQA PGQGLEWMGV IWGNGNTYYN   60
QKFQGRVTIT ADESTSTAYM ELSSLRSEDT AVYYCARWRG YKDYPFDYWG QGTLVTVSS   119

SEQ ID NO: 123           moltype = AA  length = 119
FEATURE                  Location/Qualifiers
source                   1..119
                         mol_type = protein
                         note = Anti-PAR-2 antibody P24E9 Variable Heavy Chain
                           Sequence
                         organism = synthetic construct
SEQUENCE: 123
QVQLVQSGAE VKKPGSSVKV SCKASGFSLS SYGVIWVRQA PGQGLEWMGV IWGNGNTYYN   60
QKFQGRVTIT ADESTSTAYM ELSSLRSEDT AVYYCARWRG YKDYPFDYWG QGTLVTVSS   119

SEQ ID NO: 124           moltype = AA  length = 119
FEATURE                  Location/Qualifiers
source                   1..119
                         mol_type = protein
                         note = Anti-PAR-2 antibody P24E22 Variable Heavy Chain
                           Sequence
                         organism = synthetic construct
SEQUENCE: 124
QVQLVQSGAE VKKPGSSVKV SCKASGFSLN SYGVIWVRQA PGQGLEWMGV IWGNGNTYYA   60
QKFQGRVTIT ADESTSTAYM ELSSLRSEDT AVYYCARWRG YKDYPFDYWG QGTLVTVSS   119

SEQ ID NO: 125           moltype = AA  length = 106
FEATURE                  Location/Qualifiers
source                   1..106
                         mol_type = protein
                         note = Anti-PAR-2 antibody P24E27 VAriable Light Chain
                           Sequence
                         organism = synthetic construct
SEQUENCE: 125
EIVLTQSPAT LSLSPGERAT LSCRASQNIY KYLDWYQQKP GQAPRLLIYN TNSLHTGIPA   60
RFSGSGSGRD FTLTISSLEP EDFAVYYCLQ HNSGWTFGGG TKVEIK                 106

SEQ ID NO: 126           moltype = AA  length = 106
```

```
FEATURE                 Location/Qualifiers
source                  1..106
                        mol_type = protein
                        note = Anti-PAR-2 antibody P24E29 VAriable Light Chain
                          Sequence
                        organism = synthetic construct
SEQUENCE: 126
EIVLTQSPAT LSLSPGERAT LSCKASQNVY KYLDWYQQKP GQAPRLLIYN TNSLHTGIPA    60
RFSGSGSGRD FTLTISSLEP EDFAVYYCLQ HNSGWTFGGG TKVEIK                 106

SEQ ID NO: 127          moltype = AA  length = 106
FEATURE                 Location/Qualifiers
source                  1..106
                        mol_type = protein
                        note = Anti-PAR-2 antibody P24E36 VAriable Light Chain
                          Sequence
                        organism = synthetic construct
SEQUENCE: 127
EIVLTQSPAT LSLSPGERAT LSCKASQNIY KYLDWYQQKP GQAPRLLIYN ANSLHTGIPA    60
RFSGSGSGRD FTLTISSLEP EDFAVYYCLQ HNSGWTFGGG TKVEIK                 106

SEQ ID NO: 128          moltype = AA  length = 106
FEATURE                 Location/Qualifiers
source                  1..106
                        mol_type = protein
                        note = Anti-PAR-2 antibody P24E39 VAriable Light Chain
                          Sequence
                        organism = synthetic construct
SEQUENCE: 128
EIVLTQSPAT LSLSPGERAT LSCKASQNIY KYLDWYQQKP GQAPRLLIYN TNSRHTGIPA    60
RFSGSGSGRD FTLTISSLEP EDFAVYYCLQ HNSGWTFGGG TKVEIK                 106

SEQ ID NO: 129          moltype = AA  length = 106
FEATURE                 Location/Qualifiers
source                  1..106
                        mol_type = protein
                        note = Anti-PAR-2 antibody P24E40 VAriable Light Chain
                          Sequence
                        organism = synthetic construct
SEQUENCE: 129
EIVLTQSPAT LSLSPGERAT LSCKASQNIY KYLDWYQQKP GQAPRLLIYN TNSLATGIPA    60
RFSGSGSGRD FTLTISSLEP EDFAVYYCLQ HNSGWTFGGG TKVEIK                 106

SEQ ID NO: 130          moltype = AA  length = 106
FEATURE                 Location/Qualifiers
source                  1..106
                        mol_type = protein
                        note = Anti-PAR-2 antibody P24E41 VAriable Light Chain
                          Sequence
                        organism = synthetic construct
SEQUENCE: 130
EIVLTQSPAT LSLSPGERAT LSCKASQNIY KYLDWYQQKP GQAPRLLIYD ASNRATGIPA    60
RFSGSGSGRD FTLTISSLEP EDFAVYYCLQ HNSGWTFGGG TKVEIK                 106

SEQ ID NO: 131          moltype = AA  length = 106
FEATURE                 Location/Qualifiers
source                  1..106
                        mol_type = protein
                        note = Anti-PAR-2 antibody P24E60 VAriable Light Chain
                          Sequence
                        organism = synthetic construct
SEQUENCE: 131
EIVLTQSPAT LSLSPGERAT LSCKASQNIY KWLDWYQQKP GQAPRLLIYN TNSLHTGIPA    60
RFSGSGSGRD FTLTISSLEP EDFAVYYCLQ HNSGWTFGGG TKVEIK                 106

SEQ ID NO: 132          moltype = AA  length = 106
FEATURE                 Location/Qualifiers
source                  1..106
                        mol_type = protein
                        note = Anti-PAR-2 antibody P24E61 VAriable Light Chain
                          Sequence
                        organism = synthetic construct
SEQUENCE: 132
EIVLTQSPAT LSLSPGERAT LSCKASQNIY KFLDWYQQKP GQAPRLLIYN TNSLHTGIPA    60
RFSGSGSGRD FTLTISSLEP EDFAVYYCLQ HNSGWTFGGG TKVEIK                 106

SEQ ID NO: 133          moltype = AA  length = 119
FEATURE                 Location/Qualifiers
source                  1..119
```

```
                          mol_type = protein
                          note = Anti-PAR-2 antibody P24E186 VAriable Heavy Chain
                              Sequence
                          organism = synthetic construct
SEQUENCE: 133
QVQLVQSGAE VKKPGSSVKV SCKASGFSLN SYGVIWVRQA PGQGLEWMGV IWGNGNTYYN  60
QKFQGRVTIT ADESTSTAYM ELSSLRSEDT AVYYCARWRG WKDYPFDYWG QGTLVTVSS  119

SEQ ID NO: 134            moltype = AA  length = 119
FEATURE                   Location/Qualifiers
source                    1..119
                          mol_type = protein
                          note = Anti-PAR-2 antibody P24E216 VAriable Heavy Chain
                              Sequence
                          organism = synthetic construct
SEQUENCE: 134
QVQLVQSGAE VKKPGSSVKV SCKASGFSLN YYGVIWVRQA PGQGLEWMGV IWGNGNTYYN  60
QKFQGRVTIT ADESTSTAYM ELSSLRSEDT AVYYCARWRG YKDYPFDYWG QGTLVTVSS  119

SEQ ID NO: 135            moltype = AA  length = 119
FEATURE                   Location/Qualifiers
source                    1..119
                          mol_type = protein
                          note = Anti-PAR-2 antibody P24E219 VAriable Heavy Chain
                              Sequence
                          organism = synthetic construct
SEQUENCE: 135
QVQLVQSGAE VKKPGSSVKV SCKASGFSLN SYGGIWVRQA PGQGLEWMGV IWGNGNTYYN  60
QKFQGRVTIT ADESTSTAYM ELSSLRSEDT AVYYCARWRG YKDYPFDYWG QGTLVTVSS  119

SEQ ID NO: 136            moltype = AA  length = 119
FEATURE                   Location/Qualifiers
source                    1..119
                          mol_type = protein
                          note = Anti-PAR-2 antibody P24E232 VAriable Heavy Chain
                              Sequence
                          organism = synthetic construct
SEQUENCE: 136
QVQLVQSGAE VKKPGSSVKV SCKASGFSLN SYGVIWVRQA PGQGLEWMGV IWGNGNTYYG  60
QKFQGRVTIT ADESTSTAYM ELSSLRSEDT AVYYCARWRG YKDYPFDYWG QGTLVTVSS  119

SEQ ID NO: 137            moltype = AA  length = 119
FEATURE                   Location/Qualifiers
source                    1..119
                          mol_type = protein
                          note = Anti-PAR-2 antibody P24E233 VAriable Heavy Chain
                              Sequence
                          organism = synthetic construct
SEQUENCE: 137
QVQLVQSGAE VKKPGSSVKV SCKASGFSLN SYGVIWVRQA PGQGLEWMGV IWGNGNTYYY  60
QKFQGRVTIT ADESTSTAYM ELSSLRSEDT AVYYCARWRG YKDYPFDYWG QGTLVTVSS  119

SEQ ID NO: 138            moltype = AA  length = 119
FEATURE                   Location/Qualifiers
source                    1..119
                          mol_type = protein
                          note = Anti-PAR-2 antibody
                              (P24E278,P24E279,P24E280,P24E280,andP24E282) VAriable
                              Heavy Chain Sequence
                          organism = synthetic construct
SEQUENCE: 138
QVQLVQSGAE VKKPGSSVKV SCKASGFSLS SYGVIWVRQA PGQGLEWMGV IWGNGNTYYA  60
QKFQGRVTIT ADESTSTAYM ELSSLRSEDT AVYYCARWRG YKDYPFDYWG QGTLVTVSS  119

SEQ ID NO: 139            moltype = AA  length = 119
FEATURE                   Location/Qualifiers
source                    1..119
                          mol_type = protein
                          note = Anti-PAR-2 antibody
                              (P24E283,P24E284,P24E285,P24E286,and P24E287) VAriable
                              Heavy Chain Sequence
                          organism = synthetic construct
SEQUENCE: 139
QVQLVQSGAE VKKPGSSVKV SCKASGFSLN SYAVIWVRQA PGQGLEWMGV IWGNGNTYYA  60
QKFQGRVTIT ADESTSTAYM ELSSLRSEDT AVYYCARWRG YKDYPFDYWG QGTLVTVSS  119

SEQ ID NO: 140            moltype = AA  length = 119
FEATURE                   Location/Qualifiers
source                    1..119
```

```
                        mol_type = protein
                        note = Anti-PAR-2 antibody
                          (P24E288,P24E289,P24E290,P24E291,and P24E292) VAriable
                          Heavy Chain Sequence
                        organism = synthetic construct
SEQUENCE: 140
QVQLVQSGAE VKKPGSSVKV SCKASGFSLN SYGIIWVRQA PGQGLEWMGV IWGNGNTYYA    60
QKFQGRVTIT ADESTSTAYM ELSSLRSEDT AVYYCARWRG YKDYPFDYWG QGTLVTVSS    119

SEQ ID NO: 141          moltype = AA  length = 119
FEATURE                 Location/Qualifiers
source                  1..119
                        mol_type = protein
                        note = Anti-PAR-2 antibody
                          (P24E293,P24E294,P24E295,P24E296,and P24E297) VAriable
                          Heavy Chain Sequence
                        organism = synthetic construct
SEQUENCE: 141
QVQLVQSGAE VKKPGSSVKV SCKASGFSLN SYAISWVRQA PGQGLEWMGV IWGNGNTYYA    60
QKFQGRVTIT ADESTSTAYM ELSSLRSEDT AVYYCARWRG YKDYPFDYWG QGTLVTVSS    119

SEQ ID NO: 142          moltype = AA  length = 119
FEATURE                 Location/Qualifiers
source                  1..119
                        mol_type = protein
                        note = Anti-PAR-2 antibody
                          (P24E298,P24E743,P24E794,P24E833,and P24E889)  VAriable
                          Heavy Chain Sequence
                        organism = synthetic construct
SEQUENCE: 142
QVQLVQSGAE VKKPGSSVKV SCKASGFSLS SYAISWVRQA PGQGLEWMGV IWGNGNTYYA    60
QKFQGRVTIT ADESTSTAYM ELSSLRSEDT AVYYCARWRG YKDYPFDYWG QGTLVTVSS    119

SEQ ID NO: 143          moltype = AA  length = 119
FEATURE                 Location/Qualifiers
source                  1..119
                        mol_type = protein
                        note = Anti-PAR-2 antibody (P24E300,P24E922,P24E923,and
                          P24E924)  VAriable Heavy Chain Sequence
                        organism = synthetic construct
SEQUENCE: 143
QVQLVQSGAE VKKPGSSVKV SCKASGFSLS SYAISWVRQA PGQGLEWMGV IWGNGNTYYA    60
QKFQGRVTIT ADESTSTAYM ELSSLRSEDT AVYYCARWRG WKDYPFDYWG QGTLVTVSS    119

SEQ ID NO: 144          moltype = AA  length = 119
FEATURE                 Location/Qualifiers
source                  1..119
                        mol_type = protein
                        note = Anti-PAR-2 antibody
                          (P24E301,P24E914,P24E915,P24E916,P24E917,and         P24E93
                          3) VAriable Heavy Chain Sequence
                        organism = synthetic construct
SEQUENCE: 144
QVQLVQSGAE VKKPGSSVKV SCKASGFSLS SYAISWVRQA PGQGLEWMGV IWGNGNTYYA    60
QKFQGRVTIT ADESTSTAYM ELSSLRSEDT AVYYCARWKG YKDYPFDYWG QGTLVTVSS    119

SEQ ID NO: 145          moltype = AA  length = 119
FEATURE                 Location/Qualifiers
source                  1..119
                        mol_type = protein
                        note = Anti-PAR-2 antibody (P24E918,P24E919,P24E920,and
                          P24E921) VAriable Heavy Chain Sequence
                        organism = synthetic construct
SEQUENCE: 145
QVQLVQSGAE VKKPGSSVKV SCKASGFSLS SYAISWVRQA PGQGLEWMGV IWGNGNTYYA    60
QKFQGRVTIT ADESTSTAYM ELSSLRSEDT AVYYCARWRG FKDYPFDYWG QGTLVTVSS    119

SEQ ID NO: 146          moltype = AA  length = 119
FEATURE                 Location/Qualifiers
source                  1..119
                        mol_type = protein
                        note = Anti-PAR-2 antibody
                          (P24E930,P24E931,P24E932,P24E971,P24E972,and         P24E97
                          3) VAriable Heavy Chain Sequence
                        organism = synthetic construct
SEQUENCE: 146
QVQLVQSGAE VKKPGSSVKV SCKASGFSLS SYAISWVRQA PGQGLEWMGV IWGNGNVYYA    60
QKFQGRVTIT ADESTSTAYM ELSSLRSEDT AVYYCARWKG YKDYPFDYWG QGTLVTVSS    119
```

```
SEQ ID NO: 147            moltype = AA  length = 119
FEATURE                   Location/Qualifiers
source                    1..119
                          mol_type = protein
                          note = Anti-PAR-2 antibody (P24E934,P24E935,and P24E936)
                           VAriable Heavy Chain Sequence
                          organism = synthetic construct
SEQUENCE: 147
QVQLVQSGAE VKKPGSSVKV SCKASGFSLS SYAISWVRQA PGQGLEWMGV IWGNGNVYYA    60
QKFQGRVTIT ADESTSTAYM ELSSLRSEDT AVYYCARWKG YKDHPFDYWG QGTLVTVSS    119

SEQ ID NO: 148            moltype = AA  length = 106
FEATURE                   Location/Qualifiers
source                    1..106
                          mol_type = protein
                          note = Anti-PAR-2 antibody (P24E936 and P24E973) Variable
                           Light Chain Sequence
                          organism = synthetic construct
SEQUENCE: 148
EIVLTQSPAT LSLSPGERAT LSCRASQNVY KWLDWYQQKP GQAPRLLIYN AYSRATGIPA    60
RFSGSGSGRD FTLTISSLEP EDFAVYYCQQ HGHGWTFGGG TKVEIK                  106

SEQ ID NO: 149            moltype = AA  length = 106
FEATURE                   Location/Qualifiers
source                    1..106
                          mol_type = protein
                          note = Anti-PAR-2 antibody (P24E279,P24E284,P24E289,and
                           P24E294) Variable Light Chain Sequence
                          organism = synthetic construct
SEQUENCE: 149
EIVLTQSPAT LSLSPGERAT LSCRASQNIY KYLDWYQQKP GQAPRLLIYN TNSLATGIPA    60
RFSGSGSGRD FTLTISSLEP EDFAVYYCLQ HNSGWTFGGG TKVEIK                  106

SEQ ID NO: 150            moltype = AA  length = 106
FEATURE                   Location/Qualifiers
source                    1..106
                          mol_type = protein
                          note = Anti-PAR-2 antibody (P24E280,P24E285,P24E290,and
                           P24E295) Variable Light Chain Sequence
                          organism = synthetic construct
SEQUENCE: 150
EIVLTQSPAT LSLSPGERAT LSCKASQNVY KYLDWYQQKP GQAPRLLIYN TNSLATGIPA    60
RFSGSGSGRD FTLTISSLEP EDFAVYYCLQ HNSGWTFGGG TKVEIK                  106

SEQ ID NO: 151            moltype = AA  length = 106
FEATURE                   Location/Qualifiers
source                    1..106
                          mol_type = protein
                          note = Anti-PAR-2 antibody (P24E281,P24E286,P24E291,and
                           P24E296) Variable Light Chain Sequence
                          organism = synthetic construct
SEQUENCE: 151
EIVLTQSPAT LSLSPGERAT LSCKASQNIY KYLDWYQQKP GQAPRLLIYN ANSLATGIPA    60
RFSGSGSGRD FTLTISSLEP EDFAVYYCLQ HNSGWTFGGG TKVEIK                  106

SEQ ID NO: 152            moltype = AA  length = 106
FEATURE                   Location/Qualifiers
source                    1..106
                          mol_type = protein
                          note = Anti-PAR-2 antibody (P24E282,P24E287,P24E292,and
                           P24E297) Variable Light Chain Sequence
                          organism = synthetic construct
SEQUENCE: 152
EIVLTQSPAT LSLSPGERAT LSCKASQNIY KYLDWYQQKP GQAPRLLIYN TNSRATGIPA    60
RFSGSGSGRD FTLTISSLEP EDFAVYYCLQ HNSGWTFGGG TKVEIK                  106

SEQ ID NO: 153            moltype = AA  length = 106
FEATURE                   Location/Qualifiers
source                    1..106
                          mol_type = protein
                          note = Anti-PAR-2 antibody (P24E298,P24E300,and P24E301)
                           Variable Light Chain Sequence
                          organism = synthetic construct
SEQUENCE: 153
EIVLTQSPAT LSLSPGERAT LSCKASQNIY KWLDWYQQKP GQAPRLLIYN TNSLATGIPA    60
RFSGSGSGRD FTLTISSLEP EDFAVYYCLQ HNSGWTFGGG TKVEIK                  106

SEQ ID NO: 154            moltype = AA  length = 106
FEATURE                   Location/Qualifiers
```

| | |
|---|---|
| source | 1..106<br>mol_type = protein<br>note = Anti-PAR-2 antibody (P24E743,P24E917,P24E921,and P24E931) Variable Light Chain Sequence<br>organism = synthetic construct |

SEQUENCE: 154
EIVLTQSPAT LSLSPGERAT LSCKASQNVY KWLDWYQQKP GQAPRLLIYN AYSLATGIPA 60
RFSGSGSGRD FTLTISSLEP EDFAVYYCQQ HGSGWTFGGG TKVEIK 106

| | |
|---|---|
| SEQ ID NO: 155 | moltype = AA length = 106 |
| FEATURE | Location/Qualifiers |
| source | 1..106<br>mol_type = protein<br>note = Anti-PAR-2 antibody (P24E794,P24E916,P24E920,and P24E924) Variable Light Chain Sequence<br>organism = synthetic construct |

SEQUENCE: 155
EIVLTQSPAT LSLSPGERAT LSCRASQNVY KWLDWYQQKP GQAPRLLIYN AYSRATGIPA 60
RFSGSGSGRD FTLTISSLEP EDFAVYYCQQ HNSGWTFGGG TKVEIK 106

| | |
|---|---|
| SEQ ID NO: 156 | moltype = AA length = 106 |
| FEATURE | Location/Qualifiers |
| source | 1..106<br>mol_type = protein<br>note = Anti-PAR-2 antibody (P24E883,P24E915,P24E919,and P24E923) Variable Light Chain Sequence<br>organism = synthetic construct |

SEQUENCE: 156
EIVLTQSPAT LSLSPGERAT LSCKASQNVY KWLDWYQQKP GQAPRLLIYN AYSLATGIPA 60
RFSGSGSGRD FTLTISSLEP EDFAVYYCQQ HNSGWTFGGG TKVEIK 106

| | |
|---|---|
| SEQ ID NO: 157 | moltype = AA length = 106 |
| FEATURE | Location/Qualifiers |
| source | 1..106<br>mol_type = protein<br>note = Anti-PAR-2 antibody (P24E889,P24E914,P24E918,P24E922,and P24E932) Variable Light Chain Sequence<br>organism = synthetic construct |

SEQUENCE: 157
EIVLTQSPAT LSLSPGERAT LSCRASQNIY KWLDWYQQKP GQAPRLLIYN AYSLATGIPA 60
RFSGSGSGRD FTLTISSLEP EDFAVYYCQQ HNSGWTFGGG TKVEIK 106

| | |
|---|---|
| SEQ ID NO: 158 | moltype = AA length = 106 |
| FEATURE | Location/Qualifiers |
| source | 1..106<br>mol_type = protein<br>note = Anti-PAR-2 antibody (P24E930, P24E933, and P24E933) Variable Light Chain Sequence<br>organism = synthetic construct |

SEQUENCE: 158
EIVLTQSPAT LSLSPGERAT LSCRASQNVY KWLDWYQQKP GQAPRLLIYN AYSRATGIPA 60
RFSGSGSGRD FTLTISSLEP EDFAVYYCQQ HGSGWTFGGG TKVEIK 106

| | |
|---|---|
| SEQ ID NO: 159 | moltype = AA length = 106 |
| FEATURE | Location/Qualifiers |
| source | 1..106<br>mol_type = protein<br>note = Anti-PAR-2 antibody P24E953 Variable Light Chain Sequence)<br>organism = synthetic construct |

SEQUENCE: 159
EIVLTQSPAT LSLSPGERAT LSCRASQNVY KWLDWYQQKP GQAPRLLIYD AYSRATGIPA 60
RFSGSGSGRD FTLTISSLEP EDFAVYYCQQ HGSGWTFGGG TKVEIK 106

| | |
|---|---|
| SEQ ID NO: 160 | moltype = AA length = 106 |
| FEATURE | Location/Qualifiers |
| source | 1..106<br>mol_type = protein<br>note = Anti-PAR-2 antibody (P24E935,P24E972,and P24E975) Variable Light Chain Sequence<br>organism = synthetic construct |

SEQUENCE: 160
EIVLTQSPAT LSLSPGERAT LSCRASQNVY KWLDWYQQKP GQAPRLLIYN AYSRATGIPA 60
RFSGSGSGRD FTLTISSLEP EDFAVYYCQQ HHHGWTFGGG TKVEIK 106

| | |
|---|---|
| SEQ ID NO: 161 | moltype = AA length = 106 |
| FEATURE | Location/Qualifiers |
| source | 1..106 |

```
                        mol_type = protein
                        note = Anti-PAR-2 antibody P24E977 Variable Light Chain
                          Sequence
                        organism = synthetic construct
SEQUENCE: 161
EIVLTQSPAT LSLSPGERAT LSCRASQNVY KWLDWYQQKP GQAPRLLIYD AYSRATGIPA    60
RFSGSGSGRD FTLTISSLEP EDFAVYYCQQ HHSGWTFGGG TKVEIK                  106

SEQ ID NO: 162          moltype = AA   length = 106
FEATURE                 Location/Qualifiers
source                  1..106
                        mol_type = protein
                        note = Anti-PAR-2 antibody P24E978 Variable Light Chain
                          Sequence
                        organism = synthetic construct
SEQUENCE: 162
EIVLTQSPAT LSLSPGERAT LSCRASQNVY KWLDWYQQKP GQAPRLLIYD AYSRATGIPA    60
RFSGSGSGRD FTLTISSLEP EDFAVYYCQQ HHHGWTFGGG TKVEIK                  106
```

ANTI-PAR-2 ANTIBODIES AND METHODS OF USE THEREOF

CROSS REFERENCE TO RELATED APPLICATIONS

This application is a divisional of U.S. application Ser. No. 17/405,275; filed Aug. 18, 2021, which claims the benefit of the filing date of U.S. Provisional Patent Application No. 63/067,259, filed Aug. 18, 2020, the contents of which are incorporated herein by reference in their entirety.

REFERENCE TO SEQUENCE LISTING SUBMITTED ELECTRONICALLY

The content of the electronically submitted sequence listing in .xml file (Name: 2873_3020002_SeqListing_V2_ST26; Size: 199,019 bytes; and Date of Creation: Oct. 10, 2023) filed with the application is incorporated herein by reference in its entirety.

FIELD OF THE DISCLOSURE

The present disclosure relates to antibodies and antigen-binding fragments thereof that specifically bind to human PAR-2, compositions comprising such antibodies and antigen-binding fragments thereof, and methods of making and using antibodies and antigen-binding fragments thereof that specifically bind to human PAR-2, including in the treatment of an airway disease (e.g., asthma, chronic obstructive pulmonary disease, idiopathic pulmonary fibrosis, and pulmonary arterial hypertension), cancer, a skin disease, orofacial granulomatosis, an inflammatory condition, or in relieving pain associated with various diseases or conditions.

DESCRIPTION OF THE DISCLOSURE

G-protein coupled receptors (GPCRs) are a family of 7-pass transmembrane proteins that respond to extracellular stimuli via G protein activation and subsequent second messengers. Protease-activated receptor 2 (Proteinase-Activated Receptor-2; PAR-2; GPR11; F2RL1) is a class A GPCR which is activated by protease cleavage. In humans, an N-terminal "tethered ligand" (e.g., in humans the amino acid sequence SLIGKV) is revealed by upstream proteolytic cleavage, allowing the tethered ligand to bind to extracellular loops of the receptor and induce signaling. Hollenberg M. D. and Compton S. J., Drug Dev. Res., 59(4):344-349 (2003). The N-terminal sequence of PAR-2 can be cleaved at several different sites by a variety of serine proteases including trypsin (Hollenberg M. D. and Compton S. J., Drug Dev. Res., 59(4):344-349 (2003)), tryptase (Akers, I. et al., Am J Physiol Lung Cell Mol Physiol., 278:L193-L201 (2000)), tissue factor (Larsen, K. S. et al., J Biol Chem, 285:19959-19966 (2010)), neutrophil elastase (Ramachandran, R. et al., J Biol Chem., 286:24638-24648 (2011)) and matriptase-1 (Milner, J. M. et al., Arthritis Rheum, 62:1955-1966 (2010)), and by cysteine proteases such as cathepsin S (Elmariah, S. B. et al., PLoS One, 9(6):e99702 (2014)), papain (Liang, G. et al., J Allergy Clin Immunol, 129:1377-1386 (2012)), and Der p 1 (Asosingh, K. et al., J Clin Invest, 128(7):3116-3128 (2018)). It has also been reported that PAR-2 can be transactivated by PAR-1 tethered ligand. O'Brien, P. J. et al., J Biol Chem, 275:13502-13509 (2000).

PAR-2 is expressed at very low levels on the cell surface under normal conditions. It is expressed on endothelial cells, smooth muscle cells, epithelial cells, keratinocytes, and fibroblasts (D'Andrea M R. et al., J Histochem Cytochem., 46(2):157-64(1998)), as well as immune system cells of the monocyte lineage, most notably macrophages and neutrophils (Howells, G. L. et al., Journal of Cell Science, 110: 881-887 (1997)). PAR-2 is up-regulated under inflammatory conditions, and overexpression has been associated with several diseases including for example asthma (Knight, D. A. et al., J Allergy Clin Immunol, 108:797-803 (2001)), chronic obstructive pulmonary disease (COPD) (Lee, K. H. et al., Experimental & Molecular Medicine, 50(7):1-9 (2018)), pulmonary fibrosis (Wygrecka, M. et al., Am J Respir Crit Care Med, 183:1703-1714 (2011)), rheumatoid arthritis (Tindell, A. G. et al., Rheumatol Int, 32:3077-3086 (2012)), osteoarthritis (Huesa, C. et al., Ann Rheum Dis, 75:1989-1997 (2016)), pancreatitis (Namkung, W. et al., Gastroenterology 126:1844-1859 (2004)), chronic pain (Mrozkova, P., et al., Physiol Res, 65:357-367 (2016)), atopic dermatitis (Lee, S. E., et al., Yonsei Med J, 51:808-822 (2010) and chronic itch (Akiyama, T., et al., Handb Exp Pharmacol, 226:219-235 (2015)). Mice deficient in PAR-2 have been shown to be resistant to induction of experimental asthma (de Boer, J. D. et al., Innate Immun., 20(6):618-625 (2013)), dermatitis (Kawagoe, J. et al., Jpn J Pharmacol, 88:77-84 (2002)), fibrosis (Borensztajn, K. et al., Am J Pathol 177, 2753-2764 (2010)), glomerulonephritis (Moussa, L. et al., Am J Pathol 171:800-808 (2007)), and arthritis (Busso, N. et al., Arthritis Rheum, 56:101-107 (2007)).

An antibody that specifically binds to human PAR-2 protein can be used for the diagnosis, prevention and/or treatment of diseases in which PAR-2 is overexpressed. Accordingly, there is a need to develop potent antibodies which are able to broadly antagonize activation of human PAR-2 and that are suitable for human administration.

BRIEF SUMMARY OF THE DISCLOSURE

Provided herein are isolated antibodies and antigen-binding fragments thereof that specifically bind to human PAR-2 and methods of use thereof.

In one aspect there is provided an isolated antibody or antigen-binding fragment thereof that specifically binds to human PAR-2 and which antagonizes activation of PAR-2 by a PAR-2 activating ligand. Such a PAR-2 activating ligand can include, without limitation, a PAR-2 tethered ligand (in cis or trans); a PAR-1 tethered ligand; or a soluble ligand.

In some aspects there is provided an isolated antibody or antigen-binding fragment thereof that specifically binds to human PAR-2 but does not bind to amino acids 59-63 of the N-terminus of human PAR-2 and (a) blocks the interaction between a PAR-2 activating ligand and an extracellular domain of PAR-2, and/or (b) blocks PAR-2 activation by a PAR-2 activating ligand. In some embodiments, the antibody or antigen-binding fragment thereof does not bind to the N-terminus of human PAR-2. In certain embodiments the antibody or antigen-binding fragment thereof is suitable for administration to a human subject. In certain embodiments the antibody is a humanized antibody.

In some embodiments of any of these aspects, the antibody or antigen-binding fragment thereof inhibits activation of human PAR-2 by a soluble PAR-2 activating ligand with an $IC_{50}$ from about 0.1 nM to about 17 nM, as measured by the PAR-2 β-arrestin cell assay.

In some embodiments, the antibody or antigen-binding fragment thereof inhibits interaction between the soluble PAR-2 activating ligand and PAR-2 with an $IC_{50}$ from about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, about 2 nM, 2.1 nM, about 2.2 nM, about 2.3 nM, about 2.4 nM, about 2.5 nM, about 2.6 nM, about 2.7 nM, about 2.8 nM, about 2.9 nM, about 3 nM, 3.1 nM, about 3.2 nM, about 3.3 nM, about 3.4 nM, about 3.5 nM, about 3.6 nM, about 3.7 nM, about 3.8 nM, about 3.9 nM, about 4 nM, 4.1 nM, about 4.2 nM, about 4.3 nM, about 4.4 nM, about 4.5 nM, about 4.6 nM, about 4.7 nM, about 4.8 nM, about 4.9 nM, about 5 nM, 5.1 nM, about 5.2 nM, about 5.3 nM, about 5.4 nM, about 5.5 nM, about 5.6 nM, about 5.7 nM, about 5.8 nM, about 5.9 nM, about 6 nM, 6.1 nM, about 6.2 nM, about 6.3 nM, about 6.4 nM, about 6.5 nM, about 6.6 nM, about 6.7 nM, about 6.8 nM, about 6.9 nM, about 7 nM, 7.1 nM, about 7.2 nM, about 7.3 nM, about 7.4 nM, about 7.5 nM, about 7.6 nM, about 7.7 nM, about 7.8 nM, about 7.9 nM, about 8 nM, 8.1 nM, about 8.2 nM, about 8.3 nM, about 8.4 nM, about 8.5 nM, about 8.6 nM, about 8.7 nM, about 8.8 nM, about 8.9 nM, about 9 nM, 9.1 nM, about 9.2 nM, about 9.3 nM, about 9.4 nM, about 9.5 nM, about 9.6 nM, about 9.7 nM, about 9.8 nM, about 9.9 nM, about 10 nM, 10.1 nM, about 10.2 nM, about 10.3 nM, about 10.4 nM, about 10.5 nM, about 10.6 nM, about 10.7 nM, about 10.8 nM, about 10.9 nM, about 11 nM, about 11.1 nM, about 11.2 nM, about 11.3 nM, about 11.4 nM, about 11.5 nM, about 11.6 nM, about 11.7 nM, about 11.8 nM, or about 11.9 nM.

In some embodiments, the antibody or antigen-binding fragment thereof inhibits PAR-2 activating ligand-induced and trypsin-induced calcium flux in a cell with an $IC_{50}$ from about 6 nM to about 11 nM as measured by a PAR-2 calcium flux cell assay. In some embodiments, the cell is a human lung fibroblast or epithelial cell.

In some embodiments, the antibody or antigen-binding fragment thereof inhibits PAR-2 activating ligand-induced and trypsin-induced calcium flux with an $IC_{50}$ of about 6 nM, 6.1 nM, about 6.2 nM, about 6.3 nM, about 6.4 nM, about 6.5 nM, about 6.6 nM, about 6.7 nM, about 6.8 nM, about 6.9 nM, about 7 nM, 7.1 nM, about 7.2 nM, about 7.3 nM, about 7.4 nM, about 7.5 nM, about 7.6 nM, about 7.7 nM, about 7.8 nM, about 7.9 nM, about 8 nM, 8.1 nM, about 8.2 nM, about 8.3 nM, about 8.4 nM, about 8.5 nM, about 8.6 nM, about 8.7 nM, about 8.8 nM, about 8.9 nM, about 9 nM, 9.1 nM, about 9.2 nM, about 9.3 nM, about 9.4 nM, about 9.5 nM, about 9.6 nM, about 9.7 nM, about 9.8 nM, about 9.9 nM, about 10 nM, 10.1 nM, about 10.2 nM, about 10.3 nM, about 10.4 nM, about 10.5 nM, about 10.6 nM, about 10.7 nM, about 10.8 nM, or about 10.9 nM.

In some embodiments, the antibody or antigen-binding fragment thereof inhibits PAR-2 activating ligand-induced contraction of a smooth muscle cell by at least 70%, at least 75%, at least 80%, at least 85%, at least 90%, at least 95% or at least 98% compared to a control antibody of the same isotype. In some embodiments, the smooth muscle cell is a bronchial smooth muscle cell.

In some embodiments, the antibody or antigen-binding fragment thereof inhibits the induction of a lung neutrophilia in a cynomolgus monkey by at least 70%, at least 75%, at least 80%, at least 85%, at least 90%, at least 95% or at least 98% compared to a control antibody of the same isotype.

In some aspects there is provided an isolated antibody or antigen-binding fragment thereof that specifically binds to human PAR-2, wherein the antibody or antigen-binding fragment thereof comprises the heavy chain complementarity determining region 1 (VH CDR1), VH CDR2, VH CDR3 sequences of SEQ ID NO: 1 (GFSLX$_1$X$_2$YX$_3$X$_4$X$_5$), 2 (VIWGNX$_6$N X$_7$YY X$_8$), and 3 (WX$_9$GX$_{10}$KDX$_{11}$PFDY), respectively and light chain variable region (VL) CDR1, CDR2, and CDR3 sequences, SEQ ID NO: 4 (X$_{12}$ASQNX$_{13}$YK X$_{14}$LD), 5 (X$_{15}$X$_{16}$ X$_{17}$ X$_{18}$ X$_{19}$ X$_{20}$T), and 6 (X$_{21}$QH X$_{22}$ X$_{23}$GWT), respectively, wherein:

X$_1$=Asparagine(N) or Serine(S), X$_2$=Serine(S) or Tyrosine(Y), X$_3$=Glycine(G) or Alanine(A), X$_4$=Valine(V), Glycine(G), or Isoleucine(I), X$_5$=Isoleucine(I) or Serine(S), X$_6$=Glycine(G) or Glutamine(Q), X$_7$=Threonine (T) or Valine(V), X$_8$=Asparagine(N), Alanine(A), Glycine(G), or Tyrosine(Y), X$_9$=Arginine (R) or Lysine(K), X$_{10}$=Tyrosine(Y), Tryptophan(W), or Phenylalanine(F), X$_{11}$=Tyrosine(Y) or Histidine(H), X$_{12}$=Lysine(K) or Arginine(R), X$_{13}$=Isoleucine(I) or Valine(V), X$_{14}$=Tyrosine(Y), Tryptophan(W), or Phenylalanine(F), X$_{15}$=Asparagine(N) or Aspartic acid(D), X$_{16}$=Threonine(T) or Alanine(A), X$_{17}$=Asparagine(N), Serine(S), or Tyrosine(Y), X$_{18}$=Serine(S), Threonine (T), or Asparagine(N), X$_{19}$=Leucine(L) or Arginine(R), X$_{20}$=Histidine(H) or Alanine(A), X$_{21}$=Leucine(L) or Glutamine(Q), X$_{22}$=Asparagine(N), Glycine(G), or Histidine(H), and X$_{23}$=Serine(S) or Histidine(H).

In some embodiments, the antibody or antigen-binding fragment thereof comprises VH CDR1, VH CDR2, VH CDR3 and VL CDR1, CDR2, and CDR3 sequences of SEQ ID NOs: 10, 11, 12, 16, 17, and 18, respectively.

In some embodiments, the antibody or antigen-binding fragment thereof comprises a VH comprising the amino acid sequence of SEQ ID NO: 20 or 21 and a VL comprising the amino acid sequence of SEQ ID NO: 23, 24, 25, 26, or 27.

In some embodiments, the antibody or antigen-binding fragment thereof comprises a heavy chain variable region and a light chain variable region comprising the amino acid sequences of: SEQ ID NOs: 20 and 23, respectively; SEQ ID NOs: 21 and 24, respectively; SEQ ID NOs: 21 and 25, respectively; SEQ ID NOs: 21 and 26, respectively; or SEQ ID NOs: 21 and 27, respectively.

In some aspects, an isolated antibody or antigen-binding fragment thereof comprises a heavy chain variable region and a light chain variable region, wherein the heavy chain variable region comprises the amino acid sequence of SEQ ID NO: 20 or 21.

In some aspects, an isolated antibody or antigen-binding fragment thereof comprises a heavy chain variable region and a light chain variable region, wherein the light chain variable region comprises the amino acid sequence of SEQ ID NO: 23, 24, 25, 26, or 27.

In certain embodiments, the antibody or antigen-binding fragment thereof described herein has binding affinity ($K_D$) to human PAR-2 from about 400 pM to about 1000 pM. In some embodiments, the antibody or antigen-binding fragment thereof binds specifically to human and cynomolgus monkey PAR-2. In some embodiments, the antibody or antigen-binding fragment thereof has binding affinity ($K_D$) to cynomolgus monkey PAR-2 from about 4 nM to about 5 nM. In some embodiments, the antibody or antigen-binding fragment thereof specifically binds to human PAR-2.

In some embodiments, the antibody or antigen-binding fragment thereof comprises a heavy chain constant region and a light chain constant region. In some aspects, the heavy chain constant region is an isotype selected from the group consisting of human IgG1, IgG2, IgG3, and IgG4 isotypes. In some embodiments, the heavy chain constant region is a human IgG4 heavy chain constant region. In some embodiments, the heavy chain constant region is a human IgG4 heavy chain constant region, which has one or more amino acid substitutions. In some embodiments, the light chain constant region is a human IgGκ light chain constant region.

In some embodiments, the antibody or antigen-binding fragment thereof comprises a heavy chain constant region and a light chain constant region, wherein the heavy chain constant region is a human IgG4 heavy chain constant region, and wherein the light chain constant region is a human IgGκ light chain constant region.

In some embodiments, the antibody or antigen-binding fragment thereof comprises a heavy chain constant region and a light chain constant region, wherein the heavy chain constant region is a human IgG4 heavy chain constant region comprising one or more amino acid substitutions, and wherein the light chain constant region is a human IgGκ light chain constant region. In some embodiments, the human IgG4 heavy chain constant region has one, two, three, four, five, six, seven, eight, nine, or ten amino acid substitutions.

In some embodiments, the human IgG4 heavy chain constant region comprises the S228P substitution (by EU numbering). In some embodiments, the human IgG4 heavy chain constant region comprises terminal lysine deletion (K447Δ) (by EU numbering). In some embodiments, the human IgG4 heavy chain constant region comprises the S228P substitution and K447Δ (by EU numbering).

In some embodiments, the antibody or antigen-binding fragment thereof is a chimeric antibody, a humanized antibody or antigen-binding fragment thereof.

In some embodiments, the antibody or antigen binding fragment thereof is a full length antibody.

In some embodiments, the antibody or antigen binding fragment thereof is an antigen binding fragment. In some embodiments, the antigen binding fragment is a Fab, Fab', F(ab')2, single chain Fv (scFv), disulfide linked Fv, IgNar, intrabody, IgGΔCH2, minibody, F(ab')3, tetrabody, triabody, diabody, single-domain antibody, DVD-Ig, Fcab, mAb2, (scFv)2, or scFv-Fc.

In some embodiments, the antibody or antigen-binding fragment comprises an Fc domain that is engineered to reduce effector function.

In some embodiments, the antibody or antigen-binding fragment thereof comprises a detectable label.

In other aspects there is provided an isolated polynucleotide comprising a nucleic acid sequence which encodes the heavy chain variable region or the heavy chain of the antibody or antigen-binding fragment thereof disclosed herein. In some embodiments, the nucleic acid molecule encodes the VH of SEQ ID NO: 20 or 21.

In some aspects there is provided an isolated polynucleotide which comprises a nucleic acid molecule encoding the light chain variable region or light chain of the antibody or antigen-binding fragment thereof disclosed herein. In some embodiments, the nucleic acid molecule encodes the VL of SEQ ID NO: 23, 24, 25, 26, or 27.

In some aspects there is provided an isolated polynucleotide comprising a first nucleic acid molecule encoding the light chain variable region of SEQ ID NO: 23, 24, 25, 26, or 27, and a second nucleic acid molecule encoding the heavy chain variable region of SEQ ID NO: 20 or 21. In some aspects there is provided a mixture of isolated polynucleotides comprising a first polynucleotide which comprises a nucleic acid molecule encoding the light chain variable region of SEQ ID NO: 23, 24, 25, 26, or 27, and a second polynucleotide which comprises a nucleic acid molecule encoding the heavy chain variable region of SEQ ID NO: 20 or 21.

In some aspects there is provided an isolated polynucleotide comprises a nucleic acid molecule encoding the heavy chain variable region or heavy chain of the antibody or antigen-binding fragment thereof disclosed herein and the light chain variable region or light chain of the antibody or antigen-binding fragment thereof disclosed herein.

In some aspects there is provided an isolated vector which comprises the polynucleotide disclosed herein.

In some aspects there is provided a host cell which comprises (a) a polynucleotide disclosed herein, (b) a vector disclosed herein, or (c) a first vector comprising the first polynucleotide disclosed herein and a second vector comprising the second polynucleotide disclosed herein. In some embodiments, the host cell is selected from the group consisting of E. coli, Pseudomonas, Bacillus, Streptomyces, yeast, Expi293F human cell, C6 (rat glioma cell line), U2OS, Chem-1, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture. In some embodiments, the host cell is a CHO-K1SV cell.

In some aspects there is provided a method of producing an antibody or antigen-binding fragment thereof that binds to human PAR-2, the method comprising culturing the host cell disclosed herein so that the nucleic acid molecule disclosed herein is expressed and the antibody or antigen-binding fragment thereof is produced, optionally wherein the method further comprises isolating the antibody or antigen-binding fragment thereof from the culture.

In some aspects there is provided an isolated antibody or antigen-binding fragment thereof that specifically binds to human PAR-2 and that is encoded by the polynucleotides disclosed herein or produced by the methods disclosed herein.

In some aspects there is provided a pharmaceutical composition which comprises the antibody or antigen-binding fragment thereof disclosed herein and a pharmaceutically acceptable excipient.

In some aspects there is provided a method for inhibiting activation of PAR-2 in vitro or in vivo by a PAR-2 activating ligand, the method comprising blocking the ligand binding to PAR-2 with the antibody or antigen-binding fragment thereof disclosed herein or the pharmaceutical composition disclosed herein.

In certain embodiments the PAR-2 activating ligand is a soluble PAR-2 activating ligand, a PAR-2 tethered ligand, or a PAR-1 tethered ligand.

In some aspects there is provided the antibody or antigen binding fragment thereof disclosed herein for use in treating an airway disease. In other aspects there is provided the antibody or antigen binding fragment thereof disclosed herein for use in relieving pain. In other aspects there is provided the antibody or antigen binding fragment thereof disclosed herein for use in treating cancer. In other aspects there is provided the antibody or antigen binding fragment thereof disclosed herein for use in treating a skin disease. In other aspects there is provided the antibody or antigen binding fragment thereof disclosed herein for treating an inflammatory condition.

In some aspects there is provided a method of treating an airway disease in a patient, the method comprising administering to the patient a therapeutically effective amount of the antibody or antigen binding fragment thereof disclosed herein or the pharmaceutical composition disclosed herein. In some embodiments, the airway disease is selected from the group consisting of asthma, chronic obstructive pulmonary disease, idiopathic pulmonary fibrosis, and pulmonary arterial hypertension.

In some aspects there is provided a method of relieving pain in a patient, the method comprising administering to the patient a therapeutically effective amount of the antibody or antigen binding fragment thereof disclosed herein or the pharmaceutical composition disclosed herein. In some embodiments, the pain is selected from the group consisting of cancer pain, joint pain, chemotherapy-induced peripheral neuropathy pain, dental pain, bladder pain, pancreatitis pain, irritable bowl syndrome related pain, visceral pain, osteoarthritis related pain, rheumatoid arthritis related pain, spinal cord injury pain, and migraine pain.

In some aspects there is provided a method of treating cancer in a patient, the method comprising administering to the patient a therapeutically effective amount of the antibody or antigen binding fragment thereof disclosed herein or the pharmaceutical composition disclosed herein. In some embodiments, cancer is chosen from bone cancer, pancreatic cancer, gastric cancer, colon cancer, breast cancer, glioblastoma, melanoma, prostate cancer, breast cancer, colon, or any combination thereof.

In some aspects there is provided a method of treating a skin disease in a patient, the method comprising administering to the patient a therapeutically effective amount of the antibody or antigen binding fragment thereof disclosed herein or the pharmaceutical composition disclosed herein. In some embodiments, the skin disease is selected from the group consisting of atopic dermatitis, allergic contact dermatitis, Netherton syndrome, ichthyosis, skin barrier/permeability recovery after damage, pruritus, skin cancer, skin itch, pigmentation associated with melasma, and pigmentation associated with vitiligo.

In some aspects there is provided a method of treating orofacial granulomatosis in a patient, the method comprising administering to the patient a therapeutically effective amount of the antibody or antigen binding fragment thereof disclosed herein or the pharmaceutical composition disclosed herein.

In some aspects there is provided a method of treating an inflammatory condition in a patient, the method comprising administering to the patient a therapeutically effective amount of the antibody or antigen binding fragment thereof disclosed herein or the pharmaceutical composition disclosed herein. In certain embodiments, the inflammatory condition is rheumatoid arthritis, osteoarthritis, inflammation-induced visceral hypersensitivity, periodontal disease, or a pathology associated with acute corona virus infection.

In some aspects there is provided a method for detecting PAR-2 in a sample, the method comprising contacting the sample with the antibody or antigen-binding fragment thereof disclosed herein or the pharmaceutical composition disclosed herein. In some embodiments, the sample is obtained from a human subject, optionally wherein the sample is a cancer sample. In some embodiments the sample is an in vitro sample.

BRIEF DESCRIPTION OF THE FIGURES

FIG. 1A shows an alignment of variable heavy chain sequences of humanized variants of Ab309, with the CDRs outlined by boxes.

FIG. 1B shows an alignment of variable light chain sequences of humanized variants of Ab309, with the CDRs as defined herein outlined by boxes.

FIG. 5A shows PASI score of visible skin lesions. P24E1102 or MOPC showed significant reduction in PASI score. FIG. 5B shows bouts of scratching. Only P24E1102 significantly reduced scratching, and did to levels below background.

FIGS. 6A-6C show the response of DRG neurons from wild type rats to capsaicin after treatment with the PAR2 agonist LIGRLO or a control. LIGRLO increased (~2-fold) the % of neurons increasing their response to the second capsaicin treatment, regardless to threshold sensitization set (120%-300%) (FIG. 6A). The distribution of signal in response to the second treatment with capsaicin (FIG. 6B) was increased by LIGRLO (FIG. 6C).

FIGS. 7A-7C show the response of DRG neurons from hPAR2 knock-in rats to capsaicin after treatment with the PAR2 agonist LIGRLO. Prior to LIGRLO treatment, DRG were treated with vehicle ("control"), 500 nM P24E1102. P24E1102 significantly ($p<0.05$) decreased the number of neurons sensitized by capsaicin (FIG. 7A). The distribution of second signal in response to the treatment with LIGRLO (FIG. 7B) was decreased by P24E1102 (FIG. 7C).

FIGS. 9A-9H show that SLIGKV induces changes in cell morphology and behavior consistent with metastasis, and that this is reversed by P24E1102. FIGS. 9A-9D are images of cells untreated (FIG. 9A), treated with SLIGKV (FIG. 9B), SLIGKV with 500 nM P24E1102 (FIG. 9C), or SLIGKV with 2000 nM P24E1102 (FIG. 9D). The dose-dependent inhibition by P24E1102 in the presence of SLIGKV is quantified for the % of cells with processes (FIG. 9E), mean number of outgrowths per cell (FIG. 9F), cell migration as shown by number of scattered cells, (FIG. 9G), and total area of cell clusters (FIG. 9H).

DETAILED DESCRIPTION

Figure 2:
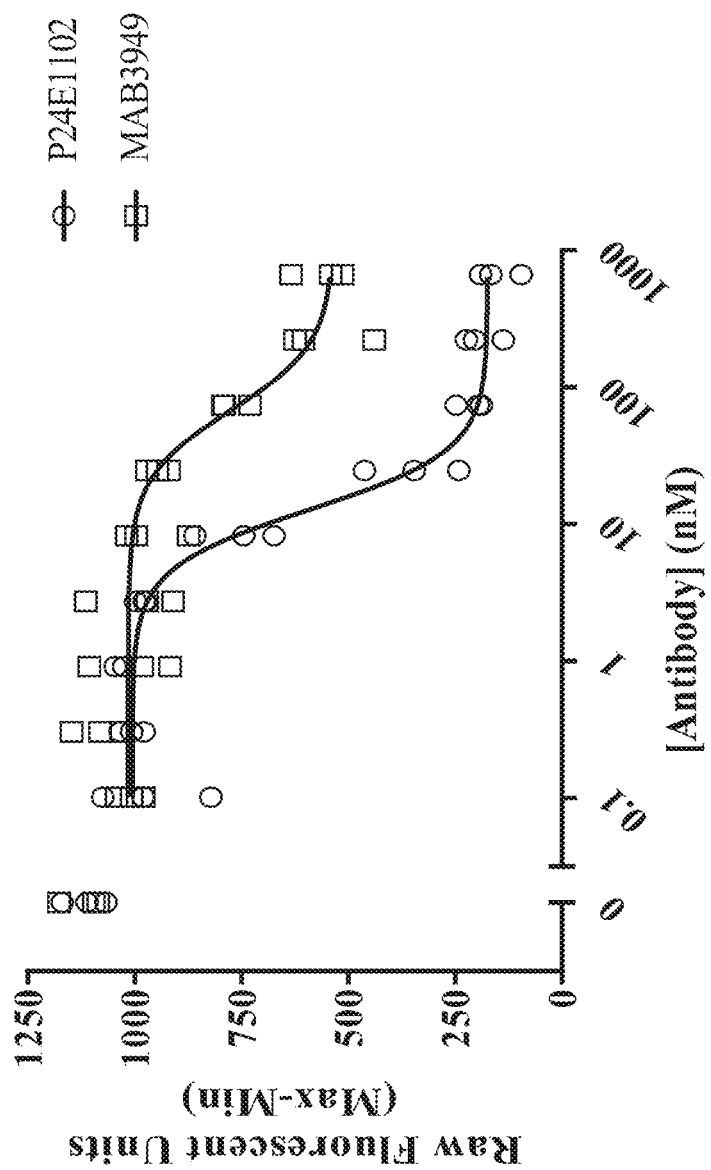
FIG. 2 shows the relative potency of P24E1102 to antagonize SLIGKV-induced PAR-2 calcium flux compared to the murine anti-human PAR-2 antibody MAb3949. (See Example 8.)

Provided herein are antibodies (e.g., humanized antibodies) and antigen-binding fragments thereof that specifically bind to human PAR-2 and exhibit one or more of the properties disclosed herein. Such antibodies or antigen-binding fragments thereof may relieve, prevent, and/or treat diseases or conditions in which PAR-2 can be increased and/or diseases or conditions that can be alleviated by antagonizing activation of PAR-2 by a PAR-2 activating ligand (e.g., airway disease, skin disease, pain relief, orofacial granulomatosis, inflammatory condition, and cancer). Such anti-human PAR-2 antibodies and antigen-binding fragments thereof can, for example, block the interaction between a PAR-2 activating ligand and an extracellular domain of PAR-2, and block PAR-2 activation by a PAR-2 activating ligand. Exemplary anti-human PAR-2 antibodies are provided herein that demonstrate these activities.

Also provided are isolated nucleic acids (polynucleotides), such as complementary DNA (cDNA), encoding such antibodies and antigen-binding fragments thereof. Further provided are vectors (e.g., expression vectors) and cells (e.g., host cells) comprising nucleic acids (polynucleotides) encoding such antibodies and antigen-binding fragments thereof. Also provided are methods of making such antibodies and antigen-binding fragments thereof.

In other aspects, provided herein are methods for using such antibodies, for example, to modulate PAR-2 activity. PAR-2 activity can be modulated, for example, by antagonizing activation of PAR-2 by a PAR-2 activating ligand. In some aspects, anti-human PAR-2 antibodies provided herein are used to block the binding of PAR-2 activating ligand to human PAR-2.

In further aspects, anti-human PAR-2 antibodies provided herein are used to block the interaction between a PAR-2 activating ligand and an extracellular domain of PAR-2. Such a PAR-2 activating ligand can include, without limitation, a PAR-2 tethered ligand (in cis or trans); a PAR-1 tethered ligand; or a soluble ligand. In further aspects, anti-human PAR-2 antibodies provided herein are used to prevent and/or treat diseases or conditions associated with increased expression of PAR-2 and/or increased activation of PAR2, and/or diseases or conditions that can be alleviated by antagonizing activation of PAR-2 by a PAR-2 activating ligand (e.g., airway diseases, skin diseases, cancer, orofacial granulomatosis, inflammatory conditions, and pain associated with various diseases or conditions).

In some aspects, such diseases or conditions include, but are not limited to asthma, chronic obstructive pulmonary disease, idiopathic pulmonary fibrosis, pulmonary arterial hypertension, atopic dermatitis, allergic contact dermatitis, Netherton syndrome, ichthyosis, skin barrier/permeability recovery after damage, pruritus, skin cancer, skin itch, pigmentation associated with melasma, pigmentation associated with vitiligo, cancer pain, joint pain, chemotherapy-induced peripheral neuropathy pain, dental pain, bladder pain, pancreatitis pain, irritable bowl syndrome related pain, visceral pain, osteoarthritis related pain, migraine, rheumatoid arthritis related pain, spinal cord injury pain, bone cancer, pancreatic cancer, gastric cancer, colon cancer, breast cancer, glioblastoma, melanoma, prostate cancer, and breast cancer. Related compositions (e.g., pharmaceutical compositions), kits, and methods are also provided.

To facilitate an understanding of the disclosure, a number of terms and phrases are defined. Additional definitions are set forth throughout the detailed description.

I. Terminology

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

As used herein, the terms "comprises", "comprising", "includes", "including", "having," and their conjugates mean "including but not limited to."

As used herein, the term "consisting of" means "including and limited to."

As used herein, the term "consisting essentially of" means the specified material of a composition, or the specified steps of a method, and those additional materials or steps that do not materially affect the basic characteristics of the material or method.

As used herein, the terms "about" and "approximately," when used to modify a numeric value or numeric range, indicate that deviations of up to 10% above and down to 10% below the value or range remain within the intended meaning of the recited value or range. It is understood that wherever aspects are described herein with the language "about" or "approximately" a numeric value or range, otherwise analogous aspects referring to the specific numeric value or range are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "protease-activated receptor 2," "PAR-2," "G-protein coupled receptor 11," "GPR11," "coagulation factor II receptor-like 1," "thrombin receptor-like 1," or "F2RL1" refers to the same G-protein coupled receptor (GPCR) superfamily member.

As used herein, the term "PAR-2" refers to mammalian PAR-2 polypeptides including, but not limited to, native PAR-2 polypeptides and isoforms of PAR-2 polypeptides. "PAR-2" encompasses full-length, unprocessed PAR-2 polypeptides as well as forms of PAR-2 polypeptides that result from processing within the cell. PAR-2, or any variants and isoforms thereof, can either be isolated from cells or tissues which naturally express them or be recombinantly produced using well-known techniques in the art and/or those described herein.

As used herein, the term "human PAR-2" refers to a polypeptide comprising the amino acid sequence of SEQ ID NO: 28; naturally occurring variants of SEQ ID NO: 28, including but not limited to variants thereof in which S or F is at position 21, N or S at position 30, R or Q at position 270, or T or A at position 291 of SEQ ID NO: 28; and processed forms of SEQ ID NO: 28, including but not limited to SEQ ID NO: 28 lacking its signal peptide. The amino acid sequence of human PAR-2 without the signal peptide is represented by the amino acid sequence of SEQ ID NO: 109. A "PAR-2 polynucleotide," or "PAR-2 nucleic acid molecule" refers to a polynucleotide encoding any PAR-2, including those described herein.

The term "antibody" means an immunoglobulin molecule that recognizes and specifically binds to a target, such as a protein, polypeptide, peptide, carbohydrate, polynucleotide, lipid, or combinations of the foregoing (e.g., a glycoprotein), through at least one antigen recognition site within the variable region of the immunoglobulin molecule. As used herein, the term "antibody" encompasses monoclonal antibodies, chimeric antibodies, humanized antibodies, human antibodies, and any other immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked, part of a fusion protein, or conjugated to other molecules such as toxins, radioisotopes, detectable labels etc.

The term "antibody fragment" refers to a portion of an antibody. An "antigen-binding fragment," "antigen-binding domain," or "antigen-binding region," as used herein, refers to one or more fragments of an antibody that retain the ability to specifically bind to an antigen (e.g., human PAR-2). It has been shown that the antigen-binding function of an antibody can be performed by fragments of a full-length antibody. Examples of binding fragments encompassed within the term "antigen-binding fragment" of an antibody, e.g., an anti-PAR-2 antibody described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv); (v) a dAb fragment (Ward et al., (1989) Nature 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see, e.g., Bird et al., (1988) Science 242:423-426; and Huston et al., (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antigen-binding fragments can be produced by recombinant DNA techniques, or by enzymatic or chemical cleavage of intact immunoglobulins.

The terms "PAR-2 inhibitor" and "PAR-2 antagonist" are used interchangeably. Each is a molecule that detectably inhibits at least one function of PAR-2. Conversely, a "PAR-2 agonist" is a molecule that detectably increases at least one function of PAR-2. The inhibition caused by a PAR-2 inhibitor need not be complete so long as it is detectable using an assay. Any assay of a function of PAR-2 can be used, examples of which are provided herein. Examples of functions of PAR-2 that can be inhibited by a PAR-2 inhibitor, or increased by a PAR-2 agonist, include protease-activated ligand binding, downstream signaling, and so on. Examples of types of PAR-2 inhibitors and PAR-2 agonists include, but are not limited to, small molecules which modulate PAR-2 activity and PAR-2 binding polypeptides such as antigen binding proteins (e.g., PAR-2 inhibiting antigen binding proteins), antibodies, antibody fragments, and antibody derivatives. See e.g., WO 2006/127379, WO 2006/127396, U.S. Pat. No. 8,927,503, WO 2012/1010453, WO 2014/020350, WO 2016/154075, WO 2010/017086, WO 2011/031695, WO 2018/167322, U.S. Pat. Nos. 8,236,305, 7,888,482, and 8,357,367.

The term "PAR-2 activating ligand," as used herein refers to a ligand that binds the protease-activated receptor 2 (PAR-2) and initiates PAR-2 activation and signaling. Such a PAR-2 activating ligand can include, without limitation, a PAR-2 tethered ligand (in cis or trans); a PAR-1 tethered ligand; or a soluble ligand. In this context, when a PAR2 molecule is activated by its own N-terminal region, the ligand is cis. When PAR2 is activated by a ligand on another PAR2 molecule, the ligand is trans. Trans activation can also occur from e.g. PAR1 ligand acting on PAR2.

The term "activation of PAR-2," as used herein refers to the PAR-2 activation in the presence of a PAR-2 ligand (e.g., a PAR-2 tethered ligand (in cis or trans); a PAR-1 tethered ligand; or a soluble ligand (e.g., a synthetic soluble PAR-2 activating ligand such as SLIGKV)).

The term "inhibiting activation of PAR-2," as used herein refers to inhibition of the PAR-2 activation by an anti-PAR-2 antibody. An $IC_{50}$ can be used as a measure of the potency of inhibition of PAR-2 activation by the anti-PAR-2 antibody (i.e., concentration of the anti-PAR-2 antibody achieving 50% inhibition of the ligand-induced PAR-2 activity, in nM).

The terms "anti-PAR-2 antibody," "PAR-2 antibody" and "antibody that binds to PAR-2" refer to an antibody that is capable of binding PAR-2 with sufficient affinity such that the antibody is useful as a diagnostic, a therapeutic, and/or as a modulator of PAR-2 activity. The extent of binding of an anti-PAR-2 antibody to PAR-2 protein can be greater than the binding of an isotype control antibody or non-PAR-2 targeting antibody to PAR-2 as measured, e.g., by flow cytometry. The extent of binding of an anti-PAR-2 antibody to an unrelated, non-PAR-2 protein can be equivalent to the binding of an isotype control antibody or non-PAR-2 targeting antibody to PAR-2 as measured, e.g., by flow cytometry. In certain embodiments, an anti-PAR-2 antibody binds exclusively to PAR-2 and not to PAR-1, PAR-3, and PAR-4.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, a "monoclonal" antibody or antigen-binding fragment thereof refers to such antibodies and antigen-binding fragments thereof made in any number of manners including but not limited to by hybridoma, phage selection, recombinant expression, and transgenic animals.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Song-sivilai & Lachmann, Clin. Exp. Immunol. 79:315-321 (1990); Kostelny et al., J. Immunol. 148, 1547-1553 (1992). For example, a bispecific antibody could include one domain that binds to the PAR2 receptor binding site, and another binding to the N-terminal portion of PAR2 before or after protease cleavage.

As used herein, the terms "variable region" or "variable domain" are used interchangeably and are common in the art. The variable region typically refers to a portion of an antibody, generally, a portion of a light or heavy chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In some aspects, the variable region is a human variable region. In some aspects, the variable region comprises rodent or murine CDRs and human framework regions (FRs). In some aspects, the variable region is a primate (e.g., non-human primate) variable region. In some aspects, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242).

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of CDR2 and inserted residues (e.g., residues 82a, 82b, and 82c, etc. according to Kabat) after heavy chain FW residue 82. See Table 1.

TABLE 1

| Loop | Kabat | Abm | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

For all heavy chain constant region amino acid positions discussed in the present disclosure, residue numbering is according to the EU index first described in Edelman et al., 1969, Proc. Natl. Acad. Sci. USA 63(1):78-85, describing the amino acid sequence of myeloma protein EU, which is the first human IgG1 sequenced. The EU index of Edelman et al. is also set forth in Kabat et al., 1991, Sequences of Proteins of Immunological Interest, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 EU antibody of Edelman et al. as set forth in Kabat 1991.

As used herein, the term "constant region" or "constant domain" are interchangeable and have the meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In some aspects, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In some aspects, the light chain is a human light chain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a CH2 domain in an Fc region, i.e., it extends from about amino acid 341 to about amino acid 447 of an IgG. As used herein, the Fc region can be a native sequence Fc, including any allotypic variant, or a variant Fc (e.g., a non-naturally-occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesion).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc includes the various allotypes of Fc (see, e.g., Jefferis et al., (2009) *mAbs* 1:1; Vidarsson G. et al. *Front Immunol.* 5:520 (published online Oct. 20, 2014)).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Human IgG1 binds to most human Fc receptors and elicits the strongest Fc effector functions. It is considered equivalent to murine IgG2a with respect to the types of activating Fc receptors that it binds to. Conversely, human IgG4 elicits the least Fc effector functions. Vidarsson G. et al. *Front Immunol.* 5:520 (published online Oct. 20, 2014).

The Fc region of the antibody may include modifications that modulate serum half-life and biodistribution, including without limitation, modifications that modulate the antibody's interaction with the neonatal Fc receptor (FcRn), a receptor with a key role in protecting IgG from catabolism, and maintaining high serum antibody concentration. These include the triple substitution of M252Y/S254T/T256E, as described in U.S. Pat. No. 7,083,784. Other substitutions may occur at positions 250 and 428, see e.g., U.S. Pat. No. 7,217,797, as well as at positions 307, 380 and 434, see, e.g., PCT Publ. No. WO 00/042072. Antibodies of any class may have the heavy chain C-terminal lysine omitted or removed to reduce heterogeneity (ΔK). The substitution of S228P (EU numbering) in the human IgG4 can stabilize antibody Fab-arm exchange in vivo (Labrin et al. (2009) Nature Biotechnol. 27:8; 767-773).

A "hinge", "hinge domain", "hinge region", or "antibody hinge region" are used interchangeably and refer to the domain of a heavy chain constant region that joins the CH1 domain to the CH2 domain and includes the upper, middle, and lower fragments of the hinge (Roux et al., *J. Immunol.* 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 *J Immunol* 161:4083). The sequences of wild-type IgG1, IgG2, IgG3 and IgG4 hinges are known in the art. See, e.g., Kabat E A et al., (1991) Sequences of Proteins of Immunological Interest, Fifth Edition, U.S. Department of Health and Human Services, NIH Publication No. 91-3242; Vidarsson G. et al. *Front Immunol.* 5:520 (published online Oct. 20, 2014). The hinge of IgG4 antibodies may be stabilized by mutating S228, such as S228P mutation. See Silva et al. (2015) The S228P mutation prevents in vivo and in vitro IgG4 Fab-arm exchange as demonstrated using a combination of novel quantitative immunoassays and physiological matrix preparation. *J Biol Chem.* 290(9):5462-9.

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH1 domains include CH1 domains with mutations that modify a biological activity of an antibody, e.g., half-life, e.g., described in U.S. Pub. No. 20120100140 and U.S. patents and publications and PCT publications cited therein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH2 domains include CH2 domains with mutations that modify a biological activity of an antibody, e.g., half-life and/or reduced Fc effector function, e.g., described in U.S. Pub. No. 20120100140 and U.S. patents and publications and PCT publications cited therein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH3 domains include CH3 domains with mutations that modify a biological activity of an antibody, e.g., half-life, e.g., described in U.S. Pub. No. 20120100140 and U.S. patents and publications and PCT publications cited therein.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally-occurring variants within a specific isotype group, which variants differ in a few amino acids (see, e.g., Jefferis et al., (2009) *mAbs* 1:1). Antibodies described herein can be of any allotype. Allotypes of IgG1, IgG2, IgG3, and IgG4 are known in the art. See, e.g., Kabat E A et al., (1991) supra; Vidarsson G. et al. *Front Immunol.* 5:520 (published online Oct. 20, 2014); and Lefranc M P, *mAbs* 1:4, 1-7(2009).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to PAR-2 is substantially free of antibodies that specifically bind antigens other than PAR-2). An isolated antibody that specifically binds to an epitope of PAR-2 can, however, have cross-reactivity to other PAR-2 proteins from different species.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementarity determining regions (CDRs) are replaced by residues from the CDRs of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). The humanized antibody or antigen-binding fragment thereof can be further modified by the substitution of additional residues either in the Fv framework region and/or within the replaced non-human residues to refine and optimize the specificity, affinity, and/or capability of the antibody or antigen-binding fragment thereof. In general, the humanized antibody or antigen-binding fragment thereof will comprise VH and VL that comprise substantially all of at least one, and typically two or three, of the CDR regions that correspond to the non-human immunoglobulin, whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some aspects, a "humanized antibody" is a resurfaced antibody.

The term "human" antibody (HuMAb) or antigen-binding fragment thereof means an antibody or antigen-binding fragment thereof having an amino acid sequence derived from a human immunoglobulin gene locus or with a sequence matching sequences from a human immunoglobulin gene locus, where such antibody or antigen-binding fragment is made using any technique known in the art. This definition of a human antibody or antigen-binding fragment thereof includes intact or full-length antibodies and fragments thereof.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

"Binding affinity" generally refers to the strength of the sum total of non-covalent interactions between a single binding site of a molecule (e.g., an antibody or antigen-binding fragment thereof) and its binding partner (e.g., an antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation rate constant of, e.g., an antibody or antigen-binding fragment thereof from an antigen. The $k_{on}$ and $k_{off}$ can be determined by techniques known to one of ordinary skill in the art, such as BIAcore© or KinExA©.

A antibody that is "blocking" or that "blocks" or that is "inhibitory" of that "inhibits" is an antibody that reduces or inhibits (partially or completely) binding of its target protein to one or more ligands when the antibody is bound to the target protein, and/or that reduces or inhibits (partially or completely) one or more activities or functions of the target protein when the antibody is bound to the target protein.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some aspects, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., alanine scanning or other site-directed mutagenesis mapping). For X-ray crystallography, crystallization can be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Crystals of an antibody or antigen-binding fragment thereof and its antigen can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

The term "epitope mapping" refers to the process of identification of the molecular determinants for antibody-antigen recognition.

A PAR-2 antibody that "binds to the same epitope" as a reference PAR-2 antibody refers to an antibody that contacts the same PAR-2 amino acid residues as the reference PAR-2 antibody. The ability of a PAR-2 antibody to bind to the same epitope as a reference PAR-2 antibody is determined using peptide scanning mutagenesis or high throughput alanine scanning mutagenesis (see Davidson and Doranz, 2014 Immunology 143, 13-20). In the latter methodology, a comprehensive mutation library of PAR-2, or a portion thereof (e.g., the extracellular domain), can be generated by mutating each individual amino acid residue to alanine (or if the amino acid residue is alanine, then to another residue such as serine) and testing each mutant for binding to an anti-PAR-2 antibody or antigen binding fragment thereof. Amino acids that are required for binding, and therefore are epitope residues, are identified by loss of immunoreactivity.

As used herein, the terms "specifically binds," "specifically recognizes," "specifically binds," "specifically recognizes," "specific binding," "selective binding," and "selectively binds," are analogous terms in the context of antibodies or antigen-binding fragments thereof and refer to antibody binding to an epitope on a predetermined antigen. Typically, the antibody (i) binds with an equilibrium dissociation constant ($K_D$) of about $10^{-8}$ M, about $10^{-9}$ M, or about $10^{-10}$ M or even lower when determined by, e.g., surface plasmon resonance (SPR) technology in a BIA-CORE© T200 instrument using the predetermined antigen, e.g., recombinant human PAR-2, as the analyte and the antibody as the ligand, or Scatchard analysis of binding of the antibody to antigen positive cells, and (ii) binds to the predetermined antigen with an affinity that is at least ten-fold greater than its affinity for binding to a non-specific antigen (e.g., BSA, casein) other than the predetermined antigen or a closely-related antigen. Accordingly, an antibody that "specifically binds to human PAR-2" refers to an antibody that binds to human PAR-2 (e.g., SEQ ID NO: 28 or amino acids 26-397 of SEQ ID NO: 28) with a $K_D$ of about $10^{-8}$ M, about $10^{-9}$ M, or about $10^{-10}$ M or even lower and can also bind to PAR-2 from other species (e.g., cynomolgus monkey PAR-2). In some aspects, the antibody or antigen-binding fragment thereof as disclosed herein does not bind to human PAR-1, PAR-3, or PAR-4.

In some aspects, the anti-PAR-2 antibody or antigen-binding fragment thereof specifically binds to human PAR-2 with high affinity, for example, with a $K_D$ of about $9.9 \times 10^{-10}$ M, about $9.8 \times 10^{-10}$ M, about $9.7 \times 10^{-10}$ M, about $9.6 \times 10^{-10}$ M, about $9.5 \times 10^{-10}$ M, about $9.4 \times 10^{-10}$ M, about $9.3 \times 10^{-10}$ M, about $9.2 \times 10^{-10}$ M, about $9.1 \times 10^{-10}$ M, about $9.0 \times 10^{-10}$ M, about $8.9 \times 10^{-10}$ M, about $8.8 \times 10^{-10}$ M, about $8.7 \times 10^{-10}$ M, about $8.6 \times 10^{-10}$ M, about $8.5 \times 10^{-10}$ M, about $8.4 \times 10^{-10}$ M, about $8.3 \times 10^{-10}$ M, about $8.2 \times 10^{-10}$ M, about $8.1 \times 10^{-10}$ M, about $8.0 \times 10^{-10}$ M, about $7.9 \times 10^{-10}$ M, about $7.8 \times 10^{-10}$ M, about $7.7 \times 10^{-10}$ M, about $7.6 \times 10^{-10}$ M, about $7.5 \times 10^{-10}$ M, about $7.4 \times 10^{-10}$ M, about $7.3 \times 10^{-10}$ M, about $7.2 \times 10^{-10}$ M, about $7.1 \times 10^{-10}$ M, about $7.0 \times 10^{-10}$ M, about $6.9 \times 10^{-10}$ M, about $6.8 \times 10^{-10}$ M, about $6.7 \times 10^{-10}$ M, about $6.6 \times 10^{-10}$ M, about $6.5 \times 10^{-10}$ M, about $6.4 \times 10^{-10}$ M, about $6.3 \times 10^{-10}$ M, about $6.2 \times 10^{-10}$ M, about $6.1 \times 10^{-10}$ M, about $6.0 \times 10^{-10}$ M, about $5.9 \times 10^{-10}$ M, about $5.8 \times 10^{-10}$ M, about $5.7 \times 10^{-10}$ M, about $5.6 \times 10^{-10}$ M, about $5.5 \times 10^{-10}$ M, about $5.4 \times 10^{-10}$ M, about $5.3 \times 10^{-10}$ M, about $5.2 \times 10^{-10}$ M, about $5.1 \times 10^{-10}$ M, about $5.0 \times 10^{-10}$ M, about $4.9 \times 10^{-10}$ M, about $4.8 \times 10^{-10}$ M, about $4.7 \times 10^{-10}$ M, about $4.6 \times 10^{-10}$ M, about $4.5 \times 10^{-10}$ M, about $4.4 \times 10^{-10}$ M, about $4.3 \times 10^{-10}$ M, about $4.2 \times 10^{-10}$ M, about $4.1 \times 10^{-10}$ M, about $4.0 \times 10^{-10}$ M, about $3.9 \times 10^{-10}$ M, about $3.8 \times 10^{-10}$ M, about $3.7 \times 10^{-10}$ M, about $3.6 \times 10^{-10}$ M, about $3.5 \times 10^{-10}$ M, about $3.4 \times 10^{-10}$ M, about $3.3 \times 10^{-10}$ M, about $3.2 \times 10^{-10}$ M, about $3.1 \times 10^{-10}$ M, about $3.0 \times 10^{-10}$ M, about $2.9 \times 10^{-10}$ M, about $2.8 \times 10^{-10}$ M, about $2.7 \times 10^{-10}$ M, about $2.6 \times 10^{-10}$ M, about $2.5 \times 10^{-10}$ M, $2.4 \times 10^{-10}$ M, about $2.3 \times 10^{-10}$ M, about $2.2 \times 10^{-10}$ M, about $2.1 \times 10^{-10}$ M, about $2.0 \times 10^{-10}$ M, about $1.9 \times 10^{-10}$ M, about $1.8 \times 10^{-10}$ M, about $1.7 \times 10^{-10}$ M, about $1.6 \times 10^{-10}$ M, about $1.5 \times 10^{-10}$ M, $1.4 \times 10^{-10}$ M, about $1.3 \times 10^{-10}$ M, about $1.2 \times 10^{-10}$ M, about $1.1 \times 10^{-10}$ M, about $1.0 \times 10^{-10}$ M, about $9 \times 10^{-11}$ M, about $8 \times 10^{-11}$ M, about $7 \times 10^{-11}$ M, about $6 \times 10^{-11}$ M, about $5 \times 10^{-11}$ M, about $4 \times 10^{-11}$ M, about $3 \times 10^{-11}$ M, about $2 \times 10^{-11}$ M, about $1 \times 10^{-11}$ M, about $9 \times 10^{-12}$ M, about $8 \times 10^{-12}$ M, about $7 \times 10^{-12}$ M, about $6 \times 10^{-12}$ M, about $5 \times 10^{-12}$ M, about $4 \times 10^{-12}$ M, about $3 \times 10^{-12}$ M, about $2 \times 10^{-12}$ M, about $1 \times 10^{-12}$ M, about $9 \times 10^{-13}$ M, or about $8 \times 10^{-13}$ M, e.g., as measured by surface plasmon resonance (SPR) technology (e.g., as described in the Example 5).

In some aspects, the anti-PAR-2 antibody or antigen-binding fragment thereof specifically binds to human PAR- 2, for example, with a $K_D$ of about $9.5 \times 10^{-10}$ M, about $9.4 \times 10^{-10}$ M, about $9.3 \times 10^{-10}$ M, about $9.2 \times 10^{-10}$ M, about $9.1 \times 10^{-10}$ M, about $9.0 \times 10^{-10}$ M, about $8.9 \times 10^{-10}$ M, about $8.8 \times 10^{-10}$ M, about $8.7 \times 10^{-10}$ M, about $8.6 \times 10^{-10}$ M, about $8.5 \times 10^{-10}$ M, about $8.4 \times 10^{-10}$ M, about $8.3 \times 10^{-10}$ M, about $8.2 \times 10^{-10}$ M, about $8.1 \times 10^{-10}$ M, about $8.0 \times 10^{-10}$ M, about $7.9 \times 10^{-10}$ M, about $7.8 \times 10^{-10}$ M, about $7.7 \times 10^{-10}$ M, about $7.6 \times 10^{-10}$ M, about $7.5 \times 10^{-10}$ M, about $7.4 \times 10^{-10}$ M, about $7.3 \times 10^{-10}$ M, about $7.2 \times 10^{-10}$ M, about $7.1 \times 10^{-10}$ M, about $7.0 \times 10^{-10}$ M, about $6.9 \times 10^{-10}$ M, about $6.8 \times 10^{-10}$ M, about $6.7 \times 10^{-10}$ M, about $6.6 \times 10^{-10}$ M, about $6.5 \times 10^{-10}$ M, about $6.4 \times 10^{-10}$ M, about $6.3 \times 10^{-10}$ M, about $6.2 \times 10^{-10}$ M, about $6.1 \times 10^{-10}$ M, about $6.0 \times 10^{-10}$ M, about $5.9 \times 10^{-10}$ M, about $5.8 \times 10^{-10}$ M, about $5.7 \times 10^{-10}$ M, about $5.6 \times 10^{-10}$ M, about $5.5 \times 10^{-10}$ M, about $5.4 \times 10^{-10}$ M, about $5.3 \times 10^{-10}$ M, about $5.2 \times 10^{-10}$ M, about $5.1 \times 10^{-10}$ M, about $5.0 \times 10^{-10}$ M, about $4.9 \times 10^{-10}$ M, about $4.8 \times 10^{-10}$ M, about $4.7 \times 10^{-10}$ M, about $4.6 \times 10^{-10}$ M, about $4.5 \times 10^{-10}$ M, about $4.4 \times 10^{-10}$ M, or about $4.3 \times 10^{-10}$ M.

In some aspects, the anti-PAR-2 antibody or antigen-binding fragment thereof specifically binds to human PAR-2 with a $K_D$ of about $9.5 \times 10^{-10}$ M. In some aspects, the anti-PAR-2 antibody or antigen-binding fragment thereof specifically binds to human PAR-2 with a $K_D$ of about $8.5 \times 10^{-10}$ M. In some aspects, the anti-PAR-2 antibody or antigen-binding fragment thereof specifically binds to human PAR-2 with a $K_D$ of about $7.5 \times 10^{-10}$ M. In some aspects, the anti-PAR-2 antibody or antigen-binding fragment thereof specifically binds to human PAR-2 with a $K_D$ of about $6.5 \times 10^{-10}$ M. In some aspects, the anti-PAR-2 antibody or antigen-binding fragment thereof specifically binds to human PAR-2 with a $K_D$ of about $5.5 \times 10^{-10}$ M. In some aspects, the anti-PAR-2 antibody or antigen-binding fragment thereof specifically binds to human PAR-2 with a $K_D$ of about $4.5 \times 10^{-10}$ M.

The term "cross-reacts," or "cross-reactivity" as used herein, refers to the ability of an antibody described herein to bind to a PAR-2 orthologue. For example, an antibody described herein that binds human PAR-2 may also bind another species of PAR-2 (e.g., cynomolgus monkey PAR-2). As used herein, cross-reactivity can be measured by detecting a specific reactivity with purified antigen in binding assays (e.g., SPR, ELISA) or binding to, or otherwise functionally interacting with, cells physiologically expressing PAR-2. Methods for determining cross-reactivity include standard binding assays as described herein, for example, by Biacore® surface plasmon resonance (SPR) analysis using a Biacore® T200 SPR instrument (Biacore AB, Uppsala, Sweden), or flow cytometric techniques. An antibody that "cross-reacts with cynomolgus monkey PAR-2" refers to an antibody that binds to cynomolgus PAR-2 with a $K_D$ of about 10-8 M, about 10-9 M, or about 10-10 M or even lower. In some aspects, such antibodies that do not cross-react with PAR-2 from a non-human species (e.g., mouse, rabbit, guinea pig, or dog PAR-2) exhibit essentially undetectable binding against these proteins in standard binding assays.

In some aspects, the anti-PAR-2 antibody or antigen-binding fragment thereof binds to cynomolgus monkey PAR-2, for example, with a $K_D$ of about $9.5 \times 10^{-9}$ M, about $9.4 \times 10^{-9}$ M, about $9.3 \times 10^{-9}$ M, about $9.2 \times 10^{-9}$ M, about $9.1 \times 10^{-9}$ M, about $9.0 \times 10^{-9}$ M, about $8.9 \times 10^{-9}$ M, about $8.8 \times 10^{-9}$ M, about $8.7 \times 10^{-9}$ M, about $8.6 \times 10^{-9}$ M, about $8.5 \times 10^{-9}$ M, about $8.4 \times 10^{-9}$ M, about $8.3 \times 10^{-9}$ M, about $8.2 \times 10^{-9}$ M, about $8.1 \times 10^{-9}$ M, about $8.0 \times 10^{-9}$ M, about $7.9 \times 10^{-9}$ M, about $7.8 \times 10^{-9}$ M, about $7.7 \times 10^{-9}$ M, about $7.6 \times 10^{-9}$ M, about $7.5 \times 10^{-9}$ M, about $7.4 \times 10^{-9}$ M, about $7.3 \times 10^{-9}$ M, about $7.2 \times 10^{-9}$ M, about $7.1 \times 10^{-9}$ M, about $7.0 \times 10^{-9}$ M, about $6.9 \times 10^{-9}$ M, about $6.8 \times 10^{-9}$ M, about $6.7 \times 10^{-9}$ M, about $6.6 \times 10^{-9}$ M, about $6.5 \times 10^{-9}$ M, about $6.4 \times 10^{-9}$ M, about $6.3 \times 10^{-9}$ M, about $6.2 \times 10^{-9}$ M, about $6.1 \times 10^{-9}$ M, about $6.0 \times 10^{-9}$ M, about $5.9 \times 10^{-9}$ M, about $5.8 \times 10^{-9}$ M, about $5.7 \times 10^{-9}$ M, about $5.6 \times 10^{-9}$ M, about $5.5 \times 10^{-9}$ M, about $5.4 \times 10^{-9}$ M, about $5.3 \times 10^{-9}$ M, about $5.2 \times 10^{-9}$ M, about $5.1 \times 10^{-9}$ M, about $5.0 \times 10^{-9}$ M, about $4.9 \times 10^{-9}$ M, about $4.8 \times 10^{-9}$ M, about $4.7 \times 10^{-9}$ M, about $4.6 \times 10^{-9}$ M, about $4.5 \times 10^{-9}$ M, about $4.4 \times 10^{-9}$ M, about $4.3 \times 10^{-9}$ M, about $4.2 \times 10^{-9}$ M, about $4.1 \times 10^{-9}$ M, about $4.0 \times 10^{-9}$ M, about $3.9 \times 10^{-9}$ M, about $3.8 \times 10^{-9}$ M, about $3.7 \times 10^{-9}$ M, about $3.6 \times 10^{-9}$ M, about $3.5 \times 10^{-9}$ M, about $3.4 \times 10^{-9}$ M, about $3.3 \times 10^{-9}$ M, about $3.2 \times 10^{-9}$ M, about $3.1 \times 10^{-9}$ M, about $3.0 \times 10^{-9}$ M, about $2.9 \times 10^{-9}$ M, about $2.8 \times 10^{-9}$ M, about $2.7 \times 10^{-9}$ M, about $2.6 \times 10^{-9}$ M, about $2.5 \times 10^{-9}$ M, about $2.4 \times 10^{-9}$ M, about $2.3 \times 10^{-9}$ M, about $2.2 \times 10^{-9}$ M, about $2.1 \times 10^{-9}$ M, about $2.0 \times 10^{-9}$ M, about $1.9 \times 10^{-9}$ M, about $1.8 \times 10^{-9}$ M, about $1.7 \times 10^{-9}$ M, about $1.6 \times 10^{-9}$ M, about $1.5 \times 10^{-9}$ M, about $1.4 \times 10^{-9}$ M, about $1.3 \times 10^{-9}$ M, about $1.2 \times 10^{-9}$ M, about $1.1 \times 10^{-9}$ M, about $1.0 \times 10^{-9}$ M, about $9.9 \times 10^{-10}$ M, about $9.8 \times 10^{-10}$ M, about $9.7 \times 10^{-10}$ M, about $9.6 \times 10^{-10}$ M, about $9.5 \times 10^{-10}$ M, about $9.4 \times 10^{-10}$ M, about $9.3 \times 10^{-10}$ M, about $9.2 \times 10^{-10}$ M, about $9.1 \times 10^{-10}$ M, about $9.0 \times 10^{-10}$ M, about $8.9 \times 10^{-10}$ M, about $8.8 \times 10^{-10}$ M, about $8.7 \times 10^{-10}$ M, about $8.6 \times 10^{-10}$ M, about $8.5 \times 10^{-10}$ M, about $8.4 \times 10^{-10}$ M, about $8.3 \times 10^{-10}$ M, about $8.2 \times 10^{-10}$ M, about $8.1 \times 10^{-10}$ M, about $8.0 \times 10^{-10}$ M, about $7.9 \times 10^{-10}$ M, about $7.8 \times 10^{-10}$ M, about $7.7 \times 10^{-10}$ M, about $7.6 \times 10^{-10}$ M, about $7.5 \times 10^{-10}$ M, about $7.4 \times 10^{-10}$ M, about $7.3 \times 10^{-10}$ M, about $7.2 \times 10^{-10}$ M, about $7.1 \times 10^{-10}$ M, about $7.0 \times 10^{-10}$ M, about $6.9 \times 10^{-10}$ M, about $6.8 \times 10^{-10}$ M, about $6.7 \times 10^{-10}$ M, about $6.6 \times 10^{-10}$ M, about $6.5 \times 10^{-10}$ M, about $6.4 \times 10^{-10}$ M, about $6.3 \times 10^{-10}$ M, about $6.2 \times 10^{-10}$ M, about $6.1 \times 10^{-10}$ M, about $6.0 \times 10^{-10}$ M, about $5.9 \times 10^{-10}$ M, about $5.8 \times 10^{-10}$ M, about $5.7 \times 10^{-10}$ M, about $5.6 \times 10^{-10}$ M, about $5.5 \times 10^{-10}$ M, about $5.4 \times 10^{-10}$ M, about $5.3 \times 10^{-10}$ M, about $5.2 \times 10^{-10}$ M, about $5.1 \times 10^{-10}$ M, about $5.0 \times 10^{-10}$ M, about $4.9 \times 10^{-10}$ M, about $4.8 \times 10^{-10}$ M, about $4.7 \times 10^{-10}$ M, about $4.6 \times 10^{-10}$ M, about $4.5 \times 10^{-10}$ M, about $4.4 \times 10^{-10}$ M, about $4.3 \times 10^{-10}$ M, about $4.2 \times 10^{-10}$ M, about $4.1 \times 10^{-10}$ M, about $4.0 \times 10^{-10}$ M, about $3.9 \times 10^{-10}$ M, about $3.8 \times 10^{-10}$ M, about $3.7 \times 10^{-10}$ M, about $3.6 \times 10^{-10}$ M, about $3.5 \times 10^{-10}$ M, about $3.4 \times 10^{-10}$ M, about $3.3 \times 10^{-10}$ M, about $3.2 \times 10^{-10}$ M, about $3.1 \times 10^{-10}$ M, about $3.0 \times 10^{-10}$ M, about $2.9 \times 10^{-10}$ M, about $2.8 \times 10^{-10}$ M, about $2.7 \times 10^{-10}$ M, about $2.6 \times 10^{-10}$ M, about $2.5 \times 10^{-10}$ M, $2.4 \times 10^{-10}$ M, about $2.3 \times 10^{-10}$ M, about $2.2 \times 10^{-10}$ M, about $2.1 \times 10^{-10}$ M, about $2.0 \times 10^{-10}$ M, about $1.9 \times 10^{-10}$ M, about $1.8 \times 10^{-10}$ M, about $1.7 \times 10^{-10}$ M, about $1.6 \times 10^{-10}$ M, about $1.5 \times 10^{-10}$ M, $1.4 \times 10^{-10}$ M, about $1.3 \times 10^{-10}$ M, about $1.2 \times 10^{-10}$ M, about $1.1 \times 10^{-10}$ M, about $1.0 \times 10^{-10}$ M, about $9 \times 10^{-11}$ M, about $8 \times 10^{-11}$ M, about $7 \times 10^{-11}$ M, about $6 \times 10^{-11}$ M, about $5 \times 10^{-11}$ M, about $4 \times 10^{-11}$ M, about $3 \times 10^{-11}$ M, about $2 \times 10^{-11}$ M, about $1 \times 10^{-11}$ M, about $9 \times 10^{-12}$ M, about $8 \times 10^{-12}$ M, about $7 \times 10^{-12}$ M, about $6 \times 10^{-12}$ M, about $5 \times 10^{-12}$ M, about $4 \times 10^{-12}$ M, about $3 \times 10^{-12}$ M, about $2 \times 10^{-12}$ M, about $1 \times 10^{-12}$ M, about $9 \times 10^{-13}$ M, or about $8 \times 10^{-13}$ M, e.g., as measured by surface plasmon resonance (SPR) technology (e.g., as described in the Example 5).

In some aspects, the anti-PAR-2 antibody or antigen-binding fragment thereof binds to cynomolgus monkey PAR-2 with a $K_D$ of about $9.5 \times 10^{-9}$ M. In some aspects, the anti-PAR-2 antibody or antigen-binding fragment thereof binds to cynomolgus monkey PAR-2 with a $K_D$ of about $8.5 \times 10^{-9}$ M. In some aspects, the anti-PAR-2 antibody or antigen-binding fragment thereof binds to cynomolgus monkey PAR-2 with a $K_D$ of about $7.5 \times 10^{-9}$ M. In some aspects, the anti-PAR-2 antibody or antigen-binding fragment thereof binds to cynomolgus monkey PAR-2 with a $K_D$ of about $6.5 \times 10^{-9}$ M. In some aspects, the anti-PAR-2 antibody or antigen-binding fragment thereof binds to cynomolgus monkey PAR-2 with a $K_D$ of about $5.5 \times 10^{-9}$ M. In some aspects, the anti-PAR-2 antibody or antigen-binding fragment thereof binds to cynomolgus monkey PAR-2 with a $K_D$ of about $4.5 \times 10^{-9}$ M.

An antibody is said to "competitively inhibit" binding of a reference antibody to a given epitope if it preferentially binds to that epitope or an overlapping epitope such that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE© surface plasmon resonance (SPR) analysis. In some aspects, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include: competition for binding to cells expressing PAR-2, e.g., by flow cytometry, such as described in the Examples. Other methods include: SPR (e.g., BIACORE©), BLI (Bio-layer interferometry), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

The term "$k_{assoc}$" or "$k_a$", as used herein, is intended to refer to the association rate of a particular antibody-antigen interaction, whereas the term "kais" or "$k_a$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. Available methods for determining the $K_D$ of an antibody include surface plasmon resonance, a biosensor system such as a BIACORE©, BLI (Bio-layer interferometry) system or flow cytometry and Scatchard analysis.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-10}$ M or less, or $10^{-8}$ M or less.

The term "$EC_{50}$" in the context of an in vitro or in vivo assay refers to the effective concentration of an agent induces a response that is 50% of the maximal response, i.e., halfway between the maximal response and the baseline. Typically this value is used when assessing antibody potency. The term "$IC_{50}$" in the context of an in vitro or in vivo assay using an antibody or antigen binding fragment thereof, refers to the inhibitory concentration of an antibody or an antigen-binding fragment thereof that inhibits a response to the level of 50% of the maximal response, i.e., halfway between the maximal response and the baseline. Typically this "inhibitory potency" value is used when assessing antibody potency.

The term "naturally-occurring" as applied to an object herein refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in some aspects, the polypeptides can occur as single chains or associated chains.

The term "nucleic acid molecule" as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some aspects, a predicted nonessential amino acid residue in an anti-PAR-2 antibody is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

The percent identity between two sequences is a function of the number of identical positions shared by the sequences (i.e., % sequence identity=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS,* 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules described herein. BLAST protein searches can be performed with the XBLAST program, score=50, word length=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, the term "host cell" or "recombinant host cell" can be any type of cell, e.g., a primary cell, a cell in culture, or a cell from a cell line. In some aspects, the term "host cell" refers to a cell transfected with a nucleic acid molecule and the progeny or potential progeny of such a cell. Progeny of such a cell cannot be identical to the parent cell transfected with the nucleic acid molecule, e.g., due to mutations or environmental influences that can occur in succeeding generations or integration of the nucleic acid molecule into the host cell genome.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the term "cytokine" refers to any one of the numerous factors that exert a variety of effects on cells, for example, inducing growth or proliferation. Non-limiting examples of cytokines which can be used alone or in combination in the practice of the present invention include, interleukin-2 (IL-2), stem cell factor (SCF), interleukin-3 (IL-3), interleukin-4 (IL-4), interleukin-6 (IL-6), interleukin-8 (IL-8), interleukin-11 (IL-11), interleukin-12 (IL-12), interleukin-13 (IL-13), interleukin-15 (IL-15), interleukin-18 (IL-18), granulocyte-colony stimulating factor (G-CSF), vascular endothelial growth factor-A (VEGF-A), granulocyte macrophage-colony stimulating factor (GM-CSF), interleukin-1 beta (IL-1β), interferon-γ (IFNγ), tumor necrosis factor (TNF), MIP-11, leukemia inhibitory factor (LIF), c-kit ligand, thrombopoietin (TPO) and flt3 ligand. Cytokines are commercially available from several vendors such as, for example, Genzyme (Framingham, Mass.), Genentech (South San Francisco, Calif.), Amgen (Thousand Oaks, Calif), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the disclosure.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer," "administering," "administration," and the like, as used herein, refer to methods that can be used to deliver a drug, e.g., an anti-human PAR-2 antibody or antigen-binding fragment thereof, to the desired site of biological action. Administration techniques that can be employed with the agents and methods described herein are found in e.g., Goodman and Gilman, *The* Pharmacological *Basis of Therapeutics*, current edition, Pergamon; and Remington's, *Pharmaceutical Sciences*, current edition, Mack Publishing Co., Easton, Pa. Routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraventricle, intravitreal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "subject" and "patient" are used interchangeably. The subject can be a mammal such as a non-human animal (e.g., cow, pig, horse, cat, dog, rat, mouse, monkey or other primate, etc.). In some aspects, the subject is a human. In some aspects, the subject is a cynomolgus monkey.

The term "effective dose" or "effective dosage" is defined as an amount of a drug, e.g., an anti-human PAR-2 antibody or antigen-binding fragment thereof, sufficient to achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, an increase in overall survival (the length of time from either the date of diagnosis or the start of treatment for a disease, such as cancer, that patients diagnosed with the disease are still alive), or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that promotes cancer regression in a subject. In some aspects, a therapeutically effective amount of the drug promotes cancer regression to the point of eliminating the cancer. "Promoting cancer regression" means that administering an effective amount of the drug, alone or in combination with an antineoplastic agent, results in a reduction in tumor growth or size, necrosis of the tumor, a decrease in severity of at least one disease symptom, an increase in frequency and duration of disease symptom-free periods, an increase in overall survival, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug inhibits cell growth or tumor growth by at least about 20%, by at least about 40%, by at least about 60%, or by at least about 80% relative to untreated subjects. In some aspects, a therapeutically effective amount or dosage of the drug completely inhibits cell growth or tumor growth, i.e., inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In some aspects described herein, tumor regression can be observed and continue for a period of at least about 20 days, at least about 40 days, or at least about 60 days.

Terms such as "treating" or "treatment" or "to treat" or "alleviating" or "to alleviate" refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis). In some aspects, a subject is successfully "treated" for cancer according to the methods provided herein if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

In some embodiments, a subject is successfully "treated" for chronic obstructive pulmonary disease (COPD) according to the methods provided herein if the patient shows one or more of the following: preventing or controlling COPD symptoms, reducing the frequency and severity of COPD exacerbations, improving health status, improving exercise tolerance, or any combination thereof. See e.g., Rabe et al., *Am J Respir Crit Care Med.*, 176:532-555 (2007).

In some embodiments, a subject is successfully "treated" for asthma according to the methods provided herein if the patient shows one or more of the following: preventing or controlling asthma symptoms, reducing the frequency and severity of asthma exacerbations, improving health status, improving exercise tolerance, or any combination thereof. See e.g., Gatheral et al., *Cochrane Database Syst Rev.*, 4(4), (2017).

The terms "cancer" and "cancerous" refer to or describe the physiological condition in mammals in which a population of cells are characterized by unregulated cell growth. Such cancers can include solid tumors, e.g., solid tumors in which myeloid cells (monocytes, macrophages, dendritic cells, granulocytes, neutrophils, microglia or other innate immune cells) have infiltrated the tumor microenvironment. Examples of such cancers include, but are not limited to, glioblastoma, head and neck cancer, kidney cancer (e.g., kidney clear cell cancer), pancreatic cancer, and breast cancer. The cancer can be a "PAR-2-positive cancer." This term refers to a cancer comprising cells that express PAR-2 mRNA or protein. The cancer can be a cancer with "increased PAR-2" mRNA or protein This refers to a cancer that has more PAR-2 (e.g., on cells that have infiltrated the cancer) than a healthy version of the same tissue.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the terms "ug" and "uM" are used interchangeably with "μg" and "μM," respectively.

Various aspects described herein are described in further detail in the following subsections. Any compositions or methods provided herein can be combined with one or more of any of the other compositions and methods provided herein.

II. Antibodies

In some embodiments, provided herein are antibodies (e.g., monoclonal antibodies, such as humanized antibodies) and antigen-binding fragments thereof which specifically bind to PAR-2, such as human, cynomolgus monkey. In some aspects, provided herein are antibodies (e.g., monoclonal antibodies, such as humanized antibodies) and antigen-binding fragments thereof which specifically bind to human PAR-2. The amino acid sequences of human, cynomolgus monkey, and rat PAR-2 are known in the art and also provided herein as represented by SEQ ID NOs: 28, 30, and 32, respectively.

Human PAR-2 (UniProt ID No. P55085-1; SEQ ID NO: 28) is comprised of 397 amino acids (including the signal peptide) and is structurally a typical class A G-protein coupled receptor superfamily member with seven transmembrane regions, an extracellular N-terminus, and an intracellular C-terminus. There is a disulfide linkage between extracellular loops 1 and 2 that is believed to stabilize the structure and potentially contributes to signaling. The crystal structure of PAR-2 has been solved. See Cheng et al., *Nature*, 545:112-115 (2017), hereby incorporated by reference in its entirety.

Below is the amino acid sequence of the one known human PAR-2 isoform. Human PAR-2 (UniProt ID No. P55085-1; SEQ ID NO: 28)

MRSPSAAWLLGAAILLAASLSCSGTIQGTNRSSKGRSLIGKVDGTSHVT

GKGVTVETVFSVDEFSASVLTGKLTTVFLPIVYTIVFVVGLPSNGMALW

VFLFRTKKKHPAVIYMANLALADLLSVIWFPLKIAYHIHGNNWIYGEAL

CNVLIGFFYGNMYCSILFMTCLSVQRYWVIVNPMGHSRKKANIAIGISL

AIWLLILLVTIPLYVVKQTIFIPALNITTCHDVLPEQLLVGDMFNYFLS

LAIGVFLFPAFLTASAYVLMIRMLRSSAMDENSEKKRKRAIKLIVTVLA

MYLICFTPSNLLLVVHYFLIKSQGQSHVYALYIVALCLSTLNSCIDPFV

YYFVSHDFRDHAKNALLCRSVRTVKQMQVSLTSKKHSRKSSSYSSSSTT

VKTSY

The signal sequence of human PAR-2 corresponds to amino acids 1-25 (underlined). Thus, the mature isoforms of human PAR-2 isoform 1 consist of amino acids 26 to 397.

Human PAR-2 (without the signal sequence) (SEQ ID NO: 109)

IQGTNRSSKGRSLIGKVDGTSHVTGKGVTVETVFSVDEFSASVLTGKLTT

VFLPIVYTIVFVVGLPSNGMALWVFLFRTKKKHPAVIYMANLALADLLSV

IWFPLKIAYHIHGNNWIYGEALCNVLIGFFYGNMYCSILFMTCLSVQRYW

VIVNPMGHSRKKANIAIGISLAIWLLILLVTIPLYVVKQTIFIPALNITT

CHDVLPEQLLVGDMFNYFLSLAIGVFLFPAFLTASAYVLMIRMLRSSAMD

ENSEKKRKRAIKLIVTVLAMYLICFTPSNLLLVVHYFLIKSQGQSHVYAL

YIVALCLSTLNSCIDPFVYYFVSHDFRDHAKNALLCRSVRTVKQMQVSLT

SKKHSRKSSSYSSSSTTVKTSY

The above human PAR-2 sequence (SEQ ID NO: 28) represents a natural sequence in which serine (S) is present at position 21, asparagine (N) is present at position 30, arginine (R) is present at position 270, and threonine (T) is present at position 291. In some embodiments, a natural variant human PAR-2 sequence is contemplated in which position 21 is occupied by a phenylalanine (F). In some embodiments, a natural variant human PAR-2 sequence is contemplated in which position 30 is occupied by a serine (S). In some embodiments, a natural variant human PAR-2 sequence is contemplated in which position 270 is occupied by a glutamine (Q). In some embodiments, a natural variant human PAR-2 sequence is contemplated in which position 291 is occupied by an alanine (A).

In some embodiments it is contemplated that the above human PAR-2 sequence lacks its signal sequence. For example, a human PAR-2 sequence can comprise amino acids 26-397 of SEQ ID NO: 28.

In some embodiments it is contemplated that the above human PAR-2 sequence lacks its signal sequence (amino acids 1-25 of SEQ ID NO: 28) and the propeptide sequence (amino acids 26-36 of SEQ ID NO: 28), which can be removed for receptor activation. The "N-terminus of human PAR2" represents amino acids 1-71 of SEQ ID NO: 28.

Other features of human PAR-2, as shown in SEQ ID NO: 28, include an extracellular domain (ECD) 1 from about amino acid 138-149, ECD2 from about amino acid 212-235, ECD3 domain from about amino acid 318-323, transmembrane domain (TM) 1 from about amino acid 72-101, TM2 from about amino acid 109-137, TM3 from about amino acid 150-177, TM4 from about amino acid 184-212, TM5 from about amino acid 236-269, TM6 from about amino acid 278-317, and TM7 from about amino acid 324-347.

Cynomolgus monkey PAR-2 (UniProt ID No. E5FAJ7; SEQ ID NO: 30)

LGHLVLTHLLVALFGMGSWAAVNGIWVELPVVVKDLPEGWSLPSYLSVI

VALGNLGLLVVTLWRRLAPGKGERVPIQVVQVLSVVGTALLAPLWHHVA

PVAGQLHSVAFLTLALVLALACCTSNVTFLPFLSHLPPPFLRSFFLGQG

LSALLPCVLALVQGVGRLECSPAPTNGTSGPPLNFPERFPASTFFWALT

ALLVTSAAAFQGLLLLLPSLPSVTTGGAGPELPLGSPGAEEEEKEEEEA

LPLQEPPSQAAGTIPGPDPEAHQLFSAHGAFLLGLLAITSALTNGVLPA

VQSFSCLPYGRLAYHLAVVLGSAANPLACFLAMGVLCRSLAGLVGLSLL

GMLFGAYLMVLAILSPCPPLVGTTAGVVLVVLSWVLCLCVFSYVKVAAS

SLLHGGGRPALLAXGVAIQVGSLLGAGTMFPPTSIYHVFQSRKDCV

In some embodiments it is contemplated that the above cynomolgus monkey PAR-2 sequence lacks its signal sequence. For example, a cynomolgus monkey PAR-2 sequence can comprise amino acids 21-438 of SEQ ID NO: 31.

Cynomolgus monkey PAR-2 (without the signal sequence) (SEQ ID NO: 31)

AVNGIWVELPVVVKDLPEGWSLPSYLSVIVALGNLGLLVVTLWRRLAPG

KGERVPIQVVQVLSVVGTALLAPLWHHVAPVAGQLHSVAFLTLALVLAL

ACCTSNVTFLPFLSHLPPPFLRSFFLGQGLSALLPCVLALVQGVGRLEC

SPAPTNGTSGPPLNFPERFPASTFFWALTALLVTSAAAFQGLLLLLPSL

PSVTTGGAGPELPLGSPGAEEEEKEEEEALPLQEPPSQAAGTIPGPDPE

AHQLFSAHGAFLLGLLAITSALTNGVLPAVQSFSCLPYGRLAYHLAVVL

GSAANPLACFLAMGVLCRSLAGLVGLSLLGMLFGAYLMVLAILSPCPPL

VGTTAGVVLVVLSWVLCLCVFSYVKVAASSLLHGGGRPALLAXGVAIQV

GSLLGAGTMFPPTSIYHVFQSRKDCV

Rat PAR-2 (UniProt ID No. Q63645; SEQ ID NO: 32)

MRSLSLAWLLGGITLLAASASCNRTVNAPGPNSKGRSLIGRLDTPPPIT

GKGAPVEPGFSVDEFSASVLTGKLTTVFLPVIYIIVFVIGLPSNGMALW

VFFFRTKKKHPAVIYMANLALADLLSVIWFPLKISYHLHGNDWTYGDAL

CKVLIGFFYGNMYCSILFMTCLSVQRYWVIVNPMGHSRKRANIAVGVSL

AIWLLIFLVTIPLYVMRQTIYIPALNITTCHDVLPEEVLVGDMFSYFLS

LAIGVFLFPALLTASAYVLMIKTLRSSAMDEHSEKKRRRAIRLIITVLS

MYFICFAPSNVLLVVHYFLIKSQRQSHVYALYLVALCLSTLNSCIDPFV

YYFVSKDFRDQARNALLCRSVRTVKRMQISLTSNKFSRKSSSYSSSSTS

VKTSY

In some embodiments it is contemplated that the above rat PAR-2 sequence lacks its signal sequence. For example, a rat PAR-2 sequence can comprise amino acids 26-397 of SEQ ID NO: 32.

In some embodiments, an antibody or antigen-binding fragment thereof described herein binds to human PAR-2 (e.g., SEQ ID NO: 28 or amino acids 26-397 of SEQ ID NO: 28, or either of the foregoing sequences in which S or F is at position 21, N or S at position 30, R or Q at position 270, or T or A at position 291).

In some embodiments, an antibody or antigen-binding fragment thereof binds to human PAR-2 and cynomolgus monkey PAR-2 (e.g., SEQ ID NO: 30 or amino acids 21-438 of SEQ ID NO: 30). In some embodiments, an antibody or antigen-binding fragment thereof binds to human PAR-2 and rat PAR-2 (e.g., SEQ ID NO: 32 or amino acids 26-397 of SEQ ID NO: 32). In some embodiments, an antibody or antigen-binding fragment thereof binds to human PAR-2, cynomolgus monkey PAR-2, and rat PAR-2. In some embodiments, an antibody or antigen-binding fragment thereof binds to human PAR-2 but does not bind to rat PAR-2 (e.g., SEQ ID NO: 32 or amino acids 26-397 of SEQ ID NO: 32). In some embodiments, an antibody or antigen-binding fragment thereof binds to human PAR-2 and optionally to rat PAR-2. In some aspects, an antibody or antigen-binding fragment thereof binds to human PAR-2, cynomolgus monkey PAR-2, and optionally to rat PAR-2.

Particular antibodies that can be used in the methods disclosed herein are antibodies, (e.g., monoclonal antibodies, such as humanized antibodies) and antigen-binding fragments thereof which specifically bind to PAR-2, such as human, cynomolgus monkey, and rat PAR-2, having the CDR and/or variable region sequences of antibody 309-4e, P24E1102, P24E976, P24E1099, and/or P24E1103 constructed in Examples 1-4, as well as antibodies having at least 80% identity (e.g., at least about 85%, at least about 90%, at least about 95%, at least about 96%, at least about 97%, at least about 98%, at least about 99%, or about 100% identity) to their variable region or CDR sequences. The VH amino acid sequences of 309-4e, P24E1102, P24E976, P24E1099, and P24E1103 are set forth in SEQ ID NOs: 20, 21, 21, 21, and 21, respectively. The VL amino acid sequences of 309-4e, P24E1102, P24E976, P24E1099, and P24E1103 are set forth in SEQ ID NOs: NOs: 23, 24, 25, 26, and 27, respectively.

In some aspects, an antibody or antigen-binding fragment thereof described herein specifically binds to human PAR-2, wherein the antibody or antigen-binding fragment thereof comprises the heavy chain variable region (VH) complementarity determining region (CDR) 1, VH CDR2, VH CDR3 and light chain variable region (VL) CDR1, VL CDR2, and VL CDR3 sequences of SEQ ID NO: 1 (GFSLX$_1$X$_2$YX$_3$X$_4$X$_5$), SEQ ID NO: 2 (VIWGNX$_6$NX$_7$YYX$_8$), SEQ ID NO: 3 (WX$_9$GX$_{10}$KDX$_{11}$PFDY), SEQ ID NO: 4 (X$_{12}$ASQNX$_{13}$YKX$_{14}$LD), SEQ ID NO: 5 (X$_{15}$X$_{16}$ X$_{17}$X$_{18}$ X$_{19}$ X$_2$MT), and SEQ ID NO: 6 (X$_{21}$QH X$_{22}$ X$_{23}$GWT), respectively, wherein:

X$_1$=Asparagine(N) or Serine(S),
X$_2$=Serine(S) or Tyrosine(Y),
X$_3$=Glycine(G) or Alanine(A),
X$_4$=Valine(V), Glycine(G) or Isoleucine(I),
X$_5$=Isoleucine(I) or Serine(S),
X$_6$=Glycine(G) or Glutamine(Q),
X$_7$=Valine(V) or Threonine (T),
X$_8$=Asparagine(N), Alanine(A), Glycine(G), or Tyrosine (Y),
X$_9$=Arginine(R) or Lysine(K),
X$_{10}$=Tyrosine(Y), Tryptophan(W), or Phenylalanine(F),
X$_{11}$=Tyrosine(Y) or Histidine(H),
X$_{12}$=Lysine(K) or Arginine(R),
X$_{13}$=Isoleucine(I) or Valine(V),
X$_{14}$=Tyrosine(Y), Tryptophan(W), or Phenylalanine(F), $X_{15}$=Asparagine(N) or Aspartic acid(D),
$X_{16}$=Threonine(T) or Alanine(A),
$X_{17}$=Asparagine(N), Serine(S), or Tyrosine(Y),
$X_{18}$=Serine(S), Threonine(T), or Asparagine(N),
$X_{19}$=Leucine(L) or Arginine(R),
$X_{20}$=Histidine(H) or Alanine(A),
$X_{21}$=Leucine(L) or Glutamine(Q),
$X_{22}$=Asparagine(N), Glycine(G), or Histidine(H), and
$X_{23}$=Serine(S) or Histidine(H).

In some embodiments, $X_1$=Serine(S), $X_2$=Serine(S), $X_3$=Alanine(A), $X_3$=Isoleucine(I), $X_5$=Serine(S), $X_6$=Glutamine(Q), $X_7$=Valine(V), $X_8$=Alanine(A), $X_9$=Lysine(K), $X_{10}$=Tyrosine(Y), $X_{11}$=Tyrosine(Y), $X_{12}$=Arginine(R), $X_{13}$=Valine(V), $X_{14}$=Tryptophan(W), $X_{15}$=Asparagine(N), $X_{16}$=Alanine(A), $X_{17}$=Asparagine(N), $X_{18}$=Threonine(T), $X_{19}$=Arginine(R), $X_{20}$=Alanine(A), $X_{21}$=Glutamine(Q), $X_{22}$=Histidine(H), and $X_{23}$=Serine(S).

In some embodiments, an antibody or antigen-binding fragment thereof described herein binds to human PAR-2 and comprises the six CDRs of an antibody listed in Table 2 (i.e., the three VH CDRs and the three VL CDRs of the same antibody listed in Table 2).

The following VH CDR residues were used to define the VH CDRs in Table 2: Heavy chain CDR1 as per AbM nomenclature (Residues H26, H27, H28, H29, H30, H31, H32, H33, H34 and H35 as defined by the Kabat numbering scheme). Heavy chain CDR2 as per Kabat but excluding the last 5 amino acids (Residues H50, H51, H52, H53, H54, H55, H56, H57, H58, H59 and H60 as defined by the Kabat numbering scheme). Heavy chain CDR3 as per Kabat (Residues H95, H96, H97, H98, H99, H100, H100A, H100B, H100C, H101 and H102 as defined by the Kabat numbering scheme). The following VL CDR residues were used to define the VL CDRs in Table 2: Light chain CDRs as per Kabat (Residues L24, L25, L26, L27, L28, L29, L30, L31, L32, L33 and L34 for CDR1; residues L50, L51, L52, L53, L54, L55 and L56 for CDR2; and residues L89, L90, L91, L92, L93, L94, L96 and L97 for CDR3 as defined by the Kabat numbering scheme).

In some aspects, an antibody or antigen-binding fragment thereof described herein binds to human PAR-2 and comprises the VH and the VL of an antibody listed in Table 3 (i.e., the VH and the VL of the same antibody listed in Table 3).

TABLE 2

Variable Heavy Chain CDR (VH CDR) and Variable Light Chain CDR (VL CDR) Amino Acid Sequences

| Antibody | VH-CDR1<br>VH-CDR2<br>VH-CDR3 | VL-CDR1<br>VL-CDR2<br>VL-CDR3 |
|---|---|---|
| Anti-PAR-2<br>("309")<br>(Parental murine antibody) | GFSLNSYGVI (SEQ ID NO: 7)<br>VIWGNGNTYYN (SEQ ID NO: 8)<br>WRGYKDYPFDY (SEQ ID NO: 9) | KASQNIYKYLD (SEQ ID NO: 13)<br>NTNSLHT (SEQ ID NO: 14)<br>LQHNSGWT (SEQ ID NO: 15) |
| Anti-PAR-2<br>("309-4e") | GFSLNSYGVI (SEQ ID NO: 7)<br>VIWGNGNTYYN (SEQ ID NO: 8)<br>WRGYKDYPFDY (SEQ ID NO: 9) | KASQNIYKYLD (SEQ ID NO: 13)<br>NTNSLHT (SEQ ID NO: 14)<br>LQHNSGWT (SEQ ID NO: 15) |
| Anti-PAR-2<br>("P24E1102") | GFSLSSYAIS (SEQ ID NO: 10)<br>VIWGNQNVYYA (SEQ ID NO: 11)<br>WKGYKDYPFDY (SEQ ID NO: 12) | RASQNVYKWLD (SEQ ID NO: 16)<br>NANTRAT (SEQ ID NO: 17)<br>QQHHSGWT (SEQ ID NO: 18) |
| Anti-PAR-2<br>("P24E976") | GFSLSSYAIS (SEQ ID NO: 10)<br>VIWGNQNVYYA (SEQ ID NO: 11)<br>WKGYKDYPFDY (SEQ ID NO: 12) | RASQNVYKWLD (SEQ ID NO: 16)<br>NAYSRAT (SEQ ID NO: 19)<br>QQHHSGWT (SEQ ID NO: 18) |
| Anti-PAR-2<br>("P24E1099") | GFSLSSYAIS (SEQ ID NO: 10)<br>VIWGNQNVYYA (SEQ ID NO: 11)<br>WKGYKDYPFDY (SEQ ID NO: 12) | RASQNVYKWLD (SEQ ID NO: 16)<br>NANSRAT (SEQ ID NO: 29)<br>QQHHSGWT (SEQ ID NO: 18) |
| Anti-PAR-2<br>("P24E1103") | GFSLSSYAIS (SEQ ID NO: 10)<br>VIWGNQNVYYA (SEQ ID NO: 11)<br>WKGYKDYPFDY (SEQ ID NO: 12) | RASQNVYKWLD (SEQ ID NO: 16)<br>NANNRAT (SEQ ID NO: 22)<br>QQHHSGWT (SEQ ID NO: 18) |

TABLE 3

Variable Heavy Chain (VH) and Variable Light Chain (VL) Amino Acid Sequences

| Antibody | VH Amino Acid Sequence (SEQ ID NO) | VL Amino Acid Sequence (SEQ ID NO) |
|---|---|---|
| Anti-PAR-2<br>("309")<br>(Parental murine antibody) | QVQLKESGPGLVQPSQTLSLTCT<br>VSGFSLNSYGVIWARQPPGKGLD<br>WMGVIWGNGNTYYNSDLKSRLS<br>ISRDTSKSQVFLKMNNLQAEDTA<br>LYFCARWRGYKDYPFDYWGQG<br>VMVTVSS (SEQ ID NO: 116) | DIQMTQSPSFLSASVGDRVTFNC<br>KASQNIYKYLDWYQQKLGEAPK<br>LLIYNTNSLHTGIPSRFSGSGFGT<br>DFTLTISSLQPEDVATYFCLQHNS<br>GWTFGGGTKLELR (SEQ ID NO: 117) |

TABLE 3-continued

Variable Heavy Chain (VH) and Variable Light Chain (VL) Amino Acid Sequences

| Antibody | VH Amino Acid Sequence (SEQ ID NO) | VL Amino Acid Sequence (SEQ ID NO) |
|---|---|---|
| Anti-PAR-2 ("309-4e") | QVQLVQSGAEVKKPGSSVKVSC KASGFSLNSYGVIWVRQAPGQG LEWMGVIWGNGNTYYNQKFQG RVTITADESTSTAYMELSSLRSED TAVYYCARWRGYKDYPFDYWG QGTLVTVSS (SEQ ID NO: 20) | EIVLTQSPATLSLSPGERATLSCK ASQNIYKYLDWYQQKPGQAPRL LIYNTNSLHTGIPARFSGSGSGRD FTLTISSLEPEDFAVYYCLQHNSG WTFGGGTKVEIK (SEQ ID NO: 23) |
| Anti-PAR-2 ("P24EH02") | QVQLVQSGAEVKKPGSSVKVSC KASGFSLSSYAISWVRQAPGQGL EWMGVIWGNQNVYYAQKFQGR VTITADESTSTAYMELSSLRSEDT AVYYCARWKGYKDYPFDYWGQ GTLVTVSS (SEQ ID NO: 21) | EIVLTQSPATLSLSPGERATLSCR ASQNVYKWLDWYQQKPGQAPR LLIYNANTRATGIPARFSGSGSGR DFTLTISSLEPEDFAVYYCQQHHS GWTFGGGTKVEIK (SEQ ID NO: 24) |
| Anti-PAR-2 ("P24E976") | QVQLVQSGAEVKKPGSSVKVSC KASGFSLSSYAISWVRQAPGQGL EWMGVIWGNQNVYYAQKFQGR VTITADESTSTAYMELSSLRSEDT AVYYCARWKGYKDYPFDYWGQ GTLVTVSS (SEQ ID NO: 21) | EIVLTQSPATLSLSPGERATLSCR ASQNVYKWLDWYQQKPGQAPR LLIYNAYSRATGIPARFSGSGSGR DFTLTISSLEPEDFAVYYCQQHHS GWTFGGGTKVEIK (SEQ ID NO: 25) |
| Anti-PAR-2 ("P24E1099") | QVQLVQSGAEVKKPGSSVKVSC KASGFSLSSYAISWVRQAPGQGL EWMGVIWGNQNVYYAQKFQGR VTITADESTSTAYMELSSLRSEDT AVYYCARWKGYKDYPFDYWGQ GTLVTVSS (SEQ ID NO: 21) | EIVLTQSPATLSLSPGERATLSCR ASQNVYKWLDWYQQKPGQAPR LLIYNANSRATGIPARFSGSGSGR DFTLTISSLEPEDFAVYYCQQHHS GWTFGGGTKVEIK (SEQ ID NO: 26) |
| Anti-PAR-2 ("P24E1103") | QVQLVQSGAEVKKPGSSVKVSC KASGFSLSSYAISWVRQAPGQGL EWMGVIWGNQNVYYAQKFQGR VTITADESTSTAYMELSSLRSEDT AVYYCARWKGYKDYPFDYWGQ GTLVTVSS (SEQ ID NO: 21) | EIVLTQSPATLSLSPGERATLSCR ASQNVYKWLDWYQQKPGQAPR LLIYNANNRATGIPARFSGSGSGR DFTLTISSLEPEDFAVYYCQQHHS GWTFGGGTKVEIK (SEQ ID NO: 27) |

Also provided is an isolated anti-PAR-2 antibody, or an antigen-binding fragment thereof, comprising heavy and light chain variable regions, (i) wherein the heavy chain variable region comprises the amino acid sequence of SEQ ID NO: 20 and wherein the light chain variable region comprises the amino acid sequence of SEQ ID NO: 23; (ii) wherein the heavy chain variable region comprises the amino acid sequence of SEQ ID NO: 21 and wherein the light chain variable region comprises the amino acid sequence of SEQ ID NO: 24; (iii) wherein the heavy chain variable region comprises the amino acid sequence of SEQ ID NO: 21 and wherein the light chain variable region comprises the amino acid sequence of SEQ ID NO: 5; (iv) wherein the heavy chain variable region comprises the amino acid sequence of SEQ ID NO: 21 and wherein the light chain variable region comprises the amino acid sequence of SEQ ID NO: 26; or (v) wherein the heavy chain variable region comprises the amino acid sequence of SEQ ID NO: 21 and wherein the light chain variable region comprises the amino acid sequence of SEQ ID NO: 27.

Provided herein is an isolated anti-PAR-2 antibody, or an antigen-binding fragment thereof, comprising a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 20 or 21, and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 23, 24, 25, 26, or 27.

In some aspects, the disclosure provides an isolated anti-PAR-2 antibody, or an antigen-binding fragment thereof, comprising:
(a) heavy and light chain variable region sequences comprising SEQ ID NOs: 20 and 23, respectively;
(b) heavy and light chain variable region sequences comprising SEQ ID NOs: 21 and 24, respectively;
(c) heavy and light chain variable region sequences comprising SEQ ID NOs: 21 and 25, respectively;
(d) heavy and light chain variable region sequences comprising SEQ ID NOs: 21 and 26, respectively; or
(e) heavy and light chain variable region sequences comprising SEQ ID NOs: 21 and 27, respectively.

The amino acid sequences of the VH CDR1, CDR2, and CDR3 for antibody P24E1102, P24E976, P24E1099, and P24E1103 are set forth in SEQ ID NOs: 10, 11, and 12, respectively. The amino acid sequences of the VH CDR1, CDR2, and CDR3 for antibody 309-4e are set forth in SEQ ID NOs: 7, 8, and 9, respectively. The amino acid sequences of the VL CDR1, CDR2, and CDR3 for antibody P24E1102 are set forth in SEQ ID NOs: 16, 17, and 18, respectively. The amino acid sequences of the VL CDR1, CDR2, and CDR3 for antibody P24E976 are set forth in SEQ ID NOs: 16, 19, and 18, respectively. The amino acid sequences of the VL CDR1, CDR2, and CDR3 for antibody P24E1099 are set forth in SEQ ID NOs: 16, 20, and 18, respectively. The amino acid sequences of the VL CDR1, CDR2, and CDR3 for antibody P24E1103 are set forth in SEQ ID NOs: 16, 21, and 18, respectively. The amino acid sequences of the VL CDR1, CDR2, and CDR3 for antibody 309-4e are set forth in SEQ ID NOs: 13, 14, and 15, respectively.

In some aspects, the anti-PAR-2 antibody or antigen-binding fragment thereof, which specifically binds to human PAR-2, comprises:
(a) a VH CDR1 comprising the amino acid sequence of SEQ ID NO: 10;
(b) a VH CDR2 comprising the amino acid sequence of SEQ ID NO: 11; (c) a VH CDR3 comprising the amino acid sequence of SEQ ID NO: 12; (d) a VL CDR1 comprising the amino acid sequence of SEQ ID NO: 16; (e) a VL CDR2 comprising the amino acid sequence of SEQ ID NO: 17; and (f) a VL CDR3 comprising the amino acid sequence of SEQ ID NO: 18.

In some aspects, the anti-PAR-2 antibody or antigen-binding fragment thereof, which specifically binds to human PAR-2, comprises:
(a) a VH CDR1 comprising the amino acid sequence of SEQ ID NO: 10;
(b) a VH CDR2 comprising the amino acid sequence of SEQ ID NO: 11;
(c) a VH CDR3 comprising the amino acid sequence of SEQ ID NO: 12;
(d) a VL CDR1 comprising the amino acid sequence of SEQ ID NO: 16;
(e) a VL CDR2 comprising the amino acid sequence of SEQ ID NO: 19; and
(f) a VL CDR3 comprising the amino acid sequence of SEQ ID NO: 18.

In some aspects, the anti-PAR-2 antibody or antigen-binding fragment thereof, which specifically binds to human PAR-2, comprises:
(a) a VH CDR1 comprising the amino acid sequence of SEQ ID NO: 10;
(b) a VH CDR2 comprising the amino acid sequence of SEQ ID NO: 11;
(c) a VH CDR3 comprising the amino acid sequence of SEQ ID NO: 12;
(d) a VL CDR1 comprising the amino acid sequence of SEQ ID NO: 16;
(e) a VL CDR2 comprising the amino acid sequence of SEQ ID NO: 29; and
(f) a VL CDR3 comprising the amino acid sequence of SEQ ID NO: 18.

In some aspects, the anti-PAR-2 antibody or antigen-binding fragment thereof, which specifically binds to human PAR-2, comprises:
(a) a VH CDR1 comprising the amino acid sequence of SEQ ID NO: 10;
(b) a VH CDR2 comprising the amino acid sequence of SEQ ID NO: 11;
(c) a VH CDR3 comprising the amino acid sequence of SEQ ID NO: 12;
(d) a VL CDR1 comprising the amino acid sequence of SEQ ID NO: 16;
(e) a VL CDR2 comprising the amino acid sequence of SEQ ID NO: 22; and
(f) a VL CDR3 comprising the amino acid sequence of SEQ ID NO: 18.

In some aspects, the anti-PAR-2 antibody or antigen-binding fragment thereof, which specifically binds to human PAR-2, comprises:
(a) a VH CDR1 comprising the amino acid sequence of SEQ ID NO: 7;
(b) a VH CDR2 comprising the amino acid sequence of SEQ ID NO: 8;
(c) a VH CDR3 comprising the amino acid sequence of SEQ ID NO: 9;
(d) a VL CDR1 comprising the amino acid sequence of SEQ ID NO: 13;
(e) a VL CDR2 comprising the amino acid sequence of SEQ ID NO: 14; and
(f) a VL CDR3 comprising the amino acid sequence of SEQ ID NO: 15.

In some aspects, provided herein are antibodies that comprise a heavy chain (HC) and a light chain (LC). With respect to the heavy chain, in some aspects, the heavy chain of an antibody described herein can be an alpha (α), delta (δ), epsilon (ε), gamma (γ) or mu (μ) heavy chain. In some aspects, the heavy chain of an antibody described can comprise a human alpha (α), delta (δ), epsilon (ε), gamma (γ) or mu (μ) heavy chain. In some aspects, an antibody described herein, which specifically binds to human PAR-2, comprises a heavy chain wherein the amino acid sequence of the VH domain comprises an amino acid sequence set forth in Table 3 and wherein the constant region of the heavy chain comprises the amino acid sequence of a human gamma (γ) heavy chain constant region. In some aspects, an antibody described herein, which specifically binds to human PAR-2, comprises a heavy chain wherein the amino acid sequence of the VH domain comprises an amino acid sequence set forth in Table 3 and wherein the constant region of the heavy chain comprises the amino acid sequence of an IgG1 heavy chain constant region. In some aspects, an antibody described herein, which specifically binds to human PAR-2, comprises a heavy chain wherein the amino acid sequence of the VH domain comprises an amino acid sequence set forth in Table 3 and wherein the constant region of the heavy chain comprises the amino acid sequence of an IgG2 (e.g., IgG2a or IgG2b) heavy chain constant region. In some aspects, an antibody described herein, which specifically binds to human PAR-2, comprises a heavy chain wherein the amino acid sequence of the VH domain comprises an amino acid sequence set forth in Table 3 and wherein the constant region of the heavy chain comprises the amino acid sequence of an IgG4 heavy chain constant region. In some aspects, an antibody described herein, which specifically binds to human PAR-2, comprises a heavy chain wherein the amino acid sequence of the VH domain comprises a sequence set forth in Table 3, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra, each of which is incorporated herein by reference in its entirety.

In some embodiments, an antibody described herein, which specifically binds to human PAR-2, can comprise modifications that modulate serum half-life and biodistribution, including without limitation, modifications that modulate the antibody's interaction with the neonatal Fc receptor (FcRn), a receptor with a key role in protecting IgG from catabolism, and maintaining high serum antibody concentration. Serum half-life modulating modifications can occur in the Fc region of IgG1, IgG2, or IgG4, including the triple substitution of M252Y/S254T/T256E (numbering according to the EU numbering system (see e.g., Edelman, G M et al., *Proc. Natl. Acad., USA* 63:78-85 (1969)), as described in U.S. Pat. No. 7,083,784. Other substitutions can occur at positions 250 and 428, see e.g., U.S. Pat. No. 7,217,797, as well as at positions 307, 380 and 434, see e.g., Int'l Publ. No. WO 00/042072. Examples of constant domain amino acid substitutions which modulate binding to Fc receptors and subsequent function mediated by these receptors, including FcRn binding and serum half-life, are described in U.S. Publ. Nos. 2009/0142340, 2009/0068175, and 2009/0092599.

Antibodies of any class can have the heavy chain C-terminal lysine omitted or removed to reduce heterogeneity (ΔK). The substitution of S228P (EU numbering) in the human IgG4 can stabilize antibody Fab-arm exchange in vivo (see e.g., Labrin et al., *Nature Biotechnol.* 27(8)767-773 (2009)), and this substitution can be present at the same time as M252Y/S254T/T256E and/or ΔK modifications.

Human heavy chain IgG4 constant regions that can be used in the disclosure are selected from the group consisting of a wild-type human IgG4 (SEQ ID NO: 33), human IgG4 (ΔK), human IgG4 S228P, human IgG4 S228P (ΔK), human IgG4 228P/252Y/254T/256E, human IgG4 228P/252Y/254T/256E (ΔK)), human IgG4 252Y/254T/256E, and human IgG4 252Y/254T/256E (ΔK). Human heavy chain IgG4 constant region (UniProt ID No. P01861; SEQ ID NO: 33)

```
                                           (SEQ ID NO: 33)
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPSCP APEFLGGPSV

FLFPPKPKDT LMISRTPEVT CVVVDVSQED PEVQFNWYVD

GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLGK
```

In some embodiments, an anti-human PAR-2 antibody contains a human IgG4 constant region, wherein the IgG4 constant region comprises an amino acid substitution corresponding to S228P (by EU numbering). In some embodiments, an anti-human PAR-2 antibody contains a human IgG4 constant region, wherein the IgG4 constant region comprises terminal lysine deletion (K447Δ). In some embodiments, an anti-human PAR-2 antibody contains a human IgG4 constant region, wherein the IgG4 constant region comprises a substitution corresponding to S228P (by EU numbering) and terminal lysine deletion (K447Δ) (e.g., as provided in SEQ ID NO: 34)

```
                                          (SEQ ID NO: 34))
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLG
```

In some aspects, an anti-human PAR-2 antibody contains a human IgG1 constant region. Human heavy chain IgG1 constant regions used in the disclosure are selected from the group consisting of a wild-type human IgG1 (SEQ ID NO: 35), human IgG1 (ΔK), human IgG1 252Y/254T/256E, human IgG1 252Y/254T/256E (ΔK), human IgG1 L235A/G237A, human IgG1 L235A/G237A (ΔK), human IgG1 L234A/L235A/G237A, and human IgG1 L234A/L235A/G237A (ΔK). Human heavy chain IgG1 constant region (UniProt ID No. P01857; SEQ ID NO: 35):

```
                                           (SEQ ID NO: 35)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK
```

In some embodiments, an anti-human PAR-2 antibody contains a human IgG2 constant region. Human heavy chain IgG2 constant regions that can be used in the disclosure are selected from the group consisting of a wild-type human IgG2 (SEQ ID NO: 36), human IgG2 (ΔK), and human IgG2 A330S/P331S. Human heavy chain IgG2 constant region (UniProt ID No. P01859; SEQ ID NO: 36):

```
                                           (SEQ ID NO: 36)
ASTKGPSVFPLAPCSRSTSESTAALGCLVKDYFPEPVTVSWNS

GALTSGVHTFPAVLQSSGLYSLSSVVTVPSSNFGTQTYTCNVD

HKPSNTKVDKTVERKCCVECPPCP APPVAGPSVF

LFPPKPKDTL MISRTPEVTC VVVDVSHEDP

EVQFNWYVDGVEVHNAKTKP REEQFNSTFR

VVSVLTVVHQDWLNGKEYKCKVSNKGLPAP

IEKTISKTKGQPREPQVYTLPPSREEMTKNQVSLTCLVKG

FYPSDISVEWESNGQPENNYKTTPPMLDSDGSFFLYSKLTVDK

SRWQQGNVFSCSVMHEALHNHYTQKSLSLSPGK
```

With respect to the light chain, in some aspects, the light chain of an antibody described herein is a kappa light chain.

In some aspects, an antibody described herein, which specifically binds to a human PAR-2, comprises a light chain wherein the amino acid sequence of the VL domain comprises a sequence set forth in Table 3, and wherein the constant region of the light chain comprises the amino acid sequence of a human kappa light chain constant region. In some embodiments, an antibody described herein, which specifically binds to human PAR-2, comprises a light chain wherein the amino acid sequence of the VL domain comprises a sequence set forth in Table 3, and wherein the constant region of the light chain comprises the amino acid sequence of a human kappa light chain constant region (e.g., as provided in SEQ ID NO: 37) Non-limiting examples of human constant region sequences have been described in the art, e.g., see U.S. Pat. No. 5,693,780 and Kabat E A et al., (1991) supra.

(SEQ ID NO: 37)
RTVAAPSVFIFPPSDEQLKSGTASVVCLLNNFYPREAKVQWKV

DNALQSGNSQESVTEQDSKDSTYSLSSTLTLSKADYEKHKVYA

CEVTHQGLSSPVTKSFNRGEC

In some aspects, an antibody described herein, which specifically binds to human PAR-2 comprises a VH domain and a VL domain comprising the amino acid sequence of any of the anti-human PAR-2 antibodies described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In some aspects, an antibody described herein, which specifically binds to human PAR-2 comprises a VH domain and a VL domain comprising the amino acid sequences of any of the anti-human PAR-2 antibodies described herein, and wherein the constant regions comprise the amino acid sequences of the constant regions of an IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule. In some aspects, the constant regions comprise the amino acid sequences of the constant regions of a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule.

Non-limiting examples of human constant regions are described in the art, e.g., see Kabat E A et al., (1991) supra.

II(a). Exemplary Fc Domains

The constant region can be manipulated, e.g., by recombinant technology, to eliminate one or more effector functions. An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as antibody dependent cellular cytotoxicity (ADCC) and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

For some therapeutic uses it can be an advantage to reduce or minimize one or more effector functions. Effector functions of an antibody can be reduced or avoided by different approaches. Effector functions of an antibody can be reduced or avoided by using antibody fragments lacking the Fc region (e.g., such as a Fab, F(ab')$_2$, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). See, e.g., U.S. Pub. No. 20120100140. Another approach is to employ Fc regions from an IgG subclass that have reduced effector function. For example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. Vidarsson G. et al. *Front Immunol.* 5:520 (published online Oct. 20, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al. *J Immunol.* 191:4769-4777 (2013)), or an Fc region with an amino acid substitution and/or addition and/or deletion that results in altered Fc effector functions, e.g., reduced or no Fc functions. Such Fc regions with the amino acid substitutions and/or additions and/or deletions are known in the art. See, e.g., U.S. Pub. No. 20120100140 and U.S. and PCT applications cited therein, An et al., *mAbs* 1(6):572-579 (2009), Wang et al., *Protein Cell* 9(1):63-73 (2018), Tam et al., Antibodies 6(3):12 (2017), Vafa et al, *Methods* 65:114-126 (2014), and Dumet et al, *mAbs* 11(8): 1341-1350 (2019), the disclosures of which are incorporated by reference to their entirety. For other uses, it may be an advantage to maintain or enhance one or more effector functions, for example where it may be desirable to kill cells such as cancer cells expressing PAR-2 on their cell surface.

In some aspects, an anti-PAR-2 antibody, and in particular, an anti-human PAR-2 antibody as provided herein, can comprise an Fc domain. In some aspects, the Fc domain is a human IgG1, IgG2, IgG3, and/or IgG4 isotype.

In certain embodiments, the Fc domain has an IgG1 isotype. In some aspects, an anti-PAR-2 antibody contains a murine IgG1 Fc domain. In some aspects, an anti-human PAR-2 antibody contains a human IgG1 Fc domain (hIgG1), e.g., as provided in SEQ ID NO: 38.

(SEQ ID NO: 38)
EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK

Human IgG1 Fc domain (without C-terminal lysine residue (ΔK); SEQ ID NO: 39)

```
                                      (SEQ ID NO: 39)
EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPG
```

In some embodiments, the human IgG1 Fc domain of an anti-human PAR-2 antibody binds an activating Fc receptor. In certain aspects, the activating Fc receptor is selected from any one or more of FcγRI, FcγRIIa and IIc, and FcγRIIIa and IIIb.

In some embodiments, the human IgG1 Fc domain of an anti-human PAR-2 antibody does not bind or has reduced binding to FcγRIII(CD16) and/or C1q. In some embodiments, the human IgG1 Fc domain of an anti-human PAR-2 antibody has reduced antibody-dependent cellular cytotoxicity (ADCC) and/or complement binding activity, respectively, compared to a wild-type human IgG1 Fc domain. The above effects can be achieved by certain amino acid modifications, e.g., the "NSLF" substitutions, in which a human IgG1 Fc domain contains the amino acid substitutions N325S and L328F (by EU numbering of the IgG1 Fc domain), as shown, e.g., in SEQ ID NO: 40. In another aspect, the human IgG1 Fc domain comprises an amino acid substitution corresponding to K322A (EU numbering), e.g., as provided in SEQ ID NO: 41.

```
                                      (SEQ ID NO: 40)
EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSSKAFPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK
```

```
                                      (SEQ ID NO: 41)
EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCAVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK
```

Exemplary modifications to the human IgG1 Fc domain are listed below in Table 4.

TABLE 4

Exemplary modifications to the human IgG1 Fc domain Substitution(s) (EU numbering scheme)

| |
| --- |
| N325S and L328F ("NSLF") |
| S267E and L328F ("SELF") |

TABLE 4-continued

Exemplary modifications to the human IgG1 Fc domain Substitution(s) (EU numbering scheme)

| |
| --- |
| P331S ("PS") |
| P331S and E430G ("PSEG") |
| K322A |
| L235E (reduces FcγR1 binding) |
| N297A (aglycosylation substitution) |
| L234A and L235A ("LALA") |
| L235A and G237A ("LAGA") |
| L234A and L235A and P329G (see for example US8969526) |
| L234A, L235A, and P331S ("LALAPS") (Substantially abolishes Fc binding to FcR) |

In certain aspects of an anti-PAR-2 antibody provided herein, the Fc domain has an IgG2 isotype. In some embodiments, an anti-human PAR-2 antibody contains a human IgG2 Fc domain (hIgG2). In some embodiments, the human IgG2 Fc domain of an anti-human PAR-2 antibody binds an activating Fc receptor. In certain embodiments, the activating Fc receptor is selected from any one or more of FcγRI, FcγRIIa and IIc, and FcγRIIIa and IIIb.

In certain aspects of an anti-PAR-2 antibody provided herein, the Fc domain has an IgG4 isotype. In some embodiments, an anti-human PAR-2 antibody contains a human IgG4 Fc domain (hIgG4), e.g., as provided in SEQ ID NO: 42. In some embodiments, the human IgG4 Fc region of the anti-human PAR-2 antibody binds an activating Fc receptor. In certain embodiments, the activating Fc receptor is selected from any one or more of FcγRI, FcγRIIa and IIc, and FcγRIIIa and IIIb. In certain embodiments, the human IgG4 Fc region comprises an amino acid substitution corresponding to S228P (by EU numbering), e.g., as provided in SEQ ID NO: 43. In certain embodiments, the human IgG4 Fc region comprises an amino acid substitution corresponding to S228P (by EU numbering) and a deletion of the terminal lysine residue (K447Δ), e.g., as provided in SEQ ID NO: 44. In certain embodiments the human IgG4 Fc region comprises an S228P substitution and an L235E substitution (to reduce FcγR interactions). In certain embodiments the human IgG4 Fc comprises an S228P substitution, an L235E substitution and a deletion of the terminal lysine residue (K447Δ).

Human IgG4 Fc domain (hIgG4)

```
                                      (SEQ ID NO: 42)
ESKYGPPCPSCPAPEFLGGPSVFLFPPKPKDTLMISRTPEVTC

VVVDVSQEDPEVQFNWYVDGVEVHNAKTKPREEQFNSTYRVVS

VLTVLHQDWLNGKEYKCKVSNKGLPSSIEKTISKAKGQPREPQ

VYTLPPSQEEMTKNQVSLTCLVKGFYPSDIAVEWESNGQPENN

YKTTPPVLDSDGSFFLYSRLTVDKSRWQEGNVFSCSVMHEALH

NHYTQKSLSLSLGK
```

Human IgG4 Fc domain with S228P

```
                                      (SEQ ID NO: 43)
ESKYGPPCPPCPAPEFLGGPSVFLFPPKPKDTLMISRTPEVTC

VVVDVSQEDPEVQFNWYVDGVEVHNAKTKPREEQFNSTYRVVS

VLTVLHQDWLNGKEYKCKVSNKGLPSSIEKTISKAKGQPREPQ

VYTLPPSQEEMTKNQVSLTCLVKGFYPSDIAVEWESNGQPENN
```

-continued

YKTTPPVLDSGSFFLYSRLTVDKSRWQEGNVFSCSVMHEALH

NHYTQKSLSLSLGK

Human IgG4 Fc domain with S228P and K447Δ

(SEQ ID NO: 44)
ESKYGPPCPPCPAPEFLGGPSVFLFPPKPKDTLMISRTPEVTC

VVVDVSQEDPEVQFNWYVDGVEVHNAKTKPREEQFNSTYRVVS

VLTVLHQDWLNGKEYKCKVSNKGLPSSIEKTISKAKGQPREPQ

VYTLPPSQEEMTKNQVSLTCLVKGFYPSDIAVEWESNGQPENN

YKTTPPVLDSGSFFLYSRLTVDKSRWQEGNVFSCSVMHEALH

NHYTQKSLSLSLG

In some aspects, any of the constant region mutations or modifications described herein can be introduced into one or both heavy chain constant regions of an antibody or antigen-binding fragment thereof described herein having two heavy chain constant regions.

In some embodiments, an antibody or antigen-binding fragment thereof described herein, which specifically binds to human PAR-2, comprises a heavy chain and a light chain, wherein (i) the heavy chain comprises a VH domain comprising the VH CDR1, VH CDR2, and VH CDR3 amino acid sequences of an antibody listed in Table 2 (e.g., SEQ ID NOs: 10, 11, and 12, respectively); (ii) the light chain comprises a VL domain comprising the VL CDR1, VL CDR2, and VL CDR3 amino acid sequences of the same antibody listed in Table 2 (e.g., SEQ ID NOs: 16, 17, and 18, respectively); (iii) the heavy chain further comprises a constant heavy chain domain comprising the amino acid sequence of the constant domain of a human IgG4 heavy chain or the amino acid sequence of the constant domain of a human IgG4 heavy chain comprising an amino acid substitution corresponding to S228P (by EU numbering) and terminal lysine deletion (K447Δ); and (iv) the light chain further comprises a constant light chain domain comprising the amino acid sequence of the constant domain of a human kappa light chain.

In some embodiments, an antibody or antigen-binding fragment thereof described herein, which specifically binds to human PAR-2, comprises a heavy chain and a light chain, wherein (i) the heavy chain comprises a VH domain comprising the amino acid sequence of an antibody listed in Table 3 (e.g., SEQ ID NO: 21); (ii) the light chain comprises a VL domain comprising the amino acid sequence of the same antibody listed in Table 3 (e.g., SEQ ID NO: 24); (iii) the heavy chain further comprises a constant heavy chain domain comprising the amino acid sequence of the constant domain of a human IgG4 heavy chain or the amino acid sequence of the constant domain of a human IgG4 heavy chain comprising an amino acid substitution corresponding to S228P (by EU numbering) and terminal lysine deletion (K447Δ); and (iv) the light chain further comprises a constant light chain domain comprising the amino acid sequence of the constant domain of a human kappa light chain.

II(b). Anti-PAR-2 Antibody Activities

An antibody or antigen-binding fragment thereof described herein, which specifically binds to human PAR-2 can block the ligand binding site on PAR-2. Blocking binding of human PAR-2 to ligand reduces signaling by PAR-2. PAR-2 signals via G proteins and β-arrestin. PAR-2 signals via a variety of Gα proteins, most notably $G\alpha_q$, $G\alpha_i$ and $G\alpha_{12/13}$. These G proteins can activate signaling via multiple pathways including ERK, NF-κB, cAMP and p85/p110. Rothmeier, A. S. and Ruf, W., *Seminars in Immunopathology*, 34:133-149 (2012). Recruitment of β-arrestin both terminates G protein-mediated signaling and initiates new signaling pathways. Nichols, H. L. et al., *Proc Natl Acad Sci USA*, 109:16660-16665 (2012). β-arrestin can activate signaling via Raf and ERK, as well as triggering actin rearrangement and hence influencing cell motility. Pal, K. et al., *J Biol Chem*, 288:3265-3274 (2013).

In some aspects, an antibody or antigen-binding fragment thereof described herein, which specifically binds to human PAR-2, (a) blocks the interaction of a PAR-2 activating ligand with an extracellular domain of PAR-2, and/or (b) blocks PAR-2 activation by a PAR-2 activating ligand, and does not bind to amino acids 59-63 of the N-terminus of human PAR-2. Such a PAR-2 activating ligand can include, without limitation, a PAR-2 tethered ligand (in cis or trans); a PAR-1 tethered ligand; or a soluble ligand (e.g., a synthetic soluble PAR-2 activating ligand such as SLIGKV (SEQ ID NO: 45), SLIGRL (SEQ ID NO: 46), or 2-Furoyl-Leu-Ile-Gly-Arg-Leu-Orn-NH2 trifluoroacetate salt (2-furoyl-LI-GRLO). Different proteases (e.g., serine proteases including, trypsin, tryptase, tissue factor, neutrophil elastase and matriptase, as well as cysteine proteases including cathepsin S, papain, and Der p) can reveal different PAR-2 tethered ligands that can bind and activate PAR-2. Soluble PAR-2 and PAR-1 ligands can also activate PAR-2. Furthermore, PAR-1 can trans-activate PAR-2.

An anti-human PAR-2 antibody that antagonizes activation of PAR-2 by a PAR-2 activating ligand can be identified for example by testing the PAR-2 activation in the presence of a PAR-2 ligand (e.g., a synthetic soluble PAR-2 activating ligand such as SLIGKV) and inhibition of the PAR-2 activation by an anti-PAR-2 antibody. An $IC_{50}$ is used as a measure of the potency of inhibition of PAR-2 activation by the anti-PAR-2 antibody in this system (i.e., concentration of the anti-PAR-2 antibody achieving 50% inhibition of the ligand-induced PAR-2 activity, in nM).

In some embodiments, the antibody or antigen-binding fragment thereof inhibits interaction between a soluble PAR-2 activating ligand (e.g., SLIGKV) and PAR-2 in a cell with an $IC_{50}$ from about 0.1 nM to about 17 nM, as measured by the PAR-2 β-arrestin cell assay described in Example 2.1

In some aspects, an antibody or antigen-binding fragment thereof described herein, which specifically binds to human PAR-2, inhibits interaction between the soluble PAR-2 activating ligand (e.g., SLIGKV) and PAR-2 with an $IC_{50}$ of about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, about 2 nM, 2.1 nM, about 2.2 nM, about 2.3 nM, about 2.4 nM, about 2.5 nM, about 2.6 nM, about 2.7 nM, about 2.8 nM, about 2.9 nM, about 3 nM, 3.1 nM, about 3.2 nM, about 3.3 nM, about 3.4 nM, about 3.5 nM, about 3.6 nM, about 3.7 nM, about 3.8 nM, about 3.9 nM, about 4 nM, 4.1 nM, about 4.2 nM, about 4.3 nM, about 4.4 nM, about 4.5 nM, about 4.6 nM, about 4.7 nM, about 4.8 nM, about 4.9 nM, about 5 nM, 5.1 nM, about 5.2 nM, about 5.3 nM, about 5.4 nM, about 5.5 nM, about 5.6 nM, about 5.7 nM, about 5.8 nM, about 5.9 nM, about 6 nM, 6.1 nM, about 6.2 nM, about 6.3 nM, about 6.4 nM, about 6.5 nM, about 6.6 nM, about 6.7 nM, about 6.8 nM, about 6.9 nM, about 7 nM, 7.1 nM, about 7.2 nM, about 7.3 nM, about 7.4 nM, about 7.5 nM, about 7.6 nM, about 7.7 nM, about 7.8 nM, about 7.9 nM, about 8 nM, 8.1 nM, about 8.2 nM, about 8.3 nM, about 8.4 nM, about 8.5 nM, about 8.6 nM, about 8.7 nM, about 8.8 nM, about 8.9 nM, about 9 nM, 9.1 nM, about 9.2 nM, about 9.3 nM, about 9.4 nM, about 9.5 nM, about 9.6 nM, about 9.7 nM, about 9.8 nM, about 9.9 nM, about 10 nM, 10.1 nM, about 10.2 nM, about 10.3 nM, about 10.4 nM, about 10.5 nM, about 10.6 nM, about 10.7 nM, about 10.8 nM, about 10.9 nM, about 11 nM, about 11.1 nM, about 11.2 nM, about 11.3 nM, about 11.4 nM, about 11.5 nM, about 11.6 nM, about 11.7 nM, about 11.8 nM, or about 11.9 nM. The inhibition of interaction between the soluble PAR-2 ligand and PAR-2 can be dependent on the dose of anti-human PAR-2 antibody.

In some aspects, an antibody or antigen-binding fragment thereof described herein, which specifically binds to human PAR-2, inhibits PAR-2 activating ligand-induced and trypsin-induced calcium flux in a cell in an $IC_{50}$ range from about 6 nM to about 11 nM as measured by the PAR-2 calcium flux cell assay described in Example 2.2

In some aspects, an antibody or antigen-binding fragment thereof described herein, which specifically binds to human PAR-2, inhibits PAR-2 activating ligand-induced and trypsin-induced calcium flux in a cell in an $IC_{50}$ range of about 6 nM, 6.1 nM, about 6.2 nM, about 6.3 nM, about 6.4 nM, about 6.5 nM, about 6.6 nM, about 6.7 nM, about 6.8 nM, about 6.9 nM, about 7 nM, 7.1 nM, about 7.2 nM, about 7.3 nM, about 7.4 nM, about 7.5 nM, about 7.6 nM, about 7.7 nM, about 7.8 nM, about 7.9 nM, about 8 nM, 8.1 nM, about 8.2 nM, about 8.3 nM, about 8.4 nM, about 8.5 nM, about 8.6 nM, about 8.7 nM, about 8.8 nM, about 8.9 nM, about 9 nM, 9.1 nM, about 9.2 nM, about 9.3 nM, about 9.4 nM, about 9.5 nM, about 9.6 nM, about 9.7 nM, about 9.8 nM, about 9.9 nM, about 10 nM, 10.1 nM, about 10.2 nM, about 10.3 nM, about 10.4 nM, about 10.5 nM, about 10.6 nM, about 10.7 nM, about 10.8 nM, or about 10.9 nM.

In some aspects, an antibody or antigen-binding fragment thereof described herein, which specifically binds to human PAR-2, inhibits PAR-2 activating ligand-induced mucin production in a cell (e.g., a human lung epithelial cell or a cell from a cynomolgus monkey bronchoalveolar lavage fluid) by at least 70%, at least 75%, at least 80%, at least 85%, at least 90%, at least 95%, at least 98%, or at least 100%, e.g., as compared to PAR-2 activating ligand-induced cytokine production in the absence of the antibody or fragment thereof or in the presence of a control antibody of the same isotype or fragment thereof. The inhibition of PAR-2 activating ligand-induced mucin production in a cell can be measured, for example, using the assay described in Example 7. The inhibition of PAR-2 activating ligand-induced mucin production in a cell can be dependent on the dose of anti-human PAR-2 antibody.

In some aspects, an antibody or antigen-binding fragment thereof described herein, which specifically binds to human PAR-2, inhibits PAR-2 activating ligand-induced contraction of a smooth muscle cell (e.g., a bronchial smooth muscle cell) by at least 70%, at least 75%, at least 80%, at least 85%, at least 90%, at least 95%, at least 98%, or at least 100%, e.g., as compared to PAR-2 activating ligand-induced contraction of a smooth muscle cell in the absence of the antibody or fragment thereof or in the presence of a control antibody of the same isotype or fragment thereof. PAR-2 activating ligand-induced contraction of a muscle cell can be measured, for example, using the assay described in Example 7. The inhibition of PAR-2 activating ligand-induced contraction of a muscle cell can be dependent on the dose of anti-human PAR-2 antibody.

In some aspects, an antibody or antigen-binding fragment thereof described herein, which specifically binds to human PAR-2, inhibits the induction of a lung neutrophilia in a cynomolgus monkey by at least 70%, at least 75%, at least 80%, at least 85%, at least 90%, at least 95%, at least 98%, or at least 100%, e.g., as compared to induction of a lung neutrophilia in the absence of the antibody or fragment thereof or in the presence of a control antibody of the same isotype or fragment thereof.

II(c). Antigen Binding Fragments

In some aspects, an antigen-binding fragment of an anti-PAR-2 antibody described herein, such as an anti-human PAR-2 antibody, is provided. Exemplary antigen-binding fragments include but are not limited to Fab, Fab', F(ab')2, and scFv, wherein the Fab, Fab', F(ab')2, or scFv comprises a heavy chain variable region sequence and a light chain variable region sequence of an anti-human PAR-2 antibody as described herein. A Fab, Fab', F(ab')2, or scFv can be produced by any technique known to those of skill in the art, including, but not limited to, those discussed in Section III, infra. In some embodiments, an antigen-binding fragment, such as a Fab, Fab', F(ab')2, or scFv, further comprises a moiety that extends the half-life of the antibody in vivo. The moiety is also termed a "half-life extending moiety." Any moiety known to those of skill in the art for extending the half-life of a an antigen-binding fragment, such as a Fab, Fab', F(ab')2, or scFv, in vivo can be used. For example, the half-life extending moiety can include an Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In some aspects, an antigen-binding fragment, such as an Fab, Fab', F(ab')2, or scFv, can be modified by the addition of one or more C-terminal amino acids for attachment of the half-life extending moiety. In some embodiments, the half-life extending moiety is polyethylene glycol or human serum albumin. In some embodiments, an antigen-binding fragment, such as a Fab, Fab', F(ab')2, or scFv, is fused to a Fc region.

An anti-PAR-2 antibody (such as an anti-human PAR-2 antibody) or antigen-binding fragment thereof can be fused or conjugated (e.g., covalently or noncovalently linked) to a detectable label or substance. Examples of detectable labels or substances include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labeled antibodies or antigen-binding fragments thereof can be used to detect PAR-2 (e.g., human PAR-2) protein. See, e.g., Sections IV and V, infra.

III. Anti-PAR-2 Antibody Production

Antibodies and antigen-binding fragments thereof that specifically bind to human PAR-2 can be produced by any method known in the art for the synthesis of antibodies and antigen-binding fragments, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates); Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In some aspects, provided herein is a method of making an antibody or antigen-binding fragment which specifically binds to human PAR-2 comprising culturing a cell or host cell described herein (e.g., a cell or a host cell comprising polynucleotides encoding an antibody or antigen-binding fragment thereof described herein). In certain embodiments, provided herein is a method of making an antibody or antigen-binding fragment thereof which specifically binds to human PAR-2 comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In some embodiments, the cell is an isolated cell. In some embodiments, the encoding polynucleotides have been introduced into the cell. In some embodiments, the method further comprises the step of purifying the antibody or antigen-binding fragment expressed by the cell or host cell.

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G& Milstein C (1975) Nature 256: 495. Examples of yeast-based presentation methods that can be employed to select and generate the antibodies described herein include those disclosed in, for example, WO2009/036379A2; WO2010/105256; and WO2012/009568, each of which is herein incorporated by reference in its entirety.

In some embodiments, a monoclonal antibody or antigen-binding fragment is an antibody or antigen-binding fragment produced by a clonal cell (e.g., hybridoma or host cell producing a recombinant antibody or antigen-binding fragment), wherein the antibody or antigen-binding fragment specifically binds to human PAR-2 as determined, e.g., by ELISA or other antigen-binding assays known in the art or in the Examples provided herein. In some embodiments, a monoclonal antibody or antigen-binding fragment thereof can be a chimeric or a humanized antibody or antigen-binding fragment thereof. In some aspects, a monoclonal antibody or antigen-binding fragment thereof can be a Fab fragment or a F(ab')2 fragment. Monoclonal antibodies or antigen-binding fragments thereof described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of a tetrameric antibody molecule and contains the complete light chain paired with the VH and CH1 domains of the heavy chain. A F(ab')2 fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that binds to a particular antigen can be selected or identified with antigen, e.g., using labeled antigen or antigen bound or captured to a solid surface or bead. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

A humanized antibody or antigen-binding fragment thereof can be selected from any class of immunoglobulins, including IgM, IgG, IgD, IgA and IgE, and any isotype, including IgG1, IgG2, IgG3 and IgG4.

Methods for making multispecific (e.g., bispecific antibodies) have been described. See, for example, U.S. Pat. Nos. 7,951,917; 7,183,076; 8,227,577; 5,837,242; 5,989,830; 5,869,620; 6,132,992 and 8,586,713.

III(a). Polynucleotides

In certain aspects, provided herein are polynucleotides comprising a nucleotide sequence encoding an antibody or antigen-binding fragment thereof described herein or a domain thereof (e.g., a variable light chain region and/or variable heavy chain region) that specifically binds to human PAR-2, and vectors, e.g., vectors comprising such polynucleotides for recombinant expression in host cells (e.g., E. coli and mammalian cells).

In some aspects, provided herein are polynucleotides comprising nucleotide sequences encoding antibodies or antigen-binding fragments thereof, which specifically bind to human PAR-2 and comprise an amino acid sequence as described herein, as well as antibodies or antigen-binding fragments that compete with such antibodies or antigen-binding fragments for binding to a human PAR-2 (e.g., in a dose-dependent manner), or which bind to the same epitope as that of such antibodies or antigen-binding fragments.

Also provided herein is an isolated polynucleotide comprising a nucleic acid sequence which encodes the heavy chain variable region or the heavy chain of the antibody or antigen-binding fragment thereof disclosed herein. In some embodiments, the nucleic acid molecule encodes the VH of SEQ ID NO: 20 or 21.

In some aspects there is provided an isolated polynucleotide which comprises a nucleic acid molecule encoding the light chain variable region or light chain of the antibody or antigen-binding fragment thereof disclosed herein. In some embodiments, the nucleic acid molecule encodes the VL of SEQ ID NO: 23, 24, 25, 26, or 27.

In some aspects there is provided an isolated polynucleotide comprising a first nucleic acid molecule encoding the light chain variable region of SEQ ID NO: 23, 24, 25, 26, or 27, and a second nucleic acid molecule encoding the heavy chain variable region of SEQ ID NO: 20 or 21. In some aspects there is provided a mixture of isolated polynucleotides comprising a first polynucleotide which comprises a nucleic acid molecule encoding the light chain variable region of SEQ ID NO: 23, 24, 25, 26, or 27, and a second polynucleotide which comprises a nucleic acid molecule encoding the heavy chain variable region of SEQ ID NO: 20 or 21.

In some aspects, an isolated polynucleotide comprises a nucleic acid molecule encoding the heavy chain variable region or heavy chain of the antibody or antigen-binding fragment thereof disclosed herein and the light chain variable region or light chain of the antibody or antigen-binding fragment thereof disclosed herein.

Also provided herein are kits, vectors, or host cells comprising (i) a first polynucleotide comprising a nucleotide sequence encoding SEQ ID NO: 20 and (ii) a second polynucleotide comprising a nucleotide sequence encoding SEQ ID NO: 23. Also provided herein are kits, vectors, or host cells comprising (i) a first polynucleotide comprising a nucleotide sequence encoding SEQ ID NO: 21 and (ii) a second polynucleotide comprising a nucleotide sequence encoding SEQ ID NO: 24. Also provided herein are kits, vectors, or host cells comprising (i) a first polynucleotide comprising a nucleotide sequence encoding SEQ ID NO: 21 and (ii) a second polynucleotide comprising a nucleotide sequence encoding SEQ ID NO: 25. Also provided herein are kits, vectors, or host cells comprising (i) a first polynucleotide comprising a nucleotide sequence encoding SEQ ID NO: 21 and (ii) a second polynucleotide comprising a nucleotide sequence encoding SEQ ID NO: 26. Also provided herein are kits, vectors, or host cells comprising (i) a first polynucleotide comprising a nucleotide sequence encoding SEQ ID NO: 21 and (ii) a second polynucleotide comprising a nucleotide sequence encoding SEQ ID NO: 27. In a kit comprising such first and second polynucleotides, the first and second polynucleotides can be in the same vector or can be in different vectors. In a host cell comprising such first and second polynucleotides, the first and second polynucleotides can be in the same vector or can be in different vectors.

In some aspects, provided herein are polynucleotides comprising a nucleotide sequence encoding three VH domain CDRs, e.g., a polypeptide containing VH CDR1, VH CDR2, and VH CDR3 of any one of the antibodies described herein (e.g., see Table 2), e.g., wherein the three VH domain CDRs are in the context of a VH. In some aspects, provided herein are polynucleotides comprising a nucleotide sequence encoding three VL domain CDRs, e.g., a polypeptide containing VL CDR1, VL CDR2, and VL CDR3 of any one of the antibodies described herein (e.g., see Table 3), e.g., wherein the three VL domain CDRs are in the context of a VL. In some aspects, provided herein are polynucleotides (or combinations of polynucleotides) comprising a nucleotide sequence encoding an anti-human PAR-2 antibody or antigen-binding fragment thereof comprising (i) three VH domain CDRs, e.g., a polypeptide containing VH CDR1, VH CDR2, and VH CDR3 of any one of antibodies described herein (e.g., see Table 2) e.g., wherein the three VH domain CDRs are in the context of a VH and (ii) three VL domain CDRs, e.g., a polypeptide containing VL CDR1, VL CDR2, and VL CDR3 of any one of antibodies described herein (e.g., see Table 2), e.g., wherein the three VL domain CDRs are in the context of a VL.

In some aspects, a polynucleotide comprises a nucleic acid sequence encoding a heavy chain variable region (e.g., a VH comprising the amino acid sequence of SEQ ID NO: 20 or 21) and a heavy chain constant region, e.g., a human gamma (γ) heavy chain constant region.

In some aspects, a polynucleotide comprises a nucleic acid sequence encoding a light chain variable region (e.g., a VL comprising the amino acid sequence of SEQ ID NO: 23, 24, 25, 26, or 27) and a light chain constant region, e.g., a human kappa light chain constant region.

Also provided herein are polynucleotides encoding an anti-human PAR-2 antibody or antigen-binding fragment thereof described herein or a domain thereof that are optimized, e.g., by codon/RNA optimization, replacement with heterologous signal sequences, and elimination of mRNA instability elements. Methods to generate optimized nucleic acids encoding an anti-human PAR-2 antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, each of which is incorporated herein by reference in its entirety.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate chimeric and humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In some embodiments, the polynucleotide is a cDNA or a DNA lacking one more endogenous introns. In some embodiments, a polynucleotide is a non-naturally occurring polynucleotide. In some embodiments, a polynucleotide is recombinantly produced. In some embodiments, the polynucleotides are isolated. In some aspects, the polynucleotides are substantially pure. In some embodiments, a polynucleotide is purified from natural components.

III(b). Cells and Vectors

In some aspects, provided herein are vectors (e.g., expression vectors) comprising polynucleotides comprising nucleotide sequences encoding anti-human PAR-2 antibodies or antigen-binding fragments thereof, or a domain thereof for recombinant expression in host cells (e.g., in mammalian cells). Also provided herein are cells, e.g. host cells, comprising such vectors for recombinantly expressing anti-human PAR-2 antibodies or antigen-binding fragments thereof described herein (e.g., human or humanized antibodies or antigen-binding fragments thereof). In some embodiments, provided herein are methods for producing an antibody or antigen-binding fragments thereof described herein, comprising expressing such antibody or antigen-binding fragment thereof in a host cell.

In some embodiments, recombinant expression of an antibody or antigen-binding fragment thereof or domain thereof described herein (e.g., a heavy or light chain described herein) that specifically binds to human PAR-2 involves construction of an expression vector containing a polynucleotide that encodes the antibody or antigen-binding fragment thereof or domain thereof. Once a polynucleotide encoding an antibody or an antigen-binding fragment thereof or domain thereof (e.g., heavy or light chain variable domain) described herein has been obtained, the vector for the production of the antibody or antigen-binding fragment thereof can be produced by recombinant DNA technology using techniques well known in the art. Thus, methods for preparing a protein by expressing a polynucleotide containing an antibody or antigen-binding fragment thereof or domain thereof (e.g., light chain or heavy chain) encoding nucleotide sequence are described herein. Methods which are well known to those skilled in the art can be used to construct expression vectors containing antibody or antigen-binding fragment thereof or domain thereof (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment thereof described herein, a heavy or light chain, a heavy or light chain variable domain, or a heavy or light chain CDR, operably linked to a promoter. Such vectors can, for example, include the nucleotide sequence encoding the constant region of the antibody or antigen-binding fragment thereof (see, e.g., International Publication Nos. WO 86/05807 and WO 89/01036; and U.S. Pat. No. 5,122,464), and variable domains of the antibody or antigen-binding fragment thereof can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody or antigen-binding fragment thereof described herein (e.g., an antibody or antigen-binding fragment thereof comprising the six CDRs, the VH, the VL, the VH and the VL, the heavy chain, the light chain, or the heavy and the light chain of P24E1102, P24E976, P24E1099, P24E1103, or 309-4e) or a domain thereof (e.g., the VH, the VL, the VH and the VL, the heavy chain, or the light chain of P24E1102, P24E976, P24E1099, P24E1103, or 309-4e). Thus, provided herein are host cells containing a polynucleotide encoding an antibody or antigen-binding fragment thereof described herein (e.g., an antibody or antigen-binding fragment thereof comprising the six CDRs, the VH, the VL, the VH and the VL, the heavy chain, the light chain, or the heavy and the light chain of P24E1102, P24E976, P24E1099, P24E1103, or 309-4e) or a domain thereof (e.g., the VH, the VL, the VH and the VL, the heavy chain, or the light chain of P24E1102, P24E976, P24E1099, P24E1103, or 309-4e), operably linked to a promoter for expression of such sequences in the host cell. In some aspects, for the expression of double-chained antibodies or antigen-binding fragments thereof, vectors encoding both the heavy and light chains, individually, can be co-expressed in the host cell for expression of the entire immunoglobulin, as detailed below. In some aspects, a host cell contains a vector comprising a polynucleotide encoding both the heavy chain and light chain of an antibody described herein (e.g., the heavy and the light chain of P24E1102, P24E976, P24E1099, P24E1103, or 309-4e), or a domain thereof (e.g., the VH and the VL of P24E1102, P24E976, P24E1099, P24E1103, or 309-4e). In some aspects, a host cell contains two different vectors, a first vector comprising a polynucleotide encoding a heavy chain or a heavy chain variable region of an antibody or antigen-binding fragment thereof described herein, and a second vector comprising a polynucleotide encoding a light chain or a light chain variable region of an antibody described herein (e.g., an antibody comprising the six CDRs of P24E1102, P24E976, P24E1099, P24E1103, or 309-4e), or a domain thereof. In some aspects, a first host cell comprises a first vector comprising a polynucleotide encoding a heavy chain or a heavy chain variable region of an antibody or antigen-binding fragment thereof described herein, and a second host cell comprises a second vector comprising a polynucleotide encoding a light chain or a light chain variable region of an antibody or antigen-binding fragment thereof described herein (e.g., an antibody or antigen-binding fragment thereof comprising the six CDRs of P24E1102, P24E976, P24E1099, P24E1103, or 309-4e). In some aspects, a heavy chain/heavy chain variable region expressed by a first cell associated with a light chain/light chain variable region of a second cell to form an human PAR-2 antibody or antigen-binding fragment thereof described herein (e.g., antibody or antigen-binding fragment thereof comprising the six CDRs of P24E1102, P24E976, P24E1099, P24E1103, or 309-4e). In some aspects, provided herein is a population of host cells comprising such first host cell and such second host cell.

In some aspects, provided herein is a population of vectors comprising a first vector comprising a polynucleotide encoding a light chain/light chain variable region of an anti-human PAR-2 antibody or antigen-binding fragment thereof described herein, and a second vector comprising a polynucleotide encoding a heavy chain/heavy chain variable region of an anti-human PAR-2 antibody or antigen-binding fragment thereof described herein (e.g., antibody or antigen-binding fragment thereof comprising the CDRs of P24E1102, P24E976, P24E1099, P24E1103, or 309-4e). Alternatively, a single vector can be used which encodes, and is capable of expressing, both heavy and light chain polypeptides.

A variety of host-expression vector systems can be utilized to express antibodies and antigen-binding fragments thereof described herein (e.g., an antibody or antigen-binding fragment thereof comprising the CDRs of P24E1102, P24E976, P24E1099, P24E1103, or 309-4e) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7030, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some aspects, cells for expressing antibodies and antigen-binding fragments thereof described herein (e.g., an antibody or antigen-binding fragment thereof comprising the CDRs of hPA-002, hPA-005, hPA-004, or hPA-001) are CHO cells, for example CHO cells from the CHO GS System™ or CHO KISV™ System (Lonza). In some aspects, cells for expressing antibodies described herein are human cells, e.g., human cell lines. In some aspects, a mammalian expression vector is pOptiVEC™ or pcDNA3.3. In some aspects, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) *Gene* 45: 101-105; and Cockett M I et al., (1990) *Biotechnology* 8: 662-667). In some aspects, antibodies or antigen-binding fragments thereof described herein are produced by CHO cells or NS0 cells.

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells which possess the cellular machinery for proper processing of the primary transcript, glycosylation, and phosphorylation of the gene product can be used. Such mammalian host cells include, but are not limited to, Expi293F human cell, C6 (rat glioma cell line), U2OS, Chem-1, CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In some aspects, anti-human PAR-2 antibodies or antigen-binding fragments thereof described herein (e.g., an antibody or antigen-binding fragment thereof comprising the CDRs of hPA-002, hPA-005, hPA-004, or hPA-001) are produced in mammalian cells, such as CHO cells.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In some aspects, an antibody or antigen-binding fragment thereof described herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in some aspects, a preparation of an antibody or antigen-binding fragment thereof described herein is substantially free of cellular material and/or chemical precursors.

IV. Bispecific Molecules

Anti-PAR-2 antibodies described herein can be used for forming bispecific molecules. An anti-PAR-2 antibody, or antigen-binding fragments thereof, can be derivatized or linked to another functional molecule, e.g., another peptide or protein (e.g., another antibody or ligand for a receptor) to generate a bispecific molecule that binds to at least two different binding sites or target molecules. For example, an anti-PAR-2 antibody can be linked to an antibody or scFv that binds specifically to any protein that can be used as potential targets for combination treatments. The antibody described herein can in fact be derived or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for PAR-2 and a second binding specificity for a second target epitope. In some embodiments described herein in which the bispecific molecule is multispecific, the molecule can further include a third binding specificity.

In some embodiments, the bispecific molecules described herein comprise as a binding specificity at least one antibody, or an antibody fragment thereof, including, e.g., an Fab, Fab', F(ab')2, Fv, or a single chain Fv (scFv). The antibody can also be a light chain or heavy chain dimer, or any minimal fragment thereof such as an Fv or a single chain construct as described in Ladner et al. U.S. Pat. No. 4,946,778.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. See, e.g., Karpovsky et al. (1984) J. Exp. Med. 160: 1686; Liu, M A et al. (1985) Proc. Natl. Acad. Sci. USA 82:8648. Other methods include those described in Paulus (1985) Behring Ins. Mitt. No. 78, 118-132; Brennan et al. (1985) Science 229:81-83), and Glennie et al. (1987) J. Immunol. 139: 2367-2375). Some conjugating agents are SATA and sulfo-SMCC, both available from Pierce Chemical Co. (Rockford, IL).

V. Pharmaceutical Compositions

Provided herein are compositions comprising an anti-PAR-2 antibody (such as an anti-human PAR-2 antibody) or antigen-binding fragment thereof, as described herein. In some aspects, the antibody or antigen-binding fragment thereof having the desired degree of purity is present in a formulation comprising, e.g., a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed. Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In some aspects, a pharmaceutical composition comprises an anti-human PAR-2 antibody or antigen-binding fragment thereof as described herein, and a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Pharmaceutical compositions described herein are, in some aspects, for use as a medicament. The compositions to be used for in vivo administration can be sterile. This is readily accomplished by filtration through, e.g., sterile filtration membranes.

A pharmaceutical composition described herein can be used to exert a biological effect(s) in vivo or in vitro. For example, a pharmaceutical composition described herein can be used to block the interaction between a PAR-2 activating ligand and an extracellular domain of PAR-2, and/or block PAR-2 activation by a PAR-2 activating ligand. Such a PAR-2 activating ligand can include, without limitation, a PAR-2 tethered ligand (in cis or trans); a PAR-1 tethered ligand; or a soluble ligand (e.g., a synthetic soluble PAR-2 activating ligand such as SLIGKV, SLIGRL, or 2-furoyl-LIGRLO.

A pharmaceutical compositions described herein can be used to treat a disease or condition, such as a disease or condition that can be alleviated by antagonizing activation of PAR-2 by a PAR-2 activating ligand.

In some embodiments, a pharmaceutical composition provided herein is used to treat diseases or conditions such as an airway disease. Examples of the airway disease include, but not limited to, asthma, chronic obstructive pulmonary disease, idiopathic pulmonary fibrosis, and pulmonary arterial hypertension.

In some embodiments, a pharmaceutical composition provided herein is used to treat diseases or conditions such as a skin disease. Examples of the skin disease include, but not limited to, skin inflammation condition, atopic dermatitis, allergic contact dermatitis, Netherton syndrome, ichthyosis, skin barrier/permeability recovery after damage, pruritus, skin cancer, skin itch, pigmentation associated with melasma, and pigmentation associated with vitiligo.

In some embodiments, a pharmaceutical composition provided herein is used to treat diseases or conditions such as cancer. Examples of cancers that can be treated as provided herein include solid tumors, e.g., solid tumors in which myeloid cells (monocytes, macrophages, dendritic cells, granulocytes, neutrophils, microglia (in the CNS) or other innate immune cells) have infiltrated the tumor microenvironment. Examples of such cancers that can be treated by the pharmaceutical compositions provided herein include, but are not limited to, glioblastoma, head and neck cancer, kidney cancer (e.g., kidney clear cell cancer), pancreatic cancer, gastric caner, and breast cancer. Other cancers include, but are not limited to, bone cancer, ovarian cancer, prostate cancer, sarcoma, colorectal cancer, lung cancer, melanoma, bladder cancer, liver cancer and uterine cancer. In some embodiments, a cancer is a hematopoietic cancer, such as a leukemia, lymphoma, or myeloma. In some embodiments, a cancer can be an early stage cancer or a late stage cancer. In some embodiments, a cancer is a primary tumor. In some embodiments, a cancer is a metastatic tumor at a second site derived from any of the above types of cancer. In some embodiments, a cancer is a PAR-2-positive cancer. In some embodiments, a cancer is a cancer with increased PAR-2 (e.g., increased PAR-2 mRNA and/or increased PAR-2 protein).

In some embodiments, a pharmaceutical composition provided herein is used to relieve pain. Examples of the pain include, but are not limited to, cancer pain, joint pain, chemotherapy-induced peripheral neuropathy pain, migraine pain, dental pain, bladder pain, pancreatitis pain, irritable bowl syndrome related pain, visceral pain, osteoarthritis related pain, rheumatoid arthritis related pain, and spinal cord injury pain.

In some embodiments, a pharmaceutical composition provided herein is used to treat orofacial granulomatosis.

In some embodiments, a pharmaceutical composition provided herein is used to treat an inflammatory condition in a patient. In certain embodiments, the inflammatory condition is rheumatoid arthritis, osteoarthritis, inflammation-induced visceral hypersensitivity, periodontal disease, or a pathology associated with acute corona virus infection.

VI. Uses and Methods

In various aspects, provided herein are in vitro and in vivo methods of using anti-human PAR-2 antibodies or antigen-binding fragments thereof as described herein, or pharmaceutical compositions thereof as described herein. In one aspect, a method for inhibiting PAR-2 activation by a ligand is provided, the method comprising contacting PAR-2 with an anti-human PAR-2 antibody or antigen-binding fragment thereof, or pharmaceutical composition thereof. In one aspect, a method for inhibiting binding of a PAR-2 activating ligand to PAR-2 is provided, the method comprising blocking the ligand binding site on PAR-2 with an anti-human PAR-2 antibody or antigen-binding fragment thereof, or pharmaceutical composition thereof. In another aspect, a method for inhibiting binding of a soluble PAR-1 or a soluble PAR-2 ligand generated from protease activity to PAR-2 is provided, the method comprising blocking the ligand binding site on PAR-2 with an anti-human PAR-2 antibody or antigen-binding fragment thereof, or pharmaceutical composition thereof. In another aspect, a method for inhibiting transactivation of PAR-2 by PAR-1, comprising blocking the ligand binding site on PAR-2 with an anti-human PAR-2 antibody or antigen-binding fragment thereof, or pharmaceutical composition thereof.

In another aspect, a method of antagonizing activation of PAR-2 by a PAR-2 activating ligand is provided, the method comprising contacting PAR-2 with an anti-human PAR-2 antibody or antigen-binding fragment thereof, or pharmaceutical composition thereof, in the presence of one or more of its ligands. Exemplary ligands include, e.g., soluble PAR-2 activating ligand SLIGKV, SLIGRL, 2-furoyl-LI-GRLO, PAR-2 tethered ligand, or PAR-1 tethered ligand.

VI(a). Therapeutic Uses and Methods

In one aspect there is provided a method for inhibiting activation of PAR-2 in vivo in a subject (e.g., a human subject) in need thereof, the method comprising administering to the subject an anti-human PAR-2 antibody or antigen-binding fragment thereof described herein, or a pharmaceutical composition described herein. In some aspects there is provided a method for inhibiting activation of PAR-2 in vivo by a PAR-2 activating ligand in a subject (e.g., a human subject) in need thereof, the method comprising administering to the subject an anti-human PAR-2 antibody or antigen-binding fragment thereof described herein, or a pharmaceutical composition described herein.
In certain embodiments, the PAR-2 activating ligand is a soluble PAR-2 activating ligand, a PAR-2 tethered ligand, or a PAR-1 tethered ligand.

PAR-2 activity has been implicated in or associated with several diseases and conditions including inflammatory diseases, pain, gastrointestinal conditions, neurological diseases, and cardiovascular disorders (see, e.g., Linder et al., *J. Immunol.* 165:6504-6510 (2000); Vergnolle et al., *Nature Medicine* 7:821-826 (2001); Cenac et al., *J. Olin. Investigation* 117:636-647 (2007); Vergnolle, *British J. Pharmacol.* 141:1264-1274 (2004); Knight et al., *J. Allergy Clin. Immunol.* 108:797-803 (2001); Schmidlin et al., *J. Immunol.* 169:5315-5321 (2002). Antibodies that bind to PAR-2 have the potential to antagonize the activity of PAR-2 in vivo. Anti-PAR-2 antibodies are therefore potentially useful for treating and/or ameliorating a variety of disease conditions. See also, US2011/0059095.

In some embodiments, provided herein are methods of treating a disease or condition associated with increased expression of PAR-2 and/or diseases or conditions that can be alleviated by blocking the interaction between a PAR-2 activating ligand with an extracellular domain of PAR-2, and/or blocking PAR-2 activation by a PAR-2 activating ligand e.g., an airway disease, a skin diseases, cancer, an inflammatory condition, orofacial granulomatosis, and pain associated with various diseases or conditions). Such methods can comprise administering an anti-human PAR-2 antibody or antigen-binding fragment thereof described herein, or a pharmaceutical composition thereof described herein, to a patient (e.g., a human patient) in need thereof.

VI(a)(1). Airway Diseases

In some aspects, provided herein are methods of treating an airway disease. Such methods can comprise administering an anti-human PAR-2 antibody or antigen-binding fragment thereof as described herein, or a pharmaceutical composition thereof as described herein, to a patient (e.g., a human patient) in need thereof.

In some embodiments, the patient has symptoms of an airway disease, and an anti-human PAR-2 antibody or antigen-binding fragment thereof as described herein, or a pharmaceutical composition thereof as described herein, is administered to treat the airway disease. In some embodiments, the patient is at risk of developing an airway disease, and the anti-human PAR-2 antibody, antigen-binding fragment, or pharmaceutical composition is administered to reduce risk, slow onset, or prevent the airway disease.

Examples of the airway diseases that can be treated as provided herein include, but are not limited to, asthma, chronic obstructive pulmonary disease (COPD), idiopathic pulmonary fibrosis, pulmonary arterial hypertension, Acute Respiratory Disorder Syndrome (ARDS), respiratory distress syndrome, cystic fibrosis, pulmonary hypertension, pulmonary vasoconstriction, acute lung injury, allergic bronchopulmonary aspergillosis, hypersensitivity pneumonia, eosinophilic pneumonia, bronchitis, allergic bronchitis bronchiectasis, tuberculosis, hypersensitivity pneumonitis, asthma-like disorders, sarcoid, reactive airway disease (or dysfunction) syndrome, byssinosis, interstitial lung disease, hyper-eosinophilic syndrome, rhinitis, sinusitis, and parasitic lung disease, and airway hyperresponsiveness associated with viral-induced conditions (e.g., respiratory syncytial virus (RSV), parainfluenza virus (PIV), rhinovirus (RV) and adenovirus).

Asthma

Asthma is a chronic inflammatory disease of the airways. The chronic inflammation is associated with airway hyper-responsiveness (an exaggerated airway-narrowing response to specific triggers such as viruses, allergens and exercise) that leads to recurrent episodes of wheezing, breathlessness, chest tightness, and/or coughing that can vary over time and in intensity. Symptom episodes are generally associated with widespread, but variable, airflow obstruction within the lungs that is usually reversible either spontaneously or with appropriate asthma treatment such as a fast-acting bronchodilator. See e.g., Quirt J. et al., *Allergy Asthma Clin Immunol.*, 14(Suppl 2):50 (2018).

PAR-2 expression is increased on multiple airway cell types in asthmatics, e.g., epithelium (Knight, D. A. et al. J Allergy Clin Immunol, 108:797-803 (2001)), smooth muscle (Aubier, M. et al., J Allergy Clin Immunol, 138: 729-739 (2016)), fibroblasts (Akers, I. A. et al., Am J Physiol Lung Cell Mol Physiol, 278:L193-201 (2000)), and endothelial cells, as well on innate immune cells including eosinophils, neutrophils (Miike, S. et al., J Immunol, 167: 6615-6622 (2001)), dendritic cells, mast cells, and monocytes (Palikhe, N. et al., PLoS One., 10(12):e0144500 (2015)). PAR-2 activation stimulates release of various inflammatory mediators, notably thymic stromal lymphopoietin (TSLP) (Kouzaki, H. et al., J Immunol, 183: 1427-1434 (2009)), as well as stimulating mucus secretion (Lee, H. J. et al., PLoS One, 7:e43188 (2012)), and increasing mucin secretion in bronchial epithelial cells (Lin, K. et al., Int J Biochem Cell Biol, 40:1379-1388 (2008)). PAR-2 activation also stimulates proliferation and migration of fibroblasts and airway smooth muscle cells (Berger, P. et al., J Appl Physiol, 91, 1372-1379 (2001); Bagher, M. et al., Cell Communication and Signaling, 16:59(2018)). PAR-2 can be activated by exogenous proteases present in common allergens (Kawabata, A. & Kawao, N., J Pharmacol Sci 97:20-24 (2005)) or by endogenous proteases released in response to asthma triggers (Cocks, T. M. et al., Nature 398:156-160 (1999)). PAR-2 expression on airway cells correlates with asthma severity (Knight, D. A. et al. J Allergy Clin Immunol, 108:797-803 (2001); Aubier, M. et al., J Allergy Clin Immunol, 138: 729-739 (2016); Palikhe, N. et al., PLoS One., 10(12):e0144500 (2015)).

Ovalbumin (OVA)-induced experimental asthma is significantly decreased in PAR-2-/- mice and significantly increased in mice engineered to overexpress PAR-2 (Schmidlin, F. et al., J Immunol, 169:5315-5321 (2002)). It can be ameliorated by administration of an anti-PAR-2 antibody or PAR-2 blocking peptide (Asaduzzaman, M. et al., Clin Exp Allergy, 45:1844-1855 (2015)). Furthermore, PAR-2 blockade with a small molecule inhibitor significantly ameliorated cockroach frass-induced experimental asthma in mice (Nadeem, A. et al., Immunology 145:391-403 (2015)).

In some embodiments, administering an anti-human PAR-2 antibody or antigen-binding fragment thereof as provided herein, or a pharmaceutical composition thereof as provided herein, can prevent, reduce the risk, and/or treat asthma, and associated conditions such as eosinophilic esophagitis. In some aspects, administering the anti-human PAR-2 antibody, antigen-binding fragment or pharmaceutical composition can modulate one or more PAR-2 activities in an individual having asthma.

Chronic Obstructive Pulmonary Disease

Chronic Obstructive Pulmonary Disease (COPD) comprises a diverse group of clinical syndromes that share the common feature of limitation of expiratory airflow. The American Thoracic Society defines COPD in terms of chronic bronchitis and emphysema. Chronic bronchitis is characterized by the clinical symptoms of excessive cough and sputum production; emphysema refers to chronic dyspnea, resulting from enlarged air spaces and destruction of lung tissue. The GOLD initiative defines COPD as "a disease state characterized by airflow limitation that is not fully reversible. The airflow limitation is usually both progressive and associated with an abnormal inflammatory response of the lungs to noxious particles or gases." Asthma is also characterized by airflow obstruction and inflammation, but in addition it involves hyperresponsiveness of the airways to stimulus; therefore, the reversibility of functional deficits in asthma differentiates it from COPD. See e.g., Devine J. F., Am Health Drug Benefits., 1(7):34-42 (2008).

PAR-2 expression does not appear to be increased in COPD patients (Cocks, T. M. & Moffatt, J. D., Pulm Pharmacol Ther 14:183-191 (2001); Miotto, D. et al., Thorax, 57:146-151 (2002)), but exposure to cigarette smoke can enhance neutrophil elastase-induced IL-8 production by human bronchial epithelial cells (Lee, K. H. et al., Experimental & Molecular Medicine 50:79 (2018)). Neutrophil elastase has also been shown to induce asthma/COPD-associated mucin, MUCSAC, release from human lung epithelial cells through PAR-2 activation (Zhou, J. et al., Mol Cell Biochem, 377:75-85 (2013)). PAR-2-mediated fibroblast proliferation and extracellular matrix deposition can contribute to COPD-associated lung fibrosis (Akers, I. A. et al., Am J Physiol Lung Cell Mol Physiol, 278:L193-201 (2000)).

In some aspects, administering an anti-human PAR-2 antibody or antigen-binding fragment thereof as provided herein, or a pharmaceutical composition thereof as provided herein, can prevent, reduce the risk, and/or treat COPD. In some embodiments, administering the anti-human PAR-2 antibody, antigen-binding fragment or pharmaceutical composition can modulate one or more PAR-2 activities in an individual having COPD.

Idiopathic Pulmonary Fibrosis

Idiopathic Pulmonary Fibrosis (IPF) is an interstitial lung disease characterized by chronic, progressive scarring of the lungs, and the pathological hallmark of usual interstitial pneumonia. Current paradigms suggest alveolar epithelial cell damage is a key initiating factor. See e.g., Barratt et al., J Clin Med., 7(8):201 (2018).

PAR-2 expression is increased on lung epithelium of IPF patients (Borensztajn, K. et al., Am J Pathol, 177:2753-2764 (2010)). Expression levels of PAR-2 correlate with disease severity (Wygrecka, M. et al., Am J Respir Crit Care Med, 183:1703-1714 (2011)) and clinical features such as honeycombing observed in chest computed tomography (CT) scans (Park, Y. S. et al., Respiratory Medicine 107:256-262 (2013)). PAR-2-/- mice are resistant to the induction of experimental pulmonary fibrosis (Borensztajn, K. et al., Am J Pathol, 177:2753-2764 (2010)). Furthermore, treatment with a PAR-2-blocking peptide ameliorated experimental pulmonary fibrosis when given either prophylactically or therapeutically (Lin, C. et al., Mol Med, 21:576-583 (2015)).

In some aspects, administering an anti-human PAR-2 antibody or antigen-binding fragment thereof as provided herein, or a pharmaceutical composition thereof as provided herein, can prevent, reduce the risk, and/or treat IPF. In some embodiments, administering the anti-human PAR-2 antibody, antigen-binding fragment or pharmaceutical composition can modulate one or more PAR-2 activities in an individual having IPF.

VI(a)(2). Skin Diseases

In some aspects, provided herein are methods of treating a skin disease. Such methods can comprise administering an anti-human PAR-2 antibody or antigen-binding fragment thereof as described herein, or a pharmaceutical composition thereof as described herein, to a patient (e.g., a human patient) in need thereof.

In some embodiments, the patient has symptoms of a skin disease, and an anti-human PAR-2 antibody or antigen-binding fragment thereof as described herein, or a pharmaceutical composition thereof as described herein, is administered to treat the skin disease. In some embodiments, the patient is at risk of developing a skin disease, and the anti-human PAR-2 antibody, antigen-binding fragment, or pharmaceutical composition is administered to reduce risk, slow onset, or prevent the skin disease.

Examples of the skin diseases that can be treated as provided herein include, but are not limited to, barrier dysfunction conditions such as atopic dermatitis (see e.g., Andersen et. al., Pain, 2017 158:1780-1791 (2017)), allergic contact dermatitis, Netherton syndrome (see e.g., Hovnanian A., Cell Tissue Research, 351:289-300 (2013); Briot et. al., Journal of Investigative Dermatology, 130:2736-2742 (2010)), ichthyosis (see e.g., Frateschi et. al., Nat Commun. 18(2):161 (2011), skin barrier/permeability recovery after damage (see e.g., Hachem et. al. Journal of Investigative Dermatology 126:2074-2086 (2006)), pruritus (see e.g., Frateschi et. al., Nat Commun. 18(2):161 (2011); Andersen et. al. Pain, 158:1780-1791 (2017)), skin cancer (see e.g., Henehan et. al. Experimental Dermatology, 28:877-885 (2019)), skin itch, pigmentation associated with melasma, and pigmentation associated with vitiligo (see e.g, Henehan et. al. Experimental Dermatology, 28:877-885 (2019)).

PAR-2 is expressed on various cell types in human skin and increased during inflammation (Steinhoff, M. et al., Exp Dermatol, 8:282-294 (1999)) where it appears to have a role in barrier maintenance, inflammation, and itch (Lee, S. E., et al., Yonsei Med J, 51:808-822 (2010). PAR-2+ mast cells are significantly increased in skin of patients with atopic dermatitis and have been associated with the development of chronic pruritus (Steinhoff, id. (1999)). A PAR-2 polymorphism has been identified as risk factor in atopy and associated with increased serum IgE and eosinophil count (Lee, J. H. et al., J Allergy Clin Immunol, 128:1326-1334 (2011)), and disease-associated polymorphisms have also been identified in PAR-2-activating proteases (Vasilopoulos, Y. et al., J Invest Dermatol, 123:62-66 (2004); Chien, Y. H. et al., Clinical Reviews in Allergy & Immunology 33:178-190 (2007)). Experimental allergic dermatitis is significantly reduced in PAR-2-/- mice (Kawagoe, J. et al., *Jpn J Pharmacol*, 88:77-84 (2002)). PAR-2 expression is also associated with periodontal disease and this condition may be treated with a PAR-2 antagonist (see for example WO 2010/132954).

VI(a)(3). Cancer

In some aspects, provided herein are methods of treating cancer. A method of treating cancer can comprise administering an anti-human PAR-2 antibody or antigen-binding fragment thereof as described herein, or a pharmaceutical composition thereof as described herein, to a patient (e.g., a human patient) in need thereof. In some embodiments, provided herein are methods of treating cancer, wherein the cancer is a solid tumor. Solid tumors include those in which myeloid cells (monocytes, macrophages, dendritic cells, granulocytes, neutrophils, microglia (in the CNS) or other innate immune cells) have infiltrated the tumor microenvironment. Examples of such cancers that can be treated as provided herein include, but are not limited to, glioblastoma, head and neck cancer, kidney cancer (e.g., kidney clear cell cancer), pancreatic cancer, and breast cancer. Other cancers include, but are not limited to, ovarian cancer, sarcoma, colorectal cancer, lung cancer, melanoma, bladder cancer, liver cancer, and uterine cancer.

In some embodiments, a cancer to be treated by the methods of the present disclosure includes, without limitation, a hematopoietic cancer, such as a leukemia, lymphoma, or myeloma. In some embodiments, a cancer to be treated by the methods of the present disclosure can be an early stage cancer or a late stage cancer. In some embodiments, a cancer can be a primary tumor. In some embodiments, a cancer can be a metastatic tumor at a second site derived from any of the above types of cancer.

In some embodiments, a cancer to be treated by the methods of the present disclosure is a PAR-2-positive cancer. In some embodiments, a cancer to be treated by the methods of the present invention is a cancer with increased PAR-2 (e.g. increased PAR-2 mRNA and/or increased PAR-2 protein). Successful treatment of a cancer can involve for example a reduction in tumor burden, or a reduction in the rate of metastasis, or a reduction in tumour invasiveness, or a reduction in the rate of tumor growth.

PAR-2 is overexpressed in various cancers and associated with malignancy, progression and poor prognosis (Schaffner, F. & Ruf, W., *Arterioscler Thromb Vasc Biol* 29: 1999-2004 (2009)). PAR-2 signaling has been reported as enhancing proliferation of several cancer cell lines: gastric (Miyata, S. et al., *J Biol Chem* 275: 4592-4598 (2000)), colon (Ducroc, R. et al., *Life Sci*, 70:1359-1367 (2002)), breast (Matej, R. et al., *Physiol Res* 56:475-484 (2007)), glioblastoma (Dutra-Oliveira, A. et al., *Biochem Biophys Res Commun*, 421:221-227 (2012)), melanoma (Kempkes, C. et al., *J Invest Dermatol*, 132:375-384 (2012)), prostate (Wilson, S. R. et al., *Prostate* 60:168-174 (2004)), breast (Ge, L. et al., *J Biol Chem* 279:55419-55424 (2004), and colon (Zhou, B. et al., *Oncol Rep*, 25:503-511 (2011)). Furthermore, PAR-2 signaling blockade suppressed growth in a pancreatic cancer xenograft model (Iwaki, K. et al., *Int J Cancer*, 122:658-663 (2008)). PAR-2-/- mice had delayed onset and reduced metastasis in a breast cancer model (Schaffner, F. et al., *Blood*, 116:6106-6113 (2010)). PAR-2 signaling blockade also inhibited proliferation and migration of malignant glioblastoma cell lines (Gessler, F. et al., *Neuroscience* 165:1312-1322 (2010)), and hepatocellular cancer lines (Kaufmann, R. et al., *Carcinogenesis* 30:1487-1496 (2009)) in vitro.

PAR-2 can promote cancer invasion and metastasis at least in part by facilitating tumor cell migration, angiogenesis, and interactions with host vascular cells, including platelets, fibroblasts, and endothelial cells lining blood vessels. Presumably inhibition of PAR-2 can inhibit these. See e.g., Wojtukiewicz et al., *Cancer Metastasis Rev*, 34:775-796 (2015).

In some embodiments, an anti-human PAR-2 antibody or antigen-binding fragment thereof, or pharmaceutical composition thereof, is administered in combination with radiation therapy and/or a chemotherapeutic agent.

VI(a)(4). Pain Associated with Various Diseases and/or Conditions

In some aspects, an anti-human PAR-2 antibody or antigen-binding fragment thereof, or pharmaceutical composition thereof, is used to relieve pain. In some embodiments, the patient has symptoms of a disease, and an anti-human PAR-2 antibody or antigen-binding fragment thereof as described herein, or a pharmaceutical composition thereof as described herein, is administered to relieve pain associated with a disease and/or a condition.

As described herein, the term "relieving pain" or "pain relief" means reducing the level of pain experienced by a subject. Pain reduction can be evaluated as described in e.g., Younger et al., *Curr Pain Headache Rep.*, 13(1):39-43 (2009).

Examples of the pain include, but not limited to, cancer pain, joint pain, chemotherapy-induced peripheral neuropathy pain, dental pain (see e.g., Ito, M. et al., Mol Pain 13:1-17 (2017)), bladder pain, pancreatitis pain (see e.g., Sharma, A. et al., *Am J Physiol Gastrointest Liver Physiol,* 288(2):G388-95 (2005), irritable bowl syndrome related pain (see e.g., Suckow et al., Mol Pain 5:54 (2009); Xu, W. et al., Evid Based Complement Alternat Med 2018:7048584 (2018), visceral pain (see e.g., Vergnolle, N., *Br J Pharmacol,* 141(8): 1264-1274 (2004); Cenac, N., *Curr Neuropharmacol,* 11, 598-605 (2013)), Osteoarthritis Related Pain, Rheumatoid Arthritis Related Pain, spinal cord injury pain (see e.g., Yoon, H. et al., *Glia,* 65(12):2070-2086 (2017)), and migraine pain.

Migraine Pain

The involvement of PAR-2 in migraine was shown in rodent models. Activation of dural PAR-2 causes local vasodilation (Dux, M. et al., *Neuroscience,* 161:887-894 (2009)), and produces migraine-like behavioral responses in wildtype mice that are absent in PAR-2−/− mice and can be blocked either by sumatriptan or a PAR-2 peptide antagonist (Hassler, S. N. et al., *Cephalalgia: An International Journal of Headache* 39:111-122 (2019)). PAR-2 activation on neuronal cells and/or on mast cells has also been considered to promote migraine-like pain in animal models.

In some embodiments, an anti-human PAR-2 antibody or antigen-binding fragment thereof as described herein, or a pharmaceutical composition thereof as described herein, is administered to relieve migraine pain, or to reduce the incidence or severity or duration of migraine pain.

Joint Pain

PAR-2 is over expressed in chondrocytes from osteoarthritis (OA) patients (Xiang, Y. et al., *Osteoarthritis Cartilage,* 14:1163-1173 (2006)) and rheumatoid arthritis (RA) patients (Busso, N. et al., *Arthritis Rheum* 56:101-107 (2007)). PAR-2 protein levels positively correlate with severity of synovitis in RA and OA patients (Tindell, A. G. et al., *Rheumatol Int,* 32(10):3077-3086 (2012)). Furthermore, in monoiodoacetate (MIA)-induced (Muley, M. et al., *Journal of neuroinflammation,* 14:168 (2017)) and surgically induced (Huesa, C. et al., *Ann Rheum Dis* 75:1989-1997 (2016)) osteoarthritis models, PAR-2−/− mice had significantly decreased synovitis, reduced nociceptive behavior, and improved weight bearing. See also, Ferrell, W. R. et al., *J Clin Invest,* 111(1): 35-41 (2003); Huesa, C. et al., *Ann Rheum Dis,* 75(11): 1989-1997 (2016).

In some embodiments, an anti-human PAR-2 antibody or antigen-binding fragment thereof as described herein, or a pharmaceutical composition thereof as described herein, is administered to relieve joint pain.

Chemotherapy-Induced Peripheral Neuropathy

Painful neuropathy is a common side-effect of cancer chemotherapy. The etiology is unclear with multiple systems being implicated, including a possible role for PAR-2 (Flatters, S. J. et al., *British Journal of Anaesthesia,* 119:737-749 (2017)). In experimental models of chemotherapy-induced pain, a PAR-2 blocking peptide reversed mechanical allodynia and heat hyperalgesia induced by paclitaxel (Chen, Y. et al., *Neuroscience* 193:440-451(2011)), mechanical pain and cold sensitivity induced by oxaliplatin (Chen, K. et al., *J Neurol Sci* 352:62-67 (2015); Tian, L. et al., *Transl Neurosci* 6:111-116 (2015)), and bortezomib (Wang, Q. et al., *Journal of biological regulators and homeostatic agents,* 31:977-983 (2017)).

In some embodiments, an anti-human PAR-2 antibody or antigen-binding fragment thereof as described herein, or a pharmaceutical composition thereof as described herein, is administered to relieve pain associated with chemotherapy-induced peripheral neuropathy.

Cancer Pain

Cancers often produce pain and this is one of the major factors affecting quality of life. The pain can be directly caused by the cancer or can be neuropathic in origin. See e.g, Portenoy, R. et al., *Pain,* 81:129-134 (1999); Lam, D., et al., *Pain,* 156(5):923-930 (2015); McCulloch, K., et al., *Front Endocrinol* (Lausanne), 9:257 (2018); Morgan, C. R., et al., *J Orofac Pain* 23(3): 265-74 (2009).

In some embodiments, an anti-human PAR-2 antibody or antigen-binding fragment thereof as described herein, or a pharmaceutical composition thereof as described herein, is administered to relieve cancer pain.

Acute and Chronic Cancer Pain

Serine proteases have been identified as possible nociceptive mediators. The membrane anchored serine protease TMPRSS2 is significantly upregulated in cancer patients, and expression levels correlate with pain severity in patients. TMPRSS2 can activate PAR-2 and TMPRSS2-induced mechanical hyperalgesia is absent in PAR-2$^{-/-}$ mice (Lam, D. K. et al., *Pain,* 156:923-930 (2015)). Serine proteases are released from head and neck cancers (Lam, D. K. et al., *Pain* 149:263-272 (2010)). Supernatants from head and neck cancer cell cultures induce mechanical allodynia in wildtype mice but not in PAR-2$^{-/-}$ mice (Lam, D. K. et al., *Pain* 149:263-272 (2010)). Furthermore, in a chemically induced head and neck cancer model in mice, cancer induced chronic allodynia was completely absent in PAR-2$^{-/-}$ mice (Lam, D. K. et al., *J Neurosci* 32:14178-14183 (2012)).

In some embodiments, an anti-human PAR-2 antibody or antigen-binding fragment thereof as described herein, or a pharmaceutical composition thereof as described herein, is administered to relieve acute and chronic cancer pain.

Bone Cancer Pain

In a tumor cell-induced model of bone cancer, pain behaviors are correlated with upregulation of PAR-2 in sciatic nerve and dorsal root ganglia. Pain behaviors were not observed in PAR-2−/− mice and could be reversed by intrathecal administration of a PAR-2 blocking peptide in wildtype mice (Liu, S. et al., *European journal of pain,* 18:326-337 (2014)). In rat bone cancer model, PAR-2 blockade was found to potentiate the analgesic effect of morphine (Bao, Y. et al., *Reg Anesth Pain Med,* 40:158-165 (2015)).

In some embodiments, an anti-human PAR-2 antibody or antigen-binding fragment thereof as described herein, or a pharmaceutical composition thereof as described herein, is administered to relieve bone cancer pain.

Pancreatic Cancer Pain

Perineural mast cell numbers are increased in pancreatic cancer patients with cancer-associated pain (Demir, I. E. et al., *PLoS One* 8:e60529 (2013)), and PAR-2+ neurons are increased in pancreatic cancer (Zhu, J. et al., *Oncotarget* 8:61810-61823 (2017)). Interactions between mast cells and PAR-2+ neurons have been implicated in the development of neuropathic pain (Sakamoto, A. et al., *Pharmacol Res,* 105:84-92 (2016)). Supernatants from pancreatic cancer cell cultures induce pain behavior in rats, which is alleviated by treatment with a PAR-2 blocking peptide, and pain behavior in a nude mouse orthotopic pancreatic cancer model was also decreased by treatment with a PAR-2 blocking peptide (Zhu, J. et al., *Oncotarget* 8:61810-61823 (2017)).

In some embodiments, an anti-human PAR-2 antibody or antigen-binding fragment thereof as described herein, or a pharmaceutical composition thereof as described herein, is administered to relieve pancreatic cancer pain.

Bladder Pain

Intravesical infusion of a PAR-2-activating peptide into the bladder causes prostanoid-dependent referred hyperalgesia in mice (Tsubota, M. et al., *J Pharmacol Sci,* 136:46-49 (2018)) and intrathecal administration of a PAR-2 blocking peptide attenuated bladder hyperactivity and pain in a mouse model of cystitis (Chen, D. et al., Transl Neurosci 7:133-138 (2016)).

In some embodiments, an anti-human PAR-2 antibody or antigen-binding fragment thereof as described herein, or a pharmaceutical composition thereof as described herein, is administered to relieve bladder pain.

Irritable Bowel Syndrome (IBS)

PAR-2 and tryptase expression were increased in biopsies from IBS patients (Liang, W. J. et al., *Gut and Liver,* 10:382-390 (2016)), and increased proteolytic activity was observed in supernatants from culture of biopsies from IBS patients compared to healthy controls (Cenac, N. et al., *J Clin Invest,* 117:636-647(2007)). When given intracolonically, these supernatants induced visceral hyperalgesia and allodynia in wildtype, but not PAR-2−/−, mice. It has been suggested that PAR-2 in endosomes can be involved in the persistent pain of IBS (Jimenez-Vargas, N. N. et al., *Proc Natl Acad Sci USA,* 115, E7438-e7447 (2018)).

In some embodiments, an anti-human PAR-2 antibody or antigen-binding fragment thereof as described herein, or a pharmaceutical composition thereof as described herein, is administered to relieve pain associated with IBS.

Pancreatitis

PAR-2 is expressed by most nociceptive neurons in the thoracic dorsal root ganglia of rats (Hoogerwerf, W. A. et al., *Gastroenterology* 127:883-891 (2004)) and is upregulated in the dorsal root ganglia of rats with experimental chronic pancreatitis (Zhang, W. et al., *Pancreas,* 40: 300-307 (2011)). Infusion of a PAR-2 activating peptide into the pancreatic duct of rats induced pain behavior (Hoogerwerf, W. A. et al., *Gastroenterology* 127:883-891 (2004)). PAR-2 has been suggested as functioning upstream of both TRPA1 (Terada, Y. et al., *J Pharmacol Sci,* 123:284-287 (2013) and TRPV1 (Nishimura, S. et al., Life Sci 87:643-650 (2010)) in pancreatic pain.

In some embodiments, an anti-human PAR-2 antibody or antigen-binding fragment thereof as described herein, or a pharmaceutical composition thereof as described herein, is administered to relieve pain associated with pancreatitis.

V(a)(5). Other Diseases and Conditions

Examples of rheumatic disorders that can be treated by the methods of the present disclosure include, but are not limited to, adult and juvenile rheumatoid arthritis, scleroderma, systemic lupus erythematosus, lupus-like syndromes, undifferentiated connective tissue disease, gout, osteoarthritis, polymyalgia rheumatica, seronegative spondylarthropathies (including ankylosing spondylitis), Reiter's disease, psoriatic arthritis, and chronic Lyme arthritis.

Examples of additional diseases or conditions that can be treated by the methods of the present disclosure, include, but are not limited to, fibrosis, arthritis, Still's disease and uveitis associated with rheumatoid arthritis, orofacial granulomatosis (see e.g., Ketabchi et al. *Oral* Diseases, 13:419-425 (2007), Guillain-Barre disease, Type I diabetes mellitus, Graves' disease, Addison's disease, Raynaud's phenomenon (including Raynaud's disease and Raynaud's syndrome), autoimmune hepatitis, GVHD (graft versus host disease), and disorders resulting in inflammation of the voluntary muscle and other muscles (including dermatomyositis, inclusion body myositis, polymyositis, and lymphangioleiomyomatosis).

Fibrosis

PAR-2 has been implicated in the development of lung (Wygrecka, M. et al., *Am J Respir Crit Care Med,* 183:703-1714 (2011)), skin (Cevikbas, F. et al., *Exp Dermatol,* 20:69-71 (2011)), kidney (Liu, H. et al., *Inflamm Res,* 59:551-559 (2010)), and cardiac fibrosis (Murray, D. B. et al., *J Cell Commun Signal,* 6:45-51 (2012)). PAR-2 levels are elevated in idiopathic pulmonary hypertension, and PAR-2 signaling blockade reverses experimental pulmonary hypertension in mice (Kwapiszewska, G. et al., *Circ Res,* 110:1179-1191 (2012)). PAR-2$^{-/-}$ mice are protected from CCl$_4$-induced liver fibrosis (Knight, V. et al., Hepatology, 55:879-887 (2012)).

In some embodiments, an anti-human PAR-2 antibody or antigen-binding fragment thereof as described herein, or a pharmaceutical composition thereof as described herein, is administered to relieve pain associated with fibrosis.

Arthritis

PAR-2 is over expressed in chondrocytes from osteoarthritis (OA) patients (Xiang, Y. et al., *Osteoarthritis Cartilage,* 14:1163-1173 (2006)) and rheumatoid arthritis (RA) patients (Busso, N. et al., *Arthritis Rheum* 56:101-107 (2007)). PAR-2 protein levels positively correlate with severity of synovitis in RA and OA patients, and in OA patients inflammation also correlates with PAR-2 levels (Tindell, A. G. et al., *Rheumatol Int,* 32(10):3077-3086 (2012)). PAR-2 expression on circulating CD14+ and CD3+ cells is elevated in RA patients (Crilly, A. et al., *Ann Rheum Dis,* 71:1049-1054 (2012)). Release of inflammatory mediators from cultured RA synoviocytes was significantly decreased in the presence of a PAR-2 antagonist (Kelso, E. B. et al., *Arthritis Rheum,* 56:765-771 (2007)). Adjuvant-induced chronic arthritis and surgically-induced osteoarthritis are both significantly reduced in PAR-2$^{-/-}$ mice (Ferrell, W. R. et al., *J Clin Invest,* 111:35-41(2003); Amiable, N. et al., *J Rheumatol,* 38:911-920 (2011)).

In some embodiments, an anti-human PAR-2 antibody or antigen-binding fragment thereof as described herein, or a pharmaceutical composition thereof as described herein, is administered to relieve pain associated with arthritis.

VI(b). Administration and Dosing

An anti-human PAR-2 antibody or antigen-binding fragment thereof as provided herein, or a pharmaceutical composition thereof as provided herein, can be administered by any suitable means, including parenteral, intrapulmonary, intranasal, intratumoral, intralesional administration, intracerebrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some aspects, the administration is subcutaneous.

The appropriate dosage and dosing regimen of an anti-human PAR-2 antibody or antigen-binding fragment thereof as provided herein, or a pharmaceutical composition thereof as provided herein, when used alone or in combination with one or more other additional therapeutic agents, will depend on the disease to be treated, the severity and course of the disease, the route of administration and other factors.

In some aspects, provided herein is an antibody or antigen-binding fragment thereof or pharmaceutical composition provided herein for use as a medicament.

In some aspects, provided herein is an antibody or antigen-binding fragment thereof or pharmaceutical composition provided herein, for use in a method for the treatment of an airway disease. In some embodiments, provided herein is an antibody or antigen-binding fragment thereof or pharmaceutical composition provided herein, for use in a method for the treatment of an airway disease in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for the treatment of a skin disease. In some embodiments, provided herein is an antibody or antigen-binding fragment thereof or pharmaceutical composition provided herein, for use in a method for the treatment of a skin disease in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for the treatment of cancer. In some embodiments, provided herein is an antibody or antigen-binding fragment thereof or pharmaceutical composition provided herein, for use in a method for the treatment of cancer in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for relieving pain associated with various diseases and/or conditions. In some aspects, provided herein is an antibody or antigen-binding fragment thereof or pharmaceutical composition provided herein, for use in a method for relieving pain associated with various diseases and/or conditions in a subject, comprising administering to the subject an effective amount of an antibody or antigen-binding fragment thereof or pharmaceutical composition provided herein.

In some embodiments, an antibody or antigen-binding fragment thereof or pharmaceutical composition provided herein is administered to adults one time per month, one time per two weeks, one time per week, two times per week, or three or more times per week, to treat diseases or conditions associated with increased expression of PAR-2 and/or diseases or conditions that can be alleviated by antagonizing activation of PAR-2 by a PAR-2 activating ligand (e.g., airway diseases, skin diseases, cancer, an inflammatory condition, orofacial granulomatosis, and pain associated with various diseases or conditions). In some embodiments one or more "loading doses" with shorter inter-dosing intervals and/or greater dosage levels may be provided in order to more swiftly raise the concentration of the antibody to a therapeutically effective level, after which longer inter-dosing intervals may be employed to maintain the concentration of the antibody at or around the therapeutically effective level.

If injected, the effective amount of an antibody or antigen-binding fragment thereof or pharmaceutical composition provided herein, per adult dose can range from about 1 mg/m2 to about 20 mg/m2. Alternatively, a fixed dose can be administered, where the amount can range from about 5 mg/dose to about 600 mg/dose or about 5 mg/dose to about 2400 mg/dose. In some embodiments the dose is 15, 30, 60, 180, 500, 1200, or 2400 mg. In some aspects, one range for a flat dose is about 20 mg/dose to about 30 mg/dose.

In some embodiments, a flat dose of 20-600 mg/dose or 25 mg/dose is repeatedly administered by injection. If a route of administration other than injection is used, the dose is appropriately adjusted in accordance with standard medical practices. One example of a therapeutic regimen involves injecting a dose of about 20-600 mg, or 20-30 mg of an antibody or antigen-binding fragment thereof or pharmaceutical composition provided herein, to one to three times per week over a period of at least three weeks, though treatment for longer periods may be necessary to induce the desired degree of improvement. For pediatric subjects (age 4-17), one exemplary suitable regimen involves the subcutaneous injection of about 0.4 mg/kg up to about 25 mg/kg of an antibody or antigen-binding fragment thereof or pharmaceutical composition provided herein, administered two or three times per week.

In some embodiments, the methods provided herein involve subcutaneous injection of from about 0.5 mg to about 10 mg of an antibody or antigen-binding fragment thereof or pharmaceutical composition provided herein, administered once or twice per week. Some aspects are directed to pulmonary administration (e.g., by nebulizer) of about 3 or more mg of an antibody or antigen-binding fragment thereof or pharmaceutical composition provided herein, administered once a week.

Examples of therapeutic regimens provided herein comprise subcutaneous injection of an antibody or antigen-binding fragment thereof or pharmaceutical composition provided herein, administered once a week, at a dose of about 1.5 mg to about 3 mg, to treat diseases or conditions associated with increased expression of PAR-2 and/or diseases or conditions that can be alleviated by antagonizing activation of PAR-2 by a PAR-2 activating ligand (e.g., airway diseases, skin diseases, cancer, orofacial granulomatosis, inflammatory conditions, and pain associated with various diseases or conditions). Weekly administration of an antibody or antigen-binding fragment thereof or pharmaceutical composition provided herein, is continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or 20 mg of an antibody or antigen-binding fragment thereof or pharmaceutical composition provided herein, per kilogram body mass of the subject (mg/kg). In some embodiments, a dose is of about 0.5 mg/kg. The dose can be administered once to the subject, or more than once at a certain interval, for example, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

VI(c). Combination Therapy

In some aspects, the present disclosure provides a method of treating a subject with an anti-human PAR-2 antibody or antigen-binding fragment thereof as provided herein, or a pharmaceutical composition thereof as provided herein, and one or more other treatments.

In some aspects, the method comprises administering one or more of the PAR-2 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

In certain embodiments, the method comprises administering one or more of the PAR-2 antagonists described herein and one or more other treatments for chronic obstructive pulmonary disease including, but not limited to e.g., short-acting bronchodilators (e.g., albuterol, ipratropium, levalbuterol, or combination thereof); long-acting bronchodilators (e.g., aclidinium, arformoterol, formoterol, indacaterol, tiotropium, salmeterol, umeclidinium, or combination thereof); inhaled steroids (e.g., fluticasone or budesonide); combination inhalers (e.g., fluticasone and vilanterol, fluticasone, umeclidinium and vilanterol, formoterol and budesonide, salmeterol and fluticasone, aclidinium and formoterol, albuterol and ipratropium, formoterol and glycopyrrolate, glycopyrrolate and indacaterol, olodaterol and tiotropium, or umeclidinium and vilanterol); phosphodiesterase-4 inhibitors; theophylline; and antibiotics.

In certain embodiments, the method comprises administering one or more of the PAR-2 antagonists described herein and one or more other treatments for asthma including, but not limited to e.g., inhaled corticosteroids (e.g., fluticasone propionate, budesonide, ciclesonide, beclomethasone, mometasone and fluticasone furoate); leukotriene modifiers (e.g., montelukast, zafirlukast, and zileuton); combination inhalers (fluticasone-salmeterol, budesonide-formoterol, formoterol-mometasone, and fluticasone furoate-vilanterol); theophylline; short-acting beta agonists (e.g., albuterol and levalbuterol); anticholinergic agents (ipratropium and tiotropium); and oral and intravenous corticosteroids (prednisone and methylprednisolone).

In certain embodiments, the method comprises administering one or more of the PAR-2 antagonists described herein and one or more other treatments for idiopathic pulmonary fibrosis including, but not limited to e.g., pirfenidone and nintedanib.

In certain embodiments, the method comprises administering one or more of the PAR-2 antagonists described herein and one or more other treatments for pulmonary arterial hypertension including, but not limited to e.g., blood vessel dilators (vasodilators) (e.g., epoprostenol); guanylate cyclase (GSC) stimulators (e.g., riociguat); endothelin receptor antagonists (e.g., bosentan, macitentan, and ambrisentan); sildenafil; tadalafil; high-dose calcium channel blockers (amlodipine, diltiazem, and nifedipine); anticoagulants (e.g., warfarin); digoxin; and diuretics.

In certain embodiments, such a combination therapy achieves synergy or an additive effect by, for example, attacking multiple sites or molecular targets in a tumor. Types of combination therapies that can be used in connection with the present disclosure include inhibiting or activating (as appropriate) multiple nodes in a single disease-related pathway, multiple pathways in a target cell, and multiple cell types within a target tissue.

VI(d). Detection and Diagnostic Uses

An anti-human PAR-2 antibody or antigen-binding fragment thereof described herein (see, e.g., Section II) can be used to assay PAR-2 protein (e.g., human PAR-2 protein) levels in a biological sample using classical methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody or antigen-binding fragment thereof described herein. Alternatively, a second antibody or antigen-binding fragment thereof that recognizes an anti-human PAR-2 antibody or antigen-binding fragment thereof described herein can be labeled and used in combination with an anti-human PAR-2 antibody or antigen-binding fragment thereof to detect PAR-2 protein (e.g., human PAR-2 protein) levels.

Assaying for the expression level of PAR-2 protein (e.g., human PAR-2 protein) is intended to include qualitatively or quantitatively measuring or estimating the level of a PAR-2 protein (e.g., human PAR-2 protein) in a first biological sample either directly (e.g., by determining or estimating absolute protein level) or relatively (e.g., by comparing to the disease associated protein level in a second biological sample). PAR-2 protein (e.g., human PAR-2 protein) expression level in the first biological sample can be measured or estimated and compared to a standard PAR-2 protein (e.g., human PAR-2 protein) level, the standard being taken from a second biological sample obtained from an individual not having the disorder or being determined by averaging levels from a population of individuals not having the disorder. As will be appreciated in the art, once the "standard" PAR-2 protein (e.g., human PAR-2 protein) level is known, it can be used repeatedly as a standard for comparison.

As used herein, the term "biological sample" refers to any biological sample obtained from a subject, cell line, tissue, or other source of cells potentially expressing PAR-2 protein (e.g., human PAR-2 protein). *Methods* for obtaining tissue biopsies and body fluids from animals (e.g., humans) are well known in the art.

An anti-human PAR-2 antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response can be utilized to predict, diagnose and monitor to evaluate patient samples including those known to have or suspected of having, e.g., airway diseases, skin diseases, cancer, and pain associated with various diseases or conditions.

Anti-human PAR-2 antibodies and antigen-binding fragments thereof described herein can carry a detectable or functional label. When fluorescence labels are used, currently available microscopy and fluorescence-activated cell sorter analysis (FACS) or combination of both methods procedures known in the art can be utilized to identify and to quantitate the specific binding members. Anti-human PAR-2 antibodies or antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-human PAR-2 antibody can carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art can be utilized to identify and quantitate the specific binding of anti-human PAR-2 antibody or antigen-binding fragment to PAR-2 protein (e.g., human PAR-2 protein). In the instance where the label is an enzyme, detection can be accomplished by any of the presently utilized colorimetric, spectrophotometric, fluorospectrophotometric, amperometric or gasometric techniques as known in the art. This can be achieved by contacting a sample or a control sample with an anti-human PAR-2 antibody or antigen-binding fragment thereof under conditions that allow for the formation of a complex between the antibody or antigen-binding fragment thereof and PAR-2 protein (e.g., human PAR-2 protein). Any complexes formed between the antibody or antigen-binding fragment thereof and PAR-2 protein (e.g., human PAR-2 protein) are detected and compared in the sample and the control. In light of the specific binding of the antibodies or antigen-binding fragments thereof described herein to human PAR-2, the antibodies or antigen-binding fragments thereof can be used to specifically detect PAR-2 protein (e.g., human PAR-2 protein) expression on the surface of cells. The antibodies or antigen-binding fragments thereof described herein can also be used to purify PAR-2 protein (e.g., human PAR-2 protein) via immunoaffinity purification.

Also included herein is an assay system which can be prepared in the form of a test kit for the quantitative analysis of the extent of the presence of PAR-2 protein (e.g., human PAR-2 protein). The system or test kit can comprise a labeled component, e.g., a labeled antibody or antigen-binding fragment, and one or more additional immunochemical reagents. See, e.g., Section VII below for more on kits.

In some aspects, methods for in vitro detection of PAR-2 protein (e.g., human PAR-2 protein) in a sample, comprising contacting said sample with an antibody or antigen-binding fragment thereof, are provided herein. In some embodiments, provided herein is the use of an antibody or antigen-binding fragment thereof provided herein, for in vitro detection of PAR-2 protein (e.g., human PAR-2 protein) in a sample. In some embodiments, provided herein is an antibody or antigen-binding fragment thereof or composition provided herein for use in the detection of PAR-2 protein (e.g., human PAR-2 protein) in a subject or a sample obtained from a subject. In some embodiments, provided herein is an antibody or antigen-binding fragment thereof provided herein for use as a diagnostic. In some aspects, the antibody comprises a detectable label.

VII. Kits

Provided herein are kits comprising one or more antibodies or antigen-binding fragments thereof described herein. In some embodiments, provided herein is a pharmaceutical pack or kit comprising one or more containers filled with one or more of the ingredients of the pharmaceutical compositions described herein, such as one or more antibodies or antigen-binding fragments thereof provided herein. Optionally associated with such container(s) can be a notice in the form prescribed by a governmental agency regulating the manufacture, use, or sale of pharmaceuticals or biological products, which notice reflects approval by the agency of manufacture, use or sale for human administration.

Also provided herein are kits that can be used in detection methods. In some aspects, a kit comprises an antibody or antigen-binding fragment thereof described herein, a purified antibody or antigen-binding fragment thereof, in one or more containers. In some embodiments, kits described herein contain a substantially isolated PAR-2 protein (e.g., human PAR-2 protein) that can be used as a control. In some embodiments, the kits described herein further comprise a control antibody or antigen-binding fragment thereof which does not react with PAR-2 protein (e.g., human PAR-2 protein). In some embodiments, kits described herein contain one or more elements for detecting the binding of an antibody or antigen-binding fragment thereof to PAR-2 protein (e.g., human PAR-2 protein) (e.g., the antibody or antigen-binding fragment thereof can be conjugated to a detectable substrate such as a fluorescent compound, an enzymatic substrate, a radioactive compound or a luminescent compound, or a second antibody or antigen-binding fragment thereof which recognizes the first antibody or antigen-binding fragment thereof can be conjugated to a detectable substrate). In some embodiments, a kit provided herein can include a recombinantly produced or chemically synthesized PAR-2 protein (e.g., human PAR-2 protein). The PAR-2 protein (e.g., human PAR-2 protein) provided in the kit can also be attached to a solid support. In some embodiments, the detecting means of the above described kit includes a solid support to which a PAR-2 protein (e.g., human PAR-2 protein) is attached. Such a kit can also include a non-attached reporter-labeled anti-human antibody or antigen-binding fragment thereof or anti-mouse/rat antibody or antigen-binding fragment thereof. In certain embodiment, binding of the antibody or antigen-binding fragment thereof to the PAR-2 protein (e.g., human PAR-2 protein) can be detected by binding of the said reporter-labeled antibody or antigen-binding fragment thereof.

VIII. Examples

The examples in this Section (i.e., Section VIII) are offered by way of illustration, and not by way of limitation.

Example 1: Generation of Selective Anti-PAR-2 Antibodies

In order to generate anti-PAR-2 antibodies, genetic immunization was performed in PAR-2 knockout (KO) mice and rats. A polynucleotide sequence encoding human PAR-2 (SEQ ID NO: 1) was cloned into a mammalian expression vector and used for immunization of PAR-2 KO mice and rats.

F2RL1 (PAR-2) knockout mice were generated by the insertion of a construct containing hygromycin and neomycin selection genes into the endogenous F2RL1 locus in mice. A targeted construct was electroporated into RW4 mouse embryonic stem (ES) cells. ES cells positive for the construct were injected into C57 mouse blastocysts. Resulting chimeric males were backcrossed to females and offspring screened for germline transmission of the vector. Positive offspring were intercrossed to generate homozygous knockout mice. F2RL1 (PAR-2) knockout rats were generated using standard techniques. The absence of F2RL1 message in the animals was confirmed by quantitative PCR.

After 4-12 rounds of immunization the serum anti-PAR-2 titre for each animal was measured using human PAR-2 transfected 3T3 cells. Animals with positive serum titers were used for monoclonal anti-PAR-2 antibody generation.

Antibody secreting plasma and memory B cells were prepared from B cell-containing tissues (spleen, lymph nodes, bone marrow) and single cells screened in a high throughput microreactor (for example as described in US 2016/0252495, U.S. Pat. No. 9,188,593, and U.S. Ser. No. 10/087,408) for secretion of antibodies selective for PAR-2 but not PAR-1 ("PAR-2 selective antibodies"), utilizing transfected 3T3 cells as source of target. Binding of secreted antibody to target was detected using fluorescently labelled secondary antibody. The screening assay included a carboxyfluorescein succinimidyl ester-labelled PAR-1-expressing cell line to enable identification of antibodies that cross-reacted with PAR-1 or other non-PAR-2 cell components. Such antibodies were eliminated from further consideration.

Over 1500 cells producing a PAR-2 selective antibody were identified. Single cells expressing PAR-2-selective antibodies were retrieved, lysed, and cellular mRNA was isolated for synthesis of cDNA using reverse transcriptase. Primer sequences complementary to rodent antibody variable regions were used to amplify the heavy and light chain antibody sequences from each antibody-expressing cell. The polynucleotide sequences encoding each antibody heavy and light chain variable region can be elucidated using next generation sequencing technology such as the Illumina MiSeq Next generation Sequencer, or as described in U.S. Pat. No. 9,188,593.

When the polynucleotides encoding each of these PAR-2 selective antibodies were sequenced, polynucleotides encoding at least 421 unique paired antibody heavy and light chain sequences were identified. Paired heavy and light chains encoded by these sequence pairs were expressed as a full length human IgG4 isotype antibodies and assessed for PAR-2 binding and selectivity by flow cytometry. Specifically, Expi293F cells were transiently transfected with a mammalian expression plasmid encoding either human PAR-2 (e.g., SEQ ID NO: 28 or amino acids 26-397 of SEQ ID NO: 28), human PAR-1 (SEQ ID NO: 47) or a chimeric molecule consisting of the N-terminal residues of PAR-2 (residues 1 to 74) fused to PAR-1 residues 102-425 ('Nt-PAR-2') (SEQ ID NO: 48) using the manufacturer's protocol. Cells were used for flow cytometric analysis 36-48 hours post-transfection. Use of Nt-PAR-2 as a target allowed antibodies which bound the N-terminal residues of PAR-2 (which comprise the protease-cleavage sites on PAR-2) to be distinguished from antibodies which bound other extracellular sites on PAR-2, such as the PAR-2-activating ligand-binding site(s). Expi293F cells, transiently expressing one of each of the different target proteins were labelled with different intensities of a single fluorophore Encoder dye (Intellicyt) for 10 mins at either 1 in 250 dilution for high intensity and/or 1 in 1500 dilution for moderate intensity, enabling simultaneous analysis of multiple cell populations. After washing the cells were then mixed in an equal ratio with the unlabeled cell type and analyzed for antibody binding.

The cells were plated in 96 well plates at 2×10$^5$ cells/well. Following a wash step using Phosphate buffered saline (PBS), the primary antibody (anti-PAR-2 antibody) was added at a concentration of 10 μg/mL in 50 μL of FACS buffer (0.5% w/v BSA in PBS) to each well and incubated for 10-15 mins. Following a wash step, secondary antibody (anti-human Fc-FITC) was added to the wells at 1:200 dilution in 50 μL for 10-15 mins. Following a washing step, the cells were re-suspended in fluorescence-activated cell sorting (FACS) buffer. The flow cytometry analysis was performed on an Intellicyt iQue screener. Gates were drawn around the different intensities of encoder dye-positive cells and these populations were analyzed separately from each other and the unlabeled cells for binding by the primary antibody.

Table 5 lists the antibodies that expressed at detectable levels and that bound to human PAR-2 (SEQ ID NO: 28) but not to human PAR-1 (SEQ ID NO: 47) as determined by flow cytometric analysis. Human PAR-1:

```
                                              (SEQ ID NO: 47)
MGPRRLLLVAACFSLCGPLLSARTRARRPESKATNATLDPRSF

LLRNPNDKYEPFWEDEEKNESGLTEYRLVSINKSSPLQKQLPA

FISEDASGYLTSSWLTLFVPSVYTGVFVVSLPLNIMAIVVFIL

KMKVKKPAVVYMLHLATADVLFVSVLPFKISYYFSGSDWQFGS

ELCRFVTAAFYCNMYASILLMTVISIDRFLAVVYPMQSLSWRT

LGRASFTCLAIWALAIAGVVPLLLKEQTIQVPGLNITTCHDVL

NETLLEGYYAYYFSAFSAVFFFVPLIISTVCYVSIIRCLSSSA

VANRSKKSRALFLSAAVFCIFIICFGPTNVLLIAHYSFLSHTS

TTEAAYFAYLLCVCVSSISCCIDPLIYYYASSECQRYVYSILC

CKESSDPSSYNSSGQLMASKMDTCSSNLNNSIYKKLLT
```

Antibodies that were positive for human PAR-2 binding and negative for PAR-1 binding were also screened with a view to eliminating antibodies which bound within the N-terminal of PAR-2 where the tethered ligand and protease cleavage sites on PAR-2 reside. This screen was performed using a chimeric construct consisting of the human PAR-2 N-terminal with the rest of the protein being human PAR1, Nt-PAR-2 (SEQ ID NO: 48). Anti-PAR-2 antibodies which did not bind the PAR-2 N-terminal were tested for function in cell-based assays. Nt-PAR-2:

```
                                              (SEQ ID NO: 48)
MRSPSAAWLLGAAILLAASLSCSGTIQGTNRSSKGRSLIGKVDGTS

HVTGKGVTVETVFSVDEFSASVLTGKLTTLFVPSVYTGVFVVSLPL

NIMAIVVFILKMKVKKPAVVYMLHLATADVLFVSVLPFKISYYFSG

SDWQFGSELCRFVTAAFYCNMYASILLMTVISIDRFLAVVYPMQSL

SWRTLGRASFTCLAIWALAIAGVVPLLLKEQTIQVPGLNITTCHDV

LNETLLEGYYAYYFSAFSAVFFFVPLIISTVCYVSIIRCLSSSAVA

NRSKKSRALFLSAAVFCIFIICFGPTNVLLIAHYSFLSHTSTTEAA

YFAYLLCVCVSSISCCIDPLIYYYASSECQRYVYSILCCKESSDPS

SYNSSGQLMASKMDTCSSNLNNSIYKKLLT
```

TABLE 5

Anti-PAR-2 antibodies binding to human PAR-1, PAR-2 and Nt-PAR-2 on PAR-1 transfected cells as measured by flow cytometry

| Anti-PAR-2 antibody # | huPAR-1 | huPAR-2 | Nt-PAR-2 on PAR-1 |
|---|---|---|---|
| 1 | − | + | − |
| 2 | − | + | + |
| 5 | − | + | − |
| 18 | − | + | − |
| 20 | − | + | − |
| 39 | − | + | − |
| 73 | + | − | − |
| 77 | − | + | − |
| 84 | − | + | − |
| 86 | − | + | − |
| 87 | − | + | − |
| 100 | − | + | − |
| 114 | − | + | − |
| 140 | − | + | − |
| 154 | − | + | − |
| 157 | − | + | − |
| 171 | − | + | − |
| 178 | − | + | − |
| 189 | − | + | − |
| 191 | − | + | − |
| 192 | − | + | − |
| 194 | − | + | − |
| 201 | − | + | − |
| 208 | − | + | − |
| 209 | − | + | − |
| 211 | − | + | − |
| 225 | − | + | − |
| 227 | − | + | − |
| 228 | − | + | − |
| 234 | − | + | − |
| 243 | − | + | + |
| 245 | − | + | − |
| 248 | − | + | − |
| 261 | − | + | − |
| 283 | − | + | − |
| 288 | − | + | − |
| 290 | − | + | − |
| 293 | − | + | − |
| 294 | − | + | − |
| 295 | − | + | − |
| 297 | − | + | − |
| 298 | − | + | − |
| 300 | − | + | − |
| 303 | − | + | − |
| 304 | − | + | − |
| 306 | − | + | − |
| 307 | − | + | − |
| 309 | − | + | − |
| 310 | − | + | − |
| 311 | − | + | − |
| 313 | − | + | − |
| 315 | − | + | − |
| 316 | − | + | − |
| 318 | − | + | + |
| 321 | − | + | − |
| 323 | − | + | − |
| 327 | − | + | − |
| 328 | − | + | − |
| 329 | − | + | − |
| 331 | − | + | − |
| 332 | − | + | − |
| 333 | − | + | − |
| 335 | − | + | − |
| 336 | − | + | − |
| 337 | − | + | − |
| 341 | − | + | − |
| 342 | − | + | − |
| 343 | − | + | − |
| 347 | − | + | − |
| 348 | − | + | − |
| 350 | − | + | + |
| 358 | − | + | − |
| 360 | − | + | − |
| 361 | − | + | + |
| 362 | − | + | + |
| 378 | − | + | + |
| 380 | − | + | − |
| 384 | − | + | − |
| 391 | − | + | − |
| 392 | − | + | − |
| 396 | − | + | − |
| 399 | − | + | − |
| 402 | − | + | − |
| 405 | − | + | − |
| 407 | − | + | − |
| 409 | − | + | − |
| 410 | − | + | − |
| 411 | − | + | − |
| 412 | − | + | − |
| 416 | − | + | − |
| 420 | − | + | − |
| 424 | − | + | − |
| 425 | − | + | − |
| 427 | − | + | − |
| 428 | − | + | − |
| 432 | − | + | + |
| 433 | − | + | − |
| 434 | − | + | − |
| 435 | − | + | − |

** + refers to binding of the antibody with a mean fluorescence intensity (MFI) at least 2-fold higher than secondary control only.

Example 2: Identification of Antagonist Anti-PAR-2 Antibodies 2.1 Screening for Antagonist Anti-PAR-2 Antibodies that Inhibit β-Arrestin Signaling In order to screen for antagonist anti-PAR-2 antibodies that inhibit β-arrestin signaling, a range of antibodies which were identified as selective for the extracellular loops of human PAR-2 (positive binding to PAR-2 but negative binding to PAR-1 and negative binding to Nt-PAR-2) were screened for their ability to antagonize SLIGKV-induced PAR-2 β-arrestin activity. Specifically, Tango™ F2RL1-bla U2OS cells (Thermo Fisher Scientific) were plated in 96 well black clear bottom plates at $4 \times 10^4$ cells/well in 128 μL assay buffer (1% dialyzed FBS, 0.1 mM non-essential amino acids, 25 mM HEPES (pH 7.3), 100 U/mL Penicillin, 100 ug/mL Streptomycin, DMEM with no phenol red). The antibody was added to the cells in 16 μL/well of assay buffer supplemented with 0.5% DMSO as a 10-point serial-dilution (including a 0 μM antibody point), starting at ~666 nM and serially diluted 1 in 4. Each concentration was tested on cells in duplicate or triplicate. Following incubation at 37° C./5% $CO_2$ for 30 min, the soluble PAR-2 agonist SLIGKV (Sigma) (SEQ ID NO: 46) was added to the cells in 16 μL/well of assay buffer with 0.5% DMSO at a concentration of 1 or 2 μM (depending on the experimental run). Plates were incubated for 16 hours at 37° C./5% $CO_2$. After loading the cell permeable LiveBLAzer™ FRET B/G substrate (Life Technologies) using the manufacturer's protocol at a final volume of 32 L/well, the plates were incubated for 2 hours in the dark at room temperature and then cellular fluorescence was measured on a Molecular Devices Flex Station 3 plate reader (excitation at 410 nm and emission at both 458 nm and 522 nm, 7 readings/well). After background subtraction using cell free wells, non-linear regression was used to fit a curve for the Blue/Green fluorescence emission ratio against the log of the molar concentration of the antibody (using a 4 parameter logistic curve fit).

Table 6 lists the potency of thirty four selected anti-PAR-2 extracellular loop-selective antibodies for inhibition of PAR-2 signalling in PAR-2 β-arrestin cell assay (where multiple independent assays were performed, a mean value is shown).

TABLE 6

Potency of anti-PAR-2 antibodies in the PAR-2 β-arrestin cell assay

| Anti-PAR-2 antibody | Variable Light Chain Sequence Identifier | Variable Heavy Chain Sequence Identifier | Potency in PAR-2 β-arrestin cell assay ($IC_{50}$ in nM) |
|---|---|---|---|
| Ab1 | SEQ ID NO: 49 | SEQ ID NO: 50 | 8.4 |
| Ab5 | SEQ ID NO: 51 | SEQ ID NO: 52 | 23.1 |
| Ab20 | SEQ ID NO: 53 | SEQ ID NO: 54 | 10.7 |
| Ab39 | SEQ ID NO: 55 | SEQ ID NO: 56 | 4.9 |
| Ab77 | SEQ ID NO: 57 | SEQ ID NO: 58 | 16.5 |
| Ab84 | SEQ ID NO: 59 | SEQ ID NO: 60 | 6.0 |
| Ab86 | SEQ ID NO: 61 | SEQ ID NO: 62 | 9.9 |
| Ab87 | SEQ ID NO: 63 | SEQ ID NO: 64 | 5.6 |
| Ab114 | SEQ ID NO: 65 | SEQ ID NO: 66 | 36.7 |
| Ab140 | SEQ ID NO: 67 | SEQ ID NO: 68 | 20.1 |
| Ab189 | SEQ ID NO: 69 | SEQ ID NO: 70 | 122.7 |
| Ab192 | SEQ ID NO: 71 | SEQ ID NO: 72 | 100.0 |
| Ab201 | SEQ ID NO: 73 | SEQ ID NO: 74 | 10.7 |
| Ab209 | SEQ ID NO: 75 | SEQ ID NO: 76 | 65.5 |
| Ab225 | SEQ ID NO: 77 | SEQ ID NO: 78 | 3.4 |
| Ab227 | SEQ ID NO: 79 | SEQ ID NO: 80 | 10.2 |
| Ab228 | SEQ ID NO: 81 | SEQ ID NO: 82 | 33.3 |
| Ab234 | SEQ ID NO: 83 | SEQ ID NO: 84 | 4.8 |
| Ab245 | SEQ ID NO: 85 | SEQ ID NO: 86 | 3.8 |
| Ab248 | SEQ ID NO: 87 | SEQ ID NO: 88 | 4.6 |
| Ab261 | SEQ ID NO: 89 | SEQ ID NO: 90 | 19.9 |
| Ab303 | SEQ ID NO: 91 | SEQ ID NO: 92 | 9.0 |
| Ab309 | SEQ ID NO: 117 | SEQ ID NO: 116 | 1.6 |
| Ab311 | SEQ ID NO: 93 | SEQ ID NO: 94 | 1.8 |
| Ab313 | SEQ ID NO: 95 | SEQ ID NO: 96 | 8.2 |
| Ab323 | SEQ ID NO: 97 | SEQ ID NO: 98 | 2.1 |
| Ab335 | SEQ ID NO: 99 | SEQ ID NO: 100 | 2.5 |
| Ab342 | SEQ ID NO: 101 | SEQ ID NO: 102 | 1.9 |
| Ab343 | SEQ ID NO: 103 | SEQ ID NO: 104 | 18.2 |
| Ab348 | SEQ ID NO: 105 | SEQ ID NO: 106 | 2.7 |
| Ab360 | SEQ ID NO: 107 | SEQ ID NO: 108 | 16 |
| Ab380 | SEQ ID NO: 110 | SEQ ID NO: 111 | 57.1 |
| Ab392 | SEQ ID NO: 112 | SEQ ID NO: 113 | 13.7 |
| Ab435 | SEQ ID NO: 114 | SEQ ID NO: 115 | 53.8 |

2.2 Screening for Anti-PAR-2 Extracellular Loop-Selective Antibodies with Broad Antagonist Activity To screen for anti-PAR-2 extracellular loop-selective antibodies with broad antagonist activity, eight anti-PAR-2 extracellular loop-selective antibodies were selected for further assessment of their ability to prevent trypsin activated PAR-2 signaling inducing calcium flux. A Chemiscreen Human PAR-2 receptor calcium-optimized stable CHEM-1 cell line (Eurofins) was used for PAR-2 calcium flux assays. CHEM-1 PAR-2 cells were plated in 96 well black clear bottom plates at 7.5×10⁴ cells/well in 100 μL serum reduced basal media (1% heat inactivated FBS, 0.1 mM non-essential amino acids, 10 mM HEPES (pH 7.3), DMEM high glucose medium (4.5 g/L D-glucose)). Plates were incubated for 20-24 hours at 37° C./5% $CO_2$. After removing the media, cells were washed in 100 μL/well assay media (1% w/v of BSA in HBSS with 20 mM HEPES) which was removed by aspiration. Fluo4NW dye (Life Technologies) reconstituted in 2.5 mM probenecid in assay buffer was added to the cells at 100 μL/well. Plates were incubated for 30 minutes at 37° C./5% $CO_2$ in the dark and then antibody was added to the cells in 50 μL/well of assay media as a 10-point serial-dilution (which included 0 μM antibody), starting at ~666 nM and serially diluted 1 in 3. Each concentration was tested on cells in duplicate or triplicate. Following incubation at room temperature for 30 min in the dark, the agonist trypsin (Sigma) was added to the cells in 50 μL/well of assay buffer at a pre-determined $EC_{80}$ concentration using the Molecular Devices FLIPR Tetra (dispense height of 200 μL, dispense speed of 75 μL/s). Cellular fluorescence was measured immediately after addition of agonist using the FLIPR Tetra (excitation at 470-495 and emission at 515 to 575, excitation intensity of 20%, gain of 80 and a variable exposure time). Non-linear regression was used to fit a curve for the Max-min fluorescence against the log of the molar concentration of the antibody (using a 4 parameter logistic curve fit).

The potency of anti-PAR-2 extracellular loop-selective antibodies for inhibition of PAR-2 signalling in a calcium flux cell assay is listed in Table 7 (where multiple independent assays were performed, a mean value is shown). These assays were carried out using $EC_{80}$ of trypsin as the PAR-2 activator.

TABLE 7

The potency of anti-PAR-2 antibodies in the PAR-2 calcium flux cell assay

| Anti-PAR-2 antibody | Variable Light Chain Sequence Identifier | Variable Heavy Chain Sequence Identifier | Potency in the PAR-2 calcium flux assay ($IC_{50}$ in nM) |
|---|---|---|---|
| Ab1 | SEQ ID NO: 49 | SEQ ID NO: 50 | 50.5 |
| Ab20 | SEQ ID NO: 53 | SEQ ID NO: 54 | 73.2 |
| Ab39 | SEQ ID NO: 55 | SEQ ID NO: 56 | 29.0 |
| Ab77 | SEQ ID NO: 57 | SEQ ID NO: 58 | 169.0 |
| Ab84 | SEQ ID NO: 59 | SEQ ID NO: 60 | Insufficient signal to obtain data |
| Ab87 | SEQ ID NO: 63 | SEQ ID NO: 64 | Insufficient signal to obtain data |
| Ab225 | SEQ ID NO: 77 | SEQ ID NO: 78 | Insufficient signal to obtain data |
| Ab309 | SEQ ID NO: 117 | SEQ ID NO: 116 | 6.7 |

Three broad groups of antibodies were identified using PAR-2 calcium flux assay: antibodies Ab84, Ab87, and Ab225 were not able to inhibit trypsin-induced calcium flux; antibodies Ab1, Ab20, Ab39, and Ab77 demonstrated low potency inhibition; and antibody 309, which was able to completely inhibit calcium flux with an $IC_{50}$ value of about 6.7 nM.

2.3 Screening for Antibodies that Inhibit the Inflammatory Cytokine Release from PAR-2 Activated A549 Cells Inhibition of PAR-2-mediated IL-6 and IL-8 cytokine release from human A549 epithelial-like cells was analyzed by a sandwich enzyme-linked immunosorbent assay (ELISA). Adherent A549 cells were plated at 2×10⁴ cells/well in flat-bottom 96-well plates at 100 l/well in Ham's F-12K nutrient media (supplemented with 10% fetal bovine serum) and incubated overnight at 37° C./5% $CO_2$. After removing the media and washing once with 200 l/well of 1× phosphate buffered saline (PBS), the cells were serum-starved by incubating with 100 l/well of serum-free media for 24 hours at 37° C./5% $CO_2$. After 24 hours, half-logarithmic serial dilutions of antibody starting at 666.7 nM and an $EC_{50}$ concentration of SLIGKV at 100 μM were added to the cells with a final volume of 200 μl/well and incubated for 24 hours at 37° C./5% $CO_2$. Following 24 hour incubation, the supernatants were harvested and assessed for IL-6 and IL-8 cytokine levels using a commercial IL-6 and IL-8 ELISA kit and assessing absorbance at 450 nm (with 570 nm wavelength subtraction) using a SpectraMax absorbance reader. After subtracting the background, expression levels of PAR-2 mediated IL-6 and IL-8 were interpolated from a standard curve and plotted using a 4 parameter logistic curve fit with the concentration of antibody plotted against the concentration of IL-6 and IL-8. Ab309 was more potent at inhibiting IL-6 and IL-8 release from A549 cells compared to Ab87.

Example 3: Humanization of Potent Anti-PAR-2 Extracellular Loop-Selective Antibody Humanization of potent anti-PAR-2 extracellular loop-selective Antibody 309 (Ab309) was performed by grafting complementarity determining regions (CDRs) from non-human 'donor' antibody variable region into human 'acceptor' variable region frameworks. The following CDR residues were used to define the CDRs: Heavy chain CDR1 as per AbM nomenclature (Residues H26, H27, H28, H29, H30, H31, H32, H33, H34 and H35 as defined by the Kabat numbering scheme); Heavy chain CDR2 as per Kabat but excluding the last 5 amino acids (Residues H50, H51, H52, H53, H54, H55, H56, H57, H58, H59 and H60 as defined by the Kabat numbering scheme); Heavy chain CDR3 as per Kabat (Residues H95, H96, H97, H98, H99, H100, H100A, H100B, H100C, H101 and H102 as defined by the Kabat numbering scheme); and Light chain CDRs as per Kabat (Residues L24, L25, L26, L27, L28, L29, L30, L31, L32, L33 and L34 for CDR1; residues L50, L51, L52, L53, L54, L55 and L56 for CDR2; and residues L89, L90, L91, L92, L93, L94, L96 and L97 for CDR3 as defined by the Kabat numbering scheme).

CDRs from the variable region of the heavy chain of Antibody 309 were grafted into human antibody variable regions as shown in FIG. 1A. CDRs from the variable region of the light chain of Antibody 309 were grafted into human antibody variable regions as shown in FIG. 1B. Antibodies with high identity to human germline sequence were favored.

Humanized antibody variable regions were converted to recombinant IgG4 and expressed. Specifically, the variable heavy and light chains for each antibody were backtranslated and codon optimized. Polynucleotides encoding antibody variable region sequences were produced by gene synthesis. All heavy chain variable regions were subcloned using standard restriction enzyme cloning into a mammalian expression vector encoding a human IgG4 (throughout specification, the term "IgG4" refers to a human IgG4 which comprises the S228P substitution and terminal lysine deletion (K447Δ) (residue numbering according to Euro Index)) (SEQ ID NO: 34). The variable light chain encoding sequences were subcloned into a mammalian expression vector encoding a human kappa constant region (SEQ ID NO:37).

Co-transfection of heavy chain and light chain plasmids was performed in Expi293F cells using the manufacturer's protocol (ThermoFisher). Cell culture supernatant was collected by centrifugation, and antibodies captured on a Protein A resin-containing column. Antibody elution was performed using either using 100 mM Acetic Acid, 100 mM Arginine HCl, 5 mM Histidine, pH 3.5 and the resultant eluent neutralized using basic buffer to pH 7-8. Antibodies were desalted into either 10 mM Histidine HCl, 100 mM Arginine HCl, pH 6 or PBS pH 6 by gel filtration or dialysis and when necessary concentrated using an Amicon Ultra-15 centrifugal filter unit (Merck Millipore).

Cell lines expressing human PAR-1, human PAR-2 or a chimera consisting of the N-terminal residues of PAR-2 (residues 1 to 74) fused to PAR-1 residues 102-425 ('Nt-PAR-2') were generated by electroporation of a mammalian expression vector coding the respective proteins (human PAR-2 (e.g., SEQ ID NO: 28 or amino acids 26-397 of SEQ ID NO: 28), human PAR-1 (SEQ ID NO: 47), Nt-PAR-2 (SEQ ID NO: 48) into the C6 rat cell line or 3T3 cell line under the selection of a stable antibiotic marker gene. Purified humanized antibodies were assessed for selectivity by flow cytometry using human PAR-2, PAR-1, and Nt-PAR-2 using transfected cells.

A subset of these antibodies (Ab309 (parental murine antibody), Ab309-4e, Ab309-6e, Ab309-11e, Ab309-12e, Ab309-4i, Ab309-6i, Ab309-11i, and Ab309-12i) were assessed for inhibition of PAR-2 signalling in β-arrestin and/or calcium flux assays, as described in Examples 2.1 and 2.2, supra. The inhibitory potencies of humanized anti-PAR-2 extracellular loop-selective antibodies (Ab309, Ab309-4e, Ab309-6e, Ab309-11e, Ab309-12e, Ab309-4i, Ab309-6i, Ab309-11i, and Ab309-12i) is listed in Table 8 (where multiple independent selected assays were performed, a mean value is shown).

TABLE 8

$IC_{50}$ values of humanized anti-PAR-2 antibodies in PAR-2 β-arrestin cell assay and PAR-2 calcium flux cell assay

| Antibody | Variable Light Chain Sequence Identifier | Variable Heavy Chain Sequence Identifier | PAR-2 β-arrestin cell assay $IC_{50}$ (nM) (assays utilizing 1 μM SLIGKV) | PAR-2 calcium flux cell assay $IC_{50}$ (nM) |
|---|---|---|---|---|
| Ab309 (Parental non-optimized antibody) | SEQ ID NO: 117 | SEQ ID NO: 116 | 4.4 | 8.6 |
| 309-4e | SEQ ID NO: 23 | SEQ ID NO: 20 | 5.8 | 7.6 |
| 309-6e | SEQ ID NO: 23 | SEQ ID NO: 118 | 5.6 | 12.7 |
| 309-11e | SEQ ID NO: 23 | SEQ ID NO: 119 | 6.1 | 22.8 |
| 309-12e | SEQ ID NO: 23 | SEQ ID NO: 120 | 2.3 | 8.3 |
| 309-4i | SEQ ID NO: 121 | SEQ ID NO: 20 | Insufficient signal to obtain data | Not tested |
| 309-6i | SEQ ID NO: 121 | SEQ ID NO: 118 | 40.58 | Not tested |
| 309-11i | SEQ ID NO: 121 | SEQ ID NO: 119 | Insufficient signal to obtain data | Not tested |
| 309-12i | SEQ ID NO: 121 | SEQ ID NO: 120 | Insufficient signal to obtain data | Not tested |

Ab309-4e, Ab309-6e, Ab309-11e, and Ab309-12e were similar in their ability to block β-arrestin signaling in this assay and were similar in activity to that of Ab309. Of the four antibodies tested, Ab309-4e and 309-12e demonstrated the most potent inhibition of trypsin-activated calcium flux or beta-arrestin activity with comparable potency to that of the parental non-optimized antibody Ab309.

Example 4: Optimization of Humanized Anti-PAR-2 Extracellular Loop-Selective Antibody The humanized anti-PAR-2 extracellular loop-selective antibody 309-4e was selected for further development and panels of variants were constructed with the aims of minimizing potential immunogenicity and manufacturing liabilities, and of enhancing potency.

Attempts to minimize potential immunogenicity included replacing rodent sequences where possible with sequences based on human germline sequences, and modifying sequences which were predicted in silico to bind human MHC class II molecules. Several software programs are available to perform this analysis such as EpiBase (Lonza) or EpiVax.

Residues or sequence motifs associated with undesirable post-translational changes such as glycosylation, aspartate isomerization, deamidation, oxidation were identified and a range of variants were constructed by making a variety of amino acid substitutions at selected residues. Attempts to improve antibody potency included making substitutions at each CDR residue which was predicted to be solvent exposed with one of each of the following amino acids: Y, W, F, K, H, N, D, G, or L. CDR residues which were predicted to not be solvent exposed were substituted with either Y or G. Additionally, CDR-targeted combinatorial scFv libraries were synthesized (Twist Biosciences), cloned into a phagemid vector pADL™-22c (Antibody Design Labs), and phage display was performed with multiple rounds of selection on PAR-2. PAR-2 binding was assessed by ELISA and confirmed by biacore.

During the selection recombinant PAR-2 was either passively adsorbed onto MaxiSorp plates or captured via the polyhistidine-tag onto Dynabeads M-280 Streptavidin (Thermo Fisher Scientific) or Sera-Mag SpeedBeads Neutravidin-Coated Magnetic Particles (GE Healthcare) which had been pre-incubated with tris-NTA biotin (Biotechrabbit) and nickel sulfate. Selections were carried out in either PBS or in HEPES-NaCl-based buffers containing lauryl maltose neopentyl glycol (LMNG) and cholesteryl hemisuccinate (CHS). Bound phages were eluted using 100 mM triethylamine. Individual clones were subsequently isolated, sequenced, and screened in a monoclonal phage ELISA for ability to bind recombinant PAR-2 (2 µg/ml), either passively adsorbed onto a MaxiSorp plate or captured onto Nunc Immobilizer Streptavidin 96-well plates which had been pre-incubated with tris-NTA biotin and nickel sulfate. Binding clones were detected using an HRP-conjugated anti-M13 antibody (GE Healthcare). Clones deemed PAR-2-specific in phage ELISA were further assessed for ability to bind recombinant PAR-2 in surface plasmon resonance (SPR) studies, with the aim of identifying clones with a dissociation rate constant slower than that of the parental 309-4e scFv. For these clones, soluble expression of scFv was induced using isopropyl β-D-1-thiogalactopyranoside (IPTG) and the soluble scFv-containing E. coli periplasmic fractions were extracted through cold osmotic shock using ice-cold 30 mM Tris-HCl, 1 mM EDTA, 20% (w/v) sucrose, pH 8.0, containing cOmplete, Mini, EDTA-free Protease Inhibitor Cocktail (Roche), according to standard methods. Soluble scFv binding to recombinant PAR-2 in SPR was assessed using Biacore T200 or S200 instruments. Briefly, an anti-hemagglutinin (HA) tag antibody (clone 3F10; Roche) was coupled to a Series S Sensor Chip CM5 using standard amine coupling methods. Soluble scFv in periplasmic extracts, diluted 1 in 2 in running buffer (50 mM HEPES, 250 mM NaCl, 0.1% w/v LMNG, 0.025% w/v CHAPS, 0.005% CHS, pH 7.4) were then injected onto the chip (and captured onto the anti-HA tag antibody via their C-terminal HA tag), after which recombinant PAR-2 (at 0 and 2 µg/ml) were injected. Resulting sensorgrams were double-referenced by buffer subtraction and by reference cell subtraction and binding curves fitted to a 1:1 binding model from which kinetic constants were derived using the Biacore S200 or T200 evaluation software.

In each case, humanized antibody variants were expressed and purified as described in Example 3, supra. Purified antibodies were assessed for selectivity by flow cytometry using human PAR-2, PAR-1 and Nt-PAR-2 using transfected cells, and for potency in PAR-2 β-arrestin cell based assay as described in Example 2.1, supra.

Variants of humanized anti-PAR-2 extracellular loop-selective antibody which exhibited improvements in at least one of the above optimization parameters, and had potency in β-arrestin assay similar or better than parental are listed in Table 9.

TABLE 9

Substitutions introduced into Antibody 309-4e during optimization and their potency in the β-arrestin cell based assay

| Antibody | Light Chain Sequence identification | Light Chain Substitution relative to 309-4e | Heavy Chain Sequence identification | Heavy Chain Substitution relative to 309-4e | Potency in PAR-2 β-arrestin cell based assay (nM) |
|---|---|---|---|---|---|
| 309-4e (Parental non-optimised antibody) | SEQ ID NO: 23 | None | SEQ ID NO: 20 | None | 2.1#, 5.9# (Results of two runs) |
| P24E5 | SEQ ID NO: 23 | None | SEQ ID NO: 122 | N30S | No IC$_{50}$ available, selected on the basis of biacore |
| P24E9 | SEQ ID NO: 23 | None | SEQ ID NO: 123 | I35S | 11.28* |
| P24E22 | SEQ ID NO: 23 | None | SEQ ID NO: 124 | N60A | 2.495* |
| P24E27 | SEQ ID NO: 125 | K24R | SEQ ID NO: 20 | None | No IC$_{50}$ available, selected on the basis of affinity |

TABLE 9-continued

Substitutions introduced into Antibody 309-4e during optimization and their potency in the β-arrestin cell based assay

| Antibody | Light Chain Sequence identification | Light Chain Substitution relative to 309-4e | Heavy Chain Sequence identification | Heavy Chain Substitution relative to 309-4e | Potency in PAR-2 β-arrestin cell based assay (nM) |
|---|---|---|---|---|---|
| P24E29 | SEQ ID NO: 126 | I29V | SEQ ID NO: 20 | None | No IC$_{50}$ available, selected on the basis of affinity |
| P24E36 | SEQ ID NO: 127 | T51A | SEQ ID NO: 20 | None | No IC$_{50}$ available, selected on the basis of biacore |
| P24E39 | SEQ ID NO: 128 | L54R | SEQ ID NO: 20 | None | No IC$_{50}$ available, selected on the basis of biacore |
| P24E40 | SEQ ID NO: 129 | H55A | SEQ ID NO: 20 | None | 2.474* |
| P24E41 | SEQ ID NO: 130 | N50D, T51A, N52S, S53N, L54R, H55A | SEQ ID NO: 20 | None | 26.93* |
| P24E60 | SEQ ID NO: 131 | Y32W | SEQ ID NO: 20 | None | 2.03* |
| P24E61 | SEQ ID NO: 132 | Y32F | SEQ ID NO: 20 | None | 2.56* |
| P24E186 | SEQ ID NO: 23 | None | SEQ ID NO: 133 | Y98W | 3.25* |
| P24E216 | SEQ ID NO: 23 | None | SEQ ID NO: 134 | S31Y | 1.95* |
| P24E219 | SEQ ID NO: 23 | None | SEQ ID NO: 135 | V34G | 1.33* |
| P24E232 | SEQ ID NO: 23 | None | SEQ ID NO: 136 | N60G | 1.99* |
| P24E233 | SEQ ID NO: 23 | None | SEQ ID NO: 137 | N60Y | 1.77* |
| P24E278 | SEQ ID NO: 129 | H55A | SEQ ID NO: 138 | N30S, N60A | 2.5# |
| P24E279 | SEQ ID NO: 149 | K24R, H55A | SEQ ID NO: 138 | N30S, N60A | 2.8# |
| P24E280 | SEQ ID NO: 150 | I29V, H55A | SEQ ID NO: 138 | N30S, N60A | 1.9# |
| P24E281 | SEQ ID NO: 151 | T51A, H55A | SEQ ID NO: 138 | N30S, N60A | 2.6# |
| P24E282 | SEQ ID NO: 152 | L54R, H55A | SEQ ID NO: 138 | N30S, N60A | 2.0# |
| P24E283 | SEQ ID NO: 129 | H55A | SEQ ID NO: 139 | G33A, N60A | 3.6# |
| P24E284 | SEQ ID NO: 149 | K24R, H55A | SEQ ID NO: 139 | G33A, N60A | 2.5# |
| P24E285 | SEQ ID NO: 150 | I29V, H55A | SEQ ID NO: 139 | G33A, N60A | 2.3# |
| P24E286 | SEQ ID NO: 151 | T51A, H55A | SEQ ID NO: 139 | G33A, N60A | 2.1# |
| P24E287 | SEQ ID NO: 152 | L54R, H55A | SEQ ID NO: 139 | G33A, N60A | 2.2# |
| P24E288 | SEQ ID NO: 129 | H55A | SEQ ID NO: 140 | V34I, N60A | 1.4# |
| P24E289 | SEQ ID NO: 149 | K24R, H55A | SEQ ID NO: 140 | V34I, N60A | 2.6# |
| P24E290 | SEQ ID NO: 150 | I29V, H55A | SEQ ID NO: 140 | V34I, N60A | 2.2# |
| P24E291 | SEQ ID NO: 151 | T51A, H55A | SEQ ID NO: 140 | V34I, N60A | 3.1# |
| P24E292 | SEQ ID NO: 152 | L54R, H55A | SEQ ID NO: 140 | V34I, N60A | 1.2# |
| P24E293 | SEQ ID NO: 129 | H55A | SEQ ID NO: 141 | G33A, V34I, I35S, N60A | 2.0# |
| P24E294 | SEQ ID NO: 149 | K24R, H55A | SEQ ID NO: 141 | G33A, V34I, I35S, N60A | 2.9# |
| P24E295 | SEQ ID NO: 150 | I29V, H55A | SEQ ID NO: 141 | G33A, V34I, I35S, N60A | 1.6# |

TABLE 9-continued

Substitutions introduced into Antibody 309-4e during optimization and their potency in the β-arrestin cell based assay

| Antibody | Light Chain Sequence identification | Light Chain Substitution relative to 309-4e | Heavy Chain Sequence identification | Heavy Chain Substitution relative to 309-4e | Potency in PAR-2 β-arrestin cell based assay (nM) |
|---|---|---|---|---|---|
| P24E296 | SEQ ID NO: 151 | T51A, H55A | SEQ ID NO: 141 | G33A, V34I, I35S, N60A | 2.4# |
| P24E297 | SEQ ID NO: 152 | L54R, H55A | SEQ ID NO: 141 | G33A, V34I, I35S, N60A | 3.0# |
| P24E298 | SEQ ID NO: 153 | Y32W, H55A | SEQ ID NO: 142 | N30S, G33A, V34I, I35S, N60A | 1.47# |
| P24E300 | SEQ ID NO: 153 | Y32W, H55A | SEQ ID NO: 143 | N30S, G33A, V34I, I35S, N60A, Y98W | 1.3# |
| P24E301 | SEQ ID NO: 153 | Y32W, H55A | SEQ ID NO: 144 | N30S, G33A, V34I, I35S, N60A, R96K | 1.48# |
| P24E743 | SEQ ID NO: 154 | I29V, Y32W, T51A, N52Y, H55A, L89Q, N92G | SEQ ID NO: 142 | N30S, G33A, V34I, I35S, N60A | 1.51# |
| P24E794 | SEQ ID NO: 155 | K24R, I29V, Y32W, T51A, N52Y, L54R, H55A, L89Q | SEQ ID NO: 142 | N30S, G33A, V34I, I35S, N60A | 0.89# |
| P24E883 | SEQ ID NO: 156 | I29V, Y32W, T51A, N52Y, H55A, L89Q | SEQ ID NO: 142 | N30S, G33A, V34I, I35S, N60A | 1.21# |
| P24E889 | SEQ ID NO: 157 | K24R, Y32W, T51A, N52Y, H55A, L89Q | SEQ ID NO: 142 | N30S, G33A, V34I, I35S, N60A | 0.97# |
| P24E914 | SEQ ID NO: 157 | K24R, Y32W, T51A, N52Y, H55A, L89Q | SEQ ID NO: 144 | N30S, G33A, V34I, I35S, N60A, R96K | 0.94# |
| P24E915 | SEQ ID NO: 156 | I29V, Y32W, T51A, N52Y, H55A, L89Q | SEQ ID NO: 144 | N30S, G33A, V34I, I35S, N60A, R96K | 1.16# |
| P24E916 | SEQ ID NO: 155 | K24R, I29V, Y32W, T51A, N52Y, L54R, H55A, L89Q | SEQ ID NO: 144 | N30S, G33A, V34I, I35S, N60A, R96K | 1.1# |
| P24E917 | SEQ ID NO: 154 | I29V, Y32W, T51A, N52Y, H55A, L89Q, N92G | SEQ ID NO: 144 | N30S, G33A, V34I, I35S, N60A, R96K | 0.93# |
| P24E918 | SEQ ID NO: 157 | K24R, Y32W, T51A, N52Y, H55A, L89Q | SEQ ID NO: 145 | N30S, G33A, V34I, I35S, N60A, Y98F | 1.18# |
| P24E919 | SEQ ID NO: 156 | I29V, Y32W, T51A, N52Y, H55A, L89Q | SEQ ID NO: 145 | N30S, G33A, V34I, I35S, N60A, Y98F | 1.44# |
| P24E920 | SEQ ID NO: 155 | K24R, I29V, Y32W, T51A, N52Y, L54R, H55A, L89Q | SEQ ID NO: 145 | N30S, G33A, V34I, I35S, N60A, Y98F | 1.32# |
| P24E921 | SEQ ID NO: 154 | I29V, Y32W, T51A, N52Y, H55A, L89Q, N92G | SEQ ID NO: 145 | N30S, G33A, V34I, I35S, N60A, Y98F | 1.9# |
| P24E922 | SEQ ID NO: 157 | K24R, Y32W, T51A, N52Y, H55A, L89Q | SEQ ID NO: 143 | N30S, G33A, V34I, I35S, N60A, Y98W | 1.01# |
| P24E923 | SEQ ID NO: 156 | I29V, Y32W, T51A, N52Y, H55A, L89Q | SEQ ID NO: 143 | N30S, G33A, V34I, I35S, N60A, Y98W | 0.99# |

TABLE 9-continued

Substitutions introduced into Antibody 309-4e during optimization and their potency in the β-arrestin cell based assay

| Antibody | Light Chain Sequence identification | Light Chain Substitution relative to 309-4e | Heavy Chain Sequence identification | Heavy Chain Substitution relative to 309-4e | Potency in PAR-2 β-arrestin cell based assay (nM) |
|---|---|---|---|---|---|
| P24E924 | SEQ ID NO: 155 | K24R, I29V, Y32W, T51A, N52Y, L54R, H55A, L89Q | SEQ ID NO: 143 | N30S, G33A, V34I, I35S, N60A, Y98W | 0.79# |
| P24E930 | SEQ ID NO: 158 | K24R, I29V, Y32W, T51A, N52Y, L54R, H55A, L89Q, N92G | SEQ ID NO: 146 | N30S, G33A, V34I, I35S, T57V, N60A, R96K | 1.7, 1.4# (Results of two runs) |
| P24E931 | SEQ ID NO: 154 | I29V, Y32W, T51A, N52Y, H55A, L89Q, N92G | SEQ ID NO: 146 | N30S, G33A, V34I, I35S, T57V, N60A, R96K | 2.0# |
| P24E932 | SEQ ID NO: 157 | K24R, Y32W, T51A, N52Y, H55A, L89Q | SEQ ID NO: 146 | N30S, G33A, V34I, I35S, T57V, N60A, R96K | 1.4# |
| P24E933 | SEQ ID NO: 158 | K24R, I29V, Y32W, T51A, N52Y, L54R, H55A, L89Q, N92G | SEQ ID NO: 144 | N30S, G33A, V34I, I35S, N60A, R96K | 1.4# |
| P24E934 | SEQ ID NO: 25 | K24R, I29V, Y32W, T51A, N52Y, L54R, H55A, L89Q, N92H | SEQ ID NO: 147 | N30S, G33A, V34I, I35S, T57V, N60A, R96K, Y101aH | 1.5# |
| P24E935 | SEQ ID NO: 160 | K24R, I29V, Y32W, T51A, N52Y, L54R, H55A, L89Q, N92H, S93H | SEQ ID NO: 147 | N30S, G33A, V34I, I35S, T57V, N60A, R96K, Y101aH | 1.5# |
| P24E936 | SEQ ID NO: 148 | K24R, I29V, Y32W, T51A, N52Y, L54R, H55A, L89Q, N92G, S93H | SEQ ID NO: 147 | N30S, G33A, V34I, I35S, T57V, N60A, R96K, Y101aH | 1.8# |
| P24E951 | SEQ ID NO: 158 | K24R, I29V, Y32W, T51A, N52Y, L54R, H55A, L89Q, N92G | SEQ ID NO: 21 | N30S, G33A, V34I, I35S, G55Q, T57V, N60A, R96K | 2.55#, 1.17# (Results of two runs) |
| P24E953 | SEQ ID NO: 159 | K24R, I29V, Y32W, N50D, T51A, N52Y, L54R, H55A, L89Q, N92G | SEQ ID NO: 21 | N30S, G33A, V34I, I35S, G55Q, T57V, N60A, R96K | 3.64#, 1.84# (Results of two runs) |
| P24E971 | SEQ ID NO: 25 | K24R, I29V, Y32W, T51A, N52Y, L54R, H55A, L89Q, N92H | SEQ ID NO: 146 | N30S, G33A, V34I, I35S, T57V, N60A, R96K | 2.40# |
| P24E972 | SEQ ID NO: 160 | K24R, I29V, Y32W, T51A, N52Y, L54R, H55A, L89Q, N92H, S93H | SEQ ID NO: 146 | N30S, G33A, V34I, I35S, T57V, N60A, R96K | 1.52# |
| P24E973 | SEQ ID NO: 148 | K24R, I29V, Y32W, T51A, N52Y, L54R, H55A, L89Q, N92G, S93H | SEQ ID NO: 146 | N30S, G33A, V34I, I35S, T57V, N60A, R96K | 2.35# |
| P24E975 | SEQ ID NO: 160 | K24R, I29V, Y32W, T51A, N52Y, L54R, H55A, L89Q, N92H, S93H | SEQ ID NO: 21 | N30S, G33A, V34I, I35S, G55Q, T57V, N60A, R96K | 0.75# |

TABLE 9-continued

Substitutions introduced into Antibody 309-4e during optimization and their potency in the β-arrestin cell based assay

| Antibody | Light Chain Sequence identification | Light Chain Substitution relative to 309-4e | Heavy Chain Sequence identification | Heavy Chain Substitution relative to 309-4e | Potency in PAR-2 β-arrestin cell based assay (nM) |
|---|---|---|---|---|---|
| P24E976 | SEQ ID NO: 25 | K24R, I29V, Y32W, T51A, N52Y, L54R, H55A, L89Q, N92H | SEQ ID NO: 21 | N30S, G33A, V34I, I35S, G55Q, T57V, N60A, R96K | 0.90#<br>1.26#<br>(Results of two runs) |
| P24E977 | SEQ ID NO: 161 | K24R, I29V, Y32W, N50D, T51A, N52Y, L54R, H55A, L89Q, N92H | SEQ ID NO: 21 | N30S, G33A, V34I, I35S, G55Q, T57V, N60A, R96K | 1.73# |
| P24E978 | SEQ ID NO: 162 | K24R, I29V, Y32W, N50D, T51A, N52Y, L54R, H55A, L89Q, N92H, S93H | SEQ ID NO: 21 | N30S, G33A, V34I, I35S, G55Q, T57V, N60A, R96K | 0.94# |
| P24E1099 | SEQ ID NO: 26 | K24R, I29V, Y32W, T51A, L54R, H55A, L89Q, N92H | SEQ ID NO: 21 | N30S, G33A, V34I, I35S, G55Q, T57V, N60A, R96K | 1.37# |
| P24E1102 | SEQ ID NO: 24 | K24R, I29V, Y32W, T51A, S53T, L54R, H55A, L89Q, N92H | SEQ ID NO: 21 | N30S, G33A, V34I, I35S, G55Q, T57V, N60A, R96K | 1.40# |
| P24E1103 | SEQ ID NO: 27 | K24R, I29V, Y32W, T51A, S53N, L54R, H55A, L89Q, N92H | SEQ ID NO: 21 | N30S, G33A, V34I, I35S, G55Q, T57V, N60A, R96K | 1.54# |

*1 μM SLIGKV added; #2 μM SLIGKV added

Modification of Ab309-4e and its Variants to Reduce Potential Immunogenic Epitopes A MAPPS (MHC Class HI Associated peptide proteomics) assay (ProImmune UK) was performed using full-length antibody P24E976 in order to identify any potential immunogenic epitopes present in the antibody. Using a 12 donor panel, the peptide sequence IYNAYSRATGIPAR, located in the CDR2 of P24E976, was identified from both the donors with the DRB1*0101 allele. Further optimization was performed to remove this motif.

The light chain CDR2 of P24E976 was modified by substituting each of the amino acids in the motif NAYSRAT with other amino acids and then performing Epibase® analysis on these variants. Variants were identified that had predicted reduced binding to DRB1*0101. It was noted that by removing the tyrosine (Y) at position 52 in this motif and then replacing it with an asparagine (N), the peptide was no longer predicted to bind to DRB1*0101. Several new antibodies were made with the N at position 52. As this would have introduced an NS motif (potential for asparagine deamidation), other antibodies with NT or NN (less prone to deamidation than NS125) were also generated. The antibody with NS at positions 52 and 53 in the light chain is P24E1099, NT is P24E1102, and NN is P24E1103. No other sequence changes were made from antibody P24E976. The heavy chain is identical to P24E976.

Four anti-PAR-2 extracellular loop-selective antibodies (P24E976, P24E1099, P24E1102, and P24E1103) were further assessed for their ability to prevent trypsin activated PAR-2 signaling inducing calcium flux, as described in Example 2.2, supra. The potency of these four antibodies in inhibiting the PAR-2 mediated release of the inflammatory cytokines IL-6 and IL-8, as described in Example 2.3, supra, was also assessed, with results listed in Table 10.

TABLE 10

Summary table for potency values (IC$_{50}$) for optimised anti-PAR-2 antibodies in various cell based assays

| Antibody | Variable Light Chain Sequence identification | Variable Heavy Chain Sequence identification | Calcium flux IC$_{50}$ (nM) | IL-6 release in A549 cells IC$_{50}$ (nM) | IL-8 release in A549 cells IC$_{50}$ (nM) |
|---|---|---|---|---|---|
| P24E976 | SEQ ID NO: 25 | SEQ ID NO: 21 | 15.94, 15.3, 7.102, 5.9 (From repeat assays) | 5.63 | 4.25 |
| P24E1099 | SEQ ID NO: 26 | SEQ ID NO: 21 | 12.35 | 6.74 | 4.89 |
| P24E1102 | SEQ ID NO: 24 | SEQ ID NO: 21 | 17.36 | 5.00 | 4.62 |
| P24E1103 | SEQ ID NO: 27 | SEQ ID NO: 21 | 12.72 | 7.18 | 5.17 |

Optimized anti-PAR-2 antibodies P24E976, P24E1099, P24E1102, and P24E1103 had similar potency across the cell based assays tested.

Example 5: Species Cross-Reactivity of Optimised Anti-PAR-2 Antibodies

Selected antibodies were tested for binding to various species of PAR-2 using surface plasmon resonance (SPR) assay for antibody binding to recombinant PAR-2, except that human PAR-2 was substituted with PAR-2 from cynomolgus monkeys, rat, or mice.

Antibodies were transfected and harvested as described in Example 3, supra. Antibodies in supernatant were diluted 1 in 50-250 in running buffer (50 mM HEPES, 250 mM NaCl, 0.1% w/v LMNG, 0.025% w/v CHAPS, 0.005% CHS, pH 7.4) and purified antibodies were diluted to 0.5 ug/mL in running buffer A Series S Protein A chip was docked into the instrument (Biacore S20) and the system was primed four times with running buffer prior to the run. Recombinant human PAR-2 was diluted to 0-5 μg/mL in running buffer. The surface was regenerated using 50 mM NaOH. The antibody was captured to between 20 to 110 Relative Units on the chip surface. The sample (recombinant PAR-2) was injected for 1 min at 30 l/min, followed by dissociation phase of 180 s. Sensorgrams were double referenced by buffer subtraction and by reference cell subtraction. Binding curves were then fit to a 1:1 binding model with kinetic constants derived from curve fits. Antibodies were ranked by dissociation rate ($k_d$) when only one concentration of antigen was injected. Antibodies were ranked by their equilibrium dissociation constant ($K_D$) when multiple concentrations of PAR-2 were injected. Of all the antibodies tested, all showed comparable binding to human and cynomolgus monkey recombinant PAR-2, borderline binding to rat PAR-2 and no binding to mouse PAR-2.

P24E1102 was tested for binding to human, cynomolgus, rat, and mouse PAR-2 by surface plasmon resonance (SPR) using PAR-2 preparations. Table 11 shows that representative antibody P24E1102 bound to human and cynomolgus PAR-2 with high affinity, only weakly bound to rat PAR-2, and did not bind mouse PAR-2.

TABLE 11

Binding Affinity of P24E1102 to human, cynomolgus, mouse and rat PAR-2

| Species | $K_D$(M) |
|---|---|
| Human | 433-946 pM |
| Cynomolgus monkey | 4.45 nM |
| Mouse | Did not bind |
| Rat | Biphasic binding could not be modeled |

P24E1102 binding was also assessed by flow cytometry, as described in Example 1 supra, using PAR-2 transiently transfected into CHEM-1 cells. In addition to human, cynomolgus, mouse and rat, guinea pig, rabbit and dog PAR-2 were also tested. P24E1102 bound well to human and cynomolgus PAR-2 but minimally to all other species tested.

Transfection into the CHEM-1 cell line also allowed for functional testing of ligand-induced calcium flux blockade, as described in Example 2.2, supra. P24E1102 blocked ligand induced calcium flux in CHEM-1 cells transiently transfected with human PAR-2, but not those transfected with rat, guinea pig, or rabbit PAR-2.

Additionally, testing for human cynomolgus binding and function was carried out using a Nomad® reporter lines stably transfected with either human or cynomolgus PAR-2 and engineered for detection of both calcium flux and β-arrestin signaling, as described in Examples 2.1 and 2.2, supra. P24E1102 bound similarly to both human and cynomolgus PAR-2 cell lines. TEV-56192 P24E1102 blocked both human and cynomolgus PAR-2 mediated calcium flux. P24E1102 blocked both human and cynomolgus PAR-2 activated β-arrestin signaling.

Table 12 shows functional inhibition of cynomolgus PAR-2 by P24E1102 over a potency range was similar to that for human PAR-2.

TABLE 12

Summary of $IC_{50}$ values for P24E1102 blockade of calcium flux and β-arrestin signaling at the respective SLIGKV $EC_{80}$ for human and cynomolgus PAR-2

| | | $IC_{50}$ (nM) P24E1102* | | SLIGKV $EC_{80}$ (μM)* | |
|---|---|---|---|---|---|
| PAR-2 | Assay | Mean | Range | Mean | Range |
| Human | Calcium flux | 2.07 | 1.27-2.86 | 3.19 | 2.58-3.78 |
| Cynomolgus | Calcium flux | 3.98 | 2.50-5.87 | 38.97 | 35.33-43.47 |
| Human | β-Arrestin | 5.38 | 3.62-6.28 | 18.29 | 16.01-19.32 |
| Cynomolgus | β-Arrestin | 15.2 | 10.53-18.09 | 107.01 | 75.56-144.8 |

*Data summary of 5 technical replicates in 2 independent experiments.

P24E1102 also showed no binding above background to recombinant human PAR-1, PAR-3, or PAR-4.

Example 6: Internalization of Humanized and Optimized Anti-PAR-2 Extracellular Loop-Selective Antibody Representative antibody P24E1102 was selected and assessed for target mediated internalization. A549 cells were plated in 96 well black clear bottom plates at $1 \times 10^4$ cells/well in 100 μL basal media (10% FBS, 100 Units/mL penicillin, 100 μg/mL streptomycin, Hams F-12K Media). Cells were incubated at 37° C./5% $CO_2$ and allowed to adhere. Test antibodies were conjugated to the pH sensitive IncuCyte Human FabFluor Red Antibody Labelling Reagent (Essen Biosciences) at a 3:1 molar excess for 15 minutes as per the manufacturer's instructions. Labelled antibody was immediately added to cells and imaged at 10× magnification every 20 minutes using an IncuCyte S3, recording both phase contrast and red fluorescence. The total integrated red fluorescence (intensity of fluorescence integrated with the area of fluorescence) was calculated using the Incucyte S3 controller and plotted against time (minutes). P24E1102 demonstrated no target-mediated internalization into A549 human epithelial cells compared to isotype control antibodies.

Example 7: Primary Cell-Based Assays to Determine Binding and Function of P24E1102 Antibody A range of human airway cell types were tested as more physiologically-relevant targets for PAR-2 binding and inhibition of PAR-2 function by a representative antibody, P24E1102.

P24E1102 was tested for binding to PAR-2 on the A549 human lung epithelial cell line by flow cytometry, as described in Example 1 supra, and was found to bind in a dose dependent manner over a concentration range of 1-133 nM.

P24E1102 was tested for binding to PAR-2 on primary human lung fibroblast cells. Cells were fixed and stained, and the average fluorescence was determined by fluorescence well scanning. P24E1102 dose dependently bound to primary human lung fibroblasts over a range of 1-133 nM.

The A549 lung epithelial cell line stimulated with PAR-2 ligand responds with calcium flux and the production of pro-inflammatory cytokines IL-6 and IL-8. P24E1102 potency in inhibiting PAR-2 mediated calcium flux and pro-inflammatory cytokines release was tested as described in Examples 2.2 and 2.3, supra. P24E1102 dose dependently blocked PAR-2 activating ligand-induced calcium flux ($IC_{50}$=13.2 nM), and IL-6 ($IC_{50}$=5.0) and IL-8 production (4.6 nM).

P24E1102 dose dependently blocked PAR-2 activating ligand-induced asthma/COPD-associated mucin MUC5AC production in the goblet cell-like lung epithelial Calu-3 cell line.

P24E1102 blocked PAR-2 activating ligand-induced calcium flux by primary human bronchial smooth muscle cells and by primary human lung fibroblasts.

Primary human bronchial smooth muscle cells were grown in a collagen matrix to form a surrogate muscle disk that contracts in response to PAR-2 ligand stimulation. PAR-2 ligand SLIGKV at 200 M caused approximately 17% disk contraction which was completely ablated by P24E1102 at a concentration of 10 µg/ml.

PAR-2 signaling has been reported as being involved in neutrophil migration and activation (Howells, G. L. et al., J Cell Sci., 110(Pt 7):881-7 (1997); Nadeem, A. et al., Chemico-Biological Interactions, 304:52-60 (2019); Lourbakos, A. et al., FEBS Lett, 435:45-48 (1998)). In experiments using fresh whole human blood from health donors, P24E1102 had no impact on neutrophil production of reactive oxygen species (ROS) induced by either N-formylmethionine-leucyl-phenylalanine (fMLF) or by Complement component 5a (C5a). In these experiments cells were pre-treated with P24E1102 or the equivalent isotype control (≤338.4 nM) followed by ROS stimulation with fMLF (10 nM) or C5a (10 nM). ROS production in neutrophils was detected via flow cytometry using dihydrorhodamine 123; a freely diffusible, uncharged non-fluorescent dye that is oxidized to fluorescent R123 in the presence of ROS and surface markers to identify human neutrophils (CD45+ CD16+CD14−). P24E1102 also had no impact on neutrophil phagocytosis of Escherichia coli (E. coli) or Staphylococcus aureus (S. aureus). To determine the impact of P24E1102 on phagocytosis, fresh human whole blood from healthy donors was pre-treated with P24E1102 or the equivalent isotype control (≤338.4 nM) and cells were treated with pHrodo™ Green E. coli and S. aureus BioParticles® Conjugate for Phagocytosis. These pHrodo™ green conjugates are non-fluorescent outside the cell at neutral pH but fluoresce green (excitation/emission 509/533) at acidic pH i.e. in phagosomes with this fluorescence measured using flow cytometry, with neutrophils the population of interest (gated using surface markers $CD45^+CD16^+CD14^-$).

Example 8: Comparison of Humanized and Optimized Anti-PAR-2 Extracellular Loop-Selective Antibody to Comparator Antibody The inhibitory potency of the humanized and optimized antibody P24E1102 to antagonize SLIGKV-induced PAR-2 β-arrestin activity was compared to the murine anti-human PAR-2 antibody MAB3949 (R&D Systems, as described in Cheng et al., Nature, 545 112-115 (2017)), as described in Example 2.1, supra. The potency of these antibodies to antagonize trypsin-induced PAR-calcium flux was also compared, as described in Example 2.2, supra.

The potency of P24E1102 relative to MAB3949 is listed in Table 13 (where multiple independent assays were performed, a range of values is shown).

TABLE 13

Potency values ($IC_{50}$) in various cell based assays

| Antibody | Variable Heavy Chain Sequence identification | Variable Light Chain Sequence identification | B-arrestin assay $IC_{50}$ (nM) (assays utilizing 2 µM SLIGKV) | Calcium flux $IC_{50}$ (nM) |
|---|---|---|---|---|
| P24E1102 | SEQ ID NO: 21 | SEQ ID NO: 24 | 0.829-1.70 | 12.49-15.25 |
| MAB3949 | Not Applicable | Not Applicable | 4.78-15.9 | 52.26-96.08 |

P24E1102 demonstrated substantially more potent activity relative to MAB3949 in inhibiting both PAR-2 mediated β-arrestin mobilization and PAR-2 mediated calcium flux. P24E1102 also exhibited more complete inhibition at higher concentrations compared to MAB3949 in the calcium flux assay as shown in FIG. 2.

Example 10. P24E1102 Significantly Reduced the Allergic Response to Ascaris in Non-Human Primates Cynomolgus monkeys (Macaca fascicularis) were sensitized to the intestinal helminth parasite Ascaris suum. This is an established model to study allergen-induced immediate asthmatic responses in the airways (Weiszer, I., et al (1968). Ascaris hypersensitivity in the rhesus monkey. I. A model for the study of immediate type hypersensitivity in the primate J. Allergy. 41:14-22; Camateros, et al. (2018) Toll-Like receptor 7/8 ligand, S28463, suppresses Ascaris suum-induced allergic asthma in nonhuman primates. Am J Respir Cell Mol Biol. 58(1): 55-65). Ascaris exposure of monkeys evokes a strong Th2-biased T cell memory response and increased levels of IgE. Subsequent airway challenge of sensitized monkeys with Ascaris extracts results in both immediate and late phase asthmatic reactions, followed by airway eosinophilia and hyperresponsiveness.

Figure 3:
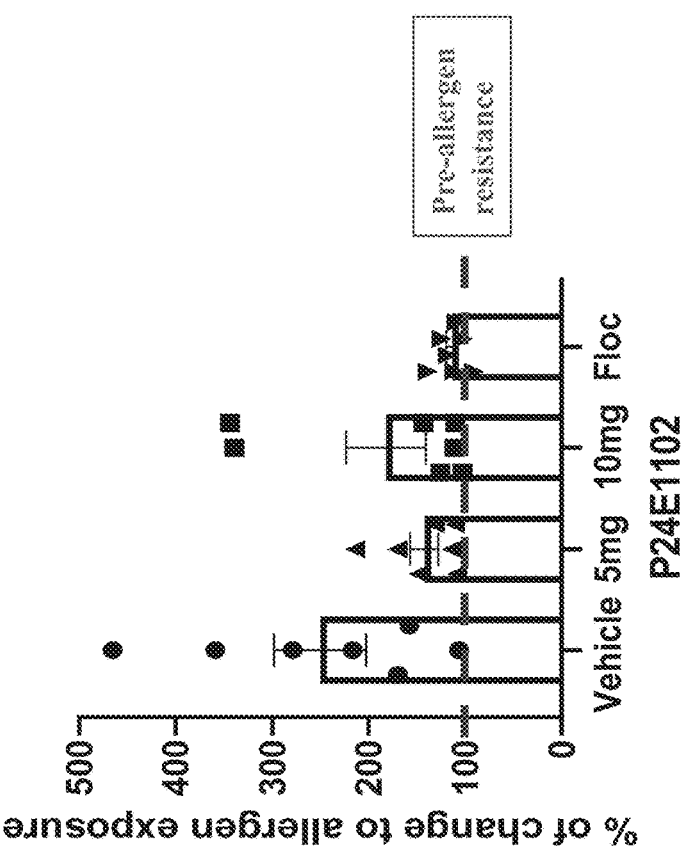
FIG. 3 shows the % change in lung resistance in cynomolgus monkey's challenged with *Ascaris* allergen following treatment with vehicle, P24E1102 (5 mg or 10 mg) or fluticasone (Floc).

Cynomolgus monkeys were sensitized by 1 mg of A. suum antigen given subcutaneously with 1 mg alum adjuvant at day 0 and 14, followed by inhailed Ascaris challenges once a week over a course of 3 weeks (5 minutes of 5 mg/ml on day 28; 30 seconds of 5 mg/ml on days 35 and 42). Based on sensitization results, monkeys were divided into 4 groups and administered vehicle, fluticasone or 5 mg and 10 mg of anti-PAR2 antibody P24E1102 4-7 days prior to Ascaris challenge. On day ~90 Ascaris was administered and lung resistance measured by a pneumotach (3500 series [0-35 L/min]; Hans Rudolph) and a differential pressure transducer (Validyne) located in front of the endotracheal tube. As shown in Table 14, 5 mg P24E1102 significantly ($p<0.05$) reduced lung resistance caused by Ascaris, to a level comparable to that achieved by the broad spectrum steroid, fluticasone. A 10 mg dose did not significantly decrease lung resistance however. The distribution of data is shown in FIG. 3. Examining individual animals, lack of response in the 10 mg dose group may be entirely explained by 2 non-responsive animals. Further experiments are being performed. If 10 mg/kg is not included, the results are also significant following a Tukey's poc-hoc analysis.

TABLE 14

% change to lung resistance following allergen exposure

| Treatment | % change |
|---|---|
| Vehicle | 250.6 |
| 5 mg P24E1102 | 142.2 * |
| 10 mg P24E1102 | 182.1 |
| 400 μg fluticasone (BID, inhalation) | 113 ** |

Numbers normalized to pre-allergen resistance in each monkey. P is One-way Anova with LSD post hoc, compared to vehicle. * p < 0.05, ** p < 0.01

These results further demonstrate that an antibody binding to the PAR2 receptor site, blocking ligand activation, can treat acute hyperresponsiveness in a model of asthma, and is predictive of effective in human asthmatics.

Example 11. P24E1102 in Skin Disease Models in hPAR2 Knock-In Rats

Background

PAR2 and skin proteases have been associated with the pathogenesis of atopic dermatitis (Lee, S. E., et al., Yonsei Med J, 51:808-822 (2010) and a PAR-2 knockout mouse showed reduced edema in an allergic dermatitis model (Kawagoe, J. et al., *Jpn J Pharmacol*, 88:77-84 (2002). PAR2 has been linked to chronic itch (Akiyama, T., et al., Handb Exp Pharmacol, 226:219-235 (2015) and skin itch and inflammation Choi and Nardo, Semin Immunopathol (2018) 40(3):249-259). An antibody that binds to the N-terminal domain of PAR2 and block protease-mediated activation of PAR2 has been reported to block scratching in a murine pruritis model (WO2011031695A1).

Construction of hPAR2 Knock-In Rats.

Knock in rats were constructed following the methods described in Li et al (2013). Simultaneous generation and germline transmission of multiple gene mutations in rat using CRISPR-Cas systems. *Nat Biotechnol*. 31(8):684-6. Briefly, small guiding RNA/CRISP/Cas9 complexes for regions flanking the coding region of the rat F2rl1 gene, and a plasmid containing the coding region for the human F2Rl1 gene with appropriate 5' and 3' homologous arms were constructed and co-injected into single cell stage embryos, which were then transferred to pseudopregnant female rats. The combination of Cas9 mediated excision and homologous recombination resulted in founder animals expressing human PAR2. A selected founder was backcrossed to wild-type rats and the resulting heterozygous offspring were intercrossed to produce animals homozygous for human PAR2.

Oxazolone-Induced Acute Dermatitis

Multiple epicutaneous administration of oxazolone, a potent hapten, induces a chronic Th2 hypersensitivity reaction resembling the features of initial human atopic dermatitis. Clinically, this model is characterized by a thickened ear/oedema, haemorrhagia, excoriations, and lichenefication. PAR2 has been implicated in both acute and chronic models of atopic dermatitis. We performed the acute model first as this type of model has reported edema that is reduced in PAR2-knockout mice.

Figure 4:
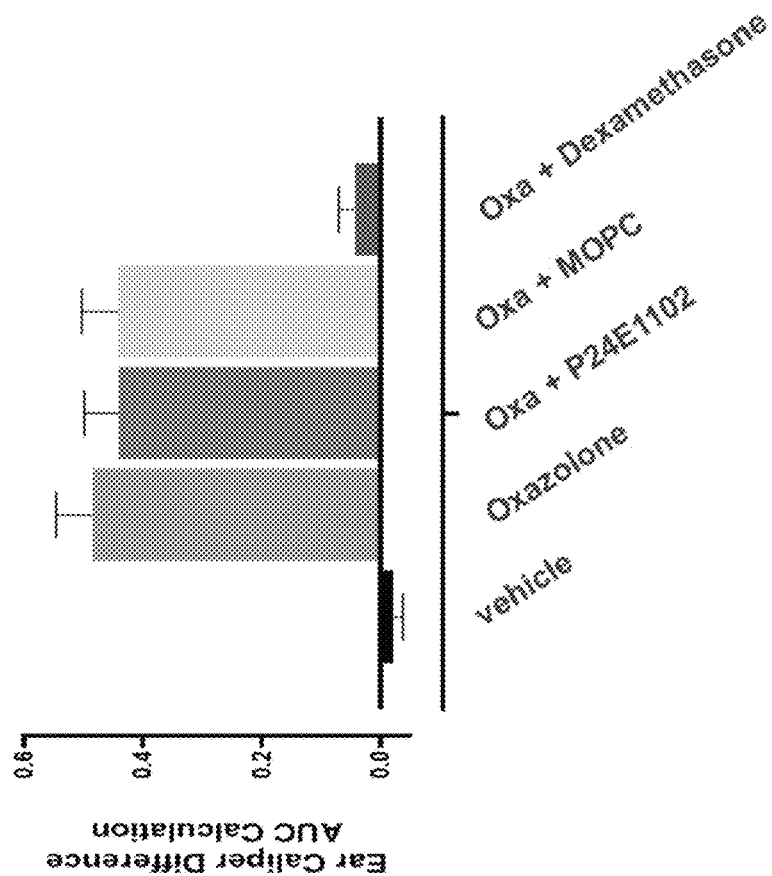
FIG. 4 shows the differences in ear caliper size in hPAR2 knock-in rats in an acute model of dermatitis. Rats were challenged with vehicle (control); topically challenged with oxazolone; or challenged with oxazolone after administration of P24E1102, MOPC isotype control, or dexamethasone. Antibody treatment did not significantly reduce inflammation in this model.

Oxazolone was administered epicutaneously on the shaved area of the abdomen of (n=8) human PAR2 knock-in rats on day 0 for the sensitization phase (Owen, 2013) On day 7, rats were administered 30 mg/kg P24E1102 IV, 30 mg/kg MOPC IV single administration. Dexamethasone 0.1 mg/kg was administered daily orally PO on day 7 through 9. One hour post-dose on day 7, rats were challenged with single topical administration of 1.6% oxazolone on the right ear. The left ear was treated in the same manner with oxazolone vehicle (acetone/olive oil). Results of treatment were determined by evaluation of ear caliper measurements and ear core weights. Efficacy evaluation was based on right-left ear caliper differentials and area under the curve (AUC) calculations As shown in FIG. 4, neither P24E1102 nor MOPC reversed oxazolone induced acute dermatitis in the rat. Because P24E1102 has shown efficacy in other disease models, and previous dermatitis models suggested a link between PAR2 and dermatitis, the lack of response in the acute dermatitis model may reflect the specific features of this acute dermatitis model, which is driven by Th1 responses. Multiple epicutaneous administration of oxazolone, shifts the model from a Th1 dominated to a chronic Th2 inflammation model. The antibody will be retested in the chronic model, and will also be assessed for other indicia of efficacy such as scratching activity.

Imiquimod-Induced Psoriasis

Imiquimod (IMQ) stimulates the innate immune system by activating toll-like receptors 7 TLR7 and 8. Daily topical application of IMQ on the back of rodents induces inflamed scaly skin lesions resembling plaque type psoriasis. These lesions shows increased epidermal proliferation, abnormal differentiation, epidermal accumulation of neutrophils in microabcesses, neoangiogenesis, and infiltrates consisting of CD4(+) T cells, CD11c(+) dendritic cells, and plasmacytoid dendritic cells. Keratinocytes and T cells can be considered the driving contributors to this model and they exist in the epidermal layer of the skin. PAR2 is expressed in the epidermal layer of the skin, and many proteases that can activate PAR2 originate from endogenous sources in the skin, including keratinocytes and immune cells.

While the IMQ model is considered a psoriasis model, it has also been considered a model for atopic dermatitis, given the complexities of this skin condition. Further, because of the itching caused by IMQ, the model is also useful for investigating impact of treatments on scratching and neuroinflammatory reactions.

Figures 5A, 5B:
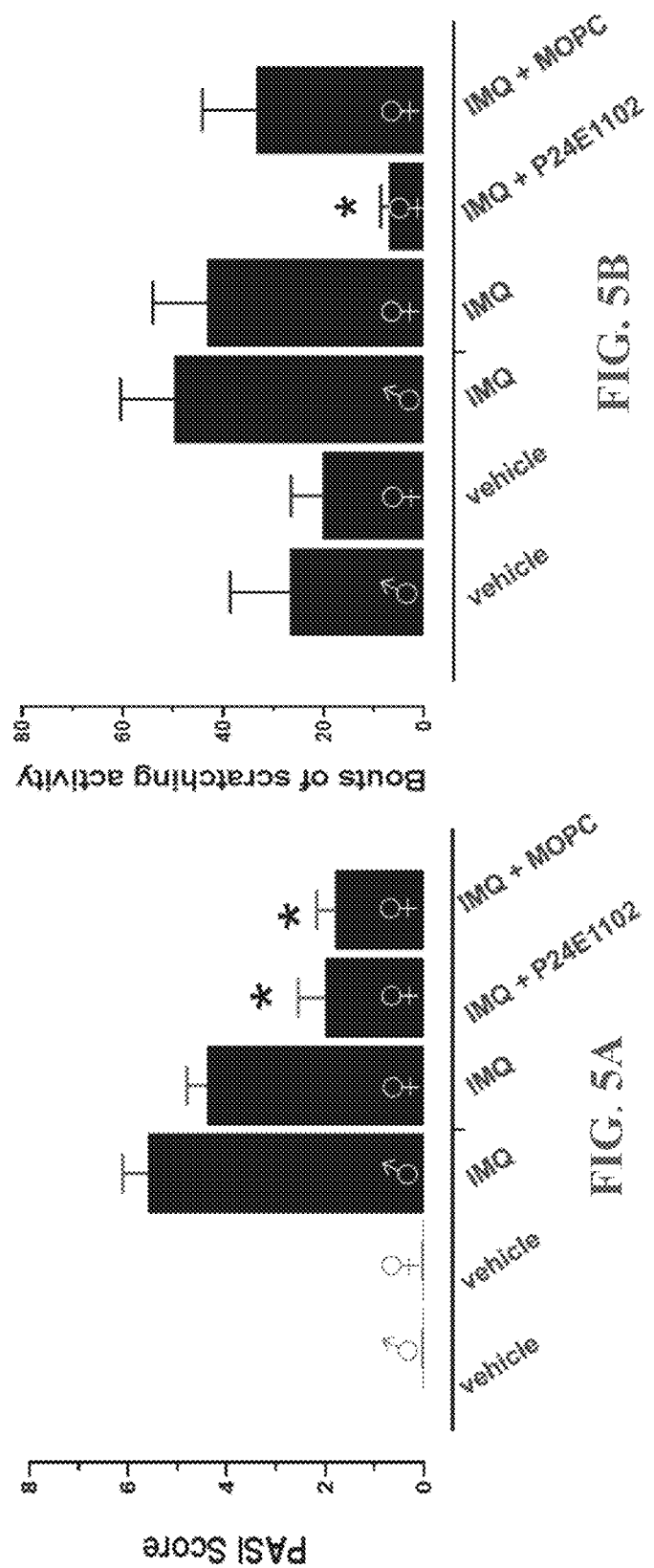
FIGS. 5A-5B show the response of hPAR2 knock in rats to imiquimod (IMQ), a model of psoriasis and dermatitis. Female and male rats were treated with vehicle, imiquimod, or imiquod after pre-treatment with P24E1102 or MOPC isotype control.

5% Aldara cream (IMQ) (37.5 mg/cm$^2$ in vaseline) was applied to the shaved back skin of rats for 9 consecutive (i.e. days 1 to day 9) (N=5). Control rats were administered vehicle (vaseline) (N=5) for 9 consecutive days. IMQ treated rats were intravenously injected with 30 mg/kg of P24E1102 or 30 mg/kg MOPC21 isotype control on day 1, 3, 5 just before Vaseline or IMQ application. Rats were evaluated on day 10 for severity of the inflammation of the back skin and for scratching behavior. (FIGS. 5A-5B).

Psoriasis Area and Severity Index (PASI) is a total quantitative sum score measuring the severity of psoriatic lesioned skin appearance (erythema, scaling and thickening). The PASI in IMQ-treated rats was clearly above rats treated with vehicle (FIG. 5A) and similar in both male and female rats. P24E1102 significantly reduced the PASI score in (unpaired student's T-test, p<0.05). At the same time, MOPC also significantly reduced PASI. This isotype effect is likely due to some non-specific non-antigen dependent mAb binding, as MOPC has no target antigen specificity in rodent. To distinguish the effect due to PAR2 binding from that which might be caused by the Fc portion, F(ab)2 derivatives of P24E1102 will be tested in the model.

Scratching is a common behavior in psoriasis, and scratching can be measured by a "bout of scratching" defined as one or more rapid movements of the hind-paws directed toward and contacting the IMQ/Vaseline treated area. The degree of scratching was quantified as the total number of bouts of scratching over a 120-minute observation period followed by manual scoring of the videotaped period. Here, IMQ increased bouts of scratching above vehicle (FIG. 5B). MOPC did not significantly reduce scratching, but P24E1102 significantly (unpaired student's T-test, p<0.05) reduced scratching not only below the levels of IMQ-treated rats, but below those treated with vehicle.

These data demonstrate that P24E1102 mitigates scratching behavior, a proxy for itch. Many conditions such as atopic dermatitis and psoriasis results in chronic itch and is a major clinical problem that remains ill-addressed. P24E1102 appears to have antipruritic properties targeting both local inflammation and sensitization of itch processing.

Example 12: P24E1102 Modulates Pain Responses

PAR2 Stimulation Positively Modulates the Capsaicin Receptor TRPV1 in Wild Type Rat Neurons The transient receptor potential cation channel subfamily V member 1 (TRPV1), (also known as the capsaicin receptor and the vanilloid receptor 1) may be activated by a wide variety of stimuli, including capsaicin.

To understand the potential interaction between PAR2 and pain receptors, dorsal root ganglia (DRG) were isolated from the spinal columns of wild type rats. Isolated DRG neurons were plated on coverslips coated with poly-lysine+laminin and kept in F12 medium supplemented with 100 ng/ml NGF. 24-48 hours after plating, the calcium sensitive dye Fura-2 was used to detect calcium flux in response to TRPV1 sensitization with or without PAR2 activation. Briefly, DRG neurons were incubated with capsaicin, a specific TRPV1 agonist for 1 minute and calcium flux was measured. Following 17 minutes of washout period, the DRG's were exposed to a sound capsaicin application for 1 min with or without prior PAR2 activation by LIGRLO 5 M for 2 min.

The addition of 50 nm capsaicin for 1 minute induced a transient calcium signal, as detected by the ratio of signal at 340 and 380 nm. After a 17 minute washout period, a second capsaicin (50 nm for 1 minute) induced calcium signal was triggered. For each individual neuron the second calcium signal was either decreased, stable, or increased in comparison to the first signal. As shown in FIG. 6A, the addition of LIGRLO led to a ~2-fold increase in the number of neurons that had an increased response to the 2nd capsaicin administration. This increase was stable across a range (20% to 300%) sensitization threshold values FIGS. 6B and 6C show the distribution of signal in response to the $2^{nd}$ capsaicin stimulation in DRG neurons. Without LIGRLO the majority of DRG showed a stable or decreased signal 2 relative to signal 1. When 5 M of the PAR2 agonist LIGRLO was added to DRG, the number of neurons showing increased sensitization increased from 19.5 to 38.5%, with fewer LIGRLO-stimulated neurons exhibiting reduced or stable signal levels (unpaired t-test, p<0.05).

These data demonstrate that PAR2 activation leads to the sensitization of TRPV1 channels.

P24E1102 Inhibits LIGRLO-Induced TRPV1 Sensitization in DRG Isolated from huPAR2 Knock in Rats.

Fibroblasts cultured from huPAR2 knock in rats were exposed to LIGRLO and tested for calcium flux in the presence of Fura-2. P24E1102 inhibited calcium flux in a dose-dependent manner (data not shown).

DRG were isolated from hPAR2 knock in rats, cultured, and subjected to TRPV1 sensitization protocol with PAR2 activation as describe above in wild type rats. Pretreatment of DRG neurons by P24E1102 (500 nM), starting two hours prior to LIGRLO incubation, reduced the number of neurons exhibiting an increased response to the $2^{nd}$ capsaicin application, from 22.05% in the absence of P24E110 to 11.2% (FIG. 7A). The amplitude of individual responses was not significantly reduced (data not shown).

Examining the distribution of responses more P24E1102 treated neurons exhibited a reduced or stable response to the $2^{nd}$ capsaicin stimulus (FIG. 7C) compared with those without P24E1102 (FIG. 7B, unpaired t-test, p<0.05).

These data demonstrate that an antibody that binds to the PAR2 receptor site, blocking ligand binding, and mitigates the effect of the PAR2 ligand in pain responses. It follows that an antibody that binds to the PAR2 receptor site has utility in the treatment of pain and related conditions.

Example 13: PAR2 Antibody Inhibition of Cancer

Effect of Antibody and PAR2 Stimulation on Cancer Cell Growth

Figure 8B:
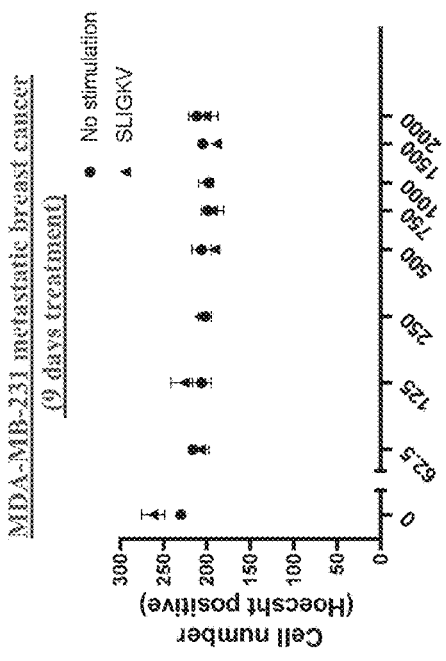
FIGS. 8A-8D show the impact on viability of cancer cells MCF (FIG. 8A), MDA-MB-231 (FIG. 8B), HepG2 (FIG. 8C), or A549 (FIG. 8D) treated with SLIGKV or no-stimulation, and with increasing concentrations of P24E1102.
Figure 8D:
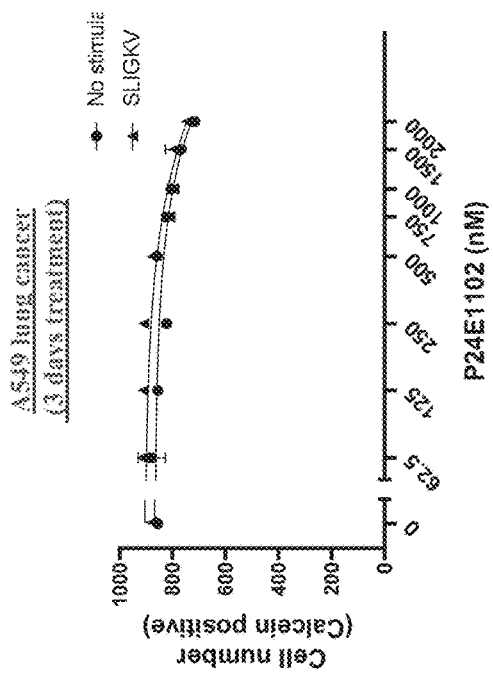

To evaluate the potential crosstalk between PAR2 and cancer progression, the following cancer cell lines: MCF-7 (breast cancer) (FIG. 8A), MDA-231 (metastatic breast cancer) (FIG. 8B), Hep-G2 (liver cancer) (FIG. 8C), and A549 (lung cancer) (FIG. 8D) were platted in 96-well plates at 2000 cell/well. Twenty-four hours after plating, the cells were treated with the PAR2 activating peptide SLIGKV (27 μM), with or without 2 hours P24E1102 (0-2000 nM) pre-treatment. After 3-9 days, cells were live stained with Hoechst 33342 (nuclei) and calcein (cytoplasm). Proliferation and morphological parameters were then analyzed using high content microscopy.

Figure 8A:
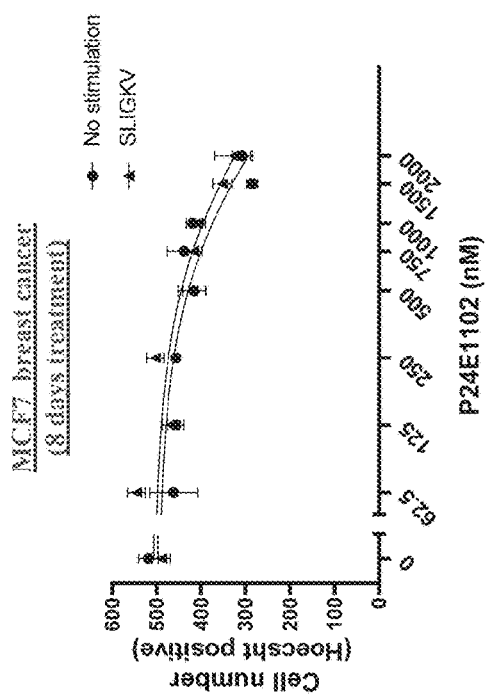
Figure 8C:
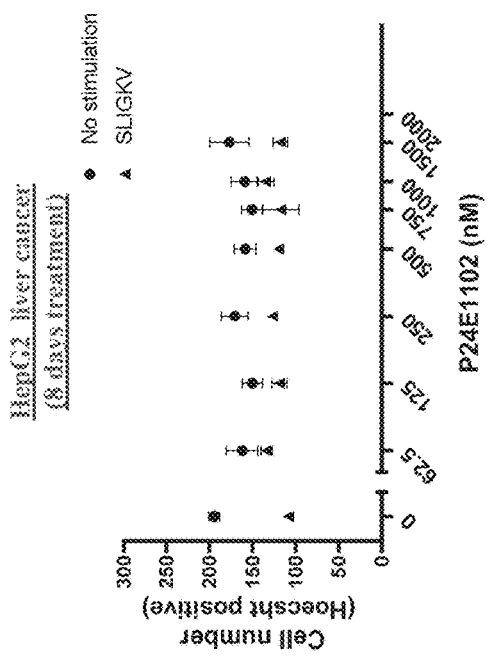

The data (FIGS. 8A-8D) shows that cells treated with P24E1102 exhibited mildly reduced (~20-40%) viability when compared to untreated cells. This holds both for SLIGKV treated cells and cells under no PAR2 stimulation. The highest effect was observed in MCF-7 breast cancer cells (FIG. 8A).

PAR2 Antibody Inhibits Cancer Metastasis

Figure 9E:
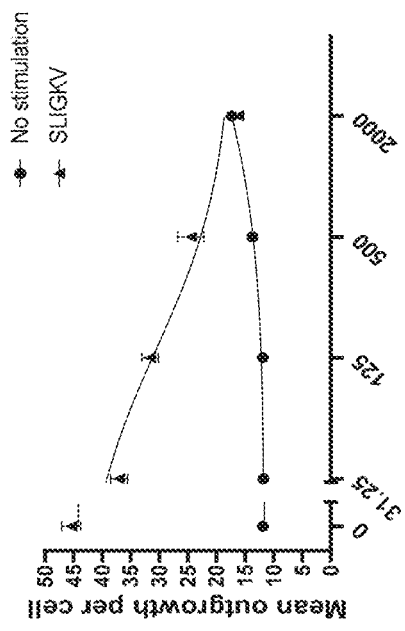

Following SLIGKV (270 μM) treatment, Hep-G2 cells exhibit morphological changes consistent with metastasic potentail. Compared to untreated cells (FIG. 9A) Briefly, following PAR2 activation (by SLIGKV), Hep-G2 cells present higher number of cellular protrusions, (resembling lamellipodia and filopodia) (FIG. 9B). Furthermore, as evident by the number of scattered cells following SLIGKV treatment, PAR2 activation promotes cell detachment and migration from cell clusters (FIG. 9B). PAR2 dependent effects were blocked by P24E1102 in a dose dependent manner. (FIGS. 9C and 9D). Complete inhibition was reached at 2000 nM. (FIG. 9D).

Figure 9F:
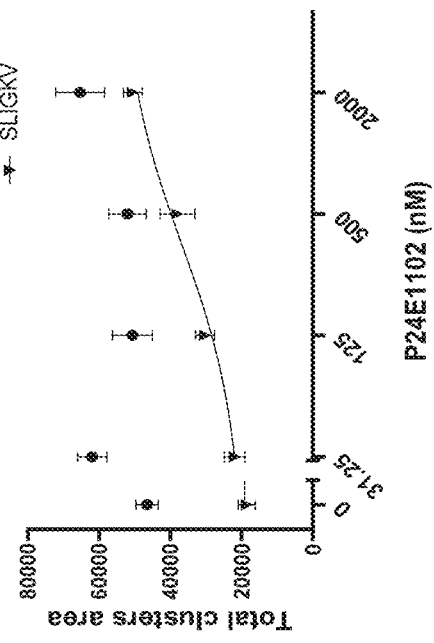
Figure 9G:
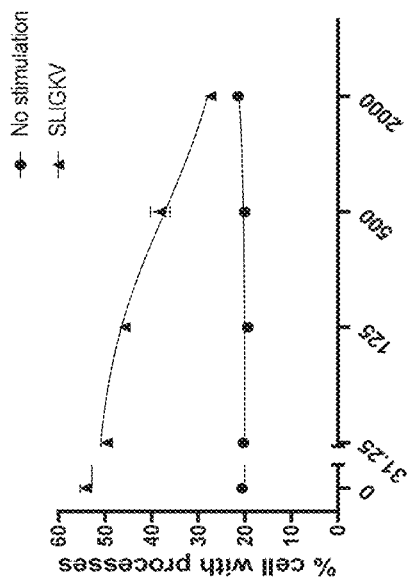
Figure 9H:
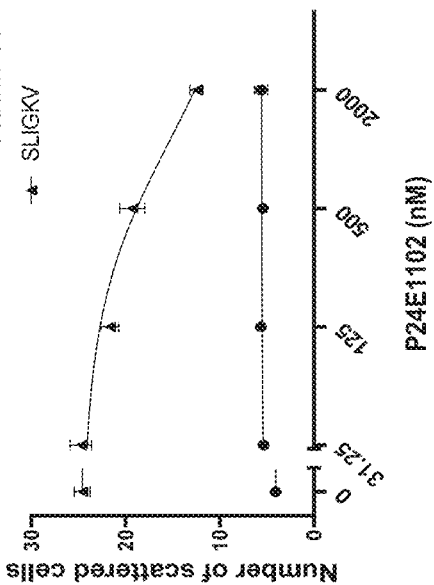

The dose-dependent inhibition by P24E1102 in the presence of SLIGKV is quantified for the % of cells with processes (FIG. 9E), mean number of outgrowths per cell (FIG. 9F), cell migration as shown by number of scattered cells, (FIG. 9G), and total area of cell clusters (FIG. 9H).

PAR2 has been linked to cancer metastasis, including a recent study showing that PAR2 expression is linked to poorer patient outcomes of hepatocellular carcinoma after hepatectomy (Tsai et al. The role of protease-activated receptor 2 in hepatocellular carcinoma after hepatectomy. *Medicina* June 2021: 57(6):574). The foregoing experiments are the first demonstrated that PAR2 stimulation appears to directly stimulate metastatic behavior, and that such metastatic behavior can be blocked by inhibiting PAR2, including by inhibiting ligand binding to the PAR2. The ability of PAR2 inhibition to inhibit cancer metastasis indicates that PAR-2 antagonists, including P24E1102, may be useful in the treatment of cancer.

Example 14: PAR2 Antibody Inhibits PAR2 Related Gene Expression Induction

PAR2 associated gene expression profile was evaluated using Clariom GOScreen high-throughput transcriptomic assay. Briefly, primary human pulmonary artery smooth muscle cells (HPASMC), primary human skin fibroblasts, and A549 human lung cancer cell line, were treated with SLIGKV (400 M), either alone or in the presence of P24E1102 (500 nM) which was administered two hours prior to SLIGKV. Cells were lysed and mRNA was extracted to reveal gene expression patterns using Afymetrix RNAchip technology. Compared to control conditions (no SLIGKV or antibody), 729, 875, 426 genes were affected (at least +/−2 fold-change) by SLIGKV in HPASMC, skin fibroblasts and A549 cells, respectively. P24E1102 at a concentration of 500 nM significantly reduced these SLIGKV-driven changes, as shown in Table 15.

TABLE 15

Differential gene expression in the presence of PAR2 agonist is reversed by PAR2 antibody

| Cells | Number of genes differentially regulated above control (at least +/− 2 fold-change) | |
|---|---|---|
| | SLIGKV | SLIGKV + P24E1102 |
| A549 lung cancer | 426 | 153 |
| Human primary airway smooth muscle cells | 729 | 75 |
| Human primary fibroblasts | 875 | 140 |

The differentially expressed (i.e. SLIGKV versus SLIGKV+P24E1102) data from Table 15 was further analyzed for relevant disease pathways. Clariom GO Screen data was analyzed using Transcriptome Analysis Console (TAC) and DAVID Gene Ontology (GO) softwares. This enabled exploratory grouping analysis and identification of gene expression differences between clusters or groupings. KEGG, GAD and WikiPathway databases were used for analysis.

Differentially Expressed Genes in HPASMC

Pathway enrichment analysis identified, among others, the IL-18 signalling pathway (44 genes, 26 up, 18 down, p=0.008506). There is considerable evidence for IL-18 having a role in various infectious, metabolic or inflammatory diseases such as influenza virus infection, atheroma, myocardial infarction, chronic obstructive pulmonary disease, or Crohn's disease. (Kaplanski. *Immunol Rev* 2018 January; 281(1):138-153). Also regulated was the NRF2 pathway (41 genes, 25 up, 16 down, p=0.052) which regulates the expression of antioxidant proteins that protect against oxidative damage triggered by injury and inflammation.

Disease annotation of differentially expressed genes in HPASMC using Genetic Associated Database (DAVID platform) identified 26 genes related to asthma, 14 related to arthritis/rheumatoid arthritis, among others Differentially Expressed Genes in Human Skin Fibroblasts Disease annotation of differentially expressed genes in human skin fibroblasts using Genetic Associated Database (DAVID platform) identified 16 genes related to asthma and Viral|Respiratory Syncytial Virus Infections, among others Differentially Expressed Genes in Human Skin Fibroblast Pathway enrichment analysis of differentially expressed genes in A549 cells. SLIGKV mediated PAR2 agonism was particularly observed in pathways associated with energy metabolism, immunity, signaling pathways, cancer and blood vessel regulation. P24E1102 at a concentration of 500 nM significantly reduced these changes SLIGKV driven changes, for most or all of the genes in each pathway.

Differentially Expressed Genes in A549 Cells

Disease annotation of differentially expressed genes in A549 using DAVID included pulmonary diseases, kidney disease, metabolic disease, cardiovascular diseases and several cancers. There were four pulmonary diseases: cystic fibrosis (8 genes), lung disease generally (8 genes), asthma (20) and COPD (20). The differential regulation of each of these genes was completely reversed by P24E1102. The results highlight the potential of P24E1102 treatment for these diseases, The invention is not to be limited in scope by the specific aspects described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

What is claimed is:

1. A method for detecting PAR-2 in a sample comprising contacting the sample with an isolated antibody or antigen-binding fragment thereof that specifically binds to human protease activated receptor 2 (PAR-2) and comprises the heavy chain variable region (VH) complementarity determining region (CDR) 1, VH CDR2, VH CDR3 and the light chain variable region (VL) CDR1, VL CDR2, and VL CDR3 amino acid sequences of:
 (a) SEQ ID NOs: 10, 11, 12, 16, 17, and 18, respectively;
 (b) SEQ ID NOs: 7, 8, 9, 13, 14, and 15, respectively;
 (c) SEQ ID NOs: 10, 11, 12, 16, 19, and 18, respectively;
 (d) SEQ ID NOs: 10, 11, 12, 16, 29, and 18, respectively; or
 (e) SEQ ID NOs: 10, 11, 12, 16, 22, and 18, respectively.

2. The method of claim 1, wherein the sample is obtained from a human subject, optionally wherein the sample is a cancer sample.

3. The method of claim 1, wherein the sample is an in vitro sample.

* * * * *